United States Patent
Sun et al.

(10) Patent No.: US 7,405,234 B2
(45) Date of Patent: Jul. 29, 2008

(54) BICYCLIC MODULATORS OF ANDROGEN RECEPTOR FUNCTION

(75) Inventors: Chong-Qing Sun, East Windsor, NJ (US); Lawrence Hamann, Cherry Hill, NJ (US); David Augeri, Princeton, NJ (US); Yingzhi Bi, Plainsboro, NJ (US); Jeffrey Robl, Newtown, PA (US); Yan-Ting Huang, Pennington, NJ (US); Tammy Wang, Lawrenceville, NJ (US); Alexandra Holubec, Yardley, PA (US); Ligaya Simpkins, Titusville, NJ (US); James C. Sutton, Princeton Junction, NJ (US); James J. Li, Pennington, NJ (US)

(73) Assignee: Bristol-Myers Squibb Company, Princeton, NJ (US)

(*) Notice: Subject to any disclaimer, the term of this patent is extended or adjusted under 35 U.S.C. 154(b) by 281 days.

(21) Appl. No.: 10/780,415

(22) Filed: Feb. 17, 2004

(65) Prior Publication Data

US 2004/0181064 A1    Sep. 16, 2004

Related U.S. Application Data

(63) Continuation-in-part of application No. 10/438,722, filed on May 15, 2003, now abandoned.

(60) Provisional application No. 60/406,711, filed on Aug. 29, 2002, provisional application No. 60/381,616, filed on May 17, 2002.

(51) Int. Cl.
    A61K 31/415    (2006.01)
    C07D 235/02    (2006.01)

(52) U.S. Cl. .................................. 514/393; 548/302.7

(58) Field of Classification Search ............... 548/302.7; 514/393
    See application file for complete search history.

(56) References Cited

U.S. PATENT DOCUMENTS

| | | | |
|---|---|---|---|
| 3,239,345 A | 3/1966 | Hodge et al. | |
| 3,948,933 A | 4/1976 | Fontanella | |
| 4,036,979 A | 7/1977 | Asato | |
| 4,411,890 A | 10/1983 | Momany | |
| 4,859,684 A * | 8/1989 | Raeymaekers et al. | 514/314 |
| 4,959,361 A | 9/1990 | Walser | |
| 5,179,080 A | 1/1993 | Rothkopf | |
| 5,403,817 A | 4/1995 | Seckinger et al. | |
| 5,482,921 A | 1/1996 | Seckinger et al. | |
| 5,488,064 A | 1/1996 | Sher | |
| 5,491,134 A | 2/1996 | Sher et al. | |
| 5,541,204 A | 7/1996 | Sher et al. | |
| 5,556,909 A | 9/1996 | Desai et al. | |
| 5,605,877 A | 2/1997 | Schafer et al. | |
| 5,612,359 A | 3/1997 | Murugesan | |
| 5,688,808 A | 11/1997 | Jones et al. | |
| 5,688,810 A | 11/1997 | Jones et al. | |
| 5,693,646 A | 12/1997 | Jones et al. | |
| 5,693,647 A | 12/1997 | Jones et al. | |
| 5,696,127 A | 12/1997 | Jones et al. | |
| 5,696,130 A | 12/1997 | Jones et al. | |
| 5,696,133 A | 12/1997 | Jones et al. | |
| 5,770,615 A | 6/1998 | Cheng et al. | |
| 5,776,983 A | 7/1998 | Washburn et al. | |
| 5,811,374 A | 9/1998 | Bertram et al. | |
| 6,011,029 A | 1/2000 | Ding et al. | |
| 6,040,321 A | 3/2000 | Kim et al. | |
| 6,043,265 A | 3/2000 | Murugesan et al. | |
| 6,184,231 B1 | 2/2001 | Hewawasam et al. | |
| 6,310,095 B1 | 10/2001 | Sebti et al. | |
| 6,365,615 B1 * | 4/2002 | Kelly et al. | 514/386 |
| 6,531,612 B2 | 3/2003 | Gabriel et al. | |
| 6,566,387 B1 * | 5/2003 | Palovich et al. | 514/401 |
| 6,670,386 B2 | 12/2003 | Sun et al. | |
| 6,710,064 B2 | 3/2004 | Launay et al. | |
| 6,897,225 B1 * | 5/2005 | Sircar et al. | 514/333 |
| 6,992,102 B2 | 1/2006 | Hamann et al. | |
| 7,256,208 B2 | 8/2007 | Yingzhi et al. | |
| 2002/0133004 A1 | 9/2002 | Takaai | |
| 2005/0059652 A1 | 3/2005 | Hamann et al. | |
| 2005/0182105 A1 | 8/2005 | Nirschl et al. | |
| 2005/0187267 A1 | 8/2005 | Hamann et al. | |

(Continued)

FOREIGN PATENT DOCUMENTS

AU    A-82875/87    6/1988

(Continued)

OTHER PUBLICATIONS

Issartel et al.,1996, CAS: 125:316198.*

(Continued)

*Primary Examiner*—Rei-tsang Shiao
(74) *Attorney, Agent, or Firm*—Daniel Feigelson; Heslin Rothenberg Farley & Mesiti P.C.

(57) ABSTRACT

The invention provides compounds according to formula I

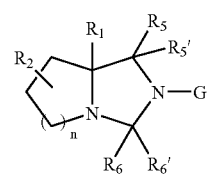

wherein the substitutents are as described herein.

Further provided are methods of using such compounds for the treatment of nuclear hormone receptor-associated conditions, such as age related diseases, for example sarcopenia. Also provided are pharmaceutical compositions containing such compounds and processes for preparing some of the compounds of the invention.

22 Claims, No Drawings

U.S. PATENT DOCUMENTS

| | | |
|---|---|---|
| 2005/0197359 A1 | 9/2005 | Nirdchl et al. |
| 2005/0197367 A1 | 9/2005 | Li et al. |
| 2007/0004717 A1 | 1/2007 | Li et al. |

FOREIGN PATENT DOCUMENTS

| | | |
|---|---|---|
| DE | 2126187 | 5/1971 |
| DE | 38 09 390 A | 9/1989 |
| EP | 0 272 594 A1 | 12/1987 |
| EP | 0 493323 B1 | 1/1992 |
| EP | 1 004 583 A3 | 5/2000 |
| EP | 1125925 | 8/2001 |
| GB | 1 503 244 A | 3/1978 |
| JP | 52 083686 A | 7/1977 |
| WO | WO89/07110 | 8/1989 |
| WO | WO89/07111 | 8/1989 |
| WO | WO93/04081 | 3/1993 |
| WO | WO94/05668 A | 3/1994 |
| WO | WO94/14817 A | 7/1994 |
| WO | WO96/19458 | 6/1996 |
| WO | WO97/19086 | 5/1997 |
| WO | WO97/21993 | 6/1997 |
| WO | WO97/30992 | 8/1997 |
| WO | WO97/49709 | 12/1997 |
| WO | WO98/22461 | 5/1998 |
| WO | WO98/25929 | 6/1998 |
| WO | WO98/38192 | 9/1998 |
| WO | WO98/54966 | 12/1998 |
| WO | WO99/00353 | 1/1999 |
| WO | WO99/01124 | 1/1999 |
| WO | WO99/02224 | 1/1999 |
| WO | WO99/02514 | 1/1999 |
| WO | WO99/03848 | 1/1999 |
| WO | WO99/07692 | 2/1999 |
| WO | WO99/24416 | 5/1999 |
| WO | WO99/27890 | 6/1999 |
| WO | WO99/28324 | 6/1999 |
| WO | WO99/43653 | 9/1999 |
| WO | WO99/54318 | 10/1999 |
| WO | WO99/54319 | 10/1999 |
| WO | WO99/54330 | 10/1999 |
| WO | WO99/65913 | 12/1999 |
| WO | WO99/67252 | 12/1999 |
| WO | WO99/67253 | 12/1999 |
| WO | WO 00/00485 | 1/2000 |
| WO | WO 00/01389 | 1/2000 |
| WO | WO 00/13508 | 3/2000 |
| WO | WO0059874 | 10/2000 |
| WO | WO00/72845 * | 12/2000 |
| WO | WO 01/07052 A | 2/2001 |
| WO | WO 01/16108 A2 | 3/2001 |
| WO | WO 01/16133 A2 | 3/2001 |
| WO | WO 01/16139 A1 | 3/2001 |
| WO | WO 01/30781 A2 | 5/2001 |
| WO | WO 01/46195 A1 | 6/2001 |
| WO | WO0154498 | 8/2001 |
| WO | WO0170684 | 9/2001 |
| WO | WO0172705 | 10/2001 |
| WO | WO 02/00653 | 1/2002 |
| WO | WO0218335 | 7/2002 |
| WO | WO 03/011824 A | 2/2003 |
| WO | WO 03/066636 A | 8/2003 |

OTHER PUBLICATIONS

Palovich et al., 2000, CAS: 134:25357.*

Panouse, J. et al., "Relations structures-Activities des immunomodulateurs apport de la modelisation moleculaire. Immunimodulator structure-Activity Relationships: Contribution of Molecular Modeling", Annales Pharmaceutiques Francaises, Masson. Paris, FR, pp. 291-302 (2000).

Talon, S. et al., "Increased rigidity of the chiral centre of tocainide favours stereoselectivity and use-dependent block of skeletal muscle $Na^+$ channels enhancing the antimyotonic activity in vivo", British J. of Pharmacology, vol. 134(7), pp. 1523-1531 (2001).

Uozumi, Y. et al., "Enantioselective desymmetrization of *meso*-cyclic anhydrides catalyzed by hexahydro-1*H*-pyrrolo [1,2-*c*] imidazolones", Tetrahedron Letters, vol. 42(3), pp. 411-414 (2001).

Alexey B. Dyatkin, (1997) Tetrahedron Letters, vol. 38, No. 12, pp. 2065-2066.

Banz, W.J. et al., "Effects of Soy Protein and Soy Phytoestrogens on Symptoms Associated with Cardiovascular Disease in Rats", Journal of Medicinal Food, vol. 2, Nos. 3-4, pp. 271-273 (1999).

Beyler, A.L. et al., "Methods for Evaluating Anabolic and Catabolic Agents in Laboratory Animals", Journal of the American Medical Women's Association, vol. 23, No. 8, pp. 708-721 (1968).

Boris, A. et al., "Comparative Androgenic, Myotrophic and Antigonadotrophic Properties of Some Anabolic Steroids", Steroids, vol. 15, pp. 61-71 (1970).

Bourguet, W. et al., "Crystal Structure of the ligand-binding domain of the human nuclear receptor RXR-α", Nature, vol. 375, pp. 377-382 (1995).

Brzozowski, A.M. et al., "Molecular basis of agonism and antagonism in the oestrogen receptor", Nature, vol. 389, pp. 753-758 (1997).

Bundgaard, H., "Design and Application of Prodrugs", A Textbook of Drug Design and Development, Harwood Academic Publishers, publ., Krogsgaard-Larsen, P. and Bundgaard, T., eds., pp. 113-191 (1991).

Bundgaard, H., ed., Design of Prodrugs, Elsevier Science Publishers B.V., publ., (table of contents) (1985).

Chalepakis, G. et al., "Differential Gene Activation by Glucocorticoids and Progestins Through the Hormone Regulatory Element of Mouse Mammary Tumor Virus", Cell, vol. 53, pp. 371-382 (1988).

Delaisi, C. et al., "RU54115, A Tight-Binding Aromatase Inhibitor Potentially Useful for the Treatment of Breast Cancer", J. Steroid Biochem. Molec. Biol., vol. 41, No. 3-8, pp. 773-777 (1992).

Edwards, J.P. et al., "Nonsteroidal Androgen Receptor Agonists Based on 4-(Trifluoromethyl)-2*H*-Pyrano[3,2-*g*]Quinolin-2-One", Bioorganic & Medicinal Chemistry Letters, vol. 9, pp. 1003-1008 (1999).

Evans, R.M., "The Steroid and Thyroid Hormone Receptor Superfamily", Science, vol. 240, pp. 889-895 (1988).

Gori, Z. et al., "La Ipertrofia Da Testosterone Del Muscolo Elevatore Dell'ano Di Ratto Castrato.—I) Dati Quantitativi", Boll.-Soc. Ital. Biol. Sper., vol. 42, 1596-1599 (1966).

Gori, Z. et al., "La Ipertrofia Da Testosterone Del Muscolo Elevatore Dell'ano Di Ratto Castrato.—II) Osservazioni Al Microscopio Elettronico", Boll.-Soc. Ital. Biol. Sper., vol. 42, 1600-1601 (1966).

Grese, T.A. et al., "Molecular determinants of tissue selectivity in estrogen receptor modulators", Proc. Natl. Acad. Sci. USA, vol. 94, pp. 14105-14110 (1997).

Hamann, L.G. et al., "Discovery of a Potent, Orally Active, Nonsteroidal Androgen Receptor Agonist: 4-Ethyl-1,2,3,4-tetrahydro-6-(trifluoromethyl)-8-pyridono[5,6-*g*]-quinoline (LG121071)", J. Med. Chem., vol. 42, pp. 210-212 (1999).

Hamann, L.G. et al, "Synthesis and Biological Activity of a Novel Series of Nonsteroidal, Peripherally Selective Androgen Receptor Antagonists Derived from 1,2-Dihydropyridono [5,6-*g*] quinolines", J. Med. Chem., vol. 41, pp. 623-639 (1998).

Heiser, W.C., "Optimizing Electroporation Conditions for the Transformation of Mammalian Cells", Methods in Molecular Biology, vol. 130, pp. 117-134 (2000).

Hempstock, J. et al., "Inhibition of Growth of Primary Human Prostate Cells by Phytoestrogens", Journal of Medicinal Food, vol. 2, Nos. 3-4, pp. 243-246 (1999).

Hershberger, L.G. et al., "Myotrophic Activity of 19-Nortestosterone and Other Steroids Determined by Modified Levator Ani Muscle Method", P.S.E.B.M., vol. 83, pp. 175-180 (1953).

Hiraoka, D. et al., "Inhibitory and Stimulatory Effects of Glucocorticoid on Androgen-induced Growth of Murine Shionogi Carcinoma 115 in Vivo and in Cell Culture", Cancer Research, vol. 47, pp. 6560-6564 (1987).

Imakura, Y. et al., Regioselective Cleavage Reaction of the Aromatic Methylenedioxy Ring. V. Cleavage with Sodium Alkoxides-Alcohols, Potassium *tert*-Butoxide-Alcohols, Dimsyl Anion-Methyl Alcohol, Metallic Sodium-Alcohols, etc., Chem. Pharm. Bull. vol. 40, No. 7, pp. 1691-1696 (1992).

Johannsson, G. et al., "Gorwth Hormone Treatment of Abdominally Obese Men Reduces Abdominal Fat Mass, Improves Glucose and Lipoprotein Metabolism, and Reduces Diastolic Blood Pressure", Journal of Clinical Endocrinology and Metabolism, vol. 82, No. 3, pp. 727-734 (1997).

Kakigami, T. et al., "Synthesis and Structure-Activity Relationship of 3-Substituted Benzamide, Benzo[*b*]furan-7-carboxamide, 2,3-Dihydrobenzo[*b*]furan-7-carboxamide, etc.", Chem. Pharm. Bull., vol. 46, No. 1, pp. 42-52 (1998).

Milata, V. et al., "Simple and Convenient Procedure for the Preparation of 1-methyl-4-nitrobenzimidazole", Org. Prep. Proced. Int., vol. 25, No. 6, pp. 703-704 (1993).

Minesita, T. et al., "An Androgen-dependent Mouse Mammary Tumor", Cancer Research, vol. 25, pp. 1168-1175 (1965).

Navone, N.M. et al., "Establishment of Two Human Prostate Cancer Cell Lines Derived from a Single Bone Metastasis", Clinical Cancer Research, vol. 3, pp. 2493-2500 (1997).

Neri, R. et al., "A Biological Profile of a Nonsteroidal Antiandrogen, SCH 13521 (4'-Nitro-3'-Trifluoromethylisobutyranilide)", Endo, vol. 91, No. 2, pp. 427-437 (1972).

Okuda, Y. et al., "Testosterone Dependant Regulation of the Enzymes Involved in DNA Synthesis in the Rat Ventral Prostate", The Journal of Urology, vol. 145, pp. 188-191 (1991).

Quella, S.K. et al., "Evaluation of Soy Phytoestrogens for the Treatment of Hot Flashes in Breast Cancer Survivors: A North Central Cancer Treatment Group Trial", Journal of Clinical Oncology, vol. 18, No. 5, pp. 1068-1074 (2000).

Regal, J.F. et al., "Dietary Phytoestrogens Have Anti-Inflammatory Activity in a Guinea Pig Model of Asthma", P.S.E.B.M., vol. 223, pp. 372-378 (2000).

Rodbard, D., "Chapter 3: Mathematics and Statistics of Ligand Assays: An Illustrated Guide", Ligand Assay, Masson Publishing USA, Inc., publ., J. Langan et al., eds, pp. 45-101 (1981).

Schuur, E.R. et al., "Prostate-Specific Antigen Expression Is Regulated by an Upstream Enhancer", The Journal of Biological Chemistry, vol. 271, No. 12, pp. 7043-7051 (1996).

Shiau, A.K. et al., "The Structural Basis of Estrogen Receptor/Coactivator Recognition and the Antagonism of This Interaction by Tamoxifen", Cell, vol. 95, pp. 927-937 (1998).

Smigel, K., "Breast Cancer Prevention Trial Shows Major Benefit, Some Risk", Journal of the National Cancer Institute, vol. 90, No. 9, pp. 647-648 (1998).

Suzuki, T. et al., "Effects of Antiandrogens on Growth of Androgen-Dependent Mouse Mammary Tumor (Shionogi Carcinoma 115) In Vivo and In Vitro", J. Steroid Biochem. Molec. Biol., vol. 37, No. 4, pp. 559-567 (1990).

Tanenbaum, D.M. et al., "Crystallographic comparison of the estrogen and progesterone receptor's ligand binding domains", Proc. Natl. Acad. Sci. USA, vol. 95, pp. 5998-6003 (1998).

Vegeto, E. et al., "The Mechanism of RU486 Antagonism is Dependent on the Conformation of the Carboxy-Terminal Tail of the Human Progesterone Receptor", Cell, vol. 69, pp. 703-713 (1992).

Venable, J.H., "Constant Cell Populations in Normal, Testosterone-Deprived and Testosterone-stimulated Levator Ani Muscles", Am. J. Anat., vol. 119, pp. 263-270 (1966).

Wermuth, C.G. et al., "Designing Prodrugs and Biopracursors I: Carrier Prodrugs", The Practice of Medicinal Chemistry, Academic Press, publ., Wermuth, C.G., ed., pp. 671-696 (1996).

Banker et al., "Modern Pharmaceuticals, 3rd ed. ". Marcel Dekker, New York, 1996, pp. 451 and 596.

Boeijen et al., Bioorg Med. Chem. Lett. 8:2375-2380.

Fernand Labrie, Int'l Braz. J. Urol. 30(1):3-11.

Hempstock et al., Brit. J. Urology 82:560-563.

Iseki, K. et al., Tet. 53(10) 3513-26.

Lalezari et al., J. Het Chem 20(2) 483-485 (1983).

Matsuki et al., Chem. Pharm. Bull. 42(1): 9-18.

Montes de Oca et al., Arkivoc, 390-403 (2003).

Taplin et al., J. Cell Biochem. 91 (3):483-490.

Uozumi, Tet Lett 42:407-410.

Wolft "Burger's Medicinal Chemistry, 5th ed. Part 1", John Wily & Sons 1995, pp. 975-977.

\* cited by examiner

BICYCLIC MODULATORS OF ANDROGEN RECEPTOR FUNCTION

CROSS-REFERENCE TO RELATED APPLICATION

This application is a Continuation-in-Part Application of U.S. patent application Ser. No. 10/438,722, filed May 15, 2003, now abandoned that claims the benefit of U.S. Provisional Application Nos. 60/381,616, filed May 17, 2002 and 60/406,711, filed Aug. 29, 2002, which are incorporated herein by reference in their entirety.

FIELD OF THE INVENTION

The present invention relates to bicyclic compounds, methods of using such compounds in the treatment of androgen receptor-associated conditions, such as age-related diseases, for example sarcopenia, and to pharmaceutical compositions containing such compounds.

BACKGROUND OF THE INVENTION

Nuclear hormone receptors (NHR's) constitute a large super-family of structurally-related and sequence-specific gene regulators scientists have named "ligand-dependent transcription factors." R. M. Evans, Science, 240:889 (1988). The steroid binding NHR's (SB—NHR's) form a recognized subset of the NHR's, including the progesterone receptor (PR), androgen receptor (AR), estrogen receptor (ER), glucocorticoid receptor (GR) and mineralocorticoid receptor (MR). The conventional nuclear hormone receptors are generally transactivators in the presence of ligand, which selectively bind to the NHR in a way that effects gene transcription. In the absence of a corresponding ligand, some of the orphan receptors behave as if they are transcriptionally inert. Others, however, behave as either constitutive activators or repressors. These orphan nuclear hormone receptors are either under the control of ubiquitous ligands that have not been identified, or do not need to bind ligand to exert these activities.

The AR is a ligand-activated transcriptional regulatory protein that mediates induction of male sexual development and function through its activity with endogenous androgens. In addition, androgens are associated with male and female maintenance of muscle mass and strength, bone mass and erythropoiesis. Androgens, such as testosterone, also play an important role in many physiological processes, such as differentiation of male internal and external genitalia, development and maintenance of male secondary sexual characteristics (e.g., the development of prostate, seminal vesicles, penis, scrotum, skeletal muscle, redistribution of body fat, stimulation of long bone growth, closure of epiphyses, development of male hair growth pattern and enlargement of larynx), the maintenance of sexual behavior and function (e.g., libido and potency) and spermatogenesis (in man).

As one ages, the serum androgen concentration in the body declines. The age dependent decline in androgens is associated with changes in body composition for men and women, such as a lower percentage of muscle mass and an increase in body fat, e.g., sarcopenia. In this regard, modulation of the AR gene can have an impact on the physiological effects associated with androgen production. However, the effectiveness of known modulators of steroid receptors is often tempered by their undesired side-effect profile, particularly during long-term administration. For example, the administration of synthetic androgens has been associated with liver damage, prostate cancer, adverse effects on male sexual function and adverse effects associated with cardiovascular and erythropoietic function.

Numerous synthetically-derived steroidal and non-steroidal agonists and antagonists have been described for the members of the SB-NHR family. Many of these agonist and antagonist ligands are used clinically in man to treat a variety of medical conditions. RU486 (mifepristone) is an example of a synthetic antagonist of the PR, which is utilized as a birth control agent (Vegeto et al., Cell 69: 703-713 (1992)). Flutamide is an example of an antagonist of the AR, which is utilized for the treatment of prostate cancer (Neri et al, Endo. 91, 427-437 (1972)). Tamoxifen is an example of a tissue-selective modulator of the ER function, that is used in the treatment of breast cancer (Smigel J. Natl. Cancer Inst. 90, 647-648 (1998)). Tamoxifen can function as an antagonist of the ER in breast tissue while acting as an agonist of the ER in bone (Grese et al., Proc. Natl. Acad. Sci. USA 94, 14105-14110 (1997)). Because of the tissue-selective effects seen for Tamoxifen, this agent, and agents like it, are referred to as tissue-selective estrogen receptor modulators. In addition to synthetically-derived non-endogenous ligands, non-endogenous ligands for NHR's can be obtained from food sources (Regal et al., Proc. Soc. Exp. Biol. Med. 223, 372-378 (2000) and Hempstock et al., J. Med. Food 2, 267-269 (1999)). The flavanoid phytoestrogens are an example of an unnatural ligand for SB-NHR's that are readily obtained from a food source such as soy (Quella et al., J. Clin. Oncol. 18, 1068-1074 (2000) and Banz et al., J. Med. Food 2, 271-273 (1999)). The ability to modulate the transcriptional activity of an individual NHR by the addition of a small molecule ligand, makes these receptors ideal targets for the development of pharmaceutical agents for a variety of disease states.

As mentioned above, non-natural ligands can be synthetically engineered to serve as modulators of the function of NHR's. In the case of SB-NHR's, engineering of an unnatural ligand can include the identification of a core structure which mimics the natural steroid core system. This can be achieved by random screening against several SB-NHR's, or through directed approaches using the available crystal structures of a variety of NHR ligand binding domains (Bourguet et al., Nature 375, 377-382 (1995), Brzozowski, et al., Nature 389, 753-758 (1997), Shiau et al., Cell 95, 927-937 (1998) and Tanenbaum et al., Proc. Natl. Acad. Sci. USA 95, 5998-6003 (1998)). Differential substitution about such a steroid mimic core can provide agents with selectivity for one receptor versus another. In addition, such modifications can be employed to obtain agents with agonist or antagonist activity for a particular SB-NHR. Differential substitution about the steroid mimic core can result in the formation of a series of high affinity agonists and antagonists with specificity for, for example, ER versus PR versus AR versus GR versus MR. Such an approach of differential substitution has been reported, for example, for quinoline based modulators of steroid NHRs in Hamann et. al., J. Med. Chem., 41, 623 (1998); Hamann et. al., J. Med. Chem. 42, 210 (1999); WO 9749709; U.S. Pat. No. 5,696,133; U.S. Pat. No. 5,696,130; U.S. Pat. No. 5,696,127; U.S. Pat. No. 5,693,647; U.S. Pat. No. 5,693,646; U.S. Pat. No. 5,688,810; U.S. Pat. No. 5,688,808 and WO 9619458, all incorporated herein by reference.

Accordingly, identification of compounds which have good specificity for one or more steroid receptors, but which have reduced or no cross-reactivity for other steroid or intracellular receptors, would be of significant value in the treatment of male and female hormone-responsive diseases. There is, therefore, a need in the art for the identification of selective modulators of the steroid binding nuclear hormone receptors, particularly non-steroidal, non-toxic tissue selective androgen receptor modulators, which activate the androgen receptor in skeletal muscle while demonstrating limited or neutral effect on other androgen responsive (e.g., prostate) tissues.

SUMMARY OF THE INVENTION

In accordance with illustrative embodiments and demonstrating features of the present invention, compounds are provided which are capable of modulating the function of a nuclear hormone receptor. Preferably the compounds are selective androgen receptor modulators, and have the general formula I

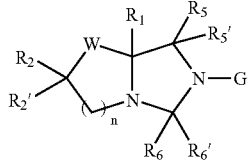

I wherein $R_1$ is selected from the group consisting of hydrogen (H), alkyl or substituted alkyl, alkenyl or substituted alkenyl, arylalkyl or substituted arylalkyl, $CO_2R_4$, $CONR_4R_4'$ and $CH_2OR_4$;

$R_2$ and $R_2'$ are independently selected from the group consisting of hydrogen (H), $OR_3$, $SR_3$, halo, $NHR_3$, $NHCOR_4$, $NHCO_2R_4$, $NHCONR_4R_4'$ and $NHSO_2R_4$;

$R_3$ in each functional group is independently selected from the group consisting of hydrogen (H), alkyl or substituted alkyl, $CHF_2$, $CF_3$ and $COR_4$;

$R_4$ and $R_4'$ in each functional group are each independently selected from the group consisting of hydrogen(H), alkyl or substituted alkyl, alkenyl or substituted alkenyl, alkynyl or substituted alkynyl, cycloalkyl or substituted cycloalkyl, arylalkyl or substituted arylalkyl, aryl or substituted aryl, and heteroaryl or substituted heteroaryl;

$R_5$ and $R_5'$ are each independently selected from the group consisting of hydrogen(H), alkyl or substituted alkyl, alkenyl or substituted alkenyl, alkynyl or substituted alkynyl, cycloalkyl or substituted cycloalkyl, arylalkyl or substituted arylalkyl, aryl or substituted aryl, and heteroaryl or substituted heteroaryl, wherein at least one of $R_5$ and $R_5'$ is hydrogen, or $R_5$ and $R_5'$ taken together can form a double bond with oxygen (O), sulfur (S), $NR_7$ or $CR_7R_7'$;

$R_6$ and $R_6'$ are each independently selected from the group consisting of hydrogen(H), alkyl or substituted alkyl, alkenyl or substituted alkenyl, alkynyl or substituted alkynyl, cycloalkyl or substituted cycloalkyl, arylalkyl or substituted arylalkyl, aryl or substituted aryl, and heteroaryl or substituted heteroaryl, wherein at least one of $R_6$ and $R_6'$ is hydrogen, or $R_6$ and $R_6'$ taken together can form a double bond with oxygen (O), sulfur (S), $NR_7$ or $CR_7R_7'$;

$R_7$ and $R_7'$ in each functional group are each independently selected from the group consisting of hydrogen(H), $OR_4$, alkyl or substituted alkyl, alkenyl or substituted alkenyl, alkynyl or substituted alkynyl, cycloalkyl or substituted cycloalkyl, arylalkyl or substituted arylalkyl, aryl or substituted aryl and heteroaryl or substituted heteroaryl G is an aryl, heterocyclo or heteroaryl group, wherein said group is mono- or polycyclic, and which is optionally substituted with one or more substituents selected from the group consisting of hydrogen, halo, CN, $CF_3$, $OR_4$, $CO_2R_4$, $NR_4R_4'$, $CONR_4R_4'$, $CH_2OR_4$, alkyl or substituted alkyl, alkenyl or substituted alkenyl, alkynyl or substituted alkynyl, cycloalkyl or substituted cycloalkyl, arylalkyl or substituted arylalkyl, aryl or substituted aryl and heteroaryl or substituted heteroaryl;

W is selected from the group consisting of $(CR_6R_6')$, $C(R_6)$ $OR_3$, $C(R_6)(NR_4R_4')$, and n is an integer of 1 or 2.

The definition of formula I above includes of all prodrug esters, stereoisomers and pharmaceutically acceptable salts of formula I.

Further embodiments of the present invention include compounds of the formula Ih

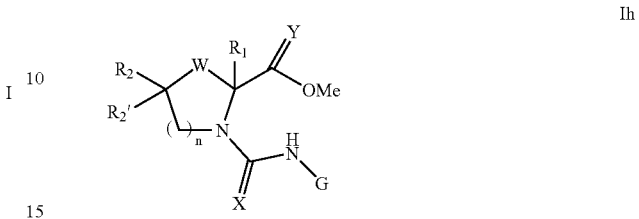

Ih wherein $R_1$ is selected from the group consisting of hydrogen (H), alkyl or substituted alkyl, alkenyl or substituted alkenyl, arylalkyl or substituted arylalkyl, $CO_2R_4$, $CONR_4R_4'$ and $CH_2OR_4$;

$R_2$ and $R_2'$ are each independently selected from the group consisting of hydrogen (H), $OR_3$, $SR_3$, halo, $NHR_3$, $NHCOR_4$, $NHCO_2R_4$, $NHCONRR'$ and $NHSO_2R_4$;

$R_3$ in each functional group is independently selected from the group consisting of hydrogen (H), alkyl or substituted alkyl, $CHF_2$, $CF_3$ and $COR_4$;

$R_4$ and $R_4'$ in each functional group are each independently selected from the group consisting of hydrogen(H), alkyl or substituted alkyl, alkenyl or substituted alkenyl, alkynyl or substituted alkynyl, cycloalkyl or substituted cycloalkyl, arylalkyl or substituted arylalkyl, aryl or substituted aryl, and heteroaryl or substituted heteroaryl;

$R_6$ and $R_6'$ are each independently selected from the group consisting of hydrogen(H), alkyl or substituted alkyl, alkenyl or substituted alkenyl, alkynyl or substituted alkynyl, cycloalkyl or substituted cycloalkyl, arylalkyl or substituted arylalkyl, aryl or substituted aryl, and heteroaryl or substituted heteroaryl, wherein at least one of $R_6$ and $R_6'$ is hydrogen, or $R_6$ and $R_6'$ taken together can form a double bond with oxygen (O), sulfur (S), $NR_7$ or $CR_7R_7'$;

X and Y are each independently oxygen (O) or sulfur (S);

G is an aryl, heterocyclo or heteroaryl group, wherein said group is mono- or polycyclic, and which is optionally substituted with one or more substituents selected from the group consisting of hydrogen, halo, CN, $CF_3$, $OR_4$, $CO_2R_4$, $NR_4R_4'$, $CONR_4R_4'$, $CH_2OR_4$, alkyl or substituted alkyl, alkenyl or substituted alkenyl, alkynyl or substituted alkynyl, cycloalkyl or substituted cycloalkyl, arylalkyl or substituted arylalkyl, aryl or substituted aryl and heteroaryl or substituted heteroaryl; and W is selected from the group consisting of $(CR_6R_6')$, $C(R_6)$ $OR_3$, $C(R_6)(NR_4R_4')$, and n is an integer of 1 or 2.

The definition of formula Ih above is inclusive of all prodrug esters, stereoisomers and pharmaceutically acceptable salts of formula Ih.

The compounds of formula I and formula Ih modulate the function of the nuclear hormone receptors, particularly the androgen receptor, and include compounds which are, for example, selective agonists, partial agonists, antagonists or partial antagonists of the androgen receptor. Preferably the compounds of formula I possess activity as agonists of the androgen receptor and may be used in the treatment of diseases or disorders associated with androgen receptor activity, such as maintenance of muscle strength and function (e.g., in the elderly); reversal or prevention of frailty or age-related functional decline ("ARFD") in the elderly (e.g., sarcopenia); prevention of catabolic side effects of glucocorticoids; prevention and treatment of reduced bone density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); acceleration of wound healing; accelerating bone fracture repair (such as accelerating the recovery of hip fracture patients); treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy.

The present invention provides for compounds of formula I and Ih, pharmaceutical compositions employing such compounds and for methods of using such compounds. In particular, the present invention provides a pharmaceutical composition comprising a therapeutically effective amount of a compound of formula I, Ih or both, alone or in combination with a pharmaceutically acceptable carrier.

Further, in accordance with the present invention, a method is provided for preventing, inhibiting or treating the progression or onset of diseases or disorders associated with nuclear hormone receptors, particularly, the androgen receptor, such as the diseases or disorders defined above and hereinafter, wherein a therapeutically effective amount of a compound of formula I, Ih or both, is administered to a mammalian, i.e., human, patient in need of treatment.

The compounds of the invention can be used alone, in combination with other compounds of the present invention, or in combination with one or more other agent(s) active in the therapeutic areas described herein.

In addition, a method is provided for preventing, inhibiting or treating the diseases as defined above and hereinafter, wherein a therapeutically effective amount of a combination of a compound of formula I, Ih or both, and another type of therapeutic agent, is administered to a human patient in need of treatment.

Preferred are compounds of formula I where $R_5$ and $R_5'$ are hydrogen or are taken together form a double bond with oxygen (O) or sulfur (S); and $R_6$ and $R_6'$ are taken together form a double bond with oxygen (O) or sulfur (S).

Additional preferred embodiments include are compounds of formula I and Ih wherein $R_1$ is hydrogen (H) or alkyl; and
$R_2$ is hydroxyl (OH).

Further preferred embodiments include compounds of formula I and Ih where G is selected from:

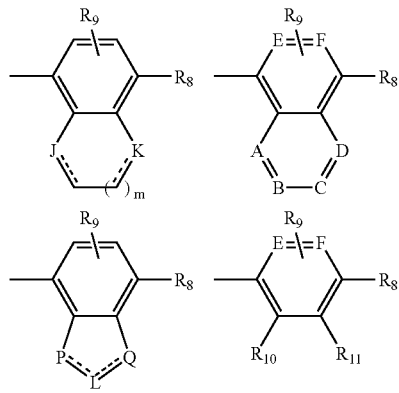

wherein
$R_8$, $R_9$, $R_{10}$ and $R_{11}$ in each functional group are each independently selected from the group consisting of hydrogen (H), $NO_2$, CN, $CF_3$, $OR_4$, $CO_2R_4$, $NR_4R_4'$, $CONR_4R_4'$, $CH_2OR_4$, alkyl or substituted alkyl, alkenyl or substituted alkenyl, alkynyl or substituted alkynyl, cycloalkyl or substituted cycloalkyl, arylalkyl or substituted arylalkyl, aryl or substituted aryl and heteroaryl or substituted heteroaryl;

A to F is each independently selected from N or $CR_1$;

J, K, L, P and Q are each independently selected from $NR_{12}$, O, S, SO, $SO_2$ or $CR_{12}R_{12}'$;

$R_{12}$ and $R_{12}'$ in each functional group are each independently selected from a bond or $R_1$; and m is an integer of 0 or 1.

Preferred are compounds of formula I and Ih where $R_8$ is CN.

The present invention also provides processes for preparing some compounds of the invention.

DETAILED DESCRIPTION OF THE INVENTION

Thus, in a first embodiment, the present invention provides compounds according to formula I

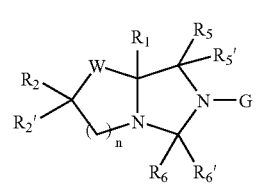

I wherein $R_1$ is selected from hydrogen (H), alkyl or substituted alkyl, alkenyl or substituted alkenyl, arylalkyl or substituted arylalkyl, $CO_2R_4$, $CONR_4R_4'$ and $CH_2OR_4$;

$R_2$ and $R_2'$ are each independently selected from hydrogen (H), alkyl, substituted alkyl, $OR_3$, $SR_3$, halo, $NHR_4$, $NHCOR_4$, $NHCO_2R_4$, $NHCONR_4R_4'$ and $NHSO_2R_4$;

and at least one of $R_2$ and $R_2'$ is H or alkyl, with the exception that $R_2$ and $R_2'$ can both be $OR_3$ when $R_3$ is not H;

$R_3$ in each functional group is independently selected from hydrogen (H), alkyl or substituted alkyl, $CHF_2$, $CF_3$ and $COR_4$;

$R_4$ and $R_4'$ in each functional group are each independently selected from hydrogen(H), alkyl or substituted alkyl, alkenyl or substituted alkenyl, alkynyl or substituted alkynyl, cycloalkyl or substituted cycloalkyl, arylalkyl or substituted arylalkyl, aryl or substituted aryl, and heteroaryl or substituted heteroaryl;

$R_5$ and $R_5'$ are each independently selected from hydrogen (H), alkyl or substituted alkyl, alkenyl or substituted alkenyl, alkynyl or substituted alkynyl, cycloalkyl or substituted cycloalkyl, arylalkyl or substituted arylalkyl, aryl or substituted aryl, and heteroaryl or substituted heteroaryl, wherein at least one of $R_5$ and $R_5'$ is hydrogen, or $R_5$ and $R_5'$ taken together can form a double bond with oxygen (O), sulfur (S), $NR_7$ or $CR_7R_7'$;

$R_6$ and $R_6'$ are each independently selected from hydrogen (H), alkyl or substituted alkyl, alkenyl or substituted alkenyl, alkynyl or substituted alkynyl, cycloalkyl or substituted cycloalkyl, arylalkyl or substituted arylalkyl, aryl or substituted aryl, and heteroaryl or substituted heteroaryl, wherein at least one of $R_6$ and $R_6'$ is hydrogen, or $R_6$ and $R_6'$ taken together can form a double bond with oxygen (O), sulfur (S), $NR_7$ or $CR_7R_7'$;

$R_7$ and $R_7'$ in each functional group are each independently selected from hydrogen(H), $OR_4$, alkyl or substituted alkyl, alkenyl or substituted alkenyl, alkynyl or substituted alkynyl, cycloalkyl or substituted cycloalkyl, arylalkyl or substituted arylalkyl, aryl or substituted aryl and heteroaryl or substituted heteroaryl;

G is an aryl, heterocyclo or heteroaryl group, wherein said group is mono- or polycyclic, and which is optionally substituted with one or more substitutents selected from hydrogen, halo, CN, $CF_3$, $OR_4$, $CO_2R_4$, $NR_4R_4'$, $CONR_4R_4'$, $CH_2OR_4$, alkyl or substituted alkyl, alkenyl or substituted alkenyl, alkynyl or substituted alkynyl, cycloalkyl or substituted cycloalkyl, arylalkyl or substituted arylalkyl, aryl or substituted aryl and heteroaryl or substituted heteroaryl; and W is selected from $(CR_6R_6')$, $C(R_6)OR_3$, $C(R_6)(NR_4R_4')$,
n is an integer of 1 or 2;

including all prodrug esters, pharmaceutically acceptable salts and stereoisomers thereof, with the following provisos:

(a) when $R_5$ and $R_5'$ and/or $R_6$ and $R_6'$ form a double bond with $CR_7R_7'$, when either $R_7$ or $R_7'$ is $OR_4$, $R_4$ is not hydrogen;

(b) excluding compounds where the following occur simultanously:

$R_2$ or $R_2'$ are hydrogen, $OR_3$, halo, $NHCOR_4$, $NHCO_2R_4$, $NHCONR_4R_4'$ or $NHSO_2R_4$;

$R_5$ and $R_5'$ are hydrogen or form a double bond with oxygen or sulfur;

$R_6$ and $R_6'$ are hydrogen, alkyl or substituted alkyl, alkenyl or substituted alkenyl, alkynyl or substituted alkynyl, cycloalkyl or substituted cycloalkyl, arylalkyl or substituted arylalkyl, aryl or substituted aryl, or heteroaryl or substituted heteroaryl, wherein at least one of $R_6$ and $R_6'$ is hydrogen, or $R_6$ and $R_6'$ taken together form a double bond with oxygen (O), sulfur (S) or $NR_7$;

$R_7$ is hydrogen, alkyl or substituted alkyl, alkenyl or substituted alkenyl, alkynyl or substituted alkynyl, cycloalkyl or substituted cycloalkyl, arylalkyl or substituted arylalkyl, aryl or substituted aryl, or heteroaryl or substituted heteroaryl; and G has the following structure:

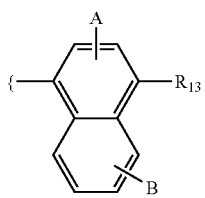

wherein $R_{13}$ is selected from hydrogen (H), cyano (—CN), nitro (—$NO_2$), halo, heterocyclo, $OR_{14}$, $CO_2R_{15}$, $CONHR_{15}$, $COR_{15}$, $S(O)_pR_{15}$, $SO_2NR_{15}R_{15}'$, $NHCOR_{15}$ and $NHSO_2R_{15}$;

$R_{14}$ in each functional group is independently selected from hydrogen (H), alkyl or substituted alkyl, $CHF_2$, $CF_3$ and $COR_{15}$;

$R_{15}$ and $R_{15}'$ in each functional group are each independently selected from hydrogen(H), alkyl or substituted alkyl, alkenyl or substituted alkenyl, alkynyl or substituted alkynyl, cycloalkyl or substituted cycloalkyl, heterocycloalkyl or substituted heterocycloalkyl, arylalkyl or substituted arylalkyl, aryl or substituted aryl, heteroaryl or substituted heteroaryl and —CN;

A and B are each independently selected from hydrogen (H), halo, cyano (—CN), nitro (—$NO_2$), alkyl or substituted alkyl and $OR_{14}$; and p is an integer from 0 to 2.

In a preferred embodiment, the present invention provides compounds according to formula I, as defined above, wherein G is selected from:

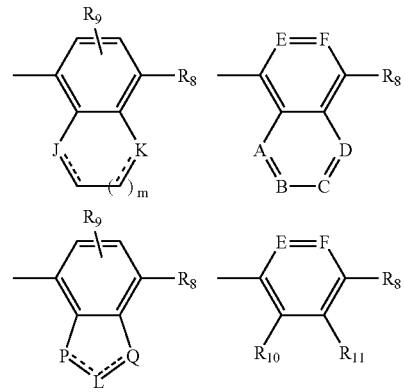

wherein $R_8$, $R_9$, $R_{10}$ and $R_{11}$ are each independently selected from hydrogen (H), $NO_2$, CN, $CF_3$, $OR_4$, $CO_2R_4$, $NR_4R_4'$, $CONR_4R_4'$, $CH_2OR_4$, alkyl or alkyl, alkenyl or substituted alkenyl, alkynyl or substituted alkynyl, cycloalkyl or substituted cycloalkyl, arylalkyl or substituted arylalkyl, aryl or substituted aryl and heteroaryl or substituted heteroaryl;

A to F is each independently selected from N or $CR_9$;

J, K, L, P and Q are each independently selected from $NR_{12}$, O, S, SO, $SO_2$ or $CR_{12}R_{12}'$;

$R_{12}$ and $R_{12}'$ in each functional group are each independently selected from a bond or $R_1$; and m is an integer of 0 or 1.

In a more preferred embodiment, the present invention provides compounds accroding to formula I, as defined above, wherein $R_1$ is hydrogen (H) or alkyl;

$R_2$ or $R_2'$ is hydroxyl (OH);

$R_5$ and $R_5'$ are hydrogen or are taken together form a double bond with oxygen (O) or sulfur (S); and $R_6$ and $R_6'$ are taken together form a double bond with oxygen (O) or sulfur (S).

In a more preferred embodiment, the present invention provides compounds according to formula I, as defined above, wherein $R_8$ is CN.

In a more preferred embodiment, the present invention provides compounds according to formula I selected from:

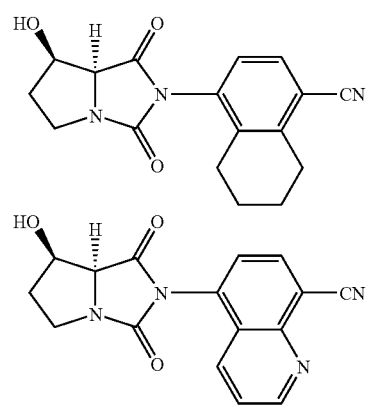

-continued
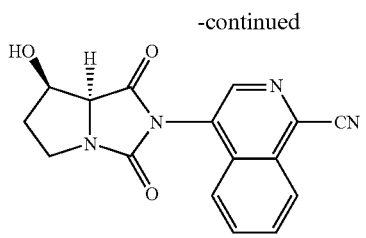
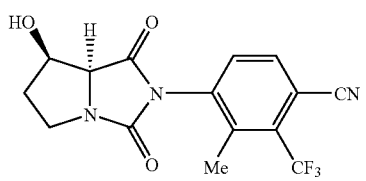
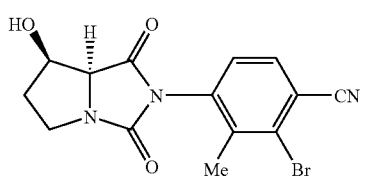
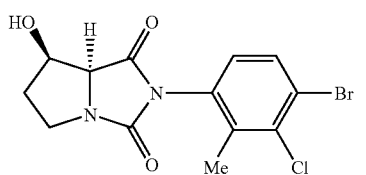
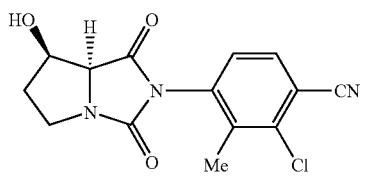
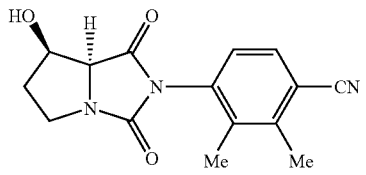
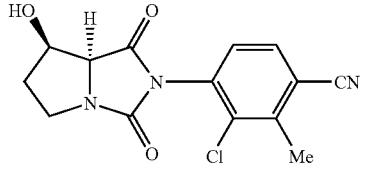
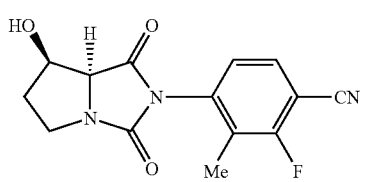
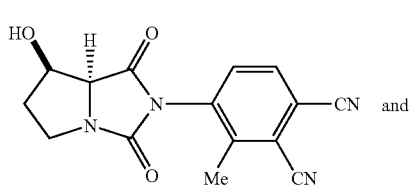 and
-continued
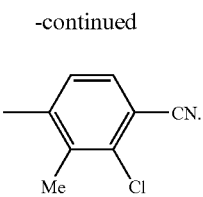
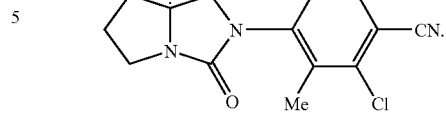
In a more preferred embodiment, the present invention provides compounds according to formula I selected from:
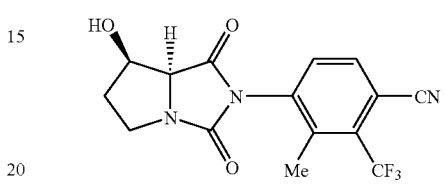
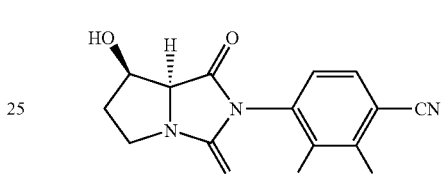
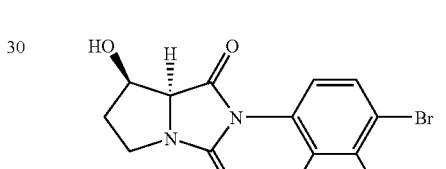
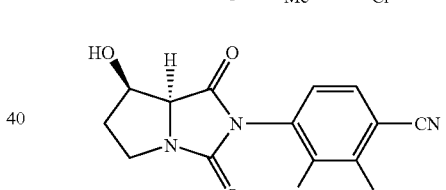
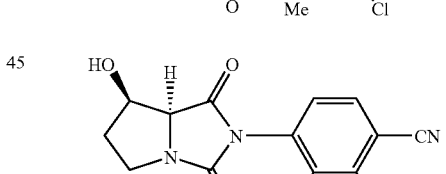
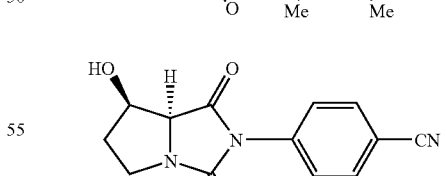
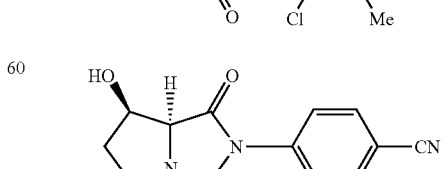
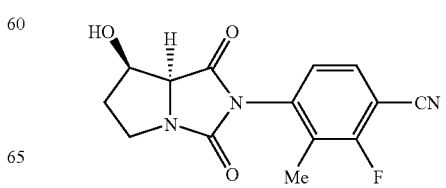

-continued

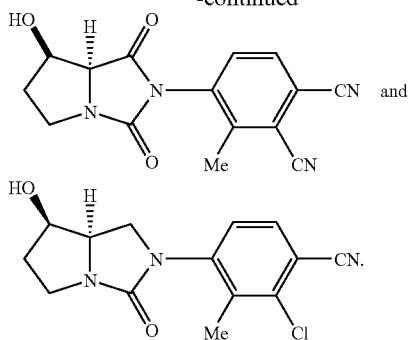

In a more preferred embodiment, the present invention provides compounds according to formula I selected from:

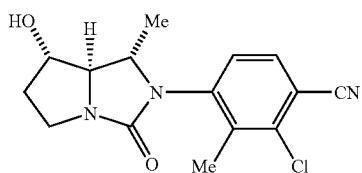
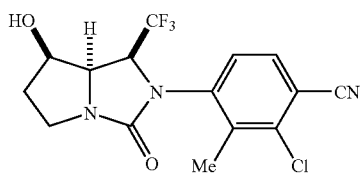
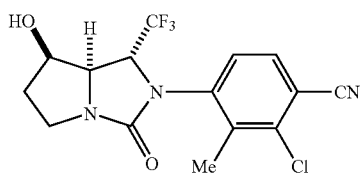
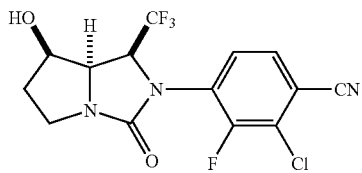
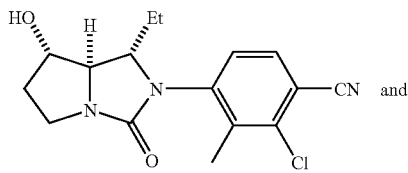
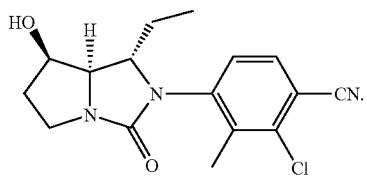

In a second embodiment, the present invention provides compounds according to formula Ih

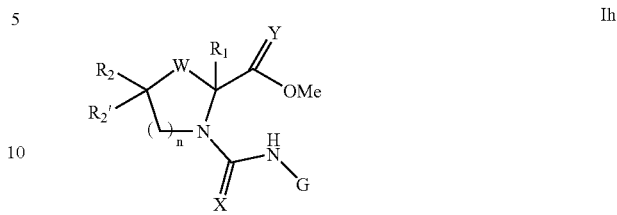

Ih wherein
$R_1$ is selected from hydrogen (H), alkyl or substituted alkyl, alkenyl or substituted alkenyl, arylalkyl or substituted arylalkyl, $CO_2R_4$, $CONR_4R_4'$ and $CH_2OR_4$;

$R_2$ and $R_2'$ are each independently selected from hydrogen (H), alkyl, substituted alkyl, $OR_3$, $SR_3$, halo, $NHR_4$, $NHCOR_4$, $NHCO_2R_4$, $NHCONR_4R_4'$ and $NHSO_2R_4$;

and at least one of $R_2$ and $R_2'$ is H or alkyl, with the exception that $R_2$ and $R_2'$ can both be $OR_3$ when $R_3$ is not H;

$R_3$ in each functional group is independently selected from hydrogen (H), alkyl or substituted alkyl, $CHF_2$, $CF_3$ and $COR_4$;

$R_4$ and $R_4'$ in each functional group are each independently selected from hydrogen(H), alkyl or substituted alkyl, alkenyl or substituted alkenyl, alkynyl or substituted alkynyl, cycloalkyl or substituted cycloalkyl, arylalkyl or substituted arylalkyl, aryl or substituted aryl, and heteroaryl or substituted heteroaryl;

X and Y are each independently oxygen (O) or sulfur (S);

G is an aryl, heterocyclo or heteroaryl group, wherein said group is mono- or polycyclic, and which is optionally substituted with one or more substitutents selected from the group consisting of hydrogen, halo, CN, $CF_3$, $OR_4$, $CO_2R_4$, $NR_4R_4'$, $CONR_4R_4'$, $CH_2OR_4$, alkyl or substituted alkyl, alkenyl or substituted alkenyl, alkynyl or substituted alkynyl, cycloalkyl or substituted cycloalkyl, arylalkyl or substituted arylalkyl, aryl or substituted aryl and heteroaryl or substituted heteroaryl; and W is selected from $(CR_6R_6')$, $C(R_6)OR_3$, $C(R_6)(NR_4R_4')$, n is an integer of 1 or 2;

including all prodrug esters, pharmaceutically acceptable salts and stereoisomers thereof, with the following proviso:

(a) excluding compounds where the following occur simultanously:

$R_2$ or $R_2'$ is hydrogen, $OR_3$, halo, $NHCOR_4$, $NHCO_2R_4$, $NHCONR_4R_4'$ or $NHSO_2R_4$; and G has the following structure:

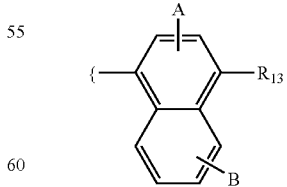

wherein
$R_{13}$ is selected from hydrogen (H), cyano (—CN), nitro (—$NO_2$), halo, heterocyclo, $OR_{14}$, $CO_2R_{15}$, $CONHR_{15}$, $COR_{15}$, $S(O)_pR_{15}$, $SO_2NR_{15}R_{15}'$, $NHCOR_{15}$ and $NHSO_2R_{15}$;

$R_{14}$ in each functional group is independently selected from (H), alkyl or substituted alkyl, $CHF_2$, $CF_3$ and $COR_{15}$;

$R_{15}$ and $R_{15}'$ in each functional group are each independently selected from hydrogen(H), alkyl or substituted alkyl, alkenyl or substituted alkenyl, alkynyl or substituted alkynyl, cycloalkyl or substituted cycloalkyl, heterocycloalkyl or substituted heterocycloalkyl, arylalkyl or substituted arylalkyl, aryl or substituted aryl, heteroaryl or substituted heteroaryl and —CN;

A and B are each independently selected from hydrogen (H), halo, cyano (—CN), nitro (—$NO_2$), alkyl or substituted alkyl and $OR_{14}$; and p is an integer from 0 to 2.

In a preferred embodiment, the present invention provides compounds according to formula Ih, as defined above, wherein G is selected from:

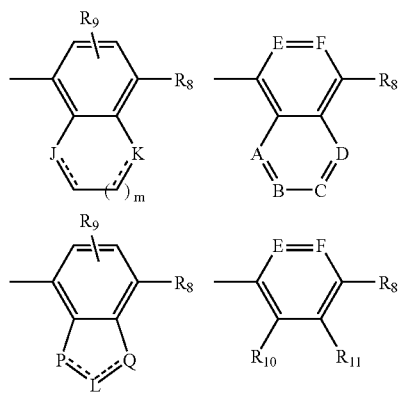

wherein $R_8$, $R_9$, $R_{10}$ and $R_{11}$ in each functional group are each independently selected from hydrogen (H), $NO_2$, CN, $CF_3$, $OR_4$, $CO_2R_4$, $NR_4R_4'$, $CONR_4R_4'$, $CH_2OR_4$, alkyl or substituted alkyl, alkenyl or substituted alkenyl, alkynyl or substituted alkynyl, cycloalkyl or substituted cycloalkyl, arylalkyl or substituted arylalkyl, aryl or substituted aryl and heteroaryl or substituted heteroaryl;

A to F is each independently selected from N or $CR_9$;

J, K, L, P and Q are each independently selected from $NR_{12}$, O, S, SO, $SO_2$ or $CR_{12}R_{12}'$;

$R_{12}$ and $R_{12}'$ in each functional group are each independently selected from a bond or $R_1$; and m is an integer of 0 or 1.

In a more preferred embodiment, the present invention provides compounds according to formula Ih, as defined above, wherein $R_1$ is hydrogen (H) or alkyl; and $R_2$ or $R_2'$ is hydroxyl (OH).

In a more preferred embodiment, the present invention provides compounds according to formula Ih, as defined above, wherein $R_8$ is CN.

In a more preferred embodiment, the present invention provides pharmaceutical composition, comprising:

(a) a compound according to formula I; and (b) at least one pharmaceutically acceptable diluent or carrier.

In a more preferred embodiment, the present invention provides the pharmaceutical compositions defined above, further comprising at least one additional therapeutic agent selected from other compounds of formula I, parathyroid hormone, bisphosphonates, estrogen, testosterone, progesterone, selective estrogen receptor modulators, growth hormone secretagogues, growth hormone, progesterone receptor modulators, anti-diabetic agents, anti-hypertensive agents, anti-inflammatory agents, anti-osteoporosis agents, anti-obesity agents, cardiac glycosides, cholesterol lowering agents, anti-depressants, anti-anxiety agents, anabolic agents, and thyroid mimetics.

In a further preferred embodiment, the present invention provides the pharmaceutical compositions defined above, wherein the additional therapeutic agent is selected from the group consisting of growth hormone secretagogues and growth hormone.

In a third embodiment, the present invention provides for a method for treating or delaying the progression or onset of muscular atrophy, lipodistrophy, long-term critical illness, sarcopenia, frailty or age-related functional decline, reduced muscle strength and function, reduced bone density or growth, the catabolic side effects of glucocorticoids, chronic fatigue syndrome, bone fracture repair, acute fatigue syndrome and muscle loss following elective surgery, cachexia, chronic catabolic state, eating disorders, side effects of chemotherapy, wasting, depression, nervousness, irritability, stress, growth retardation, reduced cognitive function, male contraception, hypogonadism, Syndrome X, diabetic complications or obesity, which comprises administering to a mammalian species in need of treatment a therapeutically effective amount of a pharmaceutical composition as defined in claim 1.

In a preferred embodiment, the present invention provides the methods defined above, further comprising administering, concurrently or sequentially, a therapeutically effective amount of at least one additional therapeutic agent selected from the group consisting of other compounds formula I, parathyroid hormone, bisphosphonates, estrogen, testosterone, progesterone, selective estrogen receptor modulators, growth hormone secretagogues, growth hormone, progesterone receptor modulators, anti-diabetic agents, anti-hypertensive agents, anti-inflammatory agents, anti-osteoporosis agents, anti-obesity agents, cardiac glycosides, cholesterol lowering agents, anti-depressants, anti-anxiety agents, anabolic agents and thyroid mimetics.

In a fourth embodiment, the present invention provides for a process for preparing a compound of formula Id

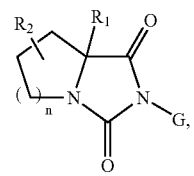

which comprises hydrolyzing a compound of formula IVa

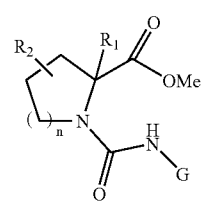

under basic conditions to give the compound of formula XIX

XIX which is then carried on to a compound of formula Id with the use of a coupling reagent.

In a fifth embodiment, the present invention provides for a process for preparing a compound of formula Ie Ie which comprises optionally protecting the compound of formula IVa, when R2 is OH, with a protecting group by treatment with a silylating reagent and then reduced with a reducing agent to give a compound of formula XX

XX which is then derivatized with a leaving group and p-toluenesulfonyl chloride and then treated with a base to give the compound of formula Ie.

In a preferred embodiment, the present invention provides for processes defined above wherein the protecting group is tert-Butyldimethylsilyl; the silylating reagent is tert-Butyldimethylsilyl (chloride); the reducing agent is lithium aluminum hydride or lithium borohydride; the leaving group is Tosyl; the base is potassium tert-butoxide.

In a sixth embodiment, the present invention provides for a process for preparing a compound of formula XII,

XII which comprises reacting an aldehyde of formula IX

IX with an amine of formula XV $H_2N$—G    XV in the presence of a reducing agent to give the compound of formula XII.

In a seventh embodiment, the present invention provides for a process for preparing a compound of formula XIV

XIV which comprises subjecting the compound of formula XII prepared by the process of claim 18 to N-deprotection to form a compound of formula XIII

XIII and reacting the compound of formula XIII with phosgene or a phosgene equivalent in the presence of a base to form the compound of formula XIV.

The following abbreviations are employed herein:
Chiralpak®=Trademark of Chiral Technologies, Inc. Eaton, Pa.
DBU=1,8-diazabicyclo[5.4.0]undec-7-ene
AcOH=acetic acid
DMPU=1,3-dimethyl-3,4,5,6-tetrahydro-2(1H)-pyrimidinone
EtOAc=ethyl acetate
HPLC=high performance liquid chromatography
MeOH=methanol
MS or Mass Spec=mass spectrometry
YMC®=trademark of YMC Co, Ltd., Kyoto, Japan
CuBr=copper(I) bromide
CuCN=copper(I) cyanide
CsF=cesium fluoride
$Et_3N$=triethylamine
DCC=1,3-dicyclohexylcarbodiimide
DEAD=diethyl azodicarboxylate
LDA=lithium diisopropylamide
NMP=1-methyl-2-pyrrolidinone
KOH=potassium hydroxide
Pd/C=palladium on activated charcoal
TFA=trifluoroacetic acid
THF=tetrahydrofuran
mp.=melting point
min=minute(s)
h=hour(s)
L=liter
mL=milliliter μL=microliter
g=gram(s)
mg=milligram(s)
mol=moles
mmol=millimole(s)
nM=nanomolar
rt=room temperature The following definitions apply to the terms as used throughout this specification, unless otherwise limited in specific instances.

As used herein, the term "alkyl" denotes branched or unbranched hydrocarbon chains, preferably having about 1 to about 8 carbons, such as, methyl, ethyl, n-propyl, iso-propyl, n-butyl, sec-butyl, iso-butyl, tert-butyl, 2-methylpentyl pentyl, hexyl, isohexyl, heptyl, 4,4-dimethyl pentyl, octyl, 2,2,4-trimethylpentyl and the like. "Substituted alkyl" includes an alkyl group optionally substituted with one or more functional groups which are attached commonly to such chains, such as, hydroxyl, bromo, fluoro, chloro, iodo, mercapto or thio, cyano, alkylthio, heterocyclyl, aryl, heteroaryl, carboxyl, carbalkoyl, alkyl, alkenyl, nitro, amino, alkoxyl, amido, and the like to form alkyl groups such as trifluoro methyl, 3-hydroxyhexyl, 2-carboxypropyl, 2-fluoroethyl, carboxymethyl, cyanobutyl and the like.

Unless otherwise indicated, the term "cycloalkyl" as employed herein alone or as part of another group includes saturated or partially unsaturated (containing 1 or more double bonds) cyclic hydrocarbon groups containing 1 to 3 rings, including monocyclicalkyl, bicyclicalkyl and tricyclicalkyl, containing a total of 3 to 20 carbons forming the rings, preferably 3 to 10 carbons, forming the ring and which may be fused to 1 or 2 aromatic rings as described for aryl, which include cyclopropyl, cyclobutyl, cyclopentyl, cyclohexyl, cycloheptyl, cyclooctyl, cyclodecyl and cyclododecyl, cyclohexenyl,

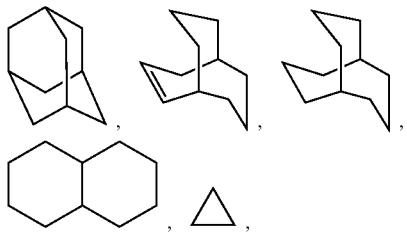

"Substituted cycloalkyl" includes a cycloalkyl group optionally substituted with 1 or more substituents such as halogen, alkyl, alkoxy, hydroxy, aryl, aryloxy, arylalkyl, cycloalkyl, alkylamido, alkanoylamino, oxo, acyl, arylcarbonylamino, amino, nitro, cyano, thiol and/or alkylthio and/or any of the substituents included in the definition of "substituted alkyl."

Unless otherwise indicated, the term "alkenyl" as used herein by itself or as part of another group refers to straight or branched chain radicals of 2 to 20 carbons, preferably 2 to 12 carbons, and more preferably 2 to 8 carbons in the normal chain, which include one or more double bonds in the normal chain, such as vinyl, 2-propenyl, 3-butenyl, 2-butenyl, 4-pentenyl, 3-pentenyl, 2-hexenyl, 3-hexenyl, 2-heptenyl, 3-heptenyl, 4-heptenyl, 3-octenyl, 3-nonenyl, 4-decenyl, 3-undecenyl, 4-dodecenyl, 4,8,12-tetradecatrienyl, and the like. "Substituted alkenyl" includes an alkenyl group optionally substituted with one or more substituents, such as the substituents included above in the definition of "substituted alkyl" and "substituted cycloalkyl."

Unless otherwise indicated, the term "alkynyl" as used herein by itself or as part of another group refers to straight or branched chain radicals of 2 to 20 carbons, preferably 2 to 12 carbons and more preferably 2 to 8 carbons in the normal chain, which include one or more triple bonds in the normal chain, such as 2-propynyl, 3-butynyl, 2-butynyl, 4-pentynyl, 3-pentynyl, 2-hexynyl, 3-hexynyl, 2-heptynyl, 3-heptynyl, 4-heptynyl, 3-octynyl, 3-nonynyl, 4-decynyl, 3-undecynyl, 4-dodecynyl and the like. "Substituted alkynyl" includes an alkynyl group optionally substituted with one or more substituents, such as the substituents included above in the definition of "substituted alkyl" and "substituted cycloalkyl."

The terms "arylalkyl", "arylalkenyl" and "arylalkynyl" as used alone or as part of another group refer to alkyl, alkenyl and alkynyl groups as described above having an aryl substituent. Representative examples of arylalkyl include, but are not limited to, benzyl, 2-phenylethyl, 3-phenylpropyl, phenethyl, benzhydryl and naphthylmethyl and the like. "Substituted arylalkyl" includes arylalkyl groups wherein the aryl portion is optionally substituted with one or more substituents, such as the substituents included above in the definition of "substituted alkyl" and "substituted cycloalkyl."

The term "halogen" or "halo" as used herein alone or as part of another group refers to chlorine, bromine, fluorine, and iodine.

Unless otherwise indicated, the term "aryl" or "Ar" as employed herein alone or as part of another group refers to monocyclic and polycyclic aromatic groups containing 6 to 10 carbons in the ring portion (such as phenyl or naphthyl including 1-naphthyl and 2-naphthyl) and may optionally include one to three additional rings fused to a carbocyclic ring or a heterocyclic ring (such as aryl, cycloalkyl, heteroaryl or cycloheteroalkyl rings), for example

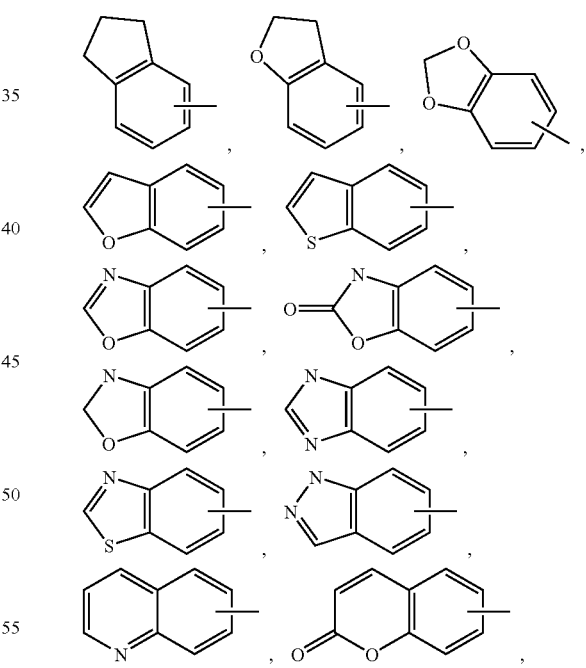

"Substituted aryl" includes an aryl group optionally substituted with one or more functional groups, such as halo, haloalkyl, alkyl, haloalkyl, alkoxy, haloalkoxy, alkenyl, trifluoromethyl, trifluoromethoxy, alkynyl, cycloalkyl-alkyl, cycloheteroalkyl, cycloheteroalkylalkyl, aryl, heteroaryl, arylalkyl, aryloxy, aryloxyalkyl, arylalkoxy, alkoxycarbonyl, arylcarbonyl, arylalkenyl, aminocarbonylaryl, arylthio, arylsulfinyl, arylazo, heteroarylalkyl, heteroarylalkenyl, heteroarylheteroaryl, heteroaryloxy, hydroxy, nitro, cyano, amino, substituted amino wherein the amino includes 1 or 2 substituents (which are alkyl, aryl or any of the other aryl compounds mentioned in the definitions), thiol, alkylthio, arylthio, heteroarylthio, arylthioalkyl, alkoxyarylthio, alkylcarbonyl, arylcarbonyl, alkylaminocarbonyl, arylaminocarbonyl, alkoxycarbonyl, aminocarbonyl, alkylcarbonyloxy, arylcarbonyloxy, alkylcarbonylamino, arylcarbonylamino, arylsulfinyl, arylsulfinylalkyl, arylsulfonylamino or arylsulfonaminocarbonyl and/or any of the alkyl substituents set out herein.

Unless otherwise indicated, the term "heteroaryl" as used herein alone or as part of another group refers to a 5- or 7-membered aromatic ring which includes 1, 2, 3 or 4 hetero atoms such as nitrogen, oxygen or sulfur and such rings fused to an aryl, cycloalkyl, heteroaryl or heterocycloalkyl ring (e.g. benzothiophenyl, indolyl), and includes possible N-oxides. "Substituted heteroaryl" includes a heteroaryl group optionally substituted with 1 to 4 substituents, such as the substituents included above in the definition of "substituted alkyl" and "substituted cycloalkyl." Examples of heteroaryl groups include the following:

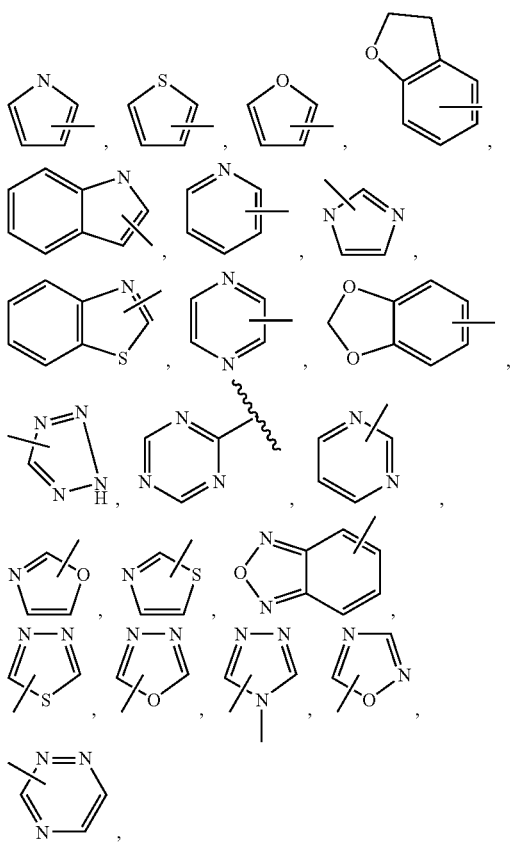

and the like.

The term "heterocyclo", heterocycle or heterocyclic ring, as used herein, represents an unsubstituted or substituted stable 5- to 7-membered monocyclic ring system which may be saturated or unsaturated, and which consists of carbon atoms and from one to four heteroatoms selected from N, O or S, and wherein the nitrogen and sulfur heteroatoms may optionally be oxidized, and the nitrogen heteroatom may optionally be quaternized. The heterocyclic ring may be attached at any heteroatom or carbon atom which results in the creation of a stable structure. Examples of such heterocy- clic groups include, but is not limited to, piperidinyl, piperazinyl, oxopiperazinyl, oxopiperidinyl, oxopyrrolidinyl, oxoazepinyl, azepinyl, pyrrolyl, pyrrolidinyl, furanyl, thienyl, pyrazolyl, pyrazolidinyl, imidazolyl, imidazolinyl, imidazolidinyl, pyridyl, pyrazinyl, pyrimidinyl, pyridazinyl, oxazolyl, oxazolidinyl, isooxazolyl, isoxazolidinyl, morpholinyl, thiazolyl, thiazolidinyl, isothiazolyl, thiadiazolyl, tetrahydropyranyl, thiamorpholinyl, thiamorpholinyl sulfoxide, thiamorpholinyl sulfone, and oxadiazolyl.

The compounds of formula I can be present as salts, which are also within the scope of this invention. Pharmaceutically acceptable (i.e., non-toxic, physiologically acceptable) salts are preferred. If the compounds of formula I have, for example, at least one basic center, they can form acid addition salts. These are formed, for example, with strong inorganic acids, such as mineral acids, for example sulfuric acid, phosphoric acid or a hydrohalic acid, with strong organic carboxylic acids, such as alkanecarboxylic acids of 1 to 4 carbon atoms which are unsubstituted or substituted, for example, by halogen, for example acetic acid, such as saturated or unsaturated dicarboxylic acids, for example oxalic, malonic, succinic, maleic, fumaric, phthalic or terephthalic acid, such as hydroxycarboxylic acids, for example ascorbic, glycolic, lactic, malic, tartaric or citric acid, such as amino acids, (for example aspartic or glutamic acid or lysine or arginine), or benzoic acid, or with organic sulfonic acids, such as ($C_1$-$C_4$) alkyl or arylsulfonic acids which are unsubstituted or substituted, for example by halogen, for example methyl- or p-toluene-sulfonic acid. Corresponding acid addition salts can also be formed having, if desired, an additionally present basic center. The compounds of formula I having at least one acid group (for example COOH) can also form salts with bases. Suitable salts with bases are, for example, metal salts, such as alkali metal or alkaline earth metal salts, for example sodium, potassium or magnesium salts, or salts with ammonia or an organic amine, such as morpholine, thiomorpholine, piperidine, pyrrolidine, a mono, di or tri-lower alkylamine, for example ethyl, tert-butyl, diethyl, diisopropyl, triethyl, tributyl or dimethyl-propylamine, or a mono, di or trihydroxy lower alkylamine, for example mono, di or triethanolamine. Corresponding internal salts may furthermore be formed. Salts which are unsuitable for pharmaceutical uses but which can be employed, for example, for the isolation or purification of free compounds of formula I or their pharmaceutically acceptable salts, are also included.

Preferred salts of the compounds of formula I which contain a basic group include monohydrochloride, hydrogensulfate, methanesulfonate, phosphate or nitrate.

Preferred salts of the compounds of formula I which contain an acid group include sodium, potassium and magnesium salts and pharmaceutically acceptable organic amines.

The term "modulator" refers to a chemical compound with capacity to either enhance (e.g., "agonist" activity) or inhibit (e.g., "antagonist" activity) a functional property of biological activity or process (e.g., enzyme activity or receptor binding); such enhancement or inhibition may be contingent on the occurrence of a specific event, such as activation of a signal transduction pathway, and/or may be manifest only in particular cell types.

The term "prodrug esters" as employed herein includes esters and carbonates formed by reacting one or more hydroxyls of compounds of formula I with alkyl, alkoxy, or aryl substituted acylating agents employing procedures known to those skilled in the art to generate acetates, pivalates, methylcarbonates, benzoates and the like.

Any compound that can be converted in vivo to provide the bioactive agent (i.e., the compound of formula I) is a prodrug within the scope and spirit of the invention.

Various forms of prodrugs are well known in the art. A comprehensive description of prodrugs and prodrug derivatives are described in:

a.) *The Practice of Medicinal Chemistry*, Camille G. Wermuth et al., Ch 31, (Academic Press, 1996);
b.) *Design of Prodrugs*, edited by H. Bundgaard, (Elsevier, 1985);
c.) *A Textbook of Drug Design and Development*, P. Krogsgaard-Larson and H. Bundgaard, eds. Ch 5, pgs 113-191 (Harwood Academic Publishers, 1991).

Said references are incorporated herein by reference.

An administration of a therapeutic agent of the invention includes administration of a therapeutically effective amount of the agent of the invention. The term "therapeutically effective amount" as used herein refers to an amount of a therapeutic agent to treat or prevent a condition treatable by administration of a composition of the invention. That amount is the amount sufficient to exhibit a detectable therapeutic or preventative or ameliorative effect. The effect may include, for example, treatment or prevention of the conditions listed herein. The precise effective amount for a subject will depend upon the subject's size and health, the nature and extent of the condition being treated, recommendations of the treating physician, and the therapeutics or combination of therapeutics selected for administration. Thus, it is not useful to specify an exact effective amount in advance.

All stereoisomers of the compounds of the instant invention are contemplated, either in admixture or in pure or substantially pure form. The compounds of the present invention can have asymmetric centers at any of the carbon atoms including any one of the R substituents. Consequently, compounds of formula I can exist in enantiomeric or diastereomeric forms or in mixtures thereof. The processes for preparation can utilize racemates, enantiomers or diastereomers as starting materials. When diastereomeric or enantiomeric products are prepared, they can be separated by conventional methods for example, chromatographic, chiral HPLC or fractional crystallization.

The compounds of formula I of the invention can be prepared as shown in the following reaction schemes and description thereof, as well as relevant published literature procedures that may be used by one skilled in the art. Exemplary reagents and procedures for these reactions appear hereinafter and in the working Examples.

Scheme I

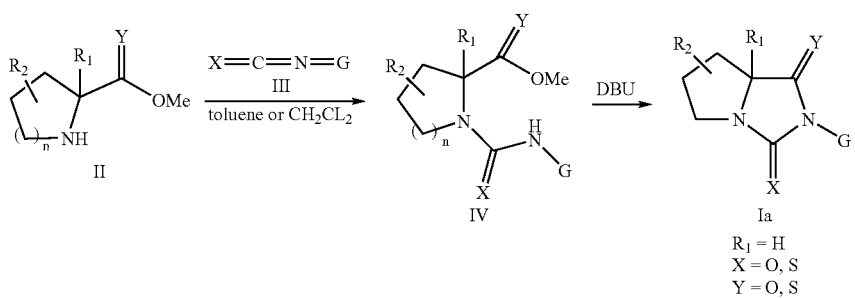

Scheme Ia

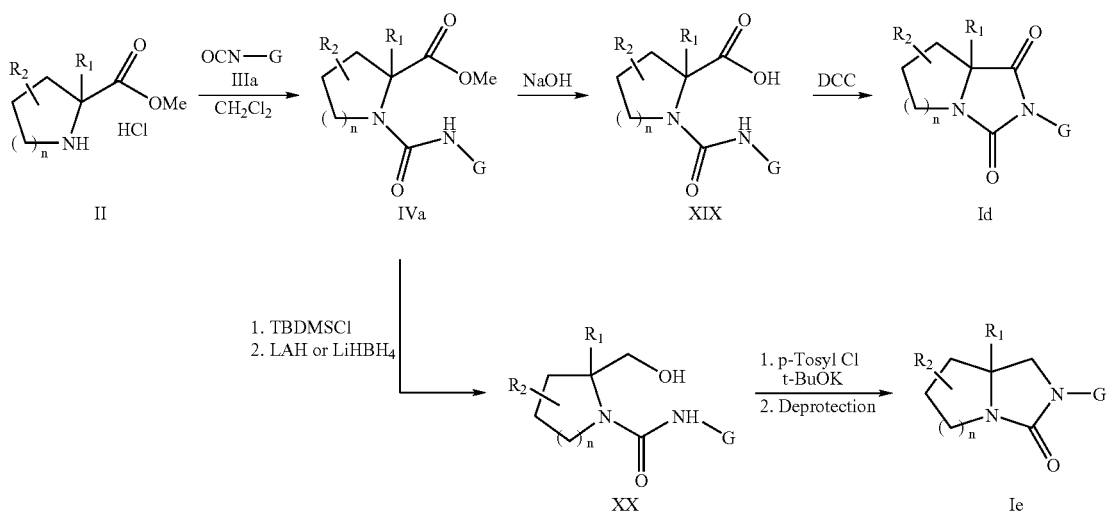

As illustrated in Scheme I, compounds of formula Ia can be prepared from suitably protected intermediates of formula II. Intermediates of formula II can be obtained commercially, can be prepared by methods known in the literature or can be readily prepared by one skilled in the art. Treatment of II with an intermediate of formula III yields an intermediate of formula of IV. The intermediates of formula III can be obtained, for example, from commercially available isocyanates and thioisocyanates and or can be readily prepared by one skilled in the art. The intermediate of formula IV can be treated with a base, such as DBU, to yield a compound of formula Ia. Compounds of formula Ia represent compounds of formula I wherein $R_1$ is H, $R_5$ and $R_5'$ are taken together to form a double bond with O or S and $R_6$ and $R_6'$ are taken together to form a double bond with O or S. As illustrated in Scheme Ia, compounds of formula Id and Ie can be prepared from suitably protected intermediates of formula II by reacting with a compound of formula IIIa to form an intermediate of formula IVa. An intermediate of the formula IVa can be hydrolysed under basic conditions to give an intermediate of the formula XIX and then carried on to a compound of the formula Id with the use of a suitable coupling reagents such as, for example DCC. Alternatively, an intermediate of the formula IVa can be optionally protected (where $R_2$=OH) with a suitable protecting group such as TBS by treatment with a silylating reagent such as TBDMSCl, and then reduced with a suitable reducing agent such as, for example LAH or $LiBH_4$ to give an intermediate of the formula XX. An intermediate of the formula XX can then be derivatized on the primary hydroxyl functionality with a suitable leaving group such as Tosyl, with, for example, p-toluenesulfonyl chloride, followed by base treatment such as with potassium tert-butoxide to give a compound of the formula Ie.

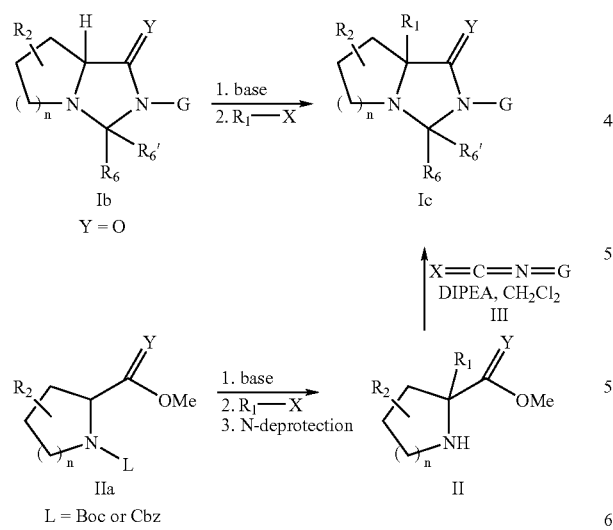

Scheme II

As illustrated in Scheme II, a compound of formula Ib, wherein $R_1$ is H, can be converted to a compound of formula Ic wherein $R_1$ is a functional group other than H, as defined herein, by treatment with a base such as LDA and an alkyl halide, such as iodomethane, preferably in a solvent such as THF at low temperatures (e.g., −78° C.). Compounds of formula Ic represent compounds of formula I wherein $R_1$ is a functional group other than H and $R_5$ and $R_5'$ are taken together to form a double bond with O. Optionally, subsequent reaction of compounds of formula Ic with a Lawesson's Reagent will convert Y from oxygen (O) to sulfur (S).

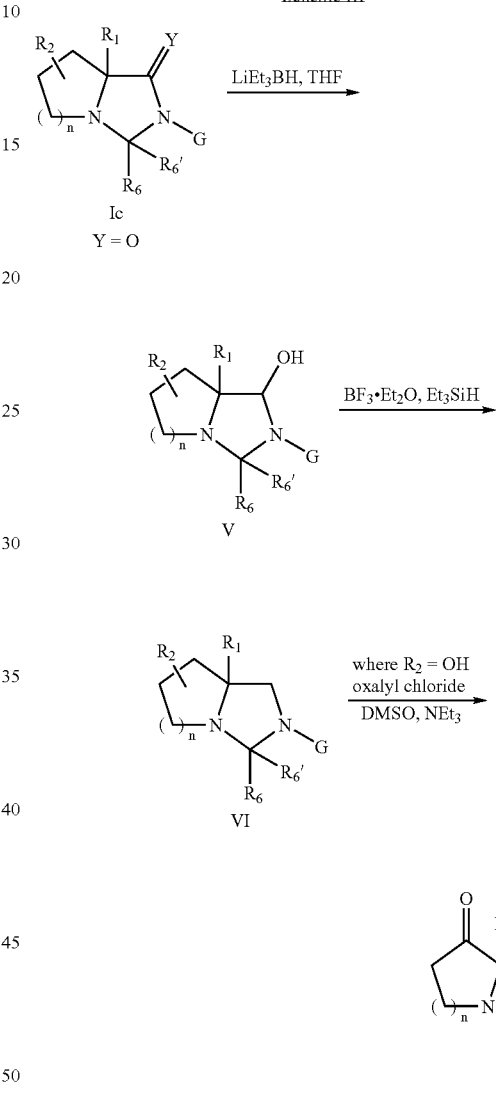

As illustrated in Scheme III, a compound of formula Ic can be converted by treatment with a reducing agent, such as $LiEt_3BH$, preferably in a solvent such as THF at low temperatures (<−40° C.) to give an intermediate V. Intermediate V is subsequently treated further with $Et_3SiH$ in the presence of boron trifluoride diethyl etherate in a halogenated solvent such as 1,2-dichloroethane at low temperatures (<0° C.) to yield a compound of formula VI. Compounds of formula VI represent compounds of formula I wherein $R_5$ and $R_5'$ are hydrogen. A compound of formula VI can be oxidized to a compound of formula VIa using standard conditions of known oxidation methods, such as, for example, Swern or Dess-Martin.

Scheme IV

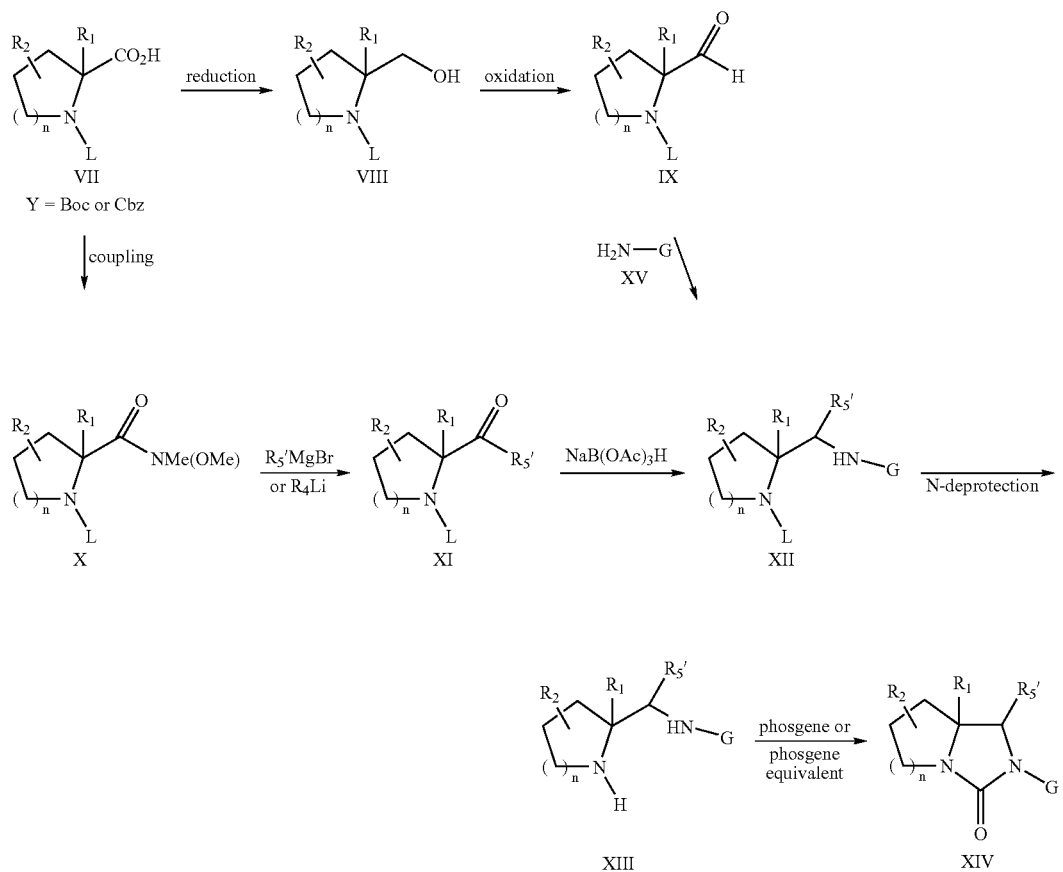

Scheme IV describes a method for preparing compounds of formula XIV from N-protected amino acids of formula VII, which can be obtained commercially or can be prepared by methods known in the literature or can be readily prepared by one skilled in the art. An intermediate of formula VII is treated with a reducing agent, such as borane, to form an alcohol intermediate VIII, which can be oxidized to an aldehyde intermediate IX. Similarly, an intermediate of formula VII can be coupled to N,O-dimethylhydroxylamine to form amide X, which can be treated with a Grignard reagent or an organolithium reagent to form an alkylketone XI. The aldehyde intermediate IX or an alkylketone XI, can be reacted with an amine of formula XV in the presence of a reducing agent, such as sodium triacetoxyborohydride to give an intermediate of formula XII. Removal of N-protecting group (L) can be achieved by methods known in the literature or by one skilled in the art to provide an intermediate of formula XIII. The intermediate of formula XIII can be treated with phosgene or phosgene equivalent in the presence of a base, such as triethylamine, to provide a compound of formula XIV. Compounds of formula XIV represent compounds of formula I wherein $R_6$ and $R_6'$ are taken together to form a double bond with oxygen and $R_5$ is hydrogen and $R_5'$ is as defined herein. In the alternative, Scheme IV may be utilized to provide compounds of formula I wherein $R_5'$ is hydrogen and $R_5$ is as defined herein. Optionally, subsequent reaction of compounds of formula XIV with a Lawesson's Reagent will provide compounds of formula I wherein $R_6$ and $R_6'$ are taken together to form a double bond with sulfur (S).

Scheme V

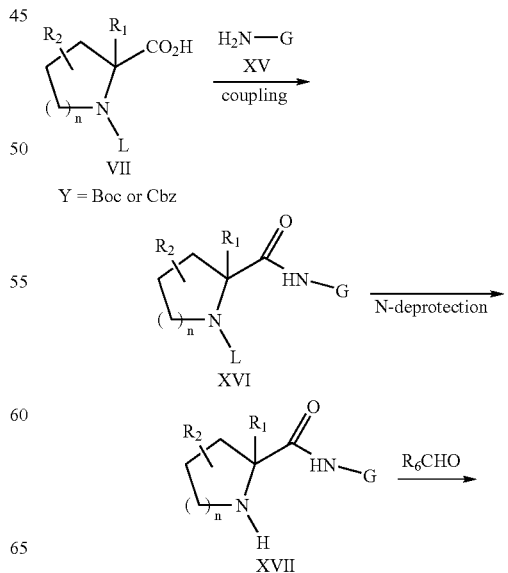

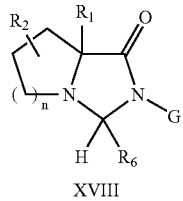

XVIII

As illustrated in Scheme V, an intermediate of formula VII as described in Scheme IV can be coupled to an amine XV using a coupling reagent, such as those described in "The Practice of Peptide Synthesis" (Spring-Verlag, $2^{nd}$ Ed., Bodanszy, Miklos, 1993), to yield an amide intermediate of formula XVI. Removal of N-protecting group can be achieved by methods known in the literature or by one skilled in the art to provide an intermediate of formula XVII. The intermediate of formula XVII is treated with an aldehyde ($R_6$CHO) in suitable solvent (such as ethanol, methanol, THF or $CH_2Cl_2$), with or without the presence of a base, such as $K_2CO_3$, NaOH or DBU, or a weak acid, such as HOAc, to give a compound of formula XVIII. Aldehydes of formula $R_6$CHO can be obtained from commercial sources, can be prepared by methods known in the literature or readily prepared by one skilled in the art. Compounds of formula XVIII represent compounds of formula I wherein $R_5$ and $R_5'$ are taken together to form a double bond with oxygen (O) and $R_6'$ is hydrogen and $R_6$ is as defined herein. In the alternative, Scheme V may be utilized to provide compounds of formula I wherein $R_6$ is hydrogen and $R_6'$ is as defined herein. Optionally, subsequent reaction of compounds of formula XVIII with a Lawesson's Reagent will provide compounds of formula I wherein $R_5$ and $R_5'$ are taken together to form a double bond with sulfur (S).

Scheme VI

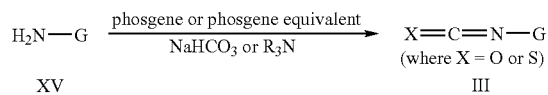

Scheme VI describes a method to prepare isocyanates of general formula III wherein intermediates XV are treated with phosgene or a phosgene like reagent in the presence of an inorganic base such as sodium bicarbonate, or a organic base such as diisopropylethylamine in a solvent such as dichloromethane to afford an isocyanate of formula III.

Scheme VIa

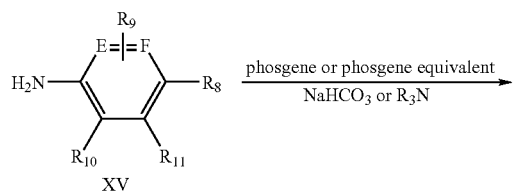

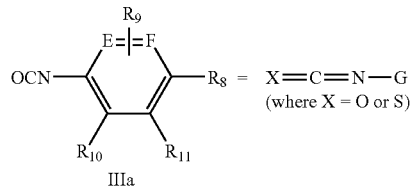

IIIa

For example, Scheme VIa describes a method for preparing isocyanates of general formula IIIa. Substituted aryl or heteroaryl amines of formula XV are treated with phosgene or a phosgene like reagent in the presence of an inorganic base such as sodium bicarbonate, or a organic base such as diisopropylethylamine in a solvent such as dichloromethane to afford an isocyanate of formula IIIa. Substituted aryl or heteroaryl amines as described above can be obtained commercially or can be prepared by methods known in the literature or by one skilled in the art.

Scheme VII describes a method to prepare aryl and heteroaryl halides of general formula XXI and XXII wherein intermediates XV are treated with tert-butylnitrite or an equivalent reagent in the presence of a halide source such as CuI or CuBr to afford an aryl or heteroaryl halide of formula XXI or XXII which are precursors suitable for the formation of the intermediates of formula XII.

Scheme VII

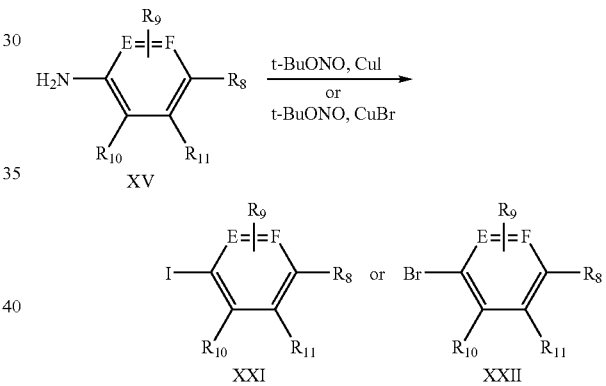

Scheme VIII describes additional methods for preparing compounds of formula XIV from N-protected aldehydes of formula IX. An intermediate of formula IX is treated with an organometalic reagent such as $R_5$MgX (X is typically a halide), $R_5$Li or alternate alkylating agents such as TMS-CF$_3$ with CsF or equivalent reagents to form an alcohol intermediate XXIII, which can be oxidized to ketone intermediate XI. The ketone intermediate XI can be reacted with an amine such as hydroxylamine or an equivalent reagent to form an imine of formula XXIV. Intermediates of formula XXIV in the presence of a reducing agents, such as hydrogen in the presence of palladium or nickel catalysts, give an amine intermediate of formula XXV. Coupling of intermediates of formula XXV with halides of formula XXI or XXII to give intermediates of formula XII can be achieved by methods known in the literature or by one skilled in the art. The intermediate of formula XII can be treated as described in Scheme IV to provide a compound of formula XIV. Alternately, intermediates of formula XXIII can be converted to intermediates of formula XXV through a three step process involving activation of the alcohol with a reagent such as mesyl or tosyl chloride in the presence of an organic or inorganic base followed by treatment with an azide source such as sodium azide and finally reduction of the azide to the amine to provide intermediates of formula XXV.

Scheme VIII

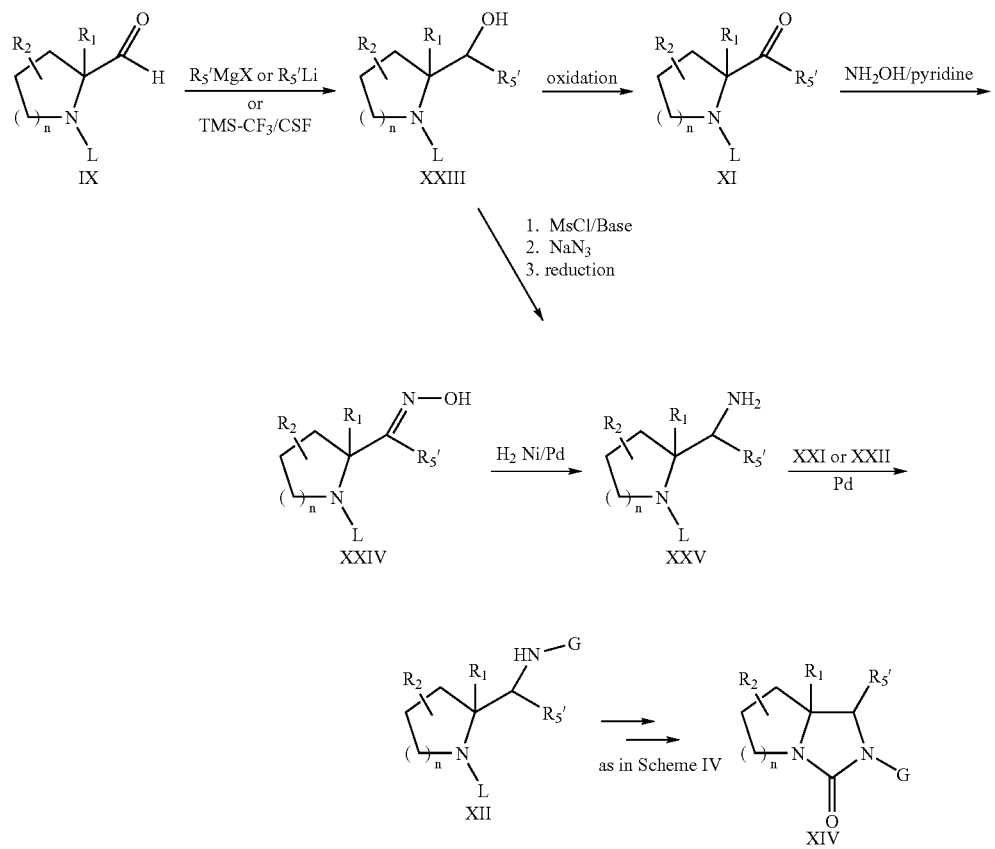

Scheme IX describes additional methods for preparing compounds of formula XIV from N-protected alcohols of formula XXIII. Removal of N-protecting group (L) can be achieved by methods known in the literature or by one skilled in the art to provide an intermediate of formula XXVI. An intermediate of formula XXVI is treated with an isocyanate of formula III to give an intermediate of formula XXVII. Treatment of intermediates of formula XXVII with an activating agent such as mesyl chloride or tosyl chloride in the presence of a base such as potassium tert-butoxide or an equivalent reagent can provide a compound of formula XIV.

Scheme IX

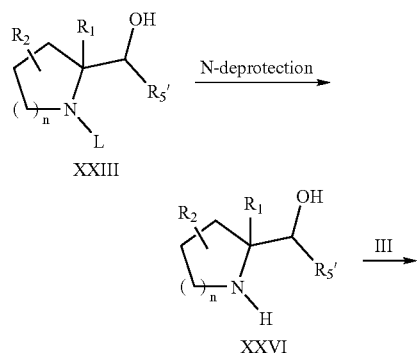

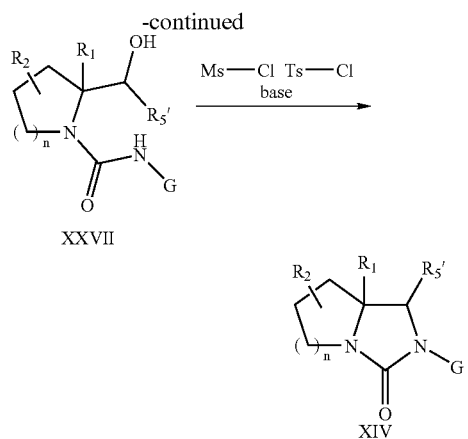

A hydroxyl group on the bicyclic core present in some compounds of the present genus can be replaced with alternative functionality, including halogens and amine-based groups according to the sequences shown in Scheme X. For example, a compound of formula XXVIII can be treated with a suitable fluorinating reagent, such as, for example, DAST, to provide compounds of formula XXIX. Compounds of formula XXVIII can alternatively be derivatised with a suitable functionality to generate a leaving group, such as, for example, conversion to a mesyl group under standard conditions to afford a compound of the formula XXX, which can then undergo a substitution reaction with a suitable nitrogen based nucleophile, such as, for example, azide anion to afford an intermediate of the formula XXXI. Intermediate azides such as those of the formula XXXI can then be reduced to the corresponding amine with a suitable reducing agent, such as, for example, $PtO_2$, to yield a primary amine such as found in compounds of the formula XXXII. Compounds of the formula XXXII can readily undergo N-acylations or N-alkylations under standard conditions to afford compounds of the formulas XXXIII and XXXIV, respectively.

In addition, a compound of formula XXVIII can be treated with a suitable oxidizing agent, such as, for example, TPAP with NMO, to provide intermediates of formula XXXV. Treatment of intermediates of formula XXXV with an amine, such as hydroxyl amine or an equivalent reagent, can give a compound of formula XXXVI.

Furthermore, alcohol diastereomers of compounds such as XXVIII can be obtained by inversion of the alcohol by methods such as the Mitsunobu reaction followed by hydrolysis or oxidation followed by reduction or other methods familiar to those trained in the art.

herein, denotes a condition or disorder which can be treated by modulating the function or activity of an AR in a subject, wherein treatment comprises prevention, partial alleviation or cure of the condition or disorder. Modulation may occur locally, for example, within certain tissues of the subject, or more extensively throughout a subject being treated for such a condition or disorder.

The compounds of the present invention can be administered to animals, preferably humans, for the treatment of a variety of conditions and disorders, including, but not limited to maintenance of muscle strength and function (e.g., in the elderly); reversal or prevention of frailty or age-related functional decline ("ARFD") in the elderly (e.g., sarcopenia); treatment of catabolic side effects of glucocorticoids; prevention and/or treatment of reduced bone mass, density or growth (e.g., osteoporosis and osteopenia); treatment of chronic fatigue syndrome (CFS); chronic myalgia; treatment of acute fatigue syndrome and muscle loss following elective surgery (e.g., post-surgical rehabilitation); accelerating of wound healing; accelerating bone fracture repair (such as accelerating the recovery of hip fracture patients); accelerating healing of complicated fractures, e.g. distraction osteogenesis; in

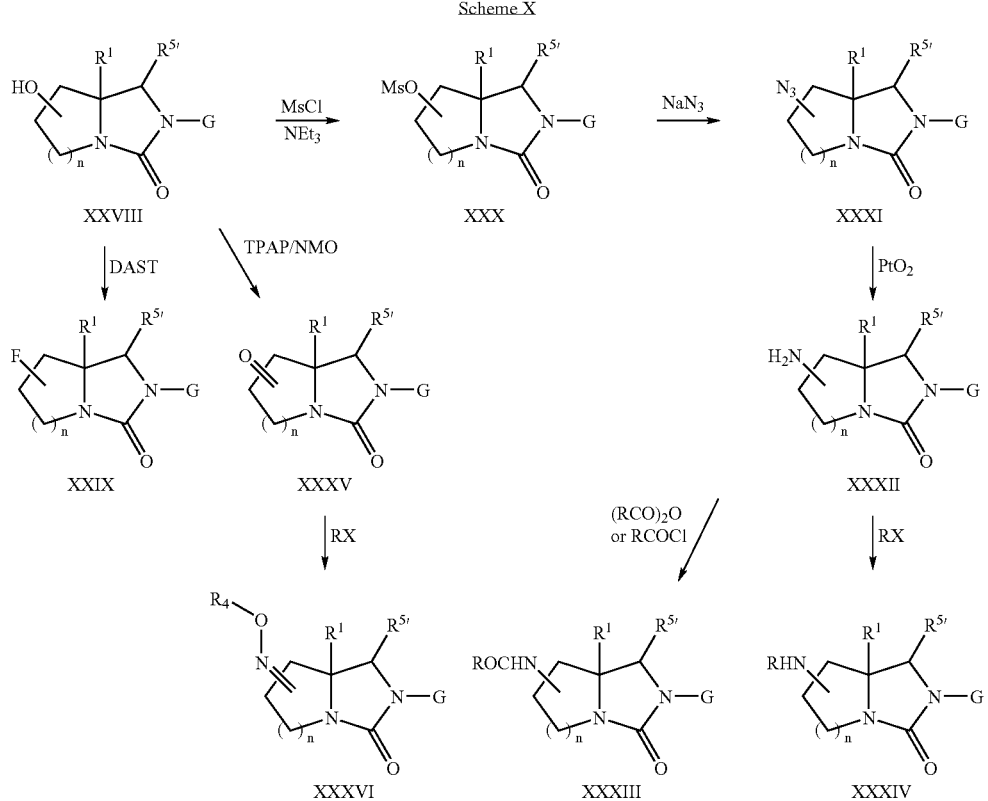

Scheme X

Use and Utility

A. Utilities

The compounds of the present invention modulate the function of the nuclear hormone receptors, particularly the androgen receptor, and include compounds which are, for example, selective agonists, partial agonists, antagonists or partial antagonists of the androgen receptor (AR). Thus, the present compounds are useful in the treatment of AR-associated conditions. An "AR-associated condition," as used joint replacement; prevention of post-surgical adhesion formation; acceleration of tooth repair or growth; maintenance of sensory function (e.g., hearing, sight, olefaction and taste); treatment of periodontal disease; treatment of wasting secondary to fractures and wasting in connection with chronic obstructive pulmonary disease (COPD), chronic liver disease, AIDS, weightlessness, cancer cachexia, burn and trauma recovery, chronic catabolic state (e.g., coma), eating disorders (e.g., anorexia) and chemotherapy; treatment of cardiomyopathy; treatment of thrombocytopenia; treatment of growth retardation in connection with Crohn's disease; treatment of short bowel syndrome; treatment of irritable bowel syndrome; treatment of inflammatory bowel disease; treatment of Crohn's disease and ulcerative colits; treatment of complications associated with transplantation; treatment of physiological short stature including growth hormone deficient children and short stature associated with chronic illness; treatment of obesity and growth retardation associated with obesity; treatment of anorexia (e.g., associated with cachexia or aging); treatment of hypercortisolism and Cushing's syndrome; Paget's disease; treatment of osteoarthritis; induction of pulsatile growth hormone release; treatment of osteochondrodysplasias; treatment of depression, nervousness, irritability and stress; treatment of reduced mental energy and low self-esteem (e.g., motivation/assertiveness); improvement of cognitive function (e.g., the treatment of dementia, including Alzheimer's disease and short term memory loss); treatment of catabolism in connection with pulmonary dysfunction and ventilator dependency; treatment of cardiac dysfunction (e.g., associated with valvular disease, myocardial infarction, cardiac hypertrophy or congestive heart failure); lowering blood pressure; protection against ventricular dysfunction or prevention of reperfusion events; treatment of adults in chronic dialysis; reversal or slowing of the catabolic state of aging; attenuation or reversal of protein catabolic responses following trauma (e.g., reversal of the catabolic state associated with surgery, congestive heart failure, cardiac myopathy, burns, cancer, COPD etc.); reducing cachexia and protein loss due to chronic illness such as cancer or AIDS; treatment of hyperinsulinemia including nesidioblastosis; treatment of immunosuppressed patients; treatment of wasting in connection with multiple sclerosis or other neurodegenerative disorders; promotion of myelin repair; maintenance of skin thickness; treatment of metabolic homeostasis and renal homeostasis (e.g., in the frail elderly); stimulation of osteoblasts, bone remodeling and cartilage growth; regulation of food intake; treatment of insulin resistance, including NIDDM, in mammals (e.g., humans); treatment of insulin resistance in the heart; improvement of sleep quality and correction of the relative hyposomatotropism of senescence due to high increase in REM sleep and a decrease in REM latency; treatment of hypothermia; treatment of congestive heart failure; treatment of lipodystrophy (e.g., in patients taking HIV or AIDS therapies such as protease inhibitors); treatment of muscular atrophy (e.g., due to physical inactivity, bed rest or reduced weight-bearing conditions); treatment of musculoskeletal impairment (e.g., in the elderly); improvement of the overall pulmonary function; treatment of sleep disorders; and the treatment of the catabolic state of prolonged critical illness; treatment of hirsutism, acne, seborrhea, androgenic alopecia, anemia, hyperpilosity, benign prostate hypertrophy, adenomas and neoplasies of the prostate (e.g., advanced metastatic prostate cancer) and malignant tumor cells containing the androgen receptor, such as is the case for breast, brain, skin, ovarian, bladder, lymphatic, liver and kidney cancers; cancers of the skin, pancreas, endometrium, lung and colon; osteosarcoma; hypercalcemia of malignancy; metastatic bone disease; treatment of spermatogenesis, endometriosis and polycystic ovary syndrome; conteracting preeclampsia, eclampsia of pregnancy and preterm labor; treatment of premenstural syndrome; treatment of vaginal dryness; age related decreased testosterone levels in men, male menopause, hypogonadism, male hormone replacement, male and female sexual dysfunction (e.g., erectile dysfunction, decreased sex drive, sexual well-being, decreased libido), urinary incontinence, male and female contraception, hair loss, Reaven's Syndrome and the enhancement of bone and muscle performance/strength. The term treatment is also intended to include prophylactic treatment.

In addition, the conditions, diseases, and maladies collectively referenced to as "Syndrome X" or Metabolic Syndrome as detailed in Johannsson *J. Clin. Endocrinol. Metab.*, 82, 727-34 (1997), may be treated employing the compounds of the invention.

B. Combinations

The present invention includes within its scope pharmaceutical compositions comprising, as an active ingredient, a therapeutically effective amount of at least one of the compounds of formula I, alone or in combination with a pharmaceutical carrier or diluent. Optionally, compounds of the present invention can be used alone, in combination with other compounds of the invention, or in combination with one or more other therapeutic agent(s), e.g., an antibiotic or other pharmaceutically active material.

The compounds of the present invention may be combined with growth promoting agents, such as, but not limited to, TRH, diethylstilbesterol, theophylline, enkephalins, E series prostaglandins, compounds disclosed in U.S. Pat. No. 3,239, 345, e.g., zeranol, and compounds disclosed in U.S. Pat. No. 4,036,979, e.g., sulbenox or peptides disclosed in U.S. Pat. No. 4,411,890.

The compounds of the invention may also be used in combination with growth hormone secretagogues such as GHRP-6, GHRP-1 (as described in U.S. Pat. No. 4,411,890 and publications WO 89/07110 and WO 89/07111), GHRP-2 (as described in WO 93/04081), NN703 (Novo Nordisk), LY444711 (Lilly), MK-677 (Merck), CP424391 (Pfizer) and B-HT920, or with growth hormone releasing factor and its analogs or growth hormone and its analogs or somatomedins including IGF-1 and IGF-2, or with alpha-adrenergic agonists, such as clonidine or serotinin 5-HT$_D$ agonists, such as sumatriptan, or agents which inhibit somatostatin or its release, such as physostigmine and pyridostigmine. A still further use of the disclosed compounds of the invention is in combination with parathyroid hormone, PTH(1-34) or bisphosphonates, such as MK-217 (alendronate).

A still further use of the compounds of the invention is in combination with estrogen, testosterone, a selective estrogen receptor modulator, such as tamoxifen or raloxifene, or other androgen receptor modulators, such as those disclosed in Edwards, J. P. et. al., *Bio. Med. Chem. Let.*, 9, 1003-1008 (1999) and Hamann, L. G. et. al., *J. Med. Chem.*, 42, 210-212 (1999).

A further use of the compounds of this invention is in combination with progesterone receptor agonists ("PRA"), such as levonorgestrel, medroxyprogesterone acetate (MPA).

The compounds of the present invention may be employed alone or in combination with each other and/or other modulators of nuclear hormone receptors or other suitable therapeutic agents useful in the treatment of the aforementioned disorders including: anti-diabetic agents; anti-osteoporosis agents; anti-obesity agents; anti-inflammatory agents; anti-anxiety agents; anti-depressants; anti-hypertensive agents; anti-platelet agents; anti-thrombotic and thrombolytic agents; cardiac glycosides; cholesterol/lipid lowering agents; mineralocorticoid receptor antagonists; phospodiesterase inhibitors; protein tyrosine kinase inhibitors; thyroid mimetics (including thyroid receptor agonists); anabolic agents; HIV or AIDS therapies; therapies useful in the treatment of Alzheimer's disease and other cognitive disorders; therapies useful in the treatment of sleeping disorders; anti-proliferative agents; and anti-tumor agents.

Examples of suitable anti-diabetic agents for use in combination with the compounds of the present invention include biguanides (e.g., metformin), glucosidase inhibitors (e.g., acarbose), insulins (including insulin secretagogues or insulin sensitizers), meglitinides (e.g., repaglinide), sulfonylureas (e.g., glimepiride, glyburide and glipizide), biguanide/glyburide combinations (e.g., Glucovance®), thiazolidinediones (e.g., troglitazone, rosiglitazone and pioglitazone), PPAR-alpha agonists, PPAR-gamma agonists, PPAR alpha/gamma dual agonists, SGLT2 inhibitors, glycogen phosphorylase inhibitors, inhibitors of fatty acid binding protein (aP2) such as those disclosed in U.S. Ser. No. 09/519,079 filed Mar. 6, 2000, glucagon-like peptide-1 (GLP-1), and dipeptidyl peptidase IV (DPP4) inhibitors such as those disclosed in WO 0168603.

Examples of suitable anti-osteoporosis agents for use in combination with the compounds of the present invention include alendronate, risedronate, PTH, PTH fragment, raloxifene, calcitonins, steroidal or non-steroidal progesterone receptor agonists, RANK ligand antagonists, calcium sensing receptor antagonists, TRAP inhibitors, selective estrogen receptor modulators (SERM's), estrogen and AP-1 inhibitors.

Examples of suitable anti-obesity agents for use in combination with the compounds of the present invention include aP2 inhibitors, such as those disclosed in U.S. Ser. No. 09/519,079 filed Mar. 6, 2000, PPAR gamma antagonists, PPAR delta agonists, beta 3 adrenergic agonists, such as AJ9677 (Takeda/Dainippon), L750355 (Merck), or CP331648 (Pfizer) or other known beta 3 agonists as disclosed in U.S. Pat. Nos. 5,541,204, 5,770,615, 5,491,134, 5,776,983 and 5,488,064, a lipase inhibitor, such as orlistat or ATL-962 (Alizyme), a serotonin (and dopamine) reuptake inhibitor, such as sibutramine, topiramate (Johnson & Johnson) or axokine (Regeneron), a thyroid receptor beta drug, such as a thyroid receptor ligand as disclosed in WO 97/21993 (U. Cal SF), WO 99/00353 (KaroBio) and GB98/284425 (KaroBio), and/or an anorectic agent, such as dexamphetamine, phentermine, phenylpropanolamine or mazindol.

Examples of suitable anti-inflammatory agents for use in combination with the compounds of the present invention include prednisone, dexamethasone, Enbrel®, cyclooxygenase inhibitors (i.e., COX-1 and/or COX-2 inhibitors such as NSAIDs, aspirin, indomethacin, ibuprofen, piroxicam, Naproxen®, Celebrex®, Vioxx®), CTLA4-Ig agonists/antagonists, CD40 ligand antagonists, IMPDH inhibitors, such as mycophenolate (CellCept®), integrin antagonists, alpha-4 beta-7 integrin antagonists, cell adhesion inhibitors, interferon gamma antagonists, ICAM-1, tumor necrosis factor (TNF) antagonists (e.g., infliximab, $OR_{1384}$), prostaglandin synthesis inhibitors, budesonide, clofazimine, CNI-1493, CD4 antagonists (e.g., priliximab), p38 mitogen-activated protein kinase inhibitors, protein tyrosine kinase (PTK) inhibitors, IKK inhibitors, and therapies for the treatment of irritable bowel syndrome (e.g., Zelmac® and Maxi-K® openers such as those disclosed in U.S. Pat. No. 6,184,231 B1).

Examples of suitable anti-anxiety agents for use in combination with the compounds of the present invention include diazepam, lorazepam, buspirone, oxazepam, and hydroxyzine pamoate.

Examples of suitable anti-depressants for use in combination with the compounds of the present invention include citalopram, fluoxetine, nefazodone, sertraline, and paroxetine.

Examples of suitable anti-hypertensive agents for use in combination with the compounds of the present invention include beta adrenergic blockers, calcium channel blockers (L-type and T-type; e.g. diltiazem, verapamil, nifedipine, amlodipine and mybefradil), diuretics (e.g., chlorothiazide, hydrochlorothiazide, flumethiazide, hydroflumethiazide, bendroflumethiazide, methylchlorothiazide, trichloromethiazide, polythiazide, benzthiazide, ethacrynic acid tricrynafen, chlorthalidone, furosemide, musolimnine, bumetanide, triamtrenene, amiloride, spironolactone), renin inhibitors, ACE inhibitors (e.g., captopril, zofenopril, fosinopril, enalapril, ceranopril, cilazopril, delapril, pentopril, quinapril, ramipril, lisinopril), AT-1 receptor antagonists (e.g., losartan, irbesartan, valsartan), ET receptor antagonists (e.g., sitaxsentan, atrsentan and compounds disclosed in U.S. Pat. Nos. 5,612,359 and 6,043,265), Dual ET/AII antagonist (e.g., compounds disclosed in WO 00/01389), neutral endopeptidase (NEP) inhibitors, vasopepsidase inhibitors (dual NEP-ACE inhibitors) (e.g., omapatrilat and gemopatrilat), and nitrates.

Examples of suitable anti-platelet agents for use in combination with the compounds of the present invention include GPIIb/IIIa blockers (e.g., abciximab, eptifibatide, tirofiban), P2Y12 antagonists (e.g., clopidogrel, ticlopidine, CS-747), thromboxane receptor antagonists (e.g., ifetroban), aspirin, and PDE-III inhibitors (e.g., dipyridamole) with or without aspirin.

Examples of suitable cardiac glycosides for use in combination with the compounds of the present invention include digitalis and ouabain.

Examples of suitable cholesterol/lipid lowering agents for use in combination with the compounds of the present invention include HMG-CoA reductase inhibitors (e.g., pravastatin, lovastatin, atorvastatin, simvastatin, NK-104 (a.k.a. itavastatin, or nisvastatin or nisbastatin) and ZD-4522 (a.k.a. rosuvastatin, or atavastatin or visastatin)), squalene synthetase inhibitors, fibrates, bile acid sequestrants, ACAT inhibitors, MTP inhibitors, lipooxygenase inhibitors, cholesterol absorption inhibitors, and cholesterol ester transfer protein inhibitors (e.g., CP-529414).

Examples of suitable mineralocorticoid receptor antagonists for use in combination with the compounds of the present invention include spironolactone and eplerinone.

Examples of suitable phospodiesterase (PDE) inhibitors for use in combination with the compounds of the present invention include PDE-3 inhibitors such as cilostazol, and phosphodiesterase-5 inhibitors (PDE-5 inhibitors) such as sildenafil.

Examples of suitable thyroid mimetics for use in combination with the compounds of the present invention include thyrotropin, polythyroid, KB-130015, and dronedarone.

Examples of suitable anabolic agents for use in combination with the compounds of the present invention include testosterone, TRH diethylstilbesterol, estrogens, β-agonists, theophylline, anabolic steroids, dehydroepiandrosterone, enkephalins, E-series prostagladins, retinoic acid and compounds as disclosed in U.S. Pat. No. 3,239,345, e.g., Zeranol®; U.S. Pat. No. 4,036,979, e.g., Sulbenox® or peptides as disclosed in U.S. Pat. No. 4,411,890.

Examples of suitable HIV or AIDS therapies for use in combination with the compounds of the present invention include indinavir sulfate, saquinavir, saquinavir mesylate, ritonavir, lamivudine, zidovudine, lamivudine/zidovudine combinations, zalcitabine, didanosine, stavudine, and megestrol acetate.

Examples of suitable therapies for treatment of Alzheimer's disease and cognitive disorders for use in combination with the compounds of the present invention include donepezil, tacrine, revastigmine, 5HT6, gamma secretase inhibitors, beta secretase inhibitors, SK channel blockers, Maxi-K blockers, and KCNQs blockers.

Examples of suitable therapies for treatment of sleeping disorders for use in combination with the compounds of the present invention include melatonin analogs, melatonin receptor antagonists, ML1B agonists, and GABA/NMDA receptor antagonists.

Examples of suitable anti-proliferative agents for use in combination with the compounds of the present invention include cyclosporin A, paclitaxel, FK-506, and adriamycin.

Examples of suitable anti-tumor agents for use in combination with the compounds of the present invention include paclitaxel, adriamycin, epothilones, cisplatin and carboplatin.

Compounds of the present invention may further be used in combination with nutritional supplements such as those described in U.S. Pat. No. 5,179,080, especially in combination with whey protein or casein, amino acids (such as leucine, branched amino acids and hydroxymethylbutyrate), triglycerides, vitamins (e.g., A, B6, B12, folate, C, D and E), minerals (e.g., selenium, magnesium, zinc, chromium, calcium and potassium), carnitine, lipoic acid, creatinine, B-hyroxy-B-methylbutyriate (Juven) and coenzyme Q-10.

In addition, compounds of the present invention may be used in combination with therapeutic agents used in the treatment of sexual dysfunction, including but not limited to PDE-5 inhibitors, such as sildenafil or IC-351.

Compounds of the present invention may further be used in combination with antiresorptive agents, hormone replacement therapies, vitamin D analogues, elemental calcium and calcium supplements, cathepsin K inhibitors, MMP inhibitors, vitronectin receptor antagonists, Src $SH_2$ antagonists, vacular —$H^+$-ATPase inhibitors, ipriflavone, fluoride, Tibolone, prostanoids, 17-beta hydroxysteroid dehydrogenase inhibitors and Src kinase inhibitors.

Compounds of the present invention may be used in combination with male contraceptives, such as nonoxynol 9 or therapeutic agents for the treatment of hair loss, such as minoxidil and finasteride or chemotherapeutic agents, such as with LHRH agonists.

Further, the compounds of the present invention may be used in combination with anti-cancer and cytotoxic agents, including but not limited to alkylating agents such as nitrogen mustards, alkyl sulfonates, nitrosoureas, ethylenimines, and triazenes; antimetabolites such as folate antagonists, purine analogues, and pyrimidine analogues; antibiotics such as anthracyclines, bleomycins, mitomycin, dactinomycin, and plicamycin; enzymes such as L-asparaginase; farnesyl-protein transferase inhibitors; 5α-reductase inhibitors; inhibitors of 17β-hydroxysteroid dehydrogenase type 3; hormonal agents such as glucocorticoids, estrogens/antiestrogens, androgens/antiandrogens, progestins, and luteinizing hormone-releasing hormone antagonists, octreotide acetate; microtubule-disruptor agents, such as ecteinascidins or their analogs and derivatives; microtubule-stabilizing agents such as taxanes, for example, paclitaxel (Taxol®), docetaxel (Taxotere®), and their analogs, and epothilones, such as epothilones A-F and their analogs; plant-derived products, such as vinca alkaloids, epipodophyllotoxins, taxanes; and topiosomerase inhibitors; prenyl-protein transferase inhibitors; and miscellaneous agents such as hydroxyurea, procarbazine, mitotane, hexamethylmelamine, platinum coordination complexes such as cisplatin and carboplatin; and other agents used as anti-cancer and cytotoxic agents such as biological response modifiers, growth factors; immune modulators and monoclonal antibodies. The compounds of the invention may also be used in conjunction with radiation therapy.

Representative examples of these classes of anti-cancer and cytotoxic agents include but are not limited to mechlorethamine hydrochloride, cyclophosphamide, chlorambucil, melphalan, ifosfamide, busulfan, carmustin, lomustine, semustine, streptozocin, thiotepa, dacarbazine, methotrexate, thioguanine, mercaptopurine, fludarabine, pentastatin, cladribin, cytarabine, fluorouracil, doxorubicin hydrochloride, daunorubicin, idarubicin, bleomycin sulfate, mitomycin C, actinomycin D, safracins, saframycins, quinocarcins, discodermolides, vincristine, vinblastine, vinorelbine tartrate, etoposide, etoposide phosphate, teniposide, paclitaxel, tamoxifen, estramustine, estramustine phosphate sodium, flutamide, buserelin, leuprolide, pteridines, diyneses, levamisole, aflacon, interferon, interleukins, aldesleukin, filgrastim, sargramostim, rituximab, BCG, tretinoin, irinotecan hydrochloride, betamethosone, gemcitabine hydrochloride, altretamine, and topoteca and any analogs or derivatives thereof.

Preferred member of these classes include, but are not limited to, paclitaxel, cisplatin, carboplatin, doxorubicin, carminomycin, daunorubicin, aminopterin, methotrexate, methopterin, mitomycin C, ecteinascidin 743, or porfiromycin, 5-fluorouracil, 6-mercaptopurine, gemcitabine, cytosine arabinoside, podophyllotoxin or podophyllotoxin derivatives such as etoposide, etoposide phosphate or teniposide, melphalan, vinblastine, vincristine, leurosidine, vindesine and leurosine.

Examples of anticancer and other cytotoxic agents include the following: epothilone derivatives as found in German Patent No. 4138042.8; WO 97/19086, WO 98/22461, WO 98/25929, WO 98/38192, WO 99/01124, WO 99/02224, WO 99/02514, WO 99/03848, WO 99/07692, WO 99/27890, WO 99/28324, WO 99/43653, WO 99/54330, WO 99/54318, WO 99/54319, WO 99/65913, WO 99/67252, WO 99/67253 and WO 00/00485; cyclin dependent kinase inhibitors as found in WO 99/24416 (see also U.S. Pat. No. 6,040,321); and prenyl-protein transferase inhibitors as found in WO 97/30992 and WO 98/54966; and agents such as those described generically and specifically in U.S. Pat. No. 6,011,029 (the compounds of which U.S. Patent can be employed together with any NHR modulators (including, but not limited to, those of present invention) such as AR modulators, ER modulators, with LHRH modulators, or with surgical castration, especially in the treatment of cancer).

The above other therapeutic agents, when employed in combination with the compounds of the present invention, may be used, for example, in those amounts indicated in the Physicians' Desk Reference (PDR) or as otherwise determined by one of ordinary skill in the art.

The compounds of the formula I can be administered for any of the uses described herein by any suitable means, for example, orally, such as in the form of tablets, capsules, granules or powders; sublingually; bucally; parenterally, such as by subcutaneous, intravenous, intramuscular, or intrastemal injection or infusion techniques (e.g., as sterile injectable aqueous or non-aqueous solutions or suspensions); nasally, including administration to the nasal membranes, such as by inhalation spray; topically, such as in the form of a cream or ointment; or rectally such as in the form of suppositories; in dosage unit formulations containing non-toxic, pharmaceutically acceptable vehicles or diluents. The present compounds can, for example, be administered in a form suitable for immediate release or extended release. Immediate release or extended release can be achieved by the use of suitable pharmaceutical compositions comprising the present compounds, or, particularly in the case of extended release, by the use of devices such as subcutaneous implants or osmotic pumps. The present compounds can also be administered liposomally.

Exemplary compositions for oral administration include suspensions which can contain, for example, microcrystalline cellulose for imparting bulk, alginic acid or sodium alginate as a suspending agent, methylcellulose as a viscosity enhancer, and sweeteners or flavoring agents such as those known in the art; and immediate release tablets which can contain, for example, microcrystalline cellulose, dicalcium phosphate, starch, magnesium stearate and/or lactose and/or other excipients, binders, extenders, disintegrants, diluents and lubricants such as those known in the art. The compounds of formula I can also be delivered through the oral cavity by sublingual and/or buccal administration. Molded tablets, compressed tablets or freeze-dried tablets are exemplary forms which may be used. Exemplary compositions include those formulating the present compound(s) with fast dissolving diluents such as mannitol, lactose, sucrose and/or cyclodextrins. Also included in such formulations may be high molecular weight excipients such as celluloses (avicel) or polyethylene glycols (PEG). Such formulations can also include an excipient to aid mucosal adhesion such as hydroxy propyl cellulose (HPC), hydroxy propyl methyl cellulose (HPMC), sodium carboxy methyl cellulose (SCMC), maleic anhydride copolymer (e.g., Gantrez), and agents to control release such as polyacrylic copolymer (e.g. Carbopol 934). Lubricants, glidants, flavors, coloring agents and stabilizers may also be added for ease of fabrication and use.

Exemplary compositions for nasal aerosol or inhalation administration include solutions in saline which can contain, for example, benzyl alcohol or other suitable preservatives, absorption promoters to enhance bioavailability, and/or other solubilizing or dispersing agents such as those known in the art.

Exemplary compositions for parenteral administration include injectable solutions or suspensions which can contain, for example, suitable non-toxic, parenterally acceptable diluents or solvents, such as mannitol, 1,3-butanediol, water, Ringer's solution, an isotonic sodium chloride solution, or other suitable dispersing or wetting and suspending agents, including synthetic mono- or diglycerides, and fatty acids, including oleic acid, or Cremaphor.

Exemplary compositions for rectal administration include suppositories which can contain, for example, a suitable non-irritating excipient, such as cocoa butter, synthetic glyceride esters or polyethylene glycols, which are solid at ordinary temperatures, but liquify and/or dissolve in the rectal cavity to release the drug.

Exemplary compositions for topical administration include a topical carrier such as Plastibase (mineral oil gelled with polyethylene).

The effective amount of a compound of the present invention can be determined by one of ordinary skill in the art, and includes exemplary dosage amounts for an adult human of from about 0.01 to 2000 mg of active compound per day, which can be administered in a single dose or in the form of individual divided doses, such as from 1 to 4 times per day. It will be understood that the specific dose level and frequency of dosage for any particular subject can be varied and will depend upon a variety of factors including the activity of the specific compound employed, the metabolic stability and length of action of that compound, the species, age, body weight, general health, sex and diet of the subject, the mode and time of administration, rate of excretion, drug combination, and severity of the particular condition. Preferred subjects for treatment include animals, most preferably mammalian species such as humans, and domestic animals such as dogs, cats and the like, subject to NHR-associated conditions.

Transactivation Assays:

AR Specific Assay:

Compounds of the present invention were tested in transactivation assays of a transfected reporter construct and using the endogenous androgen receptor of the host cells. The transactivation assay provides a method for identifying functional agonists and partial agonists that mimic, or antagonists that inhibit, the effect of native hormones, in this case, dihydrotestosterone (DHT). This assay can be used to predict in vivo activity as there is a good correlation in both series of data. See, e.g. T. Berger et al., J. Steroid Biochem. Molec. Biol. 773 (1992), the disclosure of which is herein incorporated by reference.

For the transactivation assay a reporter plasmid is introduced by transfection (a procedure to induce cells to take foreign genes) into the respective cells. This reporter plasmid, comprising the cDNA for a reporter protein, such as secreted alkaline phosphatase (SEAP), controlled by prostate specific antigen (PSA) upstream sequences containing androgen response elements (AREs). This reporter plasmid functions as a reporter for the transcription-modulating activity of the AR. Thus, the reporter acts as a surrogate for the products (mRNA then protein) normally expressed by a gene under control of the AR and its native hormone. In order to detect antagonists, the transactivation assay is carried out in the presence of constant concentration of the natural AR hormone (DHT) known to induce a defined reporter signal. Increasing concentrations of a suspected antagonist will decrease the reporter signal (e.g., SEAP production). On the other hand, exposing the transfected cells to increasing concentrations of a suspected agonist will increase the production of the reporter signal.

For this assay, LNCaP and MDA 453 cells were obtained from the American Type Culture Collection (Rockville, Md.), and maintained in RPMI 1640 or DMEM medium supplemented with 10% fetal bovine serum (FBS; Gibco) respectively. The respective cells were transiently transfected by electroporation according to the optimized procedure described by Heiser, 130 Methods Mol. Biol., 117 (2000), with the pSEAP2/PSA540/Enhancer reporter plasmid. The reporter plasmid, was constructed as follows: commercial human placental genomic DNA was used to generate by Polymerase Cycle Reaction (PCR) a fragment containing the BglII site (position 5284) and the Hind III site at position 5831 of the human prostate specific antigen promoter (Accession #U37672), Schuur, et al., J. Biol. Chem., 271 (12): 7043-51 (1996). This fragment was subcloned into the pSEAP2/basic (Clontech) previously digested with BglII and HindIII to generate the pSEAP2/PSA540 construct. Then a fragment bearing the fragment of human PSA upstream sequence between positions −5322 and −3873 was amplified by PCR from human placental genomic DNA. A XhoI and a BglII sites were introduced with the primers. The resulting fragment was subcloned into pSEAP2/PSA540 digested with XhoI and BglII respectively, to generate the pSEAP2/PSA540/Enhancer construct. LNCaP and MDA MB-453 cells were collected in media containing 10% charcoal stripped FBS. Each cell suspension was distributed into two Gene Pulser Cuvettes (Bio-Rad) which then received 8 µg of the reporter construct, and electroporated using a Bio-Rad Gene Pulser at 210 volts and 960 µ Faraday. Following the transfections the cells were washed and incubated with media containing charcoal stripped fetal bovine serum in the absence (blank) or presence (control) of 1 nM dihydrotestosterone (DHT; Sigma Chemical) and in the presence or absence of the standard anti-androgen bicalutamide or compounds of the present invention in concentrations ranging from $10^{-10}$ to $10^{-5}$ M (sample). Duplicates were used for each sample. The compound dilutions were performed on a Biomek 2000 laboratory workstation.

After 48 h, a fraction of the supernatant was assayed for SEAP activity using the Phospha-Light Chemiluminescent Reporter Gene Assay System (Tropix, Inc). Viability of the remaining cells was determined using the CellTiter 96 Aqueous Non-Radioactive Cell Proliferation Assay (MTS Assay, Promega). Briefly, a mix of a tetrazolium compound (3-(4,5-dimethylthiazol-2-yl)-5-(3-carboxymethoxyphenyl)-2-(4-sulfophenyl)-2H-tetrazolium, inner salt; MTS) and an electron coupling reagent (phenazine methosulfate; PMS) are added to the cells. MTS (Owen's reagent) is bioreduced by cells into a formazan that is soluble in tissue culture medium, and therefore its absorbance at 490 nm can be measured directly from 96 well assay plates without additional processing. The quantity of formazan product as measured by the amount of 490 nm absorbance is directly proportional to the number of living cells in culture. For each replicate the SEAP reading was normalized by the Abs490 value derived from the MTS assay. For the antagonist mode, the % Inhibition was calculated as:

% Inhibition=100×(1−[average control−average blank/average sample−average blank])

Data was plotted and the concentration of compound that inhibited 50% of the normalized SEAP was quantified ($IC_{50}$).

For the agonist mode % Control was referred as the effect of the tested compound compared to the maximal effect observed with the natural hormone, in this case DHT, and was calculated as:

% Control=100×average sample−average blank/average control−average blank

Data was plotted and the concentration of compound that activates to levels 50% of the normalized SEAP for the control was quantified ($EC_{50}$).

GR Specificity Assay:

The reporter plasmid utilized was comprised of the cDNA for the reporter SEAP protein, as described for the AR specific transactivation assay. Expression of the reporter SEAP protein was controlled by the mouse mammary tumor virus long terminal repeat (MMTV LTR) sequences that contains three hormone response elements (HREs) that can be regulated by both GR and PR see, e.g. G. Chalepakis et al., Cell, 53(3), 371 (1988). This plasmid was transfected into A549 cells, which expresses endogenous GR, to obtain a GR specific transactivation assay. A549 cells were obtained from the American Type Culture Collection (Rockville, Md.), and maintained in RPMI 1640 supplemented with 10% fetal bovine serum (FBS; Gibco). Determination of the GR specific antagonist activity of the compounds of the present invention was identical to that described for the AR specific transactivation assay, except that the DHT was replaced with 5 nM dexamethasone (Sigma Chemicals), a specific agonist for GR. Determination of the GR specific agonist activity of the compounds of the present invention was performed as described for the AR transactivation assay, wherein one measures the activation of the GR specific reporter system by the addition of a test compound, in the absence of a known GR specific agonists ligand.

PR Specific Assay:

The reporter plasmid utilized was comprised of the cDNA for the reporter SEAP protein, as described for the AR specific transactivation assay. Expression of the reporter SEAP protein was controlled by the mouse mammary tumor virus long terminal repeat (MMTV LTR) sequences that contains three hormone response elements (HRE's) that can be regulated by both GR and PR. This plasmid was transfected into T47D, which expresses endogenous PR, to obtain a PR specific transactivation assay. T47D cells were obtained from the American Type Culture Collection (Rockville, Md.), and maintained in DMEM medium supplemented with 10% fetal bovine serum (FBS; Gibco). Determination of the PR specific antagonist activity of the compounds of the present invention was identical to that described for the AR specific transactivation assay, except that the DHT was replaced with 1 nM Promegastone (NEN), a specific agonist for PR. Determination of the PR specific agonist activity of the compounds of the present invention was performed as described for the AR transactivation assay, wherein one measures the activation of the PR specific reporter system by the addition of a test compound, in the absence of a known PR specific agonists ligand.

AR Binding Assay:

For the whole-cell binding assay, human LNCaP cells (T877A mutant AR) or MDA 453 (wild type AR) in 96-well microtiter plates containing RPMI 1640 or DMEM supplemented with 10% charcoal stripped CA-FBS (Cocaleco Biologicals) respectively, were incubated at 37° C. to remove any endogenous ligand that might be complexed with the receptor in the cells. After 48 h, either a saturation analysis to determine the $K_d$ for tritiated dihydrotestosterone, $[^3H]$-DHT, or a competitive binding assay to evaluate the ability of test compounds to compete with $[^3H]$-DHT were performed. For the saturation analysis, media (RPMI 1640 or DMEM—0.2% CA-FBS) containing $[^3H]$-DHT (in concentrations ranging from 0.1 nM to 16 nM) in the absence (total binding) or presence (non-specific binding) of a 500-fold molar excess of unlabeled DHT were added to the cells. After 4 h at 37° C., an aliquot of the total binding media at each concentration of $[^3H]$-DHT was removed to estimate the amount of free $[^3H]$-DHT. The remaining media was removed, cells were washed three times with PBS and harvested onto UniFilter GF/B plates (Packard), Microscint (Packard) was added and plates counted in a Top-Counter (Packard) to evaluate the amount of bound $[^3H]$-DHT.

For the saturation analysis, the difference between the total binding and the non-specific binding, was defined as specific binding. The specific binding was evaluated by Scatchard analysis to determine the $K_d$ for $[^3H]$-DHT. See e.g. D. Rodbard, Mathematics and statistics of ligand assays: an illustrated guide: In: J. Langon and J. J. Clapp, eds., Ligand Assay, Masson Publishing U.S.A., Inc., New York, pp. 45-99, (1981), the disclosure of which is herein incorporated by reference.

For the competition studies, media containing 1 nM $[^3H]$-DHT and compounds of the invention ("test compounds") in concentrations ranging from $10^{-10}$ to $10^{-5}$ M were added to the cells. Two replicates were used for each sample. After 4 h at 37° C., cells were washed, harvested and counted as described above. The data was plotted as the amount of $[^3H]$-DHT (% of control in the absence of test compound) remaining over the range of the dose response curve for a given compound. The concentration of test compound that inhibited 50% of the amount of $[^3H]$-DHT bound in the absence of competing ligand was quantified ($IC_{50}$) after log-logit transformation. The $K_i$ values were determined by application of the Cheng-Prusoff equation to the $IC_{50}$ values, where:

$$K_1 = \frac{IC_{50}}{(1 + (^3H - DHT)/K_d \text{ for } ^3H - DHT)}.$$

After correcting for non-specific binding, $IC_{50}$ values were determined. The $IC_{50}$ is defined as the concentration of competing ligand needed to reduce specific binding by 50%. The $K_d$s for [$^3$H]-DHT for MDA 453 and LNCaP were 0.7 and 0.2 nM respectively.

C2C12 Mouse Myoblast Transactivation Assay:

Two functional transactivation assays were developed to assess the efficacy of androgen agonists in a muscle cell background using a luciferase reporter. The first assay (ARTA Stable 1) uses a cell line, Stable 1 (clone #72), which expresses the full length rat androgen receptor but requires the transient transfection of an enhancer/reporter. This cell line was derived from C2C12 mouse moyoblast cells. The second assay (ARTA Stable 2) uses a cell line, Stable 2 (clone #133), derived from Stable 1 which expresses both rAR and the enhancer/luciferase reporter.

The enhancer/reporter construct used in this system is pGL3/2XDR-1/luciferase. 2XDR-1 was reported to be an AR specific response element in CV-1 cells, Brown et. al. The Journal of Biological Chemistry 272, 8227-8235, (1997). It was developed by random mutagenesis of an AR/GR consensus enhancer sequence.

ARTA Stable 1:
1. Stable 1 cells are plated in 96 well format at 6,000 cells/well in high glucose DMEM without phenol red (Gibco BRL, Cat. No.: 21063-029) containing 10% charcoal and dextran treated FBS (HyClone Cat. No.: SH30068.02), 50 mM HEPES Buffer (Gibco BRL, Cat. No.: 15630-080), 1×MEM Na Pyruvate (Gibco BRL, Cat. No.: 11360-070), 0.5× Antibiotic-Antimycotic, and 800 μg/mL Geneticin (Gibco BRL, Cat. No.: 10131-035).
2. 48 h later, cells are transfected with pGL3/2XDR-1/luciferase using LipofectAMINE Plus™ Reagent (Gibco BRL, Cat. No.: 10964-013). Specifically, 5 ng/well pGL3/2XDR-1/luciferase DNA and 50 ng/well Salmon Sperm DNA (as carrier) are diluted with 5 □l/well Opti-MEMem media (Gibco BRL, Cat. No.: 31985-070). To this, 0.5 □l/well Plus reagent is added. This mixture is incubated for 15 min at rt. In a separate vessel, 0.385 μl/well LipofectAMINE reagent is diluted with 5 □l/well Opti-MEM. The DNA mixture is then combined with the LipofectAMINE mixture and incubated for an additional 15 min at rt. During this time, the media from the cells is removed and replaced with 60 μl/well of Opti-MEM. To this is added 10 □l/well of the DNA/LipofectAMINE transfection mixture. The cells are incubated for 4 h.
3. The transfection mixture is removed from the cells and replaced with 90 μl of media as in #1 above.
4. 10 μl/well of appropriate drug dilution is placed in each well.
5. 24 h later, the Steady-Glo™ Luciferase Assay System is used to detect activity according to the manufacturer's instructions (Promega, Cat. No.: E2520).

ARTA Stable 2:
1. Stable 2 cells are plated in 96 well format at 6,000 cells/well in high glucose DMEM without phenol red (Gibco BRL, Cat. No.: 21063-029) containing 10% charcoal and dextran treated FBS (HyClone Cat. No.: SH30068.02), 50 mM HEPES Buffer (Gibco BRL, Cat. No.: 15630-080), 1×MEM Na Pyruvate (Gibco BRL, Cat. No.: 11360-070), 0.5× Antibiotic-Antimycotic, 800 μg/mL Geneticin (Gibco BRL, Cat. No.: 10131-035) and 800 μg/mL Hygromycin P (Gibco BRL, Cat. No.: 10687-010).
2. 48 h later, the media on the cells is removed and replaced with 90 μl fresh. 10 μl/well of appropriate drug dilution is placed in each well.
3. 24 h later, the Steady-Glo™ Luciferase Assay System is used to detect activity according to the manufacturer's instructions (Promega, Cat. No. E2520).

Proliferation Assays:

Human Prostate Cell Proliferation Assay:

Compounds of the present invention were tested ("test compounds") on the proliferation of human prostate cancer cell lines. For that, MDA PCa2b cells, a cell line derived from the metastasis of a patient that failed castration, Navone et al., Clin. Cancer Res., 3, 2493-500 (1997), were incubated with or without the test compounds for 72 h and the amount of [$^3$H]-thymidine incorporated into DNA was quantified as a way to assess number of cells and therefore proliferation. The MDA PCa2b cell line was maintained in BRFF-HPC1 media (Biological Research Faculty & Facility Inc., MD) supplemented with 10% FBS. For the assay, cells were plated in Biocoated 96-well microplates and incubated at 37° C. in 10% FBS (charcoal-stripped)/BRFF-BMZERO (without androgens). After 24 h, the cells were treated in the absence (blank) or presence of 1 nM DHT (control) or with test compounds (sample) of the present invention in concentrations ranging from $10^{-10}$ to $10^{-5}$ M. Duplicates were used for each sample. The compound dilutions were performed on a Biomek 2000 laboratory work station. Seventy-two h later 0.44 uCi. of [$^3$H]-Thymidine (Amersham) was added per well and incubated for another 24 h followed by tripsinization, harvesting of the cells onto GF/B filters. Micro-scint PS were added to the filters before counting them on a Beckman TopCount.

The % Inhibition was calculated as:

% Inhibition=100×(1−[average$_{control}$−average$_{blank}$/average$_{sample}$−average$_{blank}$])

Data was plotted and the concentration of compound that inhibited 50% of the [$^3$H]-Thymidine incorporation was quantified ($IC_{50}$).

Murine Breast Cell Proliferation Assay:

The ability of compounds of the present invention ("test compounds") to modulate the function of the AR was determined by testing said compounds in a proliferation assay using the androgen responsive murine breast cell line derived from the Shionogi tumor, Hiraoka et al., Cancer Res., 47, 6560-6564 (1987). Stable AR dependent clones of the parental Shionogi line were established by passing tumor fragments under the general procedures originally described in Tetuo, et. al., Cancer Research 25, 1168-1175 (1965). From the above procedure, one stable line, SC114, was isolated, characterized and utilized for the testing of example compounds. SC114 cells were incubated with or without the test compounds for 72 h and the amount of [3H]-thymidine incorporated into DNA was quantified as a surrogate endpoint to assess the number of cells and therefore the proliferation rate as described in Suzuki et. al., J. Steroid Biochem. Mol. Biol. 37, 559-567 (1990). The SC114 cell line was maintained in MEM containing $10^{-8}$ M testosterone and 2% DCC-treated FCS. For the assay, cells were plated in 96-well microplates in the maintenance media and incubated at 37° C. On the following day, the medium was changed to serum free medium [Ham's F-12:MEM (1;1, v/v) containing 0.1% BSA] with (antagonist mode) or without (agonist mode) $10^{-8}$ M testosterone and the test compounds of the present invention in concentrations ranging from $10^{-10}$ to $10^{-5}$ M. Duplicates were used for each sample. The compound dilutions were performed on a Biomek 2000 laboratory work station. Seventy two h later 0.44 uCi of [3H]-Thymidine (Amersham) was added per well and incubated for another 2 h followed by tripsinization, and harvesting of the cells onto GF/B filters. Micro-scint PS were added to the filters before counting them on a Beckman TopCount.

For the antagonist mode, the % Inhibition was calculated as:

% Inhibition=100×(1−[average$_{sample}$−average$_{blank}$/average$_{control}$−average$_{blank}$])

Data was plotted and the concentration of compound that inhibited 50% of the [$^3$H]-Thymidine incorporation was quantified (IC$_{50}$).

For the agonist mode % Control was referred as the effect of the tested compound compared to the maximal effect observed with the natural hormone, in this case DHT, and was calculated as:

% Control=100×(average$_{sample}$−average$_{blank}$)/(average$_{control}$−average$_{blank}$)

Data was plotted and the concentration of compound that inhibited 50% of the [$^3$H]-Thymidine incorporation was quantified (EC$_{50}$).

In Vitro Assay to Measure GR-Induced AP-1 Transrepression:

The AP-1 assay is a cell-based luciferase reporter assay. A549 cells, which contain endogenous glucocorticoid receptor, were stably transfected with an AP-1 DNA binding site attached to the luciferase gene. Cells are then grown in RPMI+10% fetal calf serum (charcoal-treated)+Penicillin/Streptomycin with 0.5 mg/mL geneticin. Cells are plated the day before the assay at approximately 40000 cells/well. On assay day, the media is removed by aspiration and 20 µL assay buffer (RPMI without phenol red+10% FCS (charcoal-treated)+Pen/Strep) is added to each well. At this point either 20 µL assay buffer (control experiments), the compounds of the present invention ("test compounds") (dissolved in DMSO and added at varying concentrations) or dexamethasome (100 nM in DMSO, positive control) are added to each well. The plates are then pre-incubated for 15 min at 37° C., followed by stimulation of the cells with 10 ng/mL PMA. The plates are then incubated for 7 h at 37° C. after which 40 µL luciferase substrate reagent is added to each well. Activity is measured by analysis in a luminometer as compared to control experiments treated with buffer or dexamethasome. Activity is designated as % inhibition of the reporter system as compared to the buffer control with 10 ng/mL PMA alone. The control, dexamethasone, at a concentration of <10 □M typically suppresses activity by 65%. Test compounds which demonstrate an inhibition of PMA induction of 50% or greater at a concentration of test compound of ≦10 □M are deemed active.

In Vivo Assays

Levator Ani & Wet Prostate Weight Assay AR Agonist Assay:

The activity of compounds of the present invention as AR agonists was investigated in an immature male rat model, a recognized test of anabolic effects in muscle and sustaining effects in sex organs for a given compound, as described in L. G. Hershberger et al., *Proc. Soc. Expt. Biol. Med.*, 83, 175 (1953); B. L. Beyler et al, "Methods for evaluating anabolic and catabolic agents in laboratory animals", *J. Amer. Med. Women's Ass.*, 23, 708 (1968); H. Fukuda et al., "Investigations of the levator ani muscle as an anabolic steroid assay", *Nago Dai. Yak. Ken. Nem.* 14, 84 (1966) the disclosures of which are herein incorporated by reference.

The basis of this assay lies in the well-defined action of androgenic agents on the maintenance and growth of muscle tissues and sexual accessory organs in animals and man. Androgenic steroids, such as testosterone (T), have been well characterized for their ability to maintain muscle mass. Treatment of animals or humans after castrations with an exogenous source of T results in a reversal of muscular atrophy. The effects of T on muscular atrophy in the rat levator ani muscle have been well characterized. M. Masuoka et al., "Constant cell population in normal, testosterone deprived and testosterone stimulated levator ani muscles" *Am. J. Anat.* 119, 263 (1966); Z. Gori et al., "Testosterone hypertrophy of levator ani muscle of castrated rats. I. Quantitative data" *Boll.—Soc. Ital. Biol. Sper.* 42, 1596 (1966); Z. Gori et al., "Testosterone hypertrophy of levator ani muscle of castrated rats. II. Electron-microscopic observations" *Boll.—Soc. Ital. Biol. Sper.* 42, 1600 (1966); A. Boris et al., *Steroids* 15, 61 (1970). As described above, the effects of androgens on maintenance of male sexual accessory organs, such as the prostate and seminal vesicles, is well described. Castration results in rapid involution and atrophy of the prostate and seminal vesicles. This effect can be reversed by exogenous addition of androgens. Since both the levator ani muscle and the male sex organs are the tissues most responsive to the effects of androgenic agents, this model is used to determine the androgen dependent reversal of atrophy in the levator ani muscle and the sex accessory organs in immature castrated rats. Sexually mature rats (200-250 g, 6-8 weeks-old, Sprague-Dawley, Harlan) were acquired castrated from the vendor (Taconic). The rats were divided into groups and treated daily for 7 to 14 days with one of the following:

1. Control vehicle
2. Testosterone Propionate (TP) (3 mg/rat/day, subcutaneous)
3. TP plus Bicalutamide (administered p.o. in PEGTW, QD), a recognized antiandrogen, as a reference compound.
4. To demonstrate antagonist activity, a compound of the present invention ("test compound") was administered (p.o. in PEGTW, QD) with TP (s.c. as administered in group 2) in a range of doses.
5. To demonstrate agonist activity a compound of the present invention ("test compound") was administered alone (p.o. in PEGTW, QD) in a range of doses.

At the end of the 7-14-day treatment, the animals were sacrificed by carbon dioxide, and the levator ani, seminal vesicle and ventral prostate weighed. To compare data from different experiments, the levator ani muscle and sexual organ weights were first standardized as mg per 100 g of body weight, and the increase in organ weight induced by TP was considered as the maximum increase (100%). Super-anova (one factor) was used for statistical analysis.

The gain and loss of sexual organ weight reflect the changes of the cell number (DNA content) and cell mass (protein content), depending upon the serum androgen concentration. See Y. Okuda et al., *J. Urol.,* 145, 188-191 (1991), the disclosure of which is herein incorporated by reference. Therefore, measurement of organ wet weight is sufficient to indicate the bioactivity of androgens and androgen antagonist. In immature castrated rats, replacement of exogenous androgens increases levator ani, seminal vesicles (SV) and prostate in a dose dependent manner.

The maximum increase in organ weight was 4 to 5-fold when dosing 3 mg/rat/day of testosterone (T) or 1 mg/rat/day of testosterone propionate (TP) for 3 days. The EC$_{50}$ of T and TP were about 1 mg and 0.03 mg, respectively. The increase in the weight of the VP and SV also correlated with the increase in the serum T and DHT concentration. Although administration of T showed 5-times higher serum concentrations of T and DHT at 2 h after subcutaneous injection than that of TP, thereafter, these high levels declined very rapidly. In contrast, the serum concentrations of T and DHT in TP-treated animals were fairly consistent during the 24 h, and therefore, TP showed about 10-30-fold higher potency than free T.

The following examples serve to better illustrate, but not limit, some of the preferred embodiments of the invention.

EXAMPLE 1

(2S,3R)-3-hydroxy-2-pyrrolidinecarboxylic acid methyl ester

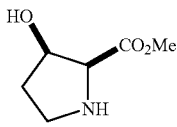

1A. (2S,3S)-3-Hydroxy-2-pyrrolidinecarboxylic acid methyl ester hydrochloride salt

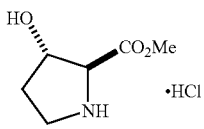

Hydrogen chloride gas was bubbled through a suspension of trans-3-hydroxy-L-proline (50 g, 0.38 mol) in MeOH (600 mL) cooled to 0° C. for 10 min. The resulting clear solution was stirred at rt for 4 h, then concentrated carefully under reduced pressure (white precipitates formed during the concentration). The resulting white solid was dried under vacuum overnight to afford the title compound (68.26 g) as a white solid.

1B. (2S,3S)-N-tert-Butyloxycarbonyl-3-hydroxy-2-pyrrolidinecarboxylic acid methyl ester

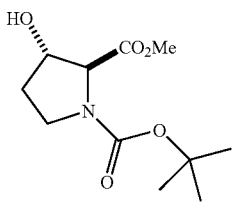

To a suspension of compound 1A (68.26 g, 0.375 mol) in CH$_2$Cl$_2$ (1.0 L) cooled to 0° C. was added Et$_3$N (105.3 mL, 0.755 mol), followed by portionwise addition of di-tert-butyl dicarbonate (82.96 g, 0.380 mol). The resulting mixture was stirred at rt for 4 h, then partitioned between water and CH$_2$Cl$_2$. The CH$_2$Cl$_2$ layer was washed with water (2×), 20% aqueous citric acid (1×), water, brine, dried (Na$_2$SO$_4$) and concentrated under reduced pressure to give an oily residue. The crude product was chromatographed (silica gel) eluting with 15%-50% EtOAc/hexane to afford compound 1B (73.3 g) as a pale yellow viscous oil.

1C. (2S,3R)-N-tert-Butyloxycarbonyl-3-benzoyloxy-2-pyrrolidine-carboxylic acid methyl ester

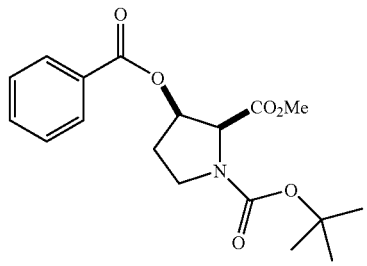

To a stirred solution of compound 1B (69.1 g, 0.282 mol), Ph$_3$P (88.7 g, 0.338 mol) and benzoic acid (41.32 g, 0.338 mol) in anhydrous THF (1.35 L) cooled to 0° C. was added a solution of DEAD (62 mL, 0.33 mol) in anhydrous THF (50 mL) dropwise over 1 h through an addition funnel. After the addition, the resulting light yellow solution was stirred at rt until the reaction was complete (~8 h). The reaction mixture was then partitioned between EtOAc and aqueous NaHCO$_3$. The organic layer was washed with saturated aqueous NaHCO$_3$, water (2×), brine, dried (Na$_2$SO$_4$) and concentrated under reduced pressure to yield a crude product as a semi-solid. The crude product was suspended in 25% EtOAc/hexane and stirred vigorously for 3 h. The resulting suspension was filtered and the collected white solid (triphenylphosphine oxide) rinsed with 20% EtOAc/hexane (2×). The combined filtrate was concentrated under reduced pressure to yield an oily residue, which was triturated twice with 20% EtOAc/hexane as described above to yield approximately 150 g of the partially purified product as a yellow oil, which was further purified by flash chromatography (silica gel) eluting with 10-20% EtOAc/hexane to furnish pure compound 1C (88.4 g) as a light yellow viscous oil.

1D. (2S,3R)-N-tert-Butyloxycarbonyl-3-hydroxy-2-pyrrolidinecarboxylic acid methyl ester

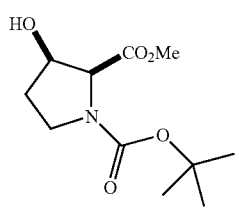

To a solution of compound 1C (88.44 g, 0.253 mol) in anhydrous MeOH (700 mL) cooled to 0° C. was slowly added a freshly prepared 1N solution of KOH in anhydrous MeOH (367 mL, 0.367 mol) over 25 min through an addition funnel. After the addition, the light yellow solution was stirred at 0° C. for 2 h, and then the reaction was quenched by slow addition (over 25 min) of a solution of 1N HCl in dioxane/EtOAc (380 mL) through an addition funnel. The resulting white suspension was concentrated under reduced pressure to remove most of the solvent, and the remaining mixture was partitioned between water and EtOAc. The separated organic phase was washed with water (2×), saturated aqueous NaHCO$_3$ (2×), water, brine, and then dried (Na$_2$SO$_4$). The filtrate was concentrated under reduced pressure to give a light yellow oily residue, which was chromatographed (silica gel) eluting first with 25-30% EtOAc/hexane, then 5% MeOH in 30% EtOAc/hexane to furnish compound 1D (44.6 g) as a pale yellow oil.

1E. (2S,3R)-3-Hydroxy-2-pyrrolidinecarboxylic acid methyl ester, trifluoroacetic acid salt

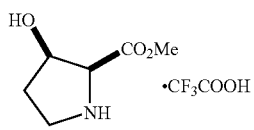

To a solution of compound 1D (44.6 g, 0.182 mol) in CH$_2$Cl$_2$ (450 mL) cooled to 0° C. was slowly added TFA (275 mL) through an addition funnel over 40 min. After addition, the reaction mixture was stirred at 0° C. for 2 h, then concentrated under reduced pressure to give a viscous oily residue which was evaporated with ether (2×), toluene (1×), ether (2×) and dried under vacuuum overnight to yield compound 1E (59.5 g) as a light yellow solid.

1F. (2S,3R)-3-Hydroxy-2-pyrrolidinecarboxylic acid methyl ester

To a solution of compound 1E (12.64 g, 48.8 mmol) in MeOH (150 mL) was added WA21J resin (60 g). The resulting suspension was stirred at rt for 1 h, and then filtered. The collected resin was rinsed with MeOH (2×) and combined filtrate concentrated carefully under reduced pressure to give compound 1F (7.7 g) as a colorless oil. [□]$_D$=14.9° (c. 1.0, MeOH); HPLC: 100% at 0.157 min (retention time) (Conditions: Phenom. Luna C18 (4.6×50 mm); Eluted with 0% to 100% B; 4 min gradient (A=90% H$_2$O—10% MeOH—0.1% H$_3$PO$_4$ and B=10% H$_2$O—90% MeOH—0.1% H$_3$PO$_4$), Flow rate at 4 mL/min., UV detection at 220 nm); MS (ES) m/z 146 [M+1]$^+$

EXAMPLE 2

(7R,7aS)-4-(7-Hydroxy-1,3-dioxo-tetrahydropyrrolo[1,2-c]imidazol-2-yl)-5,6,7,8-tetrahydronaphthalene-1-carbonitrile

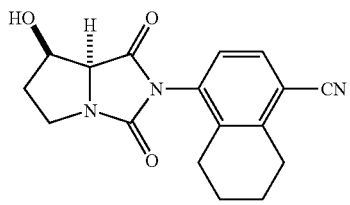

2A. N-(5,6,7,8-Tetrahydronaphthalen-1-yl)-acetamide

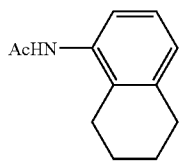

To a solution of commercially available 5,6,7,8-tetrahydronaphthylamine (2 g, 14 mmol) in EtOH (5 mL) at rt was slowly added acetic anhydride (1.28 mL, 13.6 mmol). After addition, the reaction mixture was stirred at rt for 5 min. The resulting suspension was filtered, the collected solid washed with hexane (5×) and dried under vacuum to furnish the title compound (2.5 g) as an off-white solid.

2B. N-(4-Bromo-5,6,7,8-tetrahydronaphthalen-1-yl)-acetamide

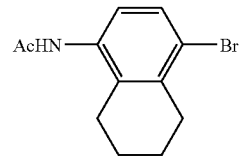

To a solution of compound 2A (2 g, 11 mmol) in AcOH (15 mL) cooled at 0° C. was added a solution of bromine (1.69 mL, 33 mmol) in AcOH (1.2 mL) slowly so that the reaction temperature was maintained below 17° C. After addition, the reaction mixture was stirred at rt until all the starting material was consumed (~4 h). The reaction mixture was then poured into ice/water and the resulting suspension filtered. The collected solid was washed with H$_2$O until the filtrate pH=6-7, and dried in a vacuum oven at 50° C. overnight to yield compound 2B (2.7 g) as an off-white solid.

2C. N-(4-Cyano-5,6,7,8-tetrahydronaphthalen-1-yl)-acetamide

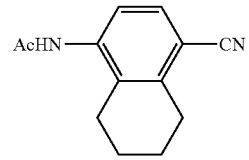

A suspension of compound 2B (1 g, 3.7 mmol) and CuCN (0.335 g, 0.374 mmol) in anhydrous DMF (8 mL) was refluxed for 5 h. After cooling to rt, the reaction mixture was concentrated under reduced pressure to remove most of the DMF and the remaining residue triturated with EtOAc (5×). The combined EtOAc was washed with water and brine, dried (Na$_2$SO$_4$), and concentrated under reduced pressure to dryness to yield compound 2C (0.8 g) as a yellow solid.

2D. 4-Amino-5,6,7,8-tetrahydronaphthalene-1-carbonitrile, hydrochloride salt

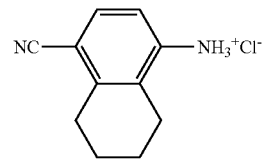

A suspension of 2C (0.40 g, 1.87 mmol) in a mixed solvent of EtOH (2 mL) and conc. HCl (2 mL) was refluxed for 2 h. The resulting solution was allowed to cool to rt and concentrated under reduced pressure. The obtained solid was evaporated with toluene (2×) to yield compound 2D (0.25 g) as a solid.

2E. 4-Isocyanato-5,6,7,8-tetrahydronaphthalene-1-carbonitrile

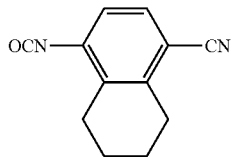

To a stirring suspension of compound 2D (0.10 g, 0.48 mmol) and NaHCO$_3$ (0.404 g, 4.80 mmol) in CH$_2$Cl$_2$ (4 mL) cooled to 0° C. was rapidly added a solution of phosgene (20%) in toluene (0.95 mL, 4.32 mmol). After addition, the mixture was stirred at rt for 2 h, then filtered to remove the solid. The filtrate was concentrated under reduced pressure, the resulting solid residue dried under vacuum for 1 h to afford compound 2E (95 mg) as a light yellow solid.

2F. (7R,7aS)-4-(7-Hydroxy-1,3-dioxotetrahydropyrrolo[1,2-c]imidazol-2-yl)-5,6,7,8-tetrahydronaphthalene-1-carbonitrile To a suspension of compound 1E (0.145 g, 0.56 mmol) in CH$_2$Cl$_2$ (2 mL) cooled at 0° C. was added i-Pr$_2$NEt (0.12 mL, 0.69 mmol). After stirring at 0° C. for 20 min, compound 2E (95 mg, 0.48 mmol) in CH$_2$Cl$_2$ (1 mL) solution was added, along with 4 Å molecular sieves (0.5 g) and the resulting mixture stirred at rt until urea formation was complete (~2 h). To the mixture was then added DBU (0.15 mL, 1.0 mmol), the resulting brown colored suspension was stirred vigorously at rt until hydantoin formation was complete (~15 h). The reaction mixture was loaded on a silica gel column, eluted with 40% EtOAc/hexane, and 5% MeOH in EtOAc/hexane (1:1) to afford 128 mg of the title compound as a white solid. HPLC: 99% at 2.42 min (retention time) (Conditions: Phenom. Luna C18 (4.6×50 mm); Eluted with 0% to 100% B; 4 min gradient (A=90% H$_2$O—10% MeOH—0.1% H$_3$PO$_4$ and B=10% H$_2$O—90% MeOH—0.1% H$_3$PO$_4$ ), Flow rate at 4 mL/min., UV detection at 220 nm). Chiral HPLC: retention time=9.01 min (99%); Conditions: (CHIRALPAK® OD column 4.6×250 mm; 25% isopropanol in hexane over 30 min at flow rate 1.0 mL/min, UV detection at 220 nm); MS (ES) m/z 312 [M+1]$^+$

EXAMPLE 3

(7R,7aS)-7-(7-Hydroxy-1,3-dioxotetrahydropyrrolo[1,2-c]imidazol-2-yl)-indan-4-carbonitrile

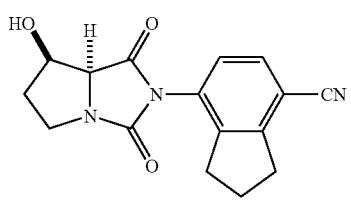

3A. N-Indan-4-yl-acetamide

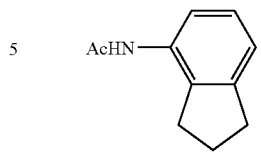

A suspension of commercially available 4-nitroindane (10 g, 61.3 mmol) and 10% Pd/C (1 g) in MeOH (200 mL) was stirred vigorously under an atmosphere of hydrogen overnight at rt. The reaction was filtered through a pad of Celite® and concentrated, and residual solvent was removed by combining the reaction with toluene followed by evaporation. The crude reaction was taken up in pyridine (100 mL), and Ac$_2$O (20 mL) was added and the reaction stirred for 16 h at rt. The reaction was evaporated and the crude product was purified by flash chromatography (5% MeOH in EtOAc/hexane(1:1) to give the title compound (9.12 g).

3B. (7R,7aS)-7-(7-Hydroxy-1,3-dioxotetrahydropyrrolo[1,2-c]imidazol-2-yl)indan-4-carbonitrile Compound 3B as a white solid was prepared from compound 3A by procedures analogous to those described in Example 2. HPLC: 97% at 2.75 min (retention time) (Conditions: YMC S5 ODS (4.6×50 mm); Eluted with 0% to 100% B; 4 min gradient; (A=90% H$_2$O—10% MeOH—0.1% H$_3$PO$_4$ and B=10% H$_2$O—90% MeOH—0.1% H$_3$PO$_4$); Flow rate at 4 mL/min. UV detection at 220 nm). LC/MS m/z 298 [M+1]$^+$.

EXAMPLE 4

(7R,7aS)-4-(7-Hydroxy-1,3-dioxotetrahydropyrrolo[1,2-c]imidazol-2-yl)-2,3-dihydrobenzofuran-7-carbonitrile

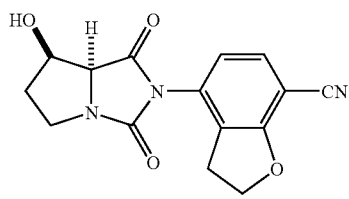

4A. 4-Acetylamino-2,3-dihydrobenzofuran-7-carboxylic acid amide

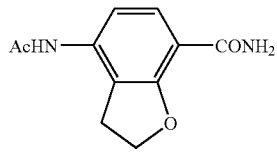

Ammonia gas was bubbled through a solution of 4-acetylamino-2,3-dihydro-benzofuran-7-carboxylic acid methyl ester (12 g, 51 mmol, prepared as described in Takuji Kakigami et al, *Chem. Pharm. Bull*, 46 (1), 42-52, (1998)) in CH$_3$OH (200 mL) in a pressure bottle at 0-5° C. until the solution was saturated. The bottle was sealed and stirred at 60° C. overnight. After cooling to 0-5° C., the reaction mixture was charged one more time with NH₃ gas, then the sealed bottle stirred at 60° C. for another 24 h. After cooling to rt, white precipitates were collected by filtration, and dried under vacuum to furnish the title compound (10.5 g) as a white solid.

4B. N-(7-Cyano-2,3-dihydrobenzofuran-4-yl)-acetamide

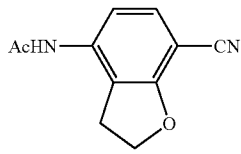

To a suspension of compound 4A (3.5 g, 16 mmol) in THF (64 mL) at 0° C. under Ar was added pyridine (6.5 mL, 80 mmol), followed by trifluoroacetic anhydride (5.6 mL, 40 mmol) dropwise. After addition, the reaction mixture was stirred at 0° C. for 5 min, then pored into H₂O (50 mL), extracted with EtOAc (3×100 mL). The combined EtOAc extracts were washed with brine, dried (Na₂SO₄), and concentrated under reduced pressure to give a crude product, which was purified by crystallization from MeOH-EtOAc-Hexane to furnish the title compound (2.3 g) as a white solid.

4C. (7R,7aS)-4-(7-Hydroxy-1,3-dioxotetrahydropyrrolo[1,2-c]imidazol-2-yl)-2,3-dihydrobenzofuran-7-carbonitrile The title compound as a white solid was prepared from compound 4B by procedures analogous to those described in Example 2 (from 2D to 2F). HPLC: 100% at 3.43 min (retention time) (Conditions: Zorbax SB C18 (4.6×75 mm); Eluted with 0% to 100% B, 8 min gradient (A=90% H₂O—10% MeOH—0.1% H₃PO₄ and B=10% H₂O—90% MeOH—0.1% H₃PO₄). Flow rate at 2.5 mL/min. UV detection at 220 nm.). Chiral HPLC: retention time=13.69 min (100%); Conditions: OD (4.6×250 mm); Eluted with 25% isopropanol in hexane for 30 min at 1 mL/min. MS (ES) m/z 300 [M+1]⁺.

EXAMPLE 5

(7R,7aS)-5-(7-Hydroxy-1,3-dioxotetrahydropyrrolo[1,2-c]imidazol-2-yl)-chroman-8-carbonitrile

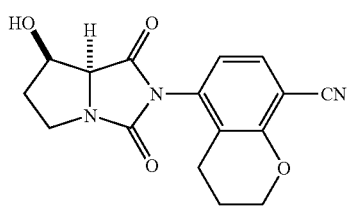

5A. 4-Acetylamino-2-hydroxy-3-(3-hydroxypropyl)-benzoic acid, methyl ester

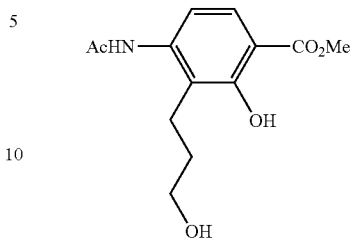

To a suspension of 4-acetylamino-3-allyl-2-hydroxy-benzoic acid methyl ester (2.49 g, 10 mmol, prepared as described in Takuji Kakigami et. al., Chem. Pharm. Bull, 46 (1), 42-52, (1998)) in THF (10 mL) at 0° C. under Argon was added a 0.5 M solution of 9-BBN in THF (80 mL, 40 mmol). The reaction mixture was stirred at 0° C. for 40 min, then at rt for 2 h. The reaction mixture was then cooled to 0° C., and 1 N aqueous NaOH (25 mL) was added dropwise over 5 min, followed by 30% aqueous H₂O₂ (20 mL) over 5 min. After addition, the reaction mixture was stirred at rt for 2 h, then extracted with EtOAc (3×60 mL). The combined EtOAc extracts were washed with brine, dried (Na₂SO₄), and concentrated under reduced pressure to give a crude product, which was chromatographed (silica gel) eluting with 30% to 80% EtOAc/hexane to afford the title compound (1.82 g) as a foam.

5B. 5-Acetylaminochroman-8-carboxylic acid, methyl ester

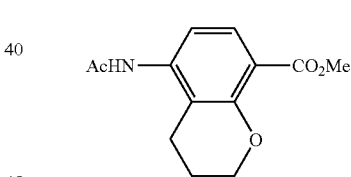

To a solution of compound 5A (1.80 g, 6.7 mmol) and Ph₃P (1.94 g, 7.4 mmol) in THF (30 mL) cooled at 0° C. was added dropwise DEAD (1.17 mL, 7.4 mmol). After addition, the reaction mixture was stirred at rt for 2 h, then concentrated under reduced pressure. The residue was chromatographed (silica gel) eluting with 50% to 100% EtOAc/hexane to furnish the title compound (1.3 g) as a white solid.

5C. (7R,7aS)-5-(7-Hydroxy-1,3-dioxotetrahydropyrrolo[1,2-c]imidazol-2-yl)chroman-8-carbonitrile The title compound was prepared from compound 5B and isolated as a white solid by procedures analogous to those described in Example 4. HPLC: 100% at 3.58 min (retention time) (Conditions: Zorbax SB C18 (4.6×75 mm); Eluted with 0% to 100% B, 8 min gradient. (A=90% H₂O—10% MeOH—0.1% H₃PO₄ and B=10% H₂O—90% MeOH—0.1% H₃PO₄). Flow rate at 2.5 mL/min. UV detection at 220 nm.). Chiral HPLC: retention time=12.35 min (99%); Con-

EXAMPLE 6

(7R,7aS)-5-(7-Hydroxy-1,3-dioxotetrahydropyrrolo[1,2-c]imidazol-2-yl)-2,2-dimethyl-2H-chromene-8-carbonitrile

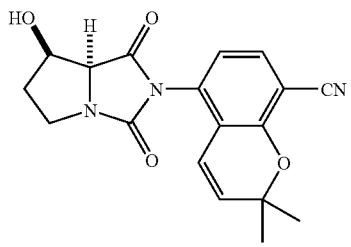

6A. 2-(1,1-Dimethylprop-2-ynyloxy)-4-nitrobenzonitrile

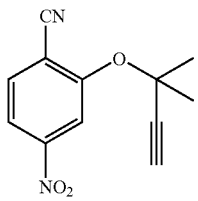

To a solution of commercially available 2-methyl-3-butyn-2-ol (0.28 mL, 2.9 mmol) in anhydrous CH₃CN (1.5 mL) cooled to −5° C. was added DBU (0.56 mL, 3.7 mmol) followed by addition of trifluoroacetic anhydride (0.41 mL, 2.9 mmol) over 25 min while maintaining the reaction temperature below 2° C. After the addition, the reaction mixture was stirred at 0° C. for 30 min before using in the following reaction.

To a solution of 2-hydroxy-4-nitro-benzonitrile (413.6 mg, 2.52 mmol, prepared as described in Yasubiro Imakura et al, *Chem. Pharm. Bull,* 40 (7), 1691-1696, (1992)) in CH₃CN (1.5 mL) cooled to −5° C. was added DBU (0.48 mL, 3.2 mmol) and CuCl₂.2H₂O (2 mg), followed by addition of a solution of trifluoroacetate prepared above over 30 min while maintaining the reaction temperature below 0° C. After addition, the reaction mixture was stirred at 0° C. for 2 h, then concentrated under reduced pressure. The residue was partitioned between EtOAc (100 mL) and water (30 mL), and the separated organic layer washed with 1 N aqueous HCl (2×20 mL), 1 N aqueous NaOH (20 mL), 1 N aqueous NaHCO₃, brine, then dried (Na₂SO₄), and concentrated under reduced pressure. The crude product was chromatographed (silica gel) eluting with 0% to 50% EtOAc/hexane to furnish the title compound (280 mg, 48%).

6B. 2,2-Dimethyl-5-nitro-2H-chromene-8-carbonitrile

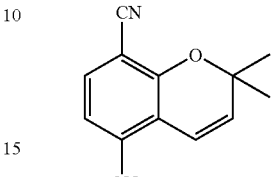

A solution of compound 6A (270 mg, 1.17 mmol) in N,N-diethylaniline (1 mL) was heated to 185° C. for 3 h. After cooling to rt, the reaction mixture was chromatographed (silica gel) eluting with 0-50% EtOAc/hexane to afford the title compound (230 mg).

6C. 5-Amino-2,2-dimethyl-2H-chromene-8-carbonitrile

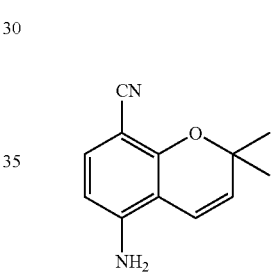

To a stirred solution of compound 6B (230 mg, 1 mmol) in EtOAc (5 mL) was added SnCl₂ 2H₂O (780 mg, 3.5 mmol). The resulting mixture was stirred at rt for 20 h, then saturated aqueous K₂CO₃ was added. After stirring for 30 min, the reaction was treated with solid K₂CO₃ (550 mg). The resulting suspension was stirred at rt for another 2 h, and then filtered. The filtrate was concentrated under reduced pressure to give a crude product, which was chromatographed (silica gel) eluting with 20% to 60% EtOAc/hexane to afford the title compound (160 mg) as a light yellow oil.

6D. (7R,7aS)-5-(7-Hydroxy-1,3-dioxotetrahydropyrrolo[1,2-c]imidazol-2-yl)-2,2-dimethyl-2H-chromene-carbonitrile The title compound was prepared from compound 6C by procedures analogous to those described in Example 2 (2E to 2F). HPLC: 100% at 4.48 min (retention time) (Conditions: Zorbax SB C18 (4.6×75 mm); Eluted with 0% to 100% B, 8 min gradient. (A=90% H₂O—10% MeOH—0.1% H₃PO₄ and B=10% H₂O—90% MeOH—0.1% H₃PO₄). Flow rate at 2.5 mL/min. UV detection at 220 nm). Chiral HPLC: retention time=9.37 min (99%); Conditions: OD (4.6×250 mm); Eluted with 25% isopropanol in hexane for 30 min at 1 mL/min. MS (ES) m/z 340 [M+1]⁺.

EXAMPLE 7

(7R,7aS)-5-(7-Hydroxy-1,3-dioxotetrahydropyrrolo[1,2-c]imidazol-2-yl)-2,2-dimethylchroman-8-carbonitrile

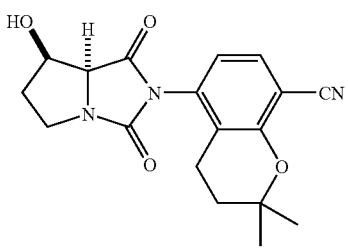

A suspension of compound 6D (50 mg, 0.15 mmol) and 5% Pd/C (10 mg) in EtOH (3 mL) was stirred at rt under an atmosphere of hydrogen for 2 h. The reaction mixture was then filtered, and the filtrate concentrated under reduced pressure to give a crude product, which was purified by crystallization from hot $CH_2Cl_2$-hexane to give the title compound (36 mg) as a white solid. HPLC: 99% at 4.52 min (retention time) (Conditions: Zorbax SB C18 (4.6×75 mm); Eluted with 0% to 100% B, 8 min gradient. (A=90% $H_2O$—10% MeOH—0.1% $H_3PO_4$ and B=10% $H_2O$—90% MeOH—0.1% $H_3PO_4$). Flow rate at 2.5 mL/min. UV detection at 220 nm.). Chiral HPLC: retention time=8.72 min (99%); Conditions: OD (4.6×250 mm); Eluted with 25% isopropanol in hexane for 30 min at 1 mL/min. MS (ES) m/z 342 $[M+1]^+$.

EXAMPLE 8

(7R,7aS)-8-(7-Hydroxy-1,3-dioxotetrahydropyrrolo[1,2-c]imidazol-2-yl)-2,3-dihydrobenzo[1,4]dioxane-5-carbonitrile

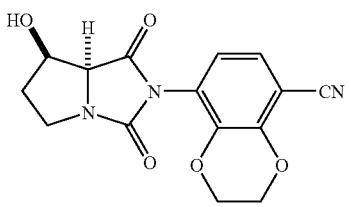

8A. 3-Nitrocatechol

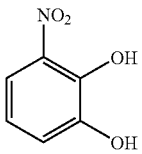

To a solution of catechol (5 g, 45 mmol) in $Et_2O$ (187 mL) cooled to 0° C. was added dropwise fuming $HNO_3$ (2 mL). After addition, the reaction was allowed to stand at rt overnight, and the $Et_2O$ was removed by evaporation under reduced pressure. The residue was triturated with pentane (3×), and the combined organics were dried ($Na_2SO_4$), filtered, and concentrated under reduced pressure. The residue was chromatographed (silica gel) eluting with 10%-20% EtOAc/hexane to give the title compound (2.94 g).

8B. 5-Nitrobenzo[1,4]dioxane

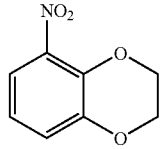

To a solution of compound 8A (3.0 g, 19.4 mmol) in DMF (40 mL) was added CsF (14.7 g, 96.8 mmol), followed by dibromoethane (1.84 mL, 21.3 mmol). The mixture was heated to 110° C. for 1.5 h, then cooled to rt, partitioned between water and $Et_2O$. The separated $Et_2O$ layer was washed with water, saturated aqueous $NaHCO_3$, brine, dried ($Na_2SO_4$), filtered and concentrated under reduced pressure. The residue was chromatographed (silica gel) eluting with 5% MeOH in $CH_2Cl_2$ to afford the title compound (0.73 g).

8C. N-(Benzo[1,4]dioxan-5-yl)-acetamide

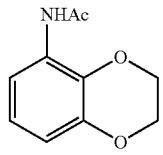

Compound 8C was prepared from 8B by procedures analogous to those described in Experiment 3A and 2A.

8D. N-(8-Bromobenzo[1,4]dioxan-5-yl)-acetamide

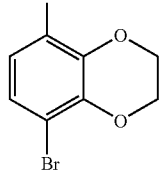

To a solution of compound 8C (0.80 g, 4.15 mmol) in chloroform (2.4 mL) cooled to −20° C. was slowly added a solution of bromine (0.22 mL, 4.35 mmol) in chloroform (1 mL) so that the reaction temperature was maintained below −10° C. The reaction was stirred at 0° C. for 5 min, and then quenched immediately with water. The mixture was extracted with $CH_2Cl_2$ (3×), the combined extracts washed with saturated $NaHCO_3$, brine, dried ($Na_2SO_4$), filtered and concentrated under reduced pressure. The residue was chromatographed (silica gel) eluting with $CH_2Cl_2$ to afford the title compound (0.98 g).

8E. (7R,7aS)-8-(7-Hydroxy-1,3-dioxotetrahydropyrrolo[1,2-c]imidazol-2-yl)benzo[1,4]dioxane-5-carbonitrile The title compound (32 mg) was prepared from compound 8D and isolated as a white solid by procedures analogous to those described in Example 2 (2C to 2F). mp196-197° C.; HPLC: 99% at 12.31 min (retention time) (CHIRALPAK® OD column 4.6×250 mm; 25% isopropanol in hexane over 30 min, 1 mL/min, UV detection at 220 nm); MS (ES) m/z 322 $[M+1]^+$.

EXAMPLE 9

(7R,7aS)-7-(7-Hydroxy-1,3-dioxotetrahydropyrrolo[1,2-c]imidazol-2-yl)-3-methyl-3H-benzimidazole-4-carbonitrile

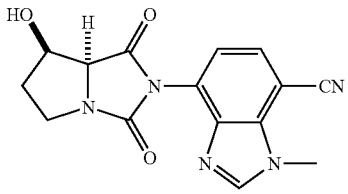

9A. 1-Methyl-1H-benzimidazol-4-ylamine

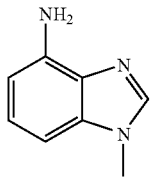

A suspension of 1-methyl-4-nitro-1H-benzimidazole [2.1 g, 12 mmol, prepared as described in Viktor Milata et. al., *Org. Prep. Proced. Int.* 25 (6), 703-704 (1993)] and 5% Pd/C (0.21 g) in EtOH (40 mL) was vigorously stirred under an atmoshphere of hydrogen at rt overnight. The reaction mixture was filtered and the filtrate concentrated under reduced pressure to afford the tiltle compound (1.65 g).

9B. 7-Amino-3-methyl-3H-benzimidazole-4-carbonitrile

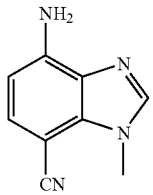

The title compound was prepared from compound 9A by procedures analogous to those described in Experiment 2 (2A to 2D).

9C. 7-Isocyanato-3-methyl-3H-benzimidazole-4-carbonitrile

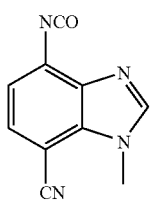

To a suspension of compound 9B (240 mg, 1.39 mmol) in CH$_2$Cl$_2$ (10 mL) under Argon was added Et$_3$N (0.97 mL, 6.95 mmol). The resulting suspension was stirred at 0° C. for 15 min, then a solution of phosgene (20%) in toluene (1.4 mL, 2.8 mmol) was added. After the addition, the mixture was stirred at rt for 2 h, then concentrated under reduced pressure. The resulting solid residue was dried under vacuum for 1 h to afford the title compound, which was used immediately in the preparation of compound 9D.

9D. (3R,2aS)-1-(7-Cyano-1-methyl-1H-benzimidazol-4-yl-carbamoyl)-3-hydroxypyrrolidine-2-carboxylic acid methyl ester

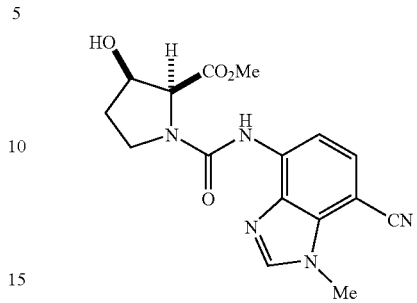

To a suspension of 1E (600 mg, 1.67 mmol) in CH$_2$Cl$_2$ (4 mL) at 0° C. was added i-Pr$_2$NEt (0.35 mL, 2.0 mmol). After 5 min, a suspension of compound 9C (1.37 mmol) in CH$_2$Cl$_2$ (3 mL) was added, followed by 4 Å molecular sieves (~1.0 g). The resulting mixture was stirred at rt for 3 h, and then concentrated under reduced pressure. The crude product was chromatographed (silica gel) eluting with 4-6% MeOH in CH$_2$Cl$_2$ to afford the title compound (250 mg) as a light yellow solid.

9E. (7R,7aS)-7-(7-Hydroxy-1,3-dioxotetrahydropyrrolo[1,2-c]imidazol-2-yl)-3-methyl-3H-benzoimidazole-4-carbonitrile To a suspension of compound 9D (51.5 mg, 0.15 mmol) in 1,2-dichloroethane (1 mL) at rt was added DBU (34 µL, 0.23 mmol), along with 4 Å molecular sieves (~0.2 g). The resulting mixture was stirred at rt for 20 h, then concentrated under reduced pressure. The crude product was chromatographed (silica gel) eluting with 4-6% MeOH in CH$_2$Cl$_2$ to give the title compound (25 mg) as a white solid. HPLC: 98% at 2.52 min (retention time) (Conditions: Zorbax SB C18 (4.6×75 mm); Eluted with 0% to 100% B, 8 min gradient. (A=90% H$_2$O—10% MeOH—0.1% H$_3$PO$_4$ and B=10% H$_2$O—90% MeOH—0.1% H$_3$PO$_4$); Flow rate at 2.5 mL/min. UV detection at 220 nm.). Chiral HPLC: retention time=62.5 min (98%); Conditions: OD (4.6×250 mm); Eluted with 45% isopropanol in hexane for 90 min at 1 mL/min. MS (ES) m/z 312 [M+1]$^+$.

EXAMPLE 10

4-(7-Hydroxy-1,3-dioxotetrahydro-pyrrolo[1,2-c]imidazol-2-yl)-2-methylbenzofuran-7-carbonitrile

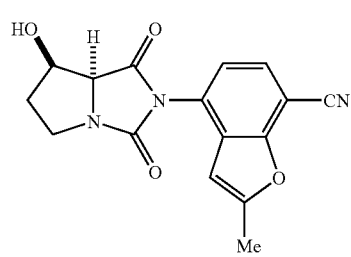

10A. 2-Allyloxy-4-nitrobenzonitrile

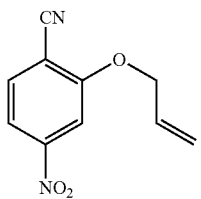

To a solution of 2-hydroxy-4-nitro-benzonitrile [164 mg, 1.0 mmol, prepared as described in Yasubiro Imakura et. al. *Chem. Pharm. Bull.* 40 (7), 1691-1696 (1992)] in anhydrous DMF (2 mL) was added allyl bromide (0.11 mL, 1.3 mmol), followed by $K_2CO_3$ (166 mg, 1.2 mmol). The resulting suspension was heated to 50° C. under Argon for 4 h. After cooling to rt, the reaction mixture was poured into ice/water, and extracted with EtOAc (3×). The combined EtOAc extracts were washed with brine, dried ($Na_2SO_4$), and concentrated under reduced pressure. The crude product was chromatographed (silica gel) eluting with 30% to 60% EtOAc/hexane to furnish the title compound (160 mg, 80% yield) as a light yellow solid.

10B. 2-Allyloxy-4-aminobenzonitrile

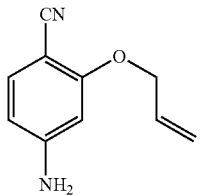

The title compound (1.70 g) as a light yellow solid was prepared from compound 10A (2.04 g, 10 mmol) by procedures analogous to those described in Experiment 6C.

10C. N-(3-Allyloxy-4-cyanophenyl)-2,2-dimethylpropionamide

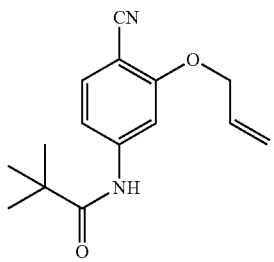

To a solution of 10B (1.9 g, 10.9 mmol) in anhydrous $CH_2Cl_2$ (16 mL) cooled at 0° C. was added 1 N aqueous NaOH solution (16.4 mL, 16.4 mmol), followed by pivaloyl chloride (1.9 mL, 15.3 mmol). After the addition, the reaction mixture was stirred at 0° C. for 2 h, then concentrated under reduced pressure to remove most of the $CH_2Cl_2$ solvent. The remaining residue was diluted with water, and the resulting precipitate collected by filtration, washed with water, hexane, and dried under vacuum to furnish the title compound as a light brown solid (2.6 g).

10D. N-(2-Allyl-4-cyano-3-hydroxyphenyl)-2,2-dimethyl-propionamide

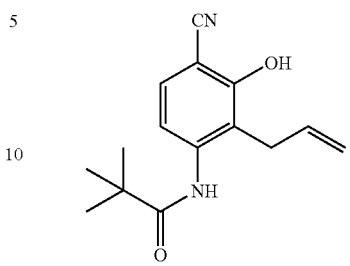

A solution of compound 10C (1.5 g, 5.8 mmol) in NMP (7 mL) was heated to 220° C. for 3 h. After cooling to rt, the reaction mixture was poured into ice/water, and extracted with EtOAc (3×). The combined EtOAc extracts were washed with brine, dried ($Na_2SO_4$), and concentrated under reduced pressure. The crude product was chromatographed (silica gel) eluting with 0% to 50% EtOAc/hexane to furnish the title compound (0.7 g).

10E. N-(7-Cyano-2-methyl-benzofuran-4-yl)-2,2-dimethyl-propionamide

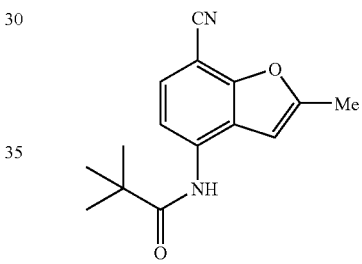

To a solution of compound 10D (0.5 g, 1.94 mmol) in a mixed solvent of DMF (2.5 mL) and water (1.9 mL) was added $Cu(OAc)_2$ (1.057 g, 5.82 mmol), followed by a 10 M aqueous solution of LiCl (0.58 mL, 5.8 mmol) and $PdCl_2$ (34.3 mg, 0.194 mmol). The resulting suspension was heated to 100° C. for 1 h. After cooling to rt, the reaction mixture was poured into ice/water, and extracted with EtOAc (3×). The combined EtOAc extracts were washed with brine, dried ($Na_2SO_4$), and concentrated under reduced pressure. The crude product was chromatographed (silica gel) eluting with 10% to 50% EtOAc/hexane to furnish the title compound (0.3 g) as a white foam.

10F. (7R,7aS)-4-(7-Hydroxy-1,3-dioxotetrahydropyrrolo[1,2-c]imidazol-2-yl)-2-methylbenzofuran-7-carbonitrile The title compound was prepared from compound 10E by procedures analogous to those described in Experiment 2 (2D to 2F). HPLC: 99% at 4.2 min (retention time) (Conditions: Zorbax SB C18 (4.6×75 mm); Eluted with 0% to 100% B, 8 min gradient. (A=90% $H_2O$—10% MeOH—0.1% $H_3PO_4$ and B=10% $H_2O$—90% MeOH—0.1% $H_3PO_4$); Flow rate at 2.5 mL/min. UV detection at 220 nm). Chiral HPLC: retention time=10.99 min (99%); Conditions: OD (4.6×250 mm); Eluted with 25% isopropanol in hexane for 30 min at 1 mL/min. MS (ES) m/z 312 $[M+1]^+$.

EXAMPLE 11

(7R,7aS)-4-(7-Hydroxy-1,3-dioxotetrahydropyrrolo[1,2-c]imidazol-2-yl)-2-methylbenzoxazole-7-carbonitrile

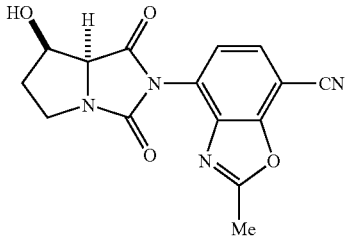

11A. 3-Amino-2-hydroxy-4-nitro-benzonitrile

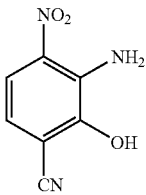

To a solution of 2-hydroxy-4-nitro-benzonitrile [1.0 g, 6.1 mmol, prepared as described in Yasubiro Imakura et. al. Chem. Pharm. Bull. 40 (7), 1691-1696 (1992)] in DMSO (60 mL) was added trimethylhydrazinium iodide (1.23 g, 6.09 mmol), followed by sodium tert-pentoxide (2.01 g, 6.09 mmol). The mixture was stirred at rt overnight, and then partitioned between 10% HCl and ether. The separated ether layer was washed with $H_2O$, brine, dried ($Na_2SO_4$), and concentrated under reduced pressure to furnish the title compound (0.78 g) as a brown solid.

11B. 2-Methyl-4-nitro-benzoxazole-7-carbonitrile

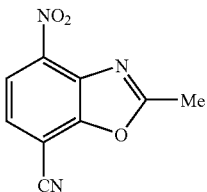

To a solution of 11A (0.2 g, 1.12 mmol) in xylene (6 mL) was added triethyl orthoacetate (0.62 mL, 3.35 mmol) and pyridinium p-toluenesulfonate (0.04 g, 1.12 mmol). The mixture was refluxed for 3 h, then allowed to cool to rt and partitioned between $H_2O$ and EtOAc. The separated EtOAc layer was concentrated under reduced pressure and the residue was chromatographed eluting with 20% EtOAc in hexane to afford compound 11B (0.16 g) as a solid.

11C. 4-Amino-2-methylbenzoxazole-7-carbonitrile

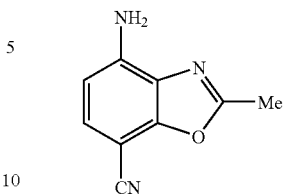

To a solution of 11B (0.16 g, 0.79 mmol) in EtOAc (2 mL) was added iron powder (0.1 g), followed by 10% aqueous AcOH (2 mL). The mixture was stirred at 60° C. for 2 h, then allowed to cool to rt and partitioned between saturated $NaHCO_3$ and EtOAc. The separated EtOAc layer was concentrated under reduced pressure to give the title compound (0.14 g) as a solid.

11D. (7R,7aS)-4-(7-Hydroxy-1,3-dioxotetrahydro-pyrrolo[1,2-c]imidazol-2-yl)-2-methylbenzoxazole-7-carbonitrile The title compound was prepared from 11C by procedures analogous to those described in Example 2 (2E to 2F) to give the product as a white foam. HPLC: 99% pure at 10.55 min (retention time) (CHIRALPAK® OD column 4.6×250 mm; 25% isopropanol in hexane over 30 min, 1 mL/min, monitoring at 220 nm); MS (ES) m/z 313 $[M+1]^+$.

EXAMPLE 12

(7R,7aS)-5-(7-Hydroxy-1,3-dioxotetrahydropyrrolo[1,2-c]imidazol-2-yl)quinoline-8-carbonitrile

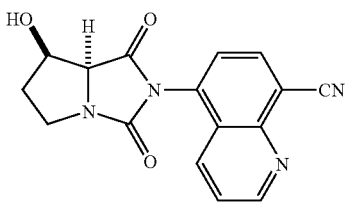

12A. 8-Methyl-5-nitroquinoline

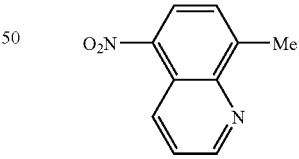

To a solution of commercially available 8-methylquinoline (5.0 g, 34 mmol) in concentrated $H_2SO_4$ (19 mL) at 0° C. was added portionwise $KNO_3$ (4.29 g, 42.4 mmol). After the addition, the reaction was stirred at rt for 17 h, then poured into ice/water and extracted with EtOAc (3×100 mL). The aqueous layer was basified to pH=9 with solid $Na_2CO_3$ and extracted with EtOAc (2×100 mL). The combined extracts were washed with brine, dried ($Na_2SO_4$), filtered and concentrated under reduced pressure. The residue was chromatographed (silica gel) to yield the title compound (5.98 g, 94%) as a light yellow solid. LC/MS m/z 189 $[M+H]^+$.

12B. 5-Nitroquinoline-8-carboxylic acid

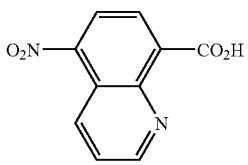

Compound 12A (1.0 g, 5.3 mmol) was dissolved in concentrated $H_2SO_4$ (7 mL), cooled to 0° C., and then $CrO_3$ (2.12 g, 21.3 mmol) was added portionwise over 30 min. After the addition, the reaction mixture was warmed to rt and then heated to 80° C. for 1 h. After cooling to rt, the reaction was diluted with water, basified with 15% aqueous NaOH, then reacidified to pH=3 with AcOH, and extracted with EtOAc (4×100 mL). The combined EtOAc extracts were washed with brine, dried ($Na_2SO_4$), filtered and concentrated under reduced pressure to yield the title compound (760 mg, 66%) as a yellow solid. LC/MS m/z 219 $[M+H]^+$.

12C. 5-Nitroquinoline-8-carbonitrile

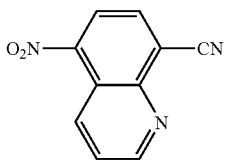

To a suspension of compound 12B (600 mg, 2.75 mmol) in anhydrous THF (25 mL) cooled to −15° C. was added $Et_3N$ (0.46 mL, 3.3 mmol), followed by a dropwise addition of ethyl chloroformate (0.33 mL, 3.44 mmol). The reaction mixture was stirred at −15° C. for 30 min, then $NH_3$ gas was bubbled into the reaction for 5 min followed by warming of the reaction to rt for 1h. The solvent was evaporated to give 850 mg (>100%) of the amide as a yellow solid which was carried on to the next step without further purification. The amide (850 mg) was dissolved in pyridine (25 mL), and imidazole (377 mg, 5.49 mmol) was added. The mixture was cooled to −30° C. under nitrogen, $POCl_3$ (1.01 mL, 10.7 mmol) was added and the reaction was warmed to 0° C. for 30 min, and then evaporated to dryness. The residue was chromatographed (silica gel) eluting with $CH_2Cl_2$ to afford the title compound (416 mg, 76%, 2 steps). LC/MS m/z 200 $[M+H]^+$.

12D. (7R,7aS)-5-(7-Hydroxy-1,3-dioxotetrahydropyrrolo[1,2-c]imidazol-2-yl)-quinoline-8-carbonitrile The title compound was synthesized from compound 12C by procedures analogous to those described in Experiment 3A and Experiment 2 (2E to 2F). 99.8% at 2.05 min (retention time) (Conditions: YMC S5 ODS (4.6×50 mm); Eluted with 0% to 100% B; 4 min gradient; (A=90% $H_2O$—10% MeOH—0.1% $H_3PO_4$ and B=10% $H_2O$—90% MeOH—0.1% $H_3PO_4$); Flow rate at 4 mL/min. UV detection at 220 nm). LC/MS m/z 309 $[M+H]^+$.

EXAMPLE 13

(7R,7aS)-4-(7-Hydroxy-1,3-dioxotetrahydropyrrolo[1,2-c]imidazol-2-yl)isoquinoline-1-carbonitrile

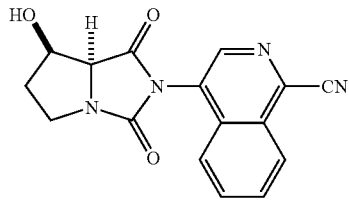

13A. 4-Bromoisoquinoline 2-oxide

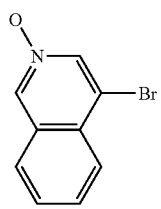

A solution of 4-bromoisoquinoline (4.16 g, 18.6 mmol) in chloroform (100 mL) was added dropwise over 1 h to a solution of 70% mCPBA (12.4 g, 50.3 mmol) in chloroform (100 mL) at rt. After stirring 18 h, the reaction mixture was washed with 1 N NaOH (2×150 mL), dried ($MgSO_4$) and concentrated under reduced pressure to afford compound 13A (4.23 g, 94%) as an off-white solid. $^1$H NMR(400 MHz, $CDCl_3$) ☐ 8.71 (s, 1H), 8.43 (s, 1H), 8.09 (d, 1H, J=8 Hz), 7.70 (m, 3H).

13B. 4-Bromoisoquinoline-1-carbonitrile

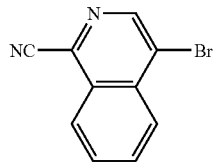

DBU (1.67 mL, 11.2 mmol) was added to a mixture of compound 13A (1.12 g, 5.00 mmol) and cyanotrimethylsilane (0.75 mL, 5.5 mmol) in THF (35 mL). The resulting homogeneous mixture was refluxed for 20 min. After concentrating under reduced pressure, the residue was purified by flash chromatography on a 5×15 cm silica gel column, eluting with 3:1 hexane:EtOAc to give compound 13B (0.95 g, 82%) as a white powder. $^1$H NMR (400 MHz, $CDCl_3$) ☐ 8.85 (s, 1H), 8.36 (d, 1H, J=8.5 Hz), 8.28 (d, 1H, J=8.5 Hz), 7.96 (t, 1H, J=8.5 Hz), 7.89 (t, 1H, J=8.5 Hz).

13C. 4-(2,4-Dimethoxybenzylamino)isoquinoline-1-carbonitrile

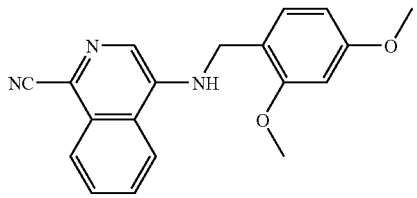

A mixture of compound 13B (699 mg, 3.00 mmol) and 2,4-dimethoxybenzylamine (4.8 mL, 30 mmol) in acetonitrile (15 mL) was refluxed for 16 h. After concentration under reduced pressure, the residue was purified on a 5×15 cm silica gel column, eluting with 3:2 hexane:EtOAc to afford compound 13C (290 mg, 30%) as a light yellow solid. HPLC: 1.76 min (retention time) (Phenomenex C-18, 5 micron column, 4.6×30 mm, eluting with 10-90% aqueous MeOH over 2 min containing 0.1% TFA, 4 mL/min, monitoring at 254 nm).

13D. 4-Aminoisoquinoline-1-carbonitrile

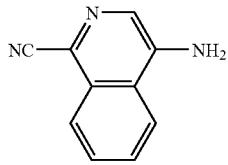

Compound 13C (50 mg, 0.16 mmol) was treated with TFA (0.5 mL) for 1 h. The highly colored mixture was partitioned between EtOAc (30 mL) and 1 N NaOH (30 mL). After washing with brine (15 mL), the organic layer was dried (MgSO$_4$) and concentrated under reduced pressure to afford compound 13D (24 mg, 92%) as a yellow solid. HPLC: 99% at 1.09 min (retention time) (Phenomenex C-18, 5 micron column, 4.6×30 mm, eluting with 10-90% aqueous MeOH over 2 min containing 0.1% TFA, 4 mL/min, monitoring at 254 nm). MS (ES+) m/z 170 [M+H]$^+$.

13E. (7R,7aS)-4-(7-Hydroxy-1,3-dioxotetrahydropyrrolo[1,2-c]imidazol-2-yl)isoquinoline-1-carbonitrile The title compound was synthesized from compound 13D by procedures analogous to those described in Experiment 2E to 2F. HPLC: 97.6% at 1.54 min (retention time) (Conditions: YMC S5 C-18 (4.6×50 mm); Eluted with 0% to 100% B; 4 min gradient; (A=90% H$_2$O—10% MeCN—0.1% TFA and B=10% H$_2$O—90% MeCN—0.1% TFA); Flow rate at 4 mL/min. UV detection at 220 nm). LC/MS m/z 309 [M+H]$^+$.

EXAMPLE 14

(7R,7aS)-3-Chloro-4-(7-hydroxy-1,3-dioxotetrahydropyrrolo[1,2-c]imidazol-2-yl)-2-methoxybenzonitrile

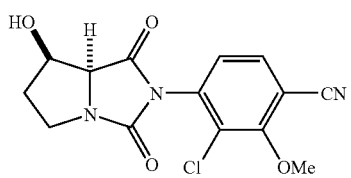

14A. 3-Amino-2-methoxy-4-nitrobenzonitrile

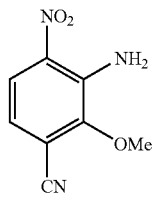

To a stirring suspension of 11A (0.34 g, 1.86 mmol) and K$_2$CO$_3$ (0.283 g, 2.05 mmol) in DMF (3 mL) was added iodomethane (0.127 mL, 2.05 mmol). After the addition, the reaction mixture was stirred at rt for 16 h, then partitioned between H$_2$O and CH$_2$Cl$_2$. The separated CH$_2$Cl$_2$ layer was washed with water, brine, dried (Na$_2$SO$_4$), filtered and concentrated under reduced pressure. The residue was chromatographed (silica gel) eluting with 5% to 40% EtOAc/hexane to yield the title compound (0.22 g) as a solid.

14B. 3-Chloro-2-methoxy-4-nitrobenzonitrile

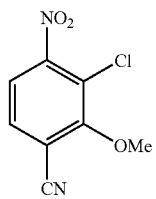

To a suspension of CuCl$_2$ (0.11 g, 0.78 mmol) in CH$_3$CN (2 mL) at rt was added tert-butyl nitrite (0.1 mL, 0.84 mmol). After addition, the mixture was heated to 65° C. while a solution of 14A (0.125 g, 0.647 mmol) in CH$_3$CN (3 mL) was slowly added. After stirring at 65° C. for 1 h, the mixture was allowed to cool to rt, and then partitioned between H$_2$O and CH$_2$Cl$_2$. The CH$_2$Cl$_2$ layer was washed with water, brine, dried (Na$_2$SO$_4$), filtered and concentrated under reduced pressure. The residue was chromatographed (silica gel) eluting with 5% to 60% EtOAc/hexane to yield the title compound (0.085 g).

14C. 4-Amino-3-chloro-2-methoxybenzonitrile

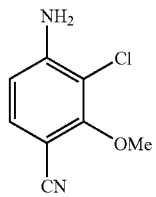

The title compound was prepared from compound 14B in a manner similar to that described in Experiment 11C.

14D. (7R,7aS)-3-Chloro-4-(7-hydroxy-1,3-dioxotetrahydropyrrolo[1,2-c]imidazol-2-yl)-2-methoxybenzonitrile The title compound was prepared from 14C by procedures analogous to those described in Example 2E to 2F. HPLC: 99% pure at 13.64 min (retention time) (CHIRALPAK® OD column 4.6×250 mm; 25% isopropanol in hexane over 30 min, 1 mL/min, monitoring at 220 nm); MS (ES) m/z 316 [M+1]$^+$.

EXAMPLE 15

(7R,7aS)-5-(7-Hydroxy-1,3-dioxotetrahydropyrrolo[1,2-c]imidazol-2-yl)-2-methoxy-3-methylbenzonitrile

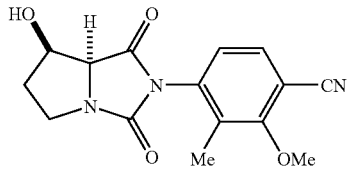

The title compound was prepared from commercially available 2-methyl-3-nitroanisole by procedures analogous to those described in Example 3A and Example 2. HPLC: 100% at 3.63 min (retention time) (Conditions: Zorbax SB C18 (4.6×75 mm); Eluted with 0% to 100% B, 8 min gradient. (A=90% $H_2O$—10% MeOH—0.1% $H_3PO_4$ and B=10% $H_2O$—90% MeOH—0.1% $H_3PO_4$); Flow rate at 2.5 mL/min. UV detection at 220 nm). Chiral HPLC: retention time=9.76 min (99%); Conditions: OD (4.6×250 mm); Eluted with 25% isopropanol in hexane for 30 min at 1 mL/min. MS (ES) m/z 302 [M+1]$^+$.

EXAMPLE 16

(7R,7aS)-2-Hydroxy-4-(7-Hydroxy-1,3-dioxotetrahydropyrrolo[1,2-c]imidazol-2-yl)-3-methylbenzonitrile

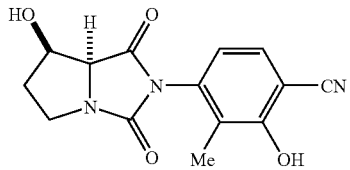

To compound 14 (90 mg, 0.3 mmol) in a 5-mL round bottom flask at 0° C. was added a 1.0 M solution of $BBr_3$ in $CH_2Cl_2$ (1 mL, 1 mmol). The reaction mixture was stirred at 0° C. for 30 min, then at rt for additional 30 min. After cooling at 0° C., MeOH (3 mL) was added, the reaction was stirred at 0° C. for 30 min, and then concentrated under reduced pressure to obtain a crude product, which was chromatographed (silica gel) eluting with 0% to 5% MeOH in $CH_2Cl_2$ to yield the title compound (12 mg). HPLC: 98% at 2.83 min (retention time) (Conditions: Zorbax SB C18 (4.6×75 mm); Eluted with 0% to 100% B, 8 min gradient. (A=90% $H_2O$—10% MeOH—0.1% $H_3PO_4$ and B=10% $H_2O$—90% MeOH—0.1% $H_3PO_4$); Flow rate at 2.5 mL/min. UV detection at 220 nm). Chiral HPLC: retention time=16.13 min (99%); Conditions: OD (4.6×250 mm); Eluted with 25% isopropanol in hexane for 30 min at 1 mL/min. MS (ES) m/z 288 [M+1]$^+$.

EXAMPLE 17

(7R,7aS)-4-(7-Hydroxy-1,3-dioxotetrahydropyrrolo[1,2-c]imidazol-2-yl)-3-methoxy-2-(trifluoromethyl)benzonitrile

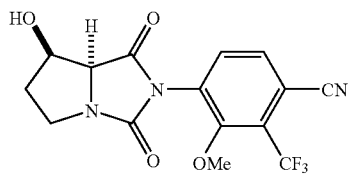

17A. 2-Nitro-6-(trifluoromethyl)phenol

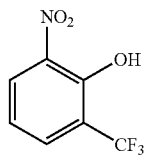

To a solution of commercially available 2-trifluoromethylphenol (2.5 g, 15.42 mmol) in AcOH (3 mL) cooled to 0° C. was added dropwise concentrated $HNO_3$ (1.5 mL). After the addition, the mixture was stirred at at 0° C. for 5 min, at rt for 10 min, then poured into ice/water, and extracted with ether (3×). The combined ether extracts were washed with water, brine, dried ($Na_2SO_4$) and concentrated under reduced pressure. The residue was chromatographed (silica gel) eluting with 0% to 10% EtOAc/hexane to yield the title compound (1.4 g, 44% yield).

17B. 2-Nitro-6-(trifluoromethyl)anisole

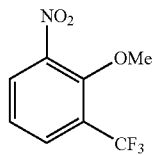

To a suspension of compound 17A (1.4 g, 6.76 mmol) and $K_2CO_3$ (1.4 g, 10 mmol) in DMF (60 mL) was added iodomethane (0.46 mL, 7.44 mmol). After the addition, the mixture was stirred at 40° C. overnight, then cooled to rt, partitioned between ether and water. The separated ether layer was washed with water and brine, then dried ($Na_2SO_4$) and concentrated under reduced pressure. The residue was chromatographed (silica gel) eluting with 10% EtOAc/hexane to yield the title compound (1.38 g, 92% yield).

17C. 2-Methoxy-3-(trifluoromethyl)aniline

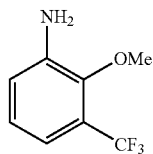

The title compound (980 mg) was prepared from compound 17B in a manner similar to that described in Experiment 11C.

17D. 4-Bromo-2-methoxy-3-(trifluoromethyl)aniline

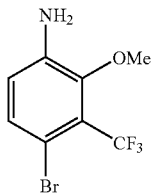

To a solution of compound 17C (200 mg, 1.05 mmol) in CH$_2$Cl$_2$ (2 mL) cooled to −20° C. was added dropwise a solution of 2,4,4,6-tetrabromo-2,5-cyclohexadienone (429 mg, 1.05 mmol) in CH$_2$Cl$_2$ (2 mL). After the addition, the reaction was stirred at rt overnight, then additional amount of 2,4,4,6-tetrabromo-2,5-cyclohexadienone (429 mg, 1.05 mmol) was added. The reaction was continued for 2 more days, then concentrated under reduced pressure. The residue was chromatographed (silica gel) eluting with 10%-20% EtOAc/hexane to yield the title compound (47mg, 16% yield).

17E. N-(4-Bromo-2-methoxy-3-(trifluoromethylphenyl)acetamide

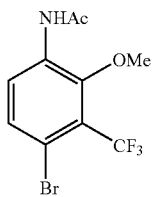

The title compound (237 mg) was prepared from compound 17D in a manner similar to that described in Experiment 2A.

17F. (7R,7aS)-4-(7-Hydroxy-1,3-dioxotetrahydropyrrolo[1,2-c]imidazol-2-yl)-3-methoxy-2-trifluoromethylbenzonitrile The title compound (55 mg) was prepared from 17E by procedures analogous to those described in Example 2 (2C to 2F). HPLC: 99% at 2.25 min (retention time) (Conditions: Phenom. Lura C18 (4.6×50 mm); Eluted with 0% to 100% B, 4 min gradient (A=90% H$_2$O—10% MeOH—0.1% TFA and B=10% H$_2$O—90% MeOH—0.1% TFA); Flow rate at 4.0 mL/min. UV detection at 220 nm.). Chiral HPLC: 99% pure at 8.98 min (retention time) (CHIRALPAK® OD column 4.6×250 mm; 30% isopropanol in hexane over 30 min, 1 mL/min, monitoring at 220 nm); MS (ES) m/z 356 [M+1]$^+$.

EXAMPLE 18

(7R,7aS)-4-(7-Hydroxy-1,3-dioxotetrahydropyrrolo[1,2-c]imidazol-2-yl)-3-methyl-2-trifluoromethylbenzonitrile

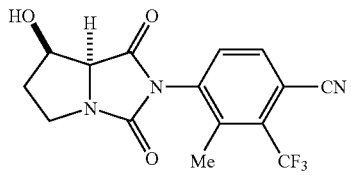

18A. N-(4-Chloro-3-trifluoromethylphenyl)-2,2-dimethylpropionamide

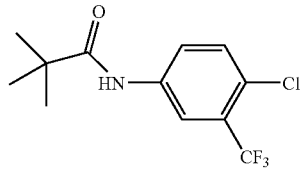

To a solution of commercially available 4-chloro-3-(trifluoromethyl)aniline (15.0 g, 76.7 mmol) in anhydrous THF (200 mL) cooled to 0-5° C. was added triethylamine (11.7 mL, 84.4 mmol) followed by pivaloyl chloride (10.4 mL, 84.4 mmol) over 30 min. The ice bath was removed and the mixture stirred at rt for 1 h. The mixture was diluted with ether and filtered. The filtrate was washed with water (2×) and brine, dried (MgSO$_4$), filtered and concentrated. The residue was triturated with hexanes and the solid was filtered and dried under vacuum to afford compound 18A (20.4 g, 95%); MS (ES) m/z 280 [M+1]$^+$.

18B. N-(4-Chloro-2-methyl-3-trifluoromethylphenyl)-2,2-dimethyl-propionamide

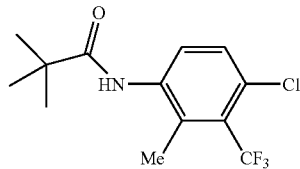

To a solution of compound 18A (2.29 g, 8.19 mmol) in anhydrous THF (25 mL) cooled to 0-5° C. was added a solution of 1.6 M n-butyllithium in hexanes (12.3 mL, 19.7 mmol) slowly, so that the reaction temperature was maintained below 5° C. The solution was stirred at 0-5° C. for 1.5 h. A solution of iodomethane (0.56 mL, 9.01 mmol) in petroleum ether (2 mL) was then added over 20 min while maintaining the temperature below 5° C. The suspension was stirred at 0-5° C. for 1 h and diluted with water and ether. The aqueous layer was extracted with ether and the combined organic layers washed with brine, dried (MgSO$_4$), filtered and concentrated. The residue was chromatographed (silica gel), eluting with CH$_2$Cl$_2$ to afford the title compound (1.60 g, 67%). MS (ES) m/z 294 [M+1]$^+$.

18C. N-(4-Cyano-2-methyl-3-trifluoromethylphenyl)-2,2-dimethyl-propionamide

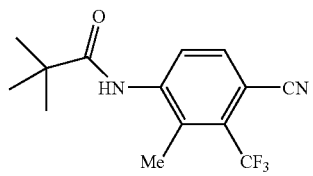

A suspension of compound 18B (8.36 g, 28.5 mmol) and CuCN (4.33 g, 65.5 mmol) in anhydrous N-methylpyrrolidinone (85 mL) was refluxed for 38 h. After cooling to rt, the suspension was poured into ice/water with stirring. The solid was filtered, washed with water and dried to yield an 85:15 mixture (7.55 g) of compounds 18C and 18D.

18D. 4-Amino-3-methyl-2-trifluoromethylbenzonitrile

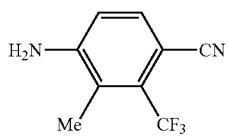

A solution of the mixed product from 18C (7.53 g, 26.5 mmol) in 120 mL of concentrated HCl/EtOH (1:1) was refluxed for 14 h. After cooling to rt, the solution was concentrated under reduced pressure. The resulting residue was dissolved in EtOAc, washed with saturated aqueous NaHCO$_3$ (2×) and brine (1×), dried (MgSO$_4$), filtered and concentrated. The residue was chromatographed (silica gel), eluting with chloroform/MeOH (98:2) to furnish the title compound (4.62 g, 87%). MS (ES) m/z 201 [M+1]$^+$.

18E. 4-Isocyanato-3-methyl-2-trifluoromethylbenzonitrile

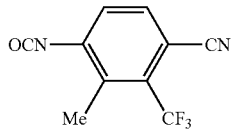

The title compound was prepared from 18D in a manner similar to that described in Experiment 2E.

18F. (7R,7aS)-4-(7-Hydroxy-1,3-dioxotetrahydropyrrolo[1,2-c]imidazol-2-yl)-3-methyl-2-trifluoromethylbenzonitrile The title compound was prepared (3.0 g, 53% yield) by procedures analogous to those described in Experiment 2 F. HPLC: 98% at 2.33, 2.58 min (retention time) (Conditions: Phenom. Lura C18 (4.6×50 mm); Eluted with 0% to 100% B, 4 min gradient (A=90% H$_2$O—10% MeOH—0.1% TFA and B=10% H$_2$O—90% MeOH—0.1% TFA); Flow rate at 4.0 mL/min. UV detection at 220 nm.). Chiral HPLC: retention time=9.71 min (98%); Conditions: OD (4.6×250 mm); Eluted with 25% isopropanol in hexane for 30 min at 1 mL/min. MS (ES) m/z 340 [M+1]$^+$.

EXAMPLE 19

(7S,7aR)-4-(7-Hydroxy-1,3-dioxotetrahydropyrrolo[1,2-c]imidazol-2-yl)-3-methyl-2-trifluoromethylbenzonitrile

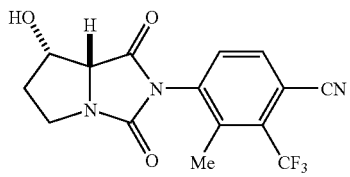

To a stirring solution of compound 1A (182 mg, 1 mmol) in MeOH (10 mL) was added WA21J resin (1 g) in one portion. The resulting suspension was stirred at rt for 30 min, then filtered and the filtrate concentrated under reduced pressure to give the corresponding free amine as a colorless oil. To a solution of the amine in CH$_2$Cl$_2$ (2 mL) was added a solution of 18E (0.7 mmol) in CH$_2$Cl$_2$ (2 mL), followed by 4 Å molecular sieves (0.5 g). The resulting suspension was stirred at rt for 20 h, and then DBU (0.2 mL, 1.5 mmol) was added. After stirring at rt for 3 days, the reaction mixture was filtered and the filtrate washed with 1 N aqueous HCl, water, brine, dried (MgSO$_4$), filtered and concentrated. The residue was chromatographed (silica gel), eluting with 5% MeOH in EtOAc/hexane (1:1) to afford the title compound (45 mg) as a white solid. HPLC: 100% at 4.32, 4.89 min (retention time) (Conditions: Zorbax SB C18 (4.6×75 mm); Eluted with 0% to 100% B, 8 min gradient (A=90% H$_2$O—10% MeOH—0.1% H$_3$PO$_4$ and B=10% H$_2$O—90% MeOH—0.1% H$_3$PO$_4$); Flow rate at 2.5 mL/min. UV detection at 220 nm.). Chiral HPLC: retention time=14.11 min (99%); Conditions: OD (4.6×250 mm); Eluted with 20% isopropanol in hexane for 30 min at 1 mL/min. MS (ES) m/z 340 [M+1]$^+$.

EXAMPLE 20

(7R,7aS)-2-Bromo-4-(7-hydroxy-1,3-dioxotetrahydropyrrolo[1,2-c]imidazol-2-yl)-3-methylbenzonitrile

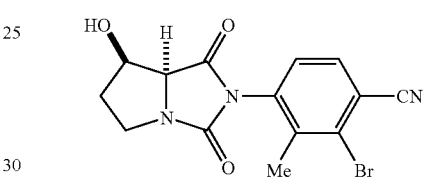

20A. 4-Amino-2-bromo-3-methylbenzaldehyde

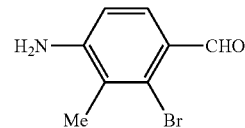

To a solution of commercially available 3-bromo-2-methyl-phenylamine (1.86 g, 10 mmol) in DMSO (200 mL) was added concentrated HCl (10 mL), followed by CuCl$_2$ (2.7 g, 20 mmol). The resulting suspension was heated to 90° C. for 6 h. After cooling to rt, the reaction mixture was poured into ice/water (600 mL) and adjusted to pH=8 by dropwise addition of 10% aqueous NaOH. The resulting greenish suspension was filtered through a pad of Celite®, and the filtrate extracted with ether (3×). The combined organics were washed with brine, dried (Na$_2$SO$_4$), filtered and concentrated. The residue was chromatographed (silica gel), eluting with 30-70% EtOAc/hexane to furnish the title compound (0.67 g, 31%).

20B. 4-Amino-2-bromo-3-methylbenzonitrile

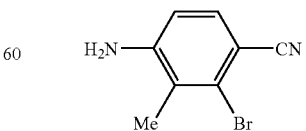

To a solution of hydroxylamine hydrochloride (109 mg, 1.58 mmol) in H$_2$O (0.37 mL) was added compound 18A (321 mg, 1.5 mmol), followed by pyridine (0.75 mL). The reaction was stirred at rt for 1 h, then CuSO₄ (75 mg, 0.3 mmol) was added, followed by Et₃N (0.44 mL, 3.2 mmol) and a solution of DCC (371 mg, 1.8 mmol) in CH₂Cl₂ (3 mL). After addition, the reaction mixture was stirred at rt until the oxime was consumed (1 h). The reaction was then treated with formic acid (0.26 mL) and stirred at rt for another 10 min to consume the excess DCC. The reaction was filtered through a pad of Celite®, and the filtrate partitioned between CH₂Cl₂ and saturated aqueous NaHCO₃. The separated organic layer was washed with brine, dried (Na₂SO₄), filtered and concentrated. The residue was chromatographed (silica gel), eluting with 10-50% EtOAc/hexane to furnish the title compound (260 mg, 83%).

20C. (7R,7aS)-2-Bromo-4-(7-hydroxy-1,3-dioxotetrahydropyrrolo[1,2-c]imidazol-2-yl)-3-methylbenzonitrile The title compound was prepared from 18B by procedures analogous to those described in Experiment 2E and 2F. HPLC: 99% at 3.99, 4.53 min (retention time) (Conditions: Zorbax SB C18 (4.6×75 mm); Eluted with 0% to 100% B, 8 min gradient (A=90% H₂O—10% MeOH—0.1% H₃PO₄ and B=10% H₂O—90% MeOH—0.1% H₃PO₄); Flow rate at 2.5 mL/min. UV detection at 220 nm). Chiral HPLC: retention time=15.4 min (99%); Conditions: OD (4.6×250 mm); Eluted with 20% isopropanol in hexane for 30 min at 1 mL/min. MS (ES) m/z 351 [M+1]⁺.

EXAMPLE 21

(7R,7aS)-2-Chloro-4-(7-hydroxy-1,3-dioxotetrahydropyrrolo[1,2-c]imidazol-2-yl)-3,6-dimethylbenzonitrile

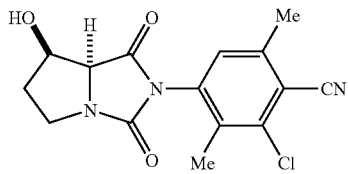

21A. 1-Chloro-2,5-dimethyl-3-nitrobenzene

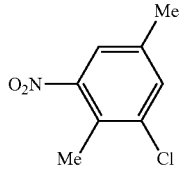

To a solution of commercially available 2-chloro-1,4-dimethylbenzene (5 mL, 37 mmol) in concentrated H₂SO₄ (5 mL) cooled to 0-5° C. was added dropwise concentrated HNO₃ (4.7 mL, 74.6 mmol) over 20 min. After the addition, the reaction was stirred at 0-5° C. for 30 min, then poured carefully into a mixture of ice and saturated aqueous K₂CO₃ solution (40 mL), and extracted with EtOAc (3×). The combined EtOAc extracts were washed with brine, dried (Na₂SO₄), filtered and concentrated under reduced pressure. The residue was chromatographed (silica gel), eluting with 10-30% EtOAc/hexane to give a mixture of the title compound and its regioisomer (1-chloro-2,5-dimethyl-4-nitrobenzene) (3.0 g). The mixture was further chromatographed (silica gel) eluting with 10% CH₂Cl₂ in hexane to afford pure compound 19A (0.2 g).

21B. 3-Chloro-2,5-dimethylaniline

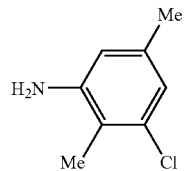

The title compound (1.70 g) was prepared from 21A (2.15 g, 11.6 mmol) in a manner similar to that described in Experiment 6C.

21C. 4-Bromo-3-chloro-2,5-dimethylaniline

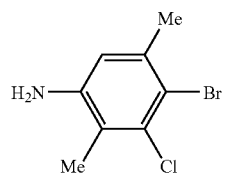

To a solution of compound 21B (1.56 g, 10 mmol) in CHCl₃ (30 mL) cooled to 0-5° C. was added portionwise tetrabutylammonium tribromide (434 mg, 9.0 mmol). After addition, the reaction was stirred at 0-5° C. for 5 min, then quenched with saturated aqueous NaHCO₃ (30 mL) and 5% aqueous Na₂S₂O₃ (30 mL). The mixture was stirred at rt for 10 min, then extracted with CH₂Cl₂ (3×). The combined organics were washed with brine, dried (Na₂SO₄), filtered and concentrated. The residue was chromatographed (silica gel), eluting with 20-60% EtOAc/hexane to give the title compound (0.75 g, 32% yield).

21D. N-(4-Bromo-3-chloro-2,5-dimethylphenyl)acetamide

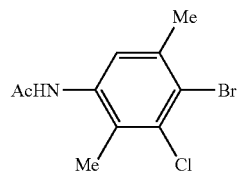

The title compound (0.82 g) was prepared from 21C (0.74 g, 3.17 mmol) in a manner similar to that described in Experiment 2A.

21E. (7R,7aS)-2-Chloro-4-(7-hydroxy-1,3-dioxotetrahydropyrrolo[1,2c]imidazol-2-yl)-3,6-dimethylbenzonitrile The title compound (30 mg) as a white solid was prepared by procedures analogous to those described in Experiment 2C to 2F. HPLC: 99% at 4.50, 4.87 min (retention time) (Conditions: Zorbax SB C18 (4.6×75 mm); Eluted with 0% to 100% B, 8 min gradient. (A=90% H₂O—10% MeOH—0.1% H₃PO₄ and B=10% H₂O—90% MeOH—0.1% H₃PO₄); Flow rate at 2.5 mL/min. UV detection at 220 nm). Chiral HPLC: retention time=12.07 min (99%); Conditions: OD (4.6×250 mm); Eluted with 20% isopropanol in hexane for 30 min at 1 mL/min. MS (ES) m/z 320 [M+1]⁺.

EXAMPLE 22

(7R,7aS)-2-(4-Bromo-3-chloro-2-methylphenyl)-7-hydroxytetrahydropyrrolo[1,2-c]imidazole-1,3-dione

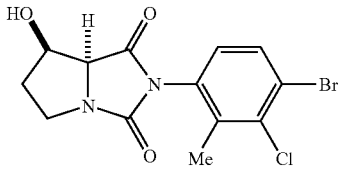

22A. N-(4-Bromo-3-chloro-2-methylphenyl)acetamide

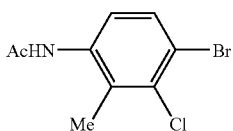

The title compound was prepared (2.75 g, 96% yield) from commercially available 3-chloro-2-methylaniline by procedures analogous to those described in Experiment 2A and 2B.

22B. 4-Bromo-3-chloro-2-methylaniline

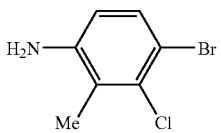

The title compound was prepared (0.70 g, 83% yield) from 22A in a manner similar to that described in Experiment 2D.

22C. (7R,7aS)-2-(4-Bromo-3-chloro-2-methylphenyl)-7-hydroxytetrahydropyrrolo[1,2-c]imidazole-1,3-dione The title compound was prepared (0.71 g, 88% yield) by procedures analogous to those described in Experiment 2E and 2F. HPLC: 99% at 2.78, 2.95 min (retention time) (Conditions: Phenom. Lura C18 (4.6×50 mm); Eluted with 0% to 100% B, 4 min gradient (A=90% $H_2O$—10% MeOH—0.1% TFA and B=10% $H_2O$—90% MeOH—0.1% TFA); Flow rate at 4.0 mL/min. UV detection at 220 nm). Chiral HPLC: retention time=7.17 min (92%); Conditions: OD (4.6×250 mm); Eluted with 25% isopropanol in hexane for 30 min at 1 mL/min MS (ES) m/z 360 [M+1]$^+$.

EXAMPLE 23

(7R,7aS)-2-Chloro-4-(7-hydroxy-1,3-dioxotetrahydropyrrolo[1,2-c]imidazol-2-yl)-3-methylbenzonitrile

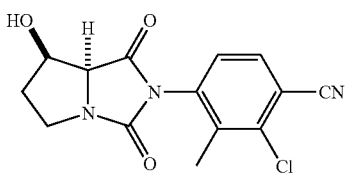

23A. 3-Chloro-2-methylphenylacetamide

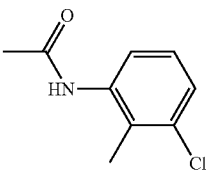

To a solution of 3-chloro-2-methylaniline (3.00 g, 21.2 mmol) in 25 mL of EtOH at rt was added acetic anhydride (2.40 mL, 25.4 mmol), and the solution was stirred at rt for 2 h. The mixture was concentrated under reduced pressure to give 3.89 g (100%) of the desired acetamide. $^1$H NMR (DMSO-$d_6$) δ 2.05 (s, 3H), 2.20 (s, 3H), 7.16 (t, J=7.7, 8.3, 1H), 7.25 (d, J=8.3, 1H), 7.31 (d, J=8.3, 1H), 9.55 (s, 1H); $^{13}$C NMR (DMSO-$d_6$) δ 15.1, 23.1, 124.4, 125.8, 126.7, 130.3, 133.7, 138.0, 168.3; HPLC a) column: Phenominex ODS C18 4.6×50 mm, 4 min gradient, 10% MeOH/90% $H_2O$/0.1% TFA to 90% MeOH/10% $H_2O$/0.1% TFA; 1 min hold, 4 mL/min UV detection at 220 nm, 2.32 min retention time; HPLC b) column: Shimadzu Shim-Pack VP-ODS C18 4.6×50 mm, 4 min gradient, 10% MeOH/90% $H_2O$/0.1% TFA to 90% MeOH/10% $H_2O$/0.1% TFA, 1 min hold; 4 mL/min, UV detection at 220 nm, 2.20 min retention time (99%); MS (ES) m/z 184 [M+H]$^+$.

23B. 4-Bromo-3-chloro-2-methylphenylacetamide

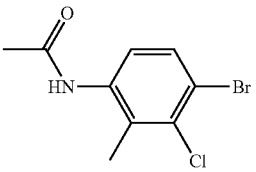

To a suspension of acetamide 23A (2.00 g, 10.9 mmol) in 15 mL of glacial AcOH cooled to approximately 15° C. was added bromine (1.67 mL, 32.7 mmol) over 20 min. The ice bath was removed and the solution was stirred for 2 h, poured into ice water with stirring, and the solid was then filtered and dried to give 2.75 g (96%) of the desired bromide. $^1$H NMR (DMSO-$d_6$) δ 2.05 (s, 3H), 2.28 (s, 3H), 7.29 (d, J=8.3, 1H), 7.56 (d, J=8.8, 1H), 9.60 (s, 1H); $^{13}$C NMR (DMSO-$d_6$) δ 16.7, 23.1, 118.1, 125.5, 130.4, 132.7, 133.4, 137.1, 168.4; HPLC a) column: Phenominex ODS C18 4.6×50 mm, 4 min gradient, 10% MeOH/90% $H_2O$/0.1% TFA to 90% MeOH/10% $H_2O$/0.1% TFA, 1 min hold, 4 mL/min, UV detection at 220 nm, 2.95 min retention time; HPLC b) column: Shimadzu Shim-Pack VP-ODS C18 4.6×50 mm, 4 min gradient, 10% MeOH/90% $H_2O$/0.1% TFA to 90% MeOH/10% $H_2O$/0.1% TFA, 1 min hold, 4 mL/min, UV detection at 220 nm, 2.87 min retention time (98%); MS (ES) m/z 263 [M+H]$^+$.

23C. 3-Chloro-4-cyano-2-methylphenylacetamide

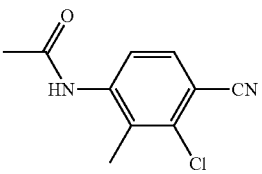

A suspension of bromide 23B (2.70 g, 10.3 mmol) and copper cyanide (0.92 g, 10.3 mmol) in DMF (30 mL) was heated to 150° C. for 4 h. The suspension was cooled, poured into water with stirring, and the solid was filtered and dried to give 1.44 g (67%) of the desired nitrile. $^1$H NMR (DMSO-$d_6$) δ 2.12 (s, 3H), 2.29 (s, 3H), 7.72 (d, J=8.8, 1H), 7.75 (d, J=8.2, 1H), 9.73 (s, 1H); $^{13}$C NMR (DMSO-$d_6$) δ 15.3, 23.5, 107.7, 116.5, 123.0, 130.1, 131.5, 135.7, 142.3, 168.8; HPLC a) column: Phenominex ODS C18 4.6×50 mm, 4 min gradient, 10% MeOH/90% $H_2O$/0.1% TFA to 90% MeOH/10% $H_2O$/0.1% TFA, 1 min hold, 4 mL/min, UV detection at 220 nm, 2.23 min retention time; HPLC b) column: Shimadzu Shim-Pack VP-ODS C18 4.6×50 mm, 4 min gradient, 10% MeOH/90% $H_2O$/0.1% TFA to 90% MeOH/10% $H_2O$/0.1% TFA, 1 min hold, 4 mL/min, UV detection at 220 nm, 2.13 min retention time (95%); MS (ES) m/z 209 [M+H]$^+$.

23D. 3-Chloro-4-cyano-2-methylphenylaniline

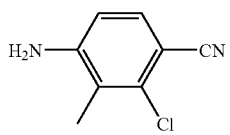

A solution of cyanoacetamide 23C (9.90 g, 47.4 mmol) in 100 mL of concentrated HCl/EtOH (1:1) was refluxed 30 min. The solution was then concentrated and dried under reduced pressure to give 9.41 g (98%) of the desired aniline as the hydrochloride salt. The free base of the aniline was obtained by suspending the salt in EtOAc and washing with saturated aqueous $NaHCO_3$ solution. The organic layer was then dried ($MgSO_4$), filtered and concentrated under reduced pressure. $^1$H NMR (DMSO-$d_6$) δ 2.12 (s, 3H), 6.30 (s, 2H), 6.61 (d, J=8.23, 1H), 7.36 (d, J=8.23, 1H); $^{13}$C NMR (DMSO-$d_6$) δ 13.8, 96.9, 112.1, 118.3, 118.85, 132.2, 135.6, 152.5; HPLC a) column: Phenominex ODS C18 4.6×50 mm, 4 min gradient, 10% MeOH/90% $H_2O$/0.1% TFA to 90% MeOH/10% $H_2O$/0.1% TFA, 1 min hold, 4 mL/min, UV detection at 220 nm, 2.43 min retention time; HPLC b):column: Shimadzu Shim-Pack VP-ODS C18 4.6×50 mm, 4 min gradient, 10% MeOH/90% $H_2O$/0.1% TFA to 90% MeOH/10% $H_2O$/0.1% TFA, 1 min hold, 4 mL/min, UV detection at 220 nm, 2.31 min retention time (99%); MS (ES) m/z 167 [M+H]$^+$.

23E. 2-Chloro-4-isocyanato-3-methylbenzonitrile

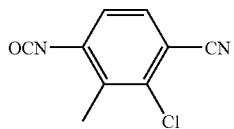

The title compound was prepared from compound 23D in a manner similar to that described in Experiments 2D to 2E.

23F. (2S,3R)-1-(3-Chloro-4-cyano-2-methylphenylcarbamoyl)-3-hydroxypyrrolidine-2-carboxylic acid methyl ester

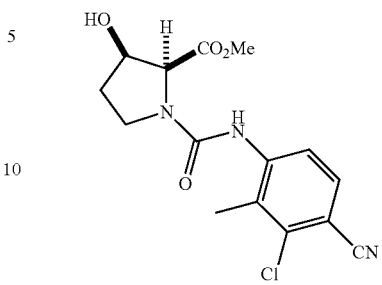

To a solution of hydroxyproline compound 1F (493 mg, 3.40 mmol) in $CH_2Cl_2$ (15 mL) was added 4 Å molecular sieves (~3.0 g), followed by isocyanate 23E (725 mg, 3.22 mmol), and the resulting mixture was stirred at rt overnight, filtered, and concentrated under reduced pressure. The residue was purified by flash chromatography (silica gel, 0.5% MeOH in EtOAc/hexane, 1:1) to afford the title compound (736 mg) as an off-white solid. HPLC column: YMC S-5 C18 (4.6×50 mm), 0% to 100% B, 4 min gradient, 1 min hold (A=90% $H_2O$—10% $CH_3CN$—0.1% TFA and B=10% $H_2O$—90% $CH_3CN$—0.1% TFA), flow rate at 4 mL/min, UV detection at 220 nm, 1.57 min retention time (100%); MS (ES) m/z 338 [M+H]$^+$.

23G. (7R,7aS)-2-Chloro-4-(7-hydroxy-1,3-dioxotetrahydropyrrolo[1,2-c]imidazol-2-yl)-3-methylbenzonitrile.

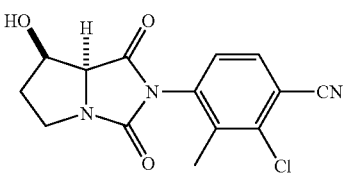

To a suspension of cis-3-hydroxyproline methyl ester, HCl salt (4.91 g, 27 mmol) in $CH_2Cl_2$ (100 mL) cooled to 0° C. was added i-$Pr_2NEt$ (4.79 mL, 27.5 mmol). After stirring at rt for 15 min, isocyanate 23E was added as a solid in one portion through a powder addition funnel, rinsing with 50 mL $CH_2Cl_2$. The resulting light brown solution was stirred at rt until urea formation was complete (~2 h). To the mixture was then added DBU (4.6 mL, 30 mmol), and the resulting brown colored solution was stirred at rt until hydantoin formation was complete (~15 h). The product (4.72 g, 62%) was collected by filtration and washing with $CH_2Cl_2$ (2×). The mother liquor was then diluted with $CH_2Cl_2$ and washed with $H_2O$ (2×), 1 N HCl (2×) and brine. After removal of most of the solvent under reduced pressure, further product (1.2 g, 16%) was collected by filtration and washing with $CH_2Cl_2$ (2×). Recrystallization of the 4.72 g of crude product from hot THF and hexane gave 4.5 g of analytically pure product. $^1$H NMR (DMSO-$d_6$) δ 2.05-2.11 (m, 1H), 2.15-2.22 (m, 1H), 2.20, 2.24 (s, 3H), 3.29-3.33 (m, 1H), 3.59-3.68 (m, 1H), 4.42-4.50 (m, 2H), 5.64, 5.72 (d, J=3.9, 3.3, 1H), 7.22, 7.51 (d, J=8.3, 1H), 7.96 (d, J=8.2, 1H); $^{13}$C NMR (DMSO-$d_6$) δ 15.4, 15.6, 35.5, 35.6, 43.3, 43.4, 68.8, 69.3, 69.8, 112.9, 113.1, 115.8, 128.1, 128.7, 132.1, 136.3, 136.4, 136.9, 137.1, 158.6, 169.1, 169.6; HPLC a) column: Phenominex ODS C18

4.6×50 mm, 4 min gradient, 10% MeOH/90% H₂O/0.1% TFA to 90% MeOH/10% H₂O/0.1% TFA; 1 min hold; 4 mL/min, UV detection at 254 nm, 2.07 and 2.32 min retention time; HPLC b) column: Shimadzu Shim-Pack VP-ODS C18 (4.6×50 mm), 4 min gradient, 10% MeOH/90% H₂O/0.1% TFA to 90% MeOH/10% H₂O/0.1% TFA, 1 min hold, 4 mL/min, UV detection at 254 nm, 1.93 and 2.23 min retention time; Chiral HPLC column: Daicel Chiralcel OD 4.6×250 mm, isocratic, 30 min, 25% isopropanol/hexanes, 1 mL/min, UV detection at 254 nm; Shimadzu HPLC: 17.99 min retention time (>99%): Column: Hypercarb 5μ, 4.6×100 mm, 25° C., isocratic, 30 min ACN/H₂O (35:65); 1 mL/min, 10.99 min retention time; MS (ES) m/z 306 [M+H]⁺. Alternatively, compound 23G can also be prepared by the following procedure: A solution of 22C (0.10 g, 0.28 mmol) and copper cyanide (0.03 g, 0.34 mmol) in DMF (1 mL) was refluxed for 3 h, cooled to rt, and diluted with water. The resulting solid was filtered, washed with water, dried and purified using preparative HPLC to afford the title compound (27 mg).

Alternatively, compound 23G can also be prepared by the following procedures: A solution of 22C (0.10 g, 0.278 mmol) and copper cyanide (0.03 g, 0.334 mmol) in DMF (1 mL) was refluxed for 3 h, cooled to rt and diluted with water. The resulting solid was filtered, washed with water, dried and purified using preparative HPLC to afford the title compound (27 mg). HPLC: 99% at 2.06, 2.34 min (retention time) (Conditions: Phenom. Lura C18 (4.6×50 mm); Eluted with 0% to 100% B, 4 min gradient (A=90% H₂O—10% MeOH—0.1% TFA and B=10% H₂O—90% MeOH—0.1% TFA); Flow rate at 4.0 mL/min. UV detection at 220 nm). Chiral HPLC: retention time=11.04 min (99%); Conditions: OD (4.6×250 mm); Eluted with 25% isopropanol in hexane for 30 min at 1 mL/min. MS (ES) m/z 306 [M+1]⁺.

EXAMPLE 24

(7S,7aR)-2-Chloro-4-(7-hydroxy-1,3-dioxotetrahydropyrrolo[1,2-c]imidazol-2-yl)-3-methylbenzonitrile

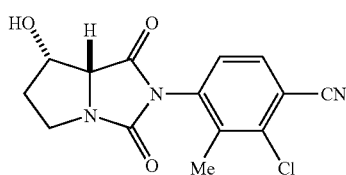

The title compound was prepared from compound 1A and compound 23E in a manner similar to that described in Example 19. mp 237-238° C.; HPLC: 100% at 2.11 and 2.36 min (retention time) (Conditions: Phenomenex Luna C18 (4.6×50 mm); Eluted with 0% to 100% B, 4 min gradient (A=90% H₂O—10% MeOH—0.1% H₃PO₄ and B=10% H₂O—90% MeOH—0.1% H₃PO₄); Flow rate at 4 mL/min. UV detection at 220 nm). Chiral HPLC: retention time=15.9 min (100%); Conditions: OD (4.6×250 mm); Eluted with 20% isopropanol in hexane for 30 min at 1 mL/min, MS (ES) m/z 306 [M+1]⁺.

EXAMPLE 25

(7R,7aS)-2-Chloro-4-(7-hydroxy-7a-methyl-1,3-dioxotetrahydropyrrolo[2-c]imidazol-2-yl)-3-methylbenzonitrile

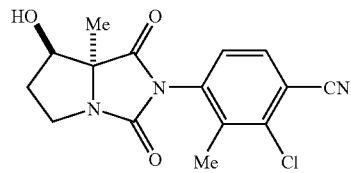

To a stirring suspension of compound 23G (600 mg, 1.96 mmol) in anhydrous THF (10 mL) at rt was added DMPU (4 mL). The resulting clear solution was cooled to −78° C., then a 2.0 M solution of LDA in THF (1.96 mL, 3.92 mmol) was added slowly so that the reaction temperature was maintained below −72° C. The resulting dark brown solution was stirred at −78° C. for 30 min, then iodomethane (0.36 mL, 3.92 mmol) was added dropwise. After addition, the reaction was stirred at −78° C. for 30 min, then at 0° C. for 3 h. The reaction was quenched with 5% aqueous KHSO₄ and extracted with EtOAc (3×). The combined extracts were washed with brine, dried (Na₂SO₄), filtered and concentrated. The residue was chromatographed (silica gel), eluting with 1% MeOH in EtOAc/CH₂Cl₂ (1:9) to give a mixture of compound 25 and compound 26 (150 mg), which was further purified using preparative HPLC to afford the title compound (20 mg). HPLC: 99% at 4.40, 5.20 min (retention time) (Conditions: Zorbax SB C18 (4.6×75 mm); Eluted with 0% to 100% B, 8 min gradient. (A=90% H₂O—10% MeOH—0.1% H₃PO₄ and B=10% H₂O—90% MeOH—0.1% H₃PO₄); Flow rate at 2.5 mL/min. UV detection at 220 nm). Chiral HPLC: retention time=7.9 min (99%); Conditions: OD (4.6×250 mm); Eluted with 20% isopropanol in hexane for 30 min at 1 mL/min, MS (ES) m/z 320 [M+1]⁺.

Alternatively, the compound of Example 25 can be prepared in the following manner 25A. (2S,3R)-3-Hydroxy-2-methylpyrrolidine-1,2-dicarboxylic acid 1-tert-butyl ester 2-methyl ester

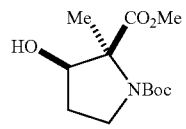

To a solution of (2S,3R)—N-tert-butyloxycarbonyl-3-hydroxy-2 pyrrolidinecarboxylic acid methyl ester (1D) (1.13 g, 4.61 mmol) in THF (73 mL) at −78° C. was slowly added a 1.8 M solution of LDA (7.70 mL, 13.86 mmol). After stirring for 1 h, iodomethane (2.87 mL, 46.10 mmol) was added, and the reaction was stirred for 1 h at −78° C., before warming gradually to −20° C. for 3 h, and then was stored at −40° C. overnight. After quenching with saturated aqueous NH₄Cl, water and EtOAc were added and the layers were separated. The organic layer was washed with brine, and the aqueous layer was extracted with EtOAc. The combined organics were dried (MgSO₄), filtered and concentrated under reduced pressure. The residue was purified using preparative HPLC (Luna C-18, 21.2×250 mm, eluting with 50-90% solvent B (A=90%

H₂O—10% MeOH and B=10% H₂O—90% MeOH) over 30 min; Flow rate at 10 mL/min. UV detection at 220 nm) to provide a mixture of the starting material and its epimer as a yellow oil (490 mg) and the title compound as a yellow oil (362 mg); LC/MS m/z 260 [M+H]⁺.

25B. (7R,7aS)-2-Chloro-4-(7-hydroxy-7a-methyl-1,3-dioxotetrahydropyrrolo[1,2-c]imidazol-2-yl)-3-methylbenzonitrile

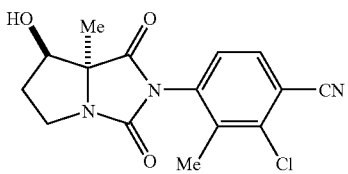

To a solution of (2S,3R)-3-hydroxy-2-methyl-pyrrolidine-1,2-dicarboxylic acid 1-tert-butyl ester 2-methyl ester (25A) (87 mg, 0.32 mmol) in CH₂Cl₂ (1.3 mL) at 0° C. was added Hunig's base (111 mL, 0.64 mmol). After stirring for 15 min, 2-chloro-4-isocyanato-3-methylbenzonitrile (23A) was added, and after an additional 10 min, the ice bath was removed. The reaction was stirred for 2 h and then diluted with water. The layers were separated and the organic layer was washed with brine, dried (MgSO₄), filtered and concentrated under reduced pressure. The resulting solid was purified using preparative HPLC (Luna C-18, 21.2×100 mm, eluting with 40-100% solvent B (A=90% H₂O—10% MeOH and B=10% H₂O—90% MeOH) over 15 min; Flow rate at 20 mL/min; UV detection at 220 nm) to provide the title compound (67 mg) as a white film; LC/MS m/z 661 [2M+23]⁺.

EXAMPLE 26

(7R,7aS)-2-Chloro-3-ethyl-4-(7-hydroxy-7a-methyl-1,3-dioxotetrahydropyrrolo[1,2-c]imidazol-2-yl)benzonitrile

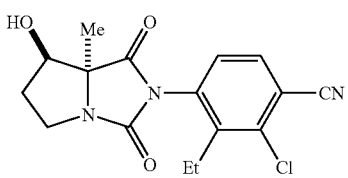

A mixed product (150 mg) from Experiment 25 was purified using preparative HPLC to afford the title compound (50 mg). HPLC: 99% at 4.75, 5.54 min (retention time) (Conditions: Zorbax SB C18 (4.6×75 mm); Eluted with 0% to 100% B, 8 min gradient. (A=90% H₂O—10% MeOH—0.1% H₃PO₄ and B=10% H₂O—90% MeOH—0.1% H₃PO₄); Flow rate at 2.5 mL/min UV detection at 220 nm). Chiral HPLC: retention time=6.4 min (99%); Conditions: OD (4.6×250 mm); Eluted with 20% isopropanol in hexane for 30 min at 1 mL/min, MS (ES) m/z 334 [M+1]⁺.

EXAMPLE 27

(7S,7aR)-2-Chloro-4-(7-hydroxy-7a-methyl-1,3-dioxotetrahydropyrrolo[1,2-c]imidazol-2-yl)-3-methylbenzonitrile

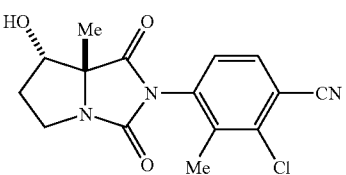

The title compound was prepared and isolated as a white solid (30 mg) from compound 24 in a manner similar to that described in Example 25. HPLC: 99% at 4.49, 5.55 min (retention time) (Conditions: Zorbax SB C18 (4.6×75 mm); Eluted with 0% to 100% B, 8 min gradient. (A=90% H₂O—10% MeOH—0.1% H₃PO₄ and B=10% H₂O—90% MeOH—0.1% H₃PO₄); Flow rate at 2.5 mL/min UV detection at 220 nm). Chiral HPLC: retention time=8.1 min (99%); Conditions: OD (4.6×250 mm); Eluted with 20% isopropanol in hexane for 30 min at 1 mL/min, MS (ES) m/z 320 [M+1]⁺.

EXAMPLE 28

(7S,7aR)-2-Chloro-3-ethyl-4-(7-hydroxy-7a-methyl-1,3-dioxotetrahydropyrrolo[1,2-c]imidazol-2-yl)benzonitrile

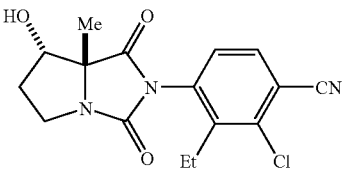

The title compound (35 mg) was obtained as a white solid in the reaction outlined in Example 27 by a procedure similar to that described in Example 26. HPLC: 99% at 4.79, 5.56 min (retention time) (Conditions: Zorbax SB C18 (4.6×75 mm); Eluted with 0% to 100% B, 8 min gradient. (A=90% H₂O—10% MeOH—0.1% H₃PO₄ and B=10% H₂O—90% MeOH—0.1% H₃PO₄); Flow rate at 2.5 mL/min UV detection at 220 nm). Chiral HPLC: retention time=7.1 min (99%); Conditions: OD (4.6×250 mm); Eluted with 20% isopropanol in hexane for 30 min at 1 mL/min, MS (ES) m/z 334 [M+1]⁺.

EXAMPLES 29 to 42

Additional compounds of the present invention were prepared by procedures analogous to those described above. The compounds of Examples 29 to 42 have the following structure:

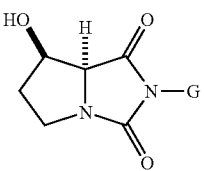

where G, the compound name, retention time, molecular mass, and the procedure employed, are set forth in Table 1. The chromatography techniques used to determine the com pound retention times of Table 1 are as follows: LC/MS=Phenom. Luna C18, 4.6×50 mm eluting with 10-90% MeOH/H₂O over 4 min containing 0.1% TFA; 4 mL/min, monitoring at 220 nm The molecular mass of the compounds listed in Table 1, where provided, were determined by MS by the formula m/z.

TABLE 1

| Example No. | G | Compound Name | Retention Time (Min)/ Molecular Mass | Proced. of Ex. |
|---|---|---|---|---|
| 29 | (4-CN-phenyl) | (7R,7aS)-4-(7-Hydroxy-1,3-dioxotetrahydropyrrolo[1,2-c]imidazol-2-yl)benzonitrile | 2.07 LCMS/ 258 [M + H]⁺ | 2 |
| 30 | (3-Et-4-CN-phenyl) | (7R,7aS)-3-Ethyl-4-(7-hydroxy-1,3-dioxotetrahydropyrrolo[1,2-c]imidazol-2-yl)benzonitrile | 2.50 LCMS/ 286 [M + H]⁺ | 2 |
| 31 | (2-OMe-4-CN-phenyl) | (7R,7aS)-4-(7-Hydroxy-1,3-dioxotetrahydropyrrolo[1,2-c]imidazol-2-yl)-2-methoxybenzonitrile | 2.35 LCMS/ 288 [M + H]⁺ | 2 |
| 32 | (3-OPr-4-CN-phenyl) | (7R,7aS)-4-(7-Hydroxy-1,3-dioxotetrahydropyrrolo[1,2-c]imidazol-2-yl)-3-propoxybenzonitrile | 2.76 LCMS/ 316 [M + H]⁺ | 2 |
| 33 | (2-OPr-4-CN-phenyl) | (7R,7aS)-4-(7-Hydroxy-1,3-dioxotetrahydropyrrolo[1,2-c]imidazol-2-yl)-2-propoxybenzonitrile | 3.10 LCMS/ 316 [M + H]⁺ | 2 |
| 34 | (3,5-diMe-4-CN-phenyl) | (7R,7aS)-4-(7-Hydroxy-1,3-dioxo-tetrahydropyrrolo[1,2-c]imidazol-2-yl)-3,5-dimethylbenzonitrile | 1.44 LCMS/ 286 [M + H]⁺ | 2 |
| 35 | (2,3-diMe-4-CN-phenyl) | (7R,7aS)-4-(7-Hydroxy-1,3-dioxotetrahydropyrrolo[1,2-c]imidazol-2-yl)-2,3-dimethylbenzonitrile | 1.79, 1.96 LCMS/ 286 [M + H]⁺ | 2 |
| 36 | (3-OMe-2-Me-4-CN-phenyl) | (7R,7aS)-4-(7-Hydroxy-1,3-dioxotetrahydropyrrolo[1,2-c]imidazol-2-yl)-3-methoxy-2-methylbenzonitrile | 1.83 LCMS/ 302 [M + H]⁺ | 21 |
| 37 | (3-Cl-2-Me-4-CN-phenyl) | (7R,7aS)-3-Chloro-4-(7-hydroxy-1,3-dioxotetrahydropyrrolo[1,2-c]imidazol-2-yl)-2-methylbenzonitrile | 1.71, 2.28 LCMS/ 306 [M + H]⁺ | 2 |

TABLE 1-continued

| Example No. | G | Compound Name | Retention Time (Min)/ Molecular Mass | Proced. of Ex. |
|---|---|---|---|---|
| 38 | ![structure with F, F, CN] | (7R,7aS)-2,3-Difluoro-4-(7-hydroxy-1,3-dioxotetrahydropyrrolo[1,2-c]imidazol-2-yl)benzonitrile | 3.59 LCMS/ 294 [M + H]$^+$ | 2 |
| 39 | ![structure with F, Cl, CN] | (7R,7aS)-2-Chloro-3-fluoro-4-(7-hydroxy-1,3-dioxotetrahydropyrrolo[1,2-c]imidazol-2-yl)benzonitrile | 2.12 LCMS/ 310 [M + H]$^+$ | 20 |
| 40 | ![structure with Et, CF3, CN] | (7R,7aS)-3-Ethyl-4-(7-hydroxy-1,3-dioxotetrahydropyrrolo[1,2-c]imidazol-2-yl)-2-(trifluoromethyl)-benzonitrile | 2.48, 2.79 LCMS/ 354 [M + H]$^+$ | 18 |
| 41 | ![structure with Me, F, CN] | (7R,7aS)-2-Fluoro-4-(7-hydroxy-1,3-dioxotetrahydropyrrolo[1,2-c]imidazol-2-yl)-3-methylbenzonitrile | 3.70 LCMS/ 290 [M + H]$^+$ | 2 |
| 42 | ![structure with Me, CO2Me, CN] | (7R,7aS)-6-Cyano-3-(7-hydroxy-1,3-dioxotetrahydropyrrolo[1,2-c]imidazol-2-yl)-2-methylbenzoic acid methyl ester | 1.95 LCMS/ 330 [M + H]$^+$ | 2 |

EXAMPLE 43

(7S,7aR)-4-(7-Hydroxy-1,3-dioxotetrahydropyrrolo[1,2-c]imidazol-2-yl)-3-methylphthalonitrile

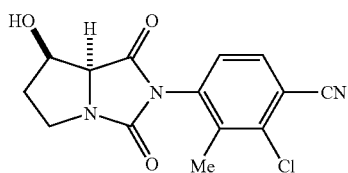

A solution of compound 23C (100 mg, 0.327 mmol), CuCN (15 mg, 0.163 mmol) and CuBr (23 mg, 0.163 mmol) in DMF (1 mL) was refluxed for 8 h, cooled to rt and diluted with water. The resulting solid was filtered, washed with water, dried and purified using preparative HPLC to afford the title compound (8 mg). HPLC: 99% at 1.83 min (retention time) (Conditions: Phenom. Lura C18 (4.6×50 mm); Eluted with 0% to 100% B, 4 min gradient (A=90% $H_2O$—10% MeOH—0.1% TFA and B=10% $H_2O$—90% MeOH—0.1% TFA); Flow rate at 4.0 mL/min UV detection at 220 nm). Chiral HPLC: retention time=21.40 min (99%); Conditions: OD (4.6×250 mm); Eluted with 25% isopropanol in hexane for 30 min at 1 mL/min MS (ES) m/z 297 [M+1]$^+$.

EXAMPLE 44

(7R,7aS)-3-Chloro-5-(7-hydroxy-1,3-dioxotetrahydropyrrolo[1,2-c]imidazol-2-yl)pyridine-2-carbonitrile

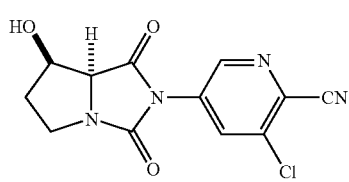

44A. 3-Chloropyridine-N-oxide

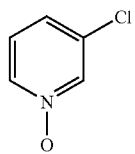

Commercially available 3-chloropyridine (11.4 g, 100 mmol) was dissolved in AcOH (60 mL) and 30% hydrogen peroxide (15 mL) was added. The mixture was heated to 70° C. for 12 h. The cooled mixture was concentrated under reduced pressure. The residue was diluted with chloroform (50 mL) and solid potassium carbonate (20 g) was added and the mixture stirred for 1 h, after which it was filtered and concentrated to give a yellow-green oil (10.21 g, 79%), which by NMR contained ~8% of starting material. The oil was used directly without further purification.

44B. 3-Chloro-2-cyanopyridine

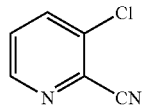

Compound 44A (2.59 g, 20 mmol), trimethylsilylcyanide (5.95 g, 60 mmol), Et$_3$N (4.05 g, 40 mmol), and acetonitrile (20 mL) were combined in a 3-necked 250-mL round-bottomed flask under nitrogen and refluxed for 6 h, at which time HPLC analysis indicated complete consumption of starting material. The cooled reaction mixture was concentrated under reduced pressure to give a brown semi-solid which was partitioned between 3 N aqueous Na$_2$CO$_3$ and CH$_2$Cl$_2$. The organic layer was washed with water, brine, dried (MgSO$_4$), filtered, and concentrated under reduced pressure. The residue was purified by flash chromatography using 5% Et$_2$O/CH$_2$Cl$_2$ as eluent to give the product 44B as a white crystalline solid (1.84 g, 67%). $^1$H NMR (CDCl$_3$) 7.37 (dd, J=4.7, 8.4 Hz, 1 H), 7.73 (dd, J=1.4, 8.2 Hz, 1 H), 8.47 (dd, J=1.3, 4.6 Hz, 1 H); LC/MS m/z 139 [M+H]$^+$.

44C. 3-Chloro-2-cyano-5-nitropyridine

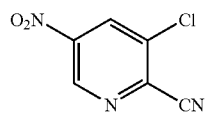

To a solution of compound 44B (1.75 g, 12.7 mmol) in CH$_2$Cl$_2$ (40 mL) cooled at 0-5° C. was added dropwise a CH$_2$Cl$_2$ solution (25 mL) containing tetrabutylammonium nitrate (5.02 g, 16.5 mmol) and trifluoroacetic anhydride (3.15 g, 15 mmol) over 20 min. The reaction was stirred for 2 h at 0-5° C., warmed to rt and stirred for two days. The mixture was stirred with saturated aqueous Na$_2$CO$_3$ for 1 h and the organic layer was washed with brine and dried (MgSO$_4$), filtered, and concentrated under reduced pressure. The residue was purified by flash chromatography using CH$_2$Cl$_2$ as eluent to give the product as a yellow solid (0.43 g, 18%). $^1$H NMR (CDCl$_3$) 8.62 (d, J=2.4 Hz, 1H), 9.33 (d, J=2.3 Hz, 1 H); LC/MS m/z 183 [M+H]$^+$.

44D. 5-Amino-3-chloro-2-cyanopyridine

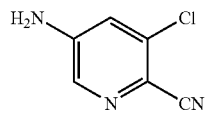

To a solution of Compound 44° C. (0.35 g, 1.9 mmol) in 90% EtOH (10 mL) was added calcium chloride (0.06 g, 0.55 mmol), followed by iron powder (0.56 g, 10 mmol). The resulting mixture was stirred at rt overnight, then filtered through a pad of Celite®, the pad washed with EtOAc, and the filtrate concentrated under reduced pressure. The residue was purified by flash chromatography using 10% Et$_2$O/CH$_2$Cl$_2$ to give a light-brown solid (0.13 g, 43%). $^1$H NMR (CDCl$_3$) 7.02 (br s, 2H), 7.28 (d, J=2.2 Hz, 1 H), 8.16 (d, J=2.2 Hz, 1 H); LC/MS m/z=154 [M+H]$^+$.

44E. (7R,7aS)-3-Chloro-5-(7-hydroxy-1,3-dioxotetrahydropyrrolo[1,2-c]imidazol-2-yl)pyridine-2-carbonitrile The title compound was synthesized from compound 44D by procedures analogous to those described for Examples 2E to 2F. HPLC: 100% at 1.67 min. (retention time) (Conditions: Shim-Pak VP-ODS (4.6×50 mm); Eluted with 0% to 100% B, 4 min gradient, 1 min hold. (A=90% H$_2$O—10% MeOH—0.1% H$_3$PO$_4$ and B=10% H$_2$O—90% MeOH—0.1% H$_3$PO$_4$); Flow rate at 4 mL/min UV detection at 220 nm); MS(ES) m/z 293 [M+H]$^+$.

EXAMPLE 45

(7R,7aS)-6-(7-Hydroxy-1,3-dioxotetrahydropyrrolo[1,2-c]imidazol-2-yl)quinoline-2-carbonitrile

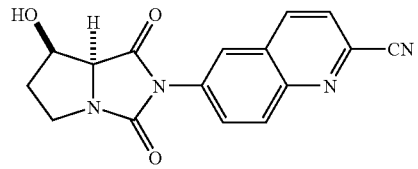

45A. 6-Nitroquinoline-N-oxide

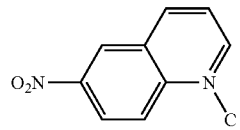

Commercially available 6-nitroquinoline (1.0 g, 5.6 mmol) was dissolved in CHCl$_3$ (30 mL) and mCPBA (1.76 g, 7.8 mmol) was added portionwise and the reactions stirred at rt for 48 h. The mixture was then washed with saturated aqueous NaHCO$_3$, 1 N aqueous NaOH, and 5% aqueous NaHSO$_3$, dried (Na$_2$SO$_4$), filtered and concentrated under reduced pressure to give compound 45A (1.0 g, 93%) as a light yellow solid. LC/MS m/z 191 [M+H]$^+$.

45B. 2-Cyano-6-nitroquinoline

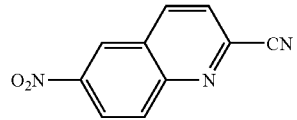

To a suspension of compound 45A (400 mg, 2.1 mmol) in MeCN (15 mL) was added trimethylsilylcyanide (0.34 mL, 2.5 mmol), followed by a slow addition of Et$_3$N (0.65 mL, 4.6 mmol). The reaction mixture was heated to 75° C. for 30 min, then cooled to rt, concentrated, dried under vacuum, and purified by silica gel flash chromatography, eluting with CH$_2$Cl$_2$ to give the title compound (150 mg, 36%) as a white solid. LC/MS m/z 200 [M+H]$^+$.

45C. 2-Cyano-6-aminoquinoline

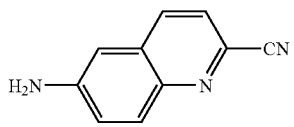

Compound 45B (212 mg, 1.1 mmol) was dissolved in 30 mL of a 1:2 mixture of EtOAc and MeOH and hydrogenated at 1 atmosphere of hydrogen in the presence of 10% Pd/C (42 mg, 20 wt. %) for 1 h. The reaction was filtered, concentrated and purified by silica gel flash chromatography eluting with 2-3% MeOH—$CH_2Cl_2$ to give the title compound (142 mg, 79%) as a light yellow solid. LC/MS m/z 170 $[M+H]^+$.

45D. (7R,7aS)-6-(7-Hydroxy-1,3-dioxotetrahydropyrrolo[1,2-c]imidazol-2-yl)quinoline-2-carbonitrile The title compound was prepared from 45C by procedures analogous to those described in Experiment 2E and 2F. HPLC: 100% at 1.81 min (retention time) (Conditions: YMC S5 C18 (4.6×50 mm); Eluted with 0% to 100% B, 8 min gradient, 3 min hold. (A=90% $H_2O$—10% MeOH—0.1% $H_3PO_4$ and B=10% $H_2O$—90% MeOH—0.1% $H_3PO_4$); Flow rate at 2.5 mL/min UV detection at 220 nm). LC/MS m/z 309 $[M+H]^+$.

EXAMPLE 46

(7R,7aS)-7-Hydroxy-2-(2-oxo-1,2-dihydroquinolin-6-yl)-tetrahydropyrrolor[1,2-c]imidazole-1,3-dione

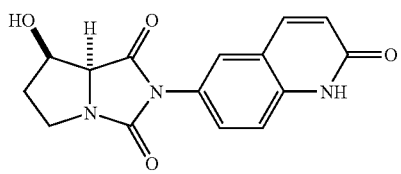

46A. 6-Nitro-2-acetoxyquinoline

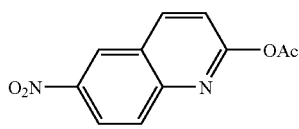

A solution of compound 45A (564 mg, 2.96 mmol) in $Ac_2O$ (20 mL) was heated to 145° C. for 5 h. After cooling to rt, the reaction was concentrated and the residue purified by silica gel flash chromatography eluting with $CH_2Cl_2$ to give the title compound (227 mg, 33%) as a beige solid. LC/MS m/z 233 $[M+H]^+$.

46B. 6-Nitro-2-quinolone

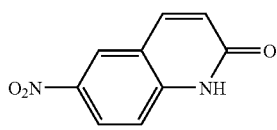

Compound 46A (210 mg, 0.90 mmol) was dissolved in MeOH (10 mL), $K_2CO_3$ was added, and the reaction was stirred at rt for 30 min. The reaction was then concentrated under reduced pressure and subsequently purified by silica gel flash chromatography eluting with 5-10% MeOH/$CH_2Cl_2$ (gradient) to give the title compound (162 mg, 94%) as a pink solid. LC/MS m/z 191 $[M+H]^+$.

46C. 6-Nitro-N-benzyl-2-quinolone

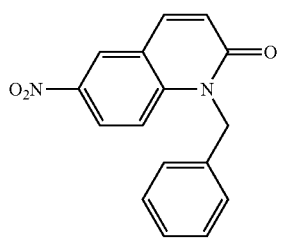

Compound 46B (50 mg, 0.26 mmol) was dissolved in DMF (1 mL), CsF (120 mg, 0.79 mmol) and benzyl chloride (0.09 mL, 0.79 mmol) were added, and the reaction was stirred at rt for 16 h. The reaction mixture was then concentrated under reduced pressure and subsequently purified by silica gel flash chromatography eluting with 0-5% EtOAc/$CH_2Cl_2$ (gradient) to give the title compound (57 mg, 77%). LC/MS m/z 281 $[M+H]^+$.

46D. 6-Amino-N-benzyl-2-quinolone

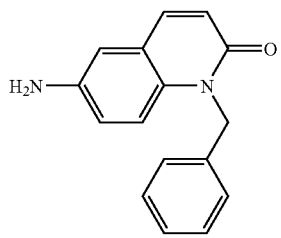

The title compound (34 mg) was prepared from compound 46C in a manner similar to that described in Experiment 45C. LC/MS m/z 251 $[M+H]^+$.

46E. (7R,7aS)-7-Hydroxy-2-(2-oxo-1,2-dihydro-N-benzylquinolin-6-yl)tetrahydropyrrolo[1,2-c]imidazole-1,3-dione

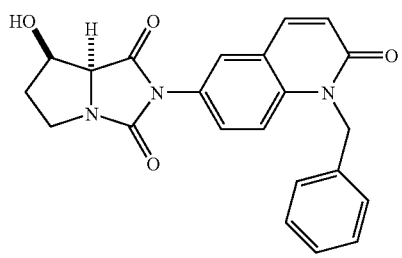

The title compound was prepared from compound 46D by procedures analogous to those described in Experiment 2E and 2F. LC/MS m/z 390 $[M+H]^+$.

46F. (7R,7aS)-7-Hydroxy-2-(2-oxo-1,2-dihydroquinolin-6-yl)tetrahydropyrrolo[1,2-c]imidazole-1,3-dione Compound 46E (80 mg, 0.20 mmol) was dissolved in MeOH (5 mL) and hydrogenated at 1 atmosphere of hydrogen for 24 h in the presence of 20 mg Pd(OH)$_2$. The reaction was then filtered, concentrated under reduced pressure, and subsequently purified by silica gel flash chromatography eluting with a gradient of 5%-10% MeOH in CH$_2$Cl$_2$ to give the title compound (16 mg) as a white solid. HPLC: 98% at 0.79 min (retention time) (Conditions: YMC S5 C18 (4.6×50 mm); Eluted with 0% to 100% B, 8 min gradient, 3 min hold. (A=90% H$_2$O—10% MeCN—0.1% TFA and B=10% H$_2$O—90% MeCN—0.1% TFA); Flow rate at 2.5 mL/min UV detection at 220 nm). LC/MS m/z 300 [M+H]$^+$.

EXAMPLE 47

(7R,7aS)-5-(7-Hydroxy-1,3-dioxotetrahydropyrrolo[1,2-c]imidazol-2-yl)biphenyl-2-carbonitrile

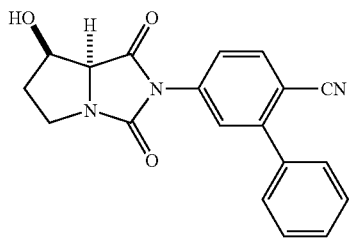

47A. 4-Cyano-3-phenylaniline

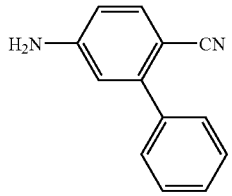

Commercially available 3-chloro-4-cyanoaniline (305 mg, 2.0 mmol) was dissolved in NMP (8 mL), and CsF (608 mg, 4.0 mmol), phenyl boronic acid (268 mg, 2.2 mmol) and dichlorobis(tricyclohexylphosphino)palladium (73mg, 0.1 mmol) were added. The reaction was then heated to 100° C. for 16 h. After cooling to rt, the reaction mixture was taken up in EtOAc, washed with water (2×), dried (Na$_2$SO$_4$), concentrated under reduced pressue, and purified by silica gel flash chromatography eluting with EtOAc/hexanes (1:1) to give compound 47A (371 mg, 96%) as a yellow solid. LC/MS m/z 195 [M+H]$^+$.

47B. (7R,7aS)-5-(7-Hydroxy-1,3-dioxotetrahydropyrrolo[1,2-c]imidazol-2-yl)biphenyl-2-carbonitrile The title compound was prepared from compound 47A by procedures analogous to those described in Experiment 2E and 2F. HPLC: 96% at 3.24 min (retention time) (Conditions: YMC S5 C18 (4.6×50 mm); Eluted with 0% to 100% B, 8 min gradient, 3 min hold. (A=90% H$_2$O—10% MeOH—0.1% H$_3$PO$_4$ and B=10% H$_2$O—90% MeOH—0.1% H$_3$PO$_4$); Flow rate at 2.5 mL/min UV detection at 220 nm). LC/MS m/z 334 [M+H]$^+$.

EXAMPLE 48

(7R,7aS)-4'-Fluoro-5-(7-hydroxy-1,3-dioxotetrahydropyrrolo[1,2-c]imidazol-2-yl)biphenyl-2-carbonitrile

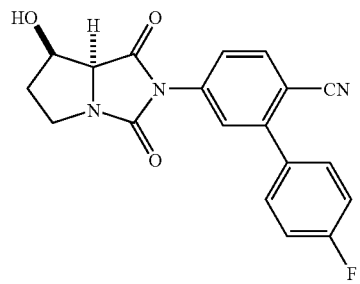

48A. 4-Cyano-3-(4-fluorophenyl)aniline

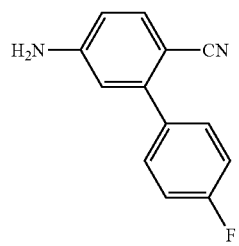

The title compound was prepared from commercially available 3-chloro-4-cyanoaniline in a similar fashion to that described in Experiment 47A and isolated as a yellow solid. LC/MS m/z 213 [M+H]$^+$.

48B. (7R,7aS)-4'-Fluoro-5-(7-hydroxy-1,3-dioxotetrahydropyrrolo[1,2-c]imidazol-2-yl)biphenyl-2-carbonitrile The title compound was prepared from compound 48A by procedures analogous to those described in Experiment 2E and 2F. HPLC: 99% at 3.32 min (retention time) (Conditions: YMC S5 C18 (4.6×50 mm); Eluted with 0% to 100% B, 8 min gradient, 3 min hold. (A=90% H$_2$O—10% MeOH—0.1% H$_3$PO$_4$ and B=10% H$_2$O—90% MeOH—0.1% H$_3$PO$_4$); Flow rate at 2.5 mL/min. UV detection at 220 nm.). LC/MS m/z 352 [M+H]$^+$.

EXAMPLE 49

(7R,7aS)-5-(7-Hydroxy-1,3-dioxotetrahydropyrrolo[1,2-c]imidazol-2-yl)-4'-methoxybiphenyl-2-carbonitrile

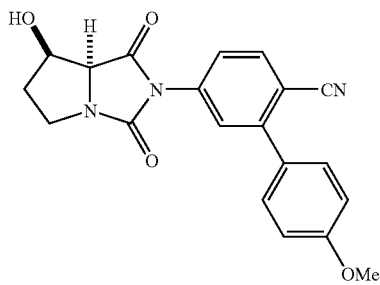

49A. 4-Cyano-3-(4-methoxyphenyl)aniline

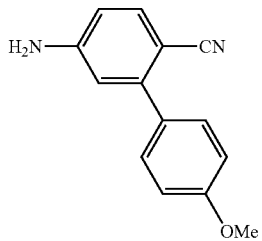

The title compound was prepared from commercially available 3-chloro-4-cyanoaniline in a manner similar to that described in Experiment 47A and isolated as a yellow solid. LC/MS m/z 225 [M+H]⁺.

49B. (7R,7aS)-5-(7-Hydroxy-1,3-dioxo-tetrahydro-pyrrolo[1,2-c]imidazol-2-yl)-4'-methoxybiphenyl-2-carbonitrile The title compound was prepared from compound 49A by procedures analogous to those described in Experiment 2E and 2F. HPLC: 96% at 3.24 min (retention time) (Conditions: YMC S5 C18 (4.6×50 mm); Eluted with 0% to 100% B, 8 min gradient, 3 min hold. (A=90% H₂O—10% MeOH—0.1% H₃PO₄ and B=10% H₂O—90% MeOH—0.1% H₃PO₄); Flow rate at 2.5 mL/min UV detection at 220 nm). LC/MS m/z 364 [M+H]⁺.

EXAMPLE 50

(7R,7aR)-7-(7-Hydroxy-1,3-dioxotetrahydropyrrolo[1,2-c]imidazol-2-yl)benzo[1,2,5]thiadiazole-4-carbonitrile

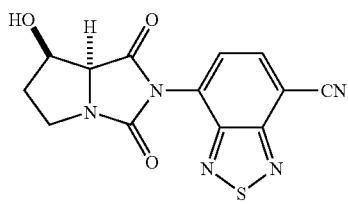

50A. 4-Cyano-7-amino-benzothiadiazole

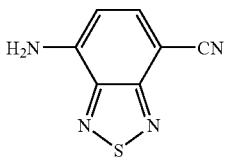

A solution of 2-cyano-5-nitrophenylenediamine (78 mg, 0.44 mmol, prepared as described in WO 0076501) in SOCl₂ (2 mL) was heated to reflux for 3 h. The resulting mixture was allowed to cool to rt and was then poured into ice/water. CH₂Cl₂ was added, the layers were separated and the aqueous layer was extracted twice with CH₂Cl₂. The combined organic phases were dried (MgSO₄), concentrated under reduced pressure and purified by flash chromatography on silica gel eluting with 50% EtOAc in hexanes to give 4-cyano-7-nitrobenzothiadiazole. This material was dissolved in AcOH (2 mL) containing EtOAc (1 mL) and H₂O (0.2 mL) and heated to 70° C. At this temperature, iron powder (78 mg, 1.41 mmol) was added in one portion and the dark mixture was stirred for 20 min before cooling to rt. The reaction mixture was then filtered through a pad of Celite® eluting with EtOAc, washed with saturated Na₂CO₃ solution, dried (MgSO₄) and concentrated under reduced pressure. Purification by flash chromatography on silica gel eluting with 20-70% EtOAc in hexanes afforded the title compound (47 mg, 67%) as a brown solid.

50B. (7R,7aR)-7-(7-Hydroxy-1,3-dioxotetrahydropyrrolo[1,2-c]imidazol-2-yl)benzo[1,2,5]thiadiazole-4-carbonitrile The title compound (12.2 mg) was prepared from compound 50A by procedures analogous to those described in Experiment 2E and 2F. HPLC: 99% at 1.57 min (retention time) (Conditions: Phenom. Luna. (4.6×50 mm); Eluted with 0% to 100% B, 4 min gradient, 1 min hold. (A=90% H₂O—10% MeOH—0.1% TFA and B=10% H₂O—90% MeOH—0.1% TFA); Flow rate at 4.0 mL/min UV detection at 220 nm). Chiral HPLC: retention time=22.68 min (98%); Conditions: OD (4.6×250 mm); Eluted with 25% isopropanol in hexane for 30 min at 1 mL/min; MS (ES) m/z 316 [M+1]⁺.

EXAMPLE 51

(7R,7aR)-2-Chloro-4-(7-hydroxy-3-oxotetrahydropyrrolo[1,2-c]imidazol-2-yl)3-methylbenzonitrile

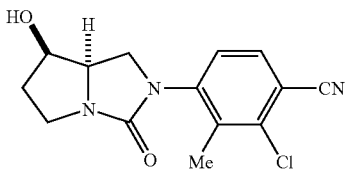

To a solution of compound 23G (150 mg, 0.5 mmol) in anhydrous THF (12 mL) cooled to −78° C. was added dropwise 1.0 M LiEt₃BH solution in THF (0.5 mL, 0.5 mmol). After addition, the reaction was stirred at −78° C. for 4 h, then quenched by addition of saturated aqueous Na₂CO₃ (5 mL). The reaction was warmed to 0° C., 30% H₂O₂ (~0.5 mL) was added, and the reaction was stirred at 0° C. for 30 min, then extracted with CH₂Cl₂ (3×). The combined extracts were washed with brine, dried (Na₂SO₄), filtered, and concentrated under reduced pressure overnight. The residue (~120 mg) was dissolved in anhydrous CH₂Cl₂, and to the resulting solution cooled to −78° C. was added dropwise triethylsilane (0.5 mL, 3.1 mmol), followed by boron trifluoride diethyl etherate (0.5 mL, 3.9 mmol). The reaction mixture was stirred at −78° C. for 2 h, then additional triethylsilane (0.3 mL, 1.88 mmol) and boron trifluoride diethyl etherate (0.3 mL, 2.35 mmol) were added, and the reaction was stirred at 0° C. overnight. The reaction was then quenched with saturated aqueous Na₂CO₃ (10 mL), then extracted with CH₂Cl₂ (3×). The combined extracts were washed with brine, dried (Na₂SO₄), filtered, and concentrated under reduced pressure to give a crude product (~100 mg). The crude product was purified using preparative HPLC to give 30 mg, which was further purified using chiral preparative HPLC to afford the title compound (9 mg). HPLC: 98% at 4.39 min (retention time) (Conditions: Zorbax SB C18 (4.6×75 mm); Eluted with 0% to 100% B, 8 min gradient (A=90% H₂O—10% MeOH—0.1% H₃PO₄ and B=10% H₂O—90% MeOH—0.1% H₃PO₄); Flow rate at 2.5 mL/min UV detection at 220 nm). Chiral HPLC: retention time=10.59 min (99%); Conditions: OD (4.6×250 mm); Eluted with 20% isopropanol in hexane for 30 min at 1 mL/min; MS (ES) m/z 292 [M+1]⁺.

Alternatively, the Compound of Example 51 can be prepared by the following sequence:

51A. (2S,3R)-3-(tert-Butyldimethylsilanyloxy)pyrrolidine-1,2-dicarboxylic acid 1-tert-butyl ester 2-methyl ester

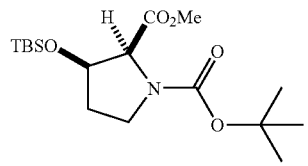

To a solution of (2S,3R)—N-tert-butyloxycarbonyl-3-hydroxy-2 pyrrolidinecarboxylic acid methyl ester (1D) (0.63 g, 2.56 mmol) in CH₂Cl₂ (12 mL) at rt was added imidazole (0.35 g, 5.14 mmol), and then tert-butydimethylsilyl chloride (0.43 g, 2.83 mmol). After stirring for 3 h, the reaction mixture was partitioned between H₂O and CH₂Cl₂. The CH₂Cl₂ layer was washed with 1 M H₃PO₄, NaHCO₃ and brine, dried (MgSO₄), then filtered and concentrated under reduced pressure. The residue was chromatographed (silica gel) eluting with 30% EtOAc/hexane to yield the title compound (0.91 g). LC/MS m/z 360 [M+H]⁺.

51B. (2R,3R)-3-(tert-Butyldimethylsilanyloxy)-2-hydroxymethylpyrrolidine-1-carboxylic acid tert-butyl ester

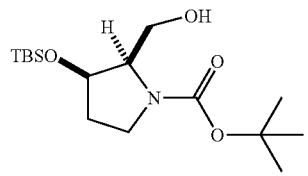

To (2S,3R)-3-(tert-Butyl-dimethyl-silanyloxy)-pyrrolidine-1,2-dicarboxylic acid 1-tert-butyl ester 2-methyl ester (51A) (8.05 g, 22.39 mmol) in THF (90 mL) at −78° C. was added a 1 M solution of Super-Hydride® in THF (112 mL, 112 mmol) in five portions over 15 min The cold bath was removed and the reaction was allowed to warm to rt. After 3 h, the reaction was poured into a 1-L Erlenmeyer flask and was carefully quenched with ice while stirring and then diluted with EtOAc. The layers were separated and the organic layer washed with 1 M H₃PO₄, NaHCO₃ and brine, dried (MgSO₄), filtered and concentrated. The residue was diluted with CH₂Cl₂, stirred with silica gel overnight, then concentrated and purified via flash chromatography eluting with 30% EtOAc/hexane to obtain the title compound (6.70 g) as a clear oil.

51C. (2S,3R)-3-(tert-Butyldimethylsilanyloxy)-2-formylpyrrolidine-1-carboxylic acid tert-butyl ester

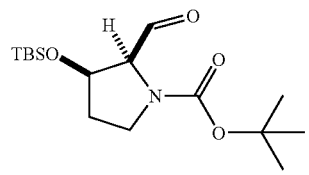

To (2R,3R)-3-(tert-Butyl-dimethyl-silanyloxy)-2-hydroxymethyl-pyrrolidine-1-carboxylic acid tert-butyl ester (51B) (6.70 g, 20.24 mmol) in CH₂Cl₂ (100 mL) at 0° C. was added Dess-Martin periodinane. The ice bath was removed and the reaction was warmed to rt. After 2 h, saturated aqueous Na₂S₂O₃ and NaHCO₃ (ca. 100 mL each) were added and the reaction mixture was stirred vigorously for 0.5 h. The layers were separated, the organic layer was washed with a mixture of saturated aqueous Na₂S₂O₃ and NaHCO₃ followed by brine, dried (MgSO₄), and was then filtered and concentrated to obtain the title compound (7.20 g) as a yellow oil.

51D. (2R,3R)—N-tert-Butyloxycarbonyl-3-(tert-butyldimethylsiloxy)-2-[(3-chloro-4-cyano-2-methylphenylamino) methyl]pyrrolidine

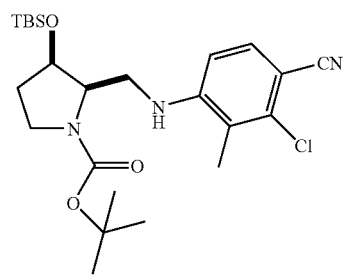

To a solution of (2S,3R)-3-(tert-Butyldimethylsilanyloxy)-2-formyl-pyrrolidine-1-carboxylic acid tert-butyl ester (51C) (661 mg, 2.0 mmol) in 5% DMF in CH₂Cl₂ (10 mL) at rt was added 4-amino-2-chloro-3-methyl-benzonitrile (340 mg, 2.04 mmol) followed by NaBH(OAc)₃ (636 mg, 3.0 mmol) and HOAc (180 μL, 3 mmol). The reaction was stirred under nitrogen at rt for 18 h. Additional portions of NaBH (OAc)₃ (424 mg, 2.0 mmol) and HOAc (120 μL, 2 mmol) were added, and the reaction was stirred for an additional 18 h. The reaction was diluted with EtOAc (50 mL) and the organic layer was washed with saturated aqueous NaHCO₃ (50 ml), dried (MgSO₄), filtered and concentrated. Purification via flash chromatography (silica gel, 0 to 15% EtOAc/hexanes) provided the title compound (605 mg, 1.26 mmol, 63%). MS m/z 480 [M+H]⁺.

51E. (2R,3R)-3-(tert-Butyldimethylsilanyloxy)-2-[(3-chloro-4-cyano-2-methylphenylamino)methyl]pyrrolidine-1-carboxylic acid tert-butyl ester

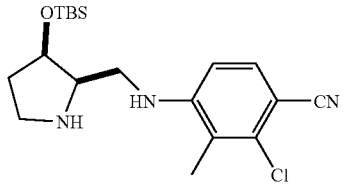

(2R,3R)—N-tert-Butyloxycarbonyl-3-(tert-butyldimethylsiloxy)-2-[(3-chloro-4-cyano-2-methylphenylamino)methyl]pyrrolidine (51D) (35 mg, 0.07 mmol) was dissolved in 50% TFA/CH$_2$Cl$_2$ and stirred for 2 h then concentrated. The residue was dissolved in EtOAc, saturated aqueous NaHCO$_3$ was added and the reaction mixture was stirred vigorously for 0.5 h. The layers were separated, and the organic layer was washed with NaHCO$_3$ and brine, dried (MgSO$_4$), filtered and concentrated to provide the title compound (22 mg) as a yellow film. LC/MS m/z 380 [M+H]$^+$.

51F. (7R,7aR)-2-Chloro-4-(7-hydroxy-3-oxotetrahydropyrrolo[1,2-c]imidazol-2-yl)-3-methylbenzonitrile

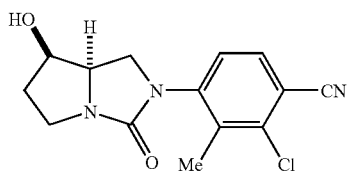

To a solution of (2R,3R)-3-(tert-Butyldimethylsilanyloxy)-2-[(3-chloro-4-cyano-2-methylphenylamino)methyl]pyrrolidine-1-carboxylic acid tert-butyl ester (51E) (22 mg, 0.06 mmol) dissolved in THF (1 mL) was added 1,1'-carbonyldiimidazole (9.40 mg, 0.06 mmol) and the mixture was stirred at rt for 3 days, and then brought to reflux for 1 h. An aliquot (~half of the reaction mixture) was treated with DBU (10 µL, 0.07 mmol) and the reaction mixture was heated at reflux overnight. The reaction was then diluted with EtOAc and water, and the layers were separated. The organic layer was washed with brine, concentrated under reduced pressure, and purified via preparative HPLC (Luna C-18, 21.2×100 mm, eluting with 60-100% solvent B (A=90% H$_2$O—10% MeOH—0.1% TFA and B=10% H$_2$O—90% MeOH—0.1% TFA) over 12 min; Flow rate at 20 mL/min. UV detection at 220 nm). The major peak was collected, concentrated and treated with TFA (2 mL) overnight. The reaction was concentrated and purified via preparative HPLC (Luna C-18, 21.2×100 mm, eluting with 40-100% solvent B (A=90% H$_2$O—10% MeOH—0.1% TFA and B=10% H$_2$O—90% MeOH—0.1% TFA) over 10 min; Flow rate at 20 mL/min. UV detection at 220 nm) to provide the title compound (1 mg). LC/MS m/z 292 [M+H]$^+$.

EXAMPLE 52

2-Chloro-4-[3,7-dioxotetrahydropyrrolo[1,2-c]imidazol-2-yl]-3-methylbenzonitrile

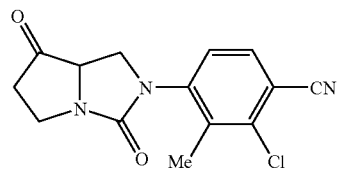

To a solution of compound 51 (0.02 g, 0.07 mmol) in CH$_2$Cl$_2$ (0.5 mL) was added a solution of Dess-Martin periodinane (0.038 g, 0.086 mmol) at rt. The reaction mixture was stirred at rt for 2 h. The reaction mixture was washed with NaHCO$_3$ (2×2 mL), brine, and dried (Na$_2$SO$_4$). The CH$_2$Cl$_2$ layer was then evaporated and the crude product was purified by preparative HPLC to yield 0.01 g of the title compound as a white powder. HPLC: 99% at 1.92 min; Conditions: Phenom. Luna C18 (4.6×50 mm); eluted with 0% to 100% B; 4 min gradient (A=90% H$_2$O—10% ACN—0.1% H$_3$PO$_4$ and B=10% H$_2$O—90% ACN—0.1% H$_3$PO$_4$; flow rate at 4 mL/min., UV detection at 220 nm. Chiral HPLC: 98% at 34.2 min; Conditions: (CHIRALPAK® OD column 4.6×250 mm; 25% isopropanol in hexane over 40 min at flow rate 1.0 mL/min, UV detection at 220 nm); MS (ES) m/z 299 [M+1]$^+$.

EXAMPLES 53a and 53b

2-Chloro-4-(8-hydroxy-1,3-dioxohexahydroimidazo[1,5-a]pyridin-2-yl)-3-methylbenzonitrile

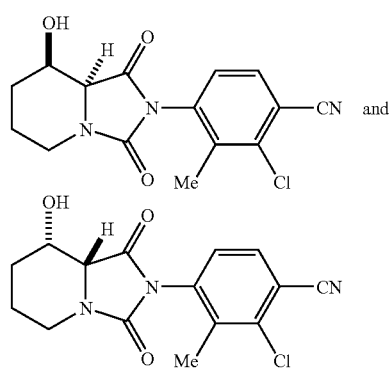

53A. (±)-cis-3-hydroxypyridine-2-carboxylic acid

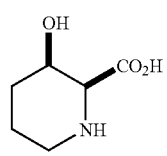

A sample of Rh(OH)$_3$ was prepared according to the procedure described in *Tetrahedron Lett.* 1967, 17, 1663-1664.

The 3-hydroxypyridine-2-carboxylic acid (0.5 g, 3.6 mmol) was dissolved in aqueous NH₄OH and then added H₂O in a ratio of 1 to 7. Rh(OH)₃ (0.2 g) was added and the reaction mixture was stirred at rt under 70-80 psi of H₂ for 4 h. The catalyst was filtered through a cake of celite and the filtrate was evaporated under reduced pressure to afford compound 53A (0.50 g) as a white foam.

53B. (±)-cis-3-Hydoxypiperidine-2-carboxylic acid methyl ester

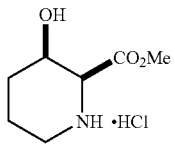

Hydrogen chloride gas was bubbled through a suspension of 3-hydroxy-piperidine-2-carboxylic acid (0.54 g, 0.370 mol) in MeOH (100 mL) cooled to 0° C. for 10 min. The resulting clear solution was stirred at rt for 4 h, then evaporated carefully under reduced pressure (white precipitates formed during the concentration). The resulting white solid was dried overnight under vacuum to afford 0.86 g of the title compound as an off-white powder.

53C. 2-Chloro-4-(8-hydroxy-1,3-dioxohexahydroimidazo[1,5-a]pyridin-2-yl)-3-methylbenzonitrile To a suspension of compound 53B (0.20 g, 0.77 mmol) in CH₂Cl₂ (3 mL) cooled to 0° C. was added i-Pr₂EtN (0.178 mL, 1.00 mmol). After stirring at 0° C. for 20 min, compound 23E (0.095 g, 0.59 mmol) in CH₂Cl₂ (1 mL) solution was added, along with 4 Å molecular sieves (0.5 g), and the resulting mixture stirred at rt until urea formation was completed (~2 h). The mixture was then stirred at rt until hydantoin formation was complete (~15 h). The reaction mixture was loaded on a silica gel column, eluted with 40% EtOAc/hexane, and 5% MeOH in EtOAc/hexane (1:1) to afford 0.11 g of the title compound as an off-white powder. HPLC: 99% at 1.67-1.79 min; Conditions: Phenom. Luna C18 (4.6×50 mm); Eluted with 0% to 100% B; 4 min gradient (A=90% H₂O—10% ACN—0.1% H₃PO₄ and B=10% H₂O—90% ACN—0.1% H₃PO₄), Flow rate at 4 mL/min., UV detection at 220 nm). The compound was further loaded on a Chiral AD column, eluted with 25% isopropanol in hexane isocratic to afford 50 mg each of enantiomer 53a (isomer A; retention time=14.2 min; 100% e.e.) and enantiomer 53b (isomer B; retention time=20 min; 100% e.e.) of the title compound as white powders. Chiral HPLC Conditions: (CHIRALPAK® AD column 4.6×250 mm; 25% isopropanol in hexane over 30 min at flow rate 1.0 mL/min, UV detection at 220 nm); MS (ES) m/z 320 [M+1]⁺.

EXAMPLE 54

(7S,7aS)-2-Chloro-4-(7-hydroxy-1,3-dioxotetrahydropyrrolo[1,2-c]imidazol-2-yl)-3-methylbenzonitrile

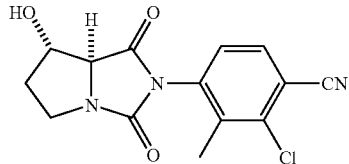

54A. (2S,3S)-1-(3-Chloro-4-cyano-2-methylphenylcarbamoyl)-3-hydroxy-pyrrolidine-2-carboxylic acid methyl ester.

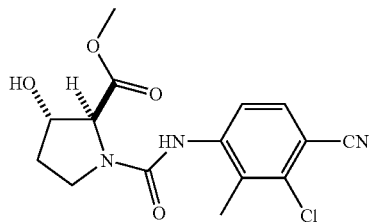

To a suspension of trans-3-hydroxyproline methyl ester, HCl salt (207 mg, 1.14 mmol) in 1.5 mL of CH₂Cl₂ cooled to 0° C. was added diisopropylethylamine (0.23 mL, 1.30 mmol) followed by a suspension of isocyanate 23E (200 mg, 1.04 mmol) in 2 mL of CH₂Cl₂. The suspension was allowed to warm to rt and stir for 1 h. The reaction mixture was then washed with water, and a solid precipitated which was filtered and dried under vacuum to afford the title compound (210 mg) as a white solid. ¹H NMR (CD₃OD) 1.98-2.01 (m, 1H), 2.13-2.17 (m, 1H), 2.30 (s, 3H), 3.69-3.72 (m, 5H), 4.36 (br s, 1H), 4.40 (br s, 1H), 7.41 (d, J=8.80, 1H), 7.55 (d, J=8.25, 1H); ¹³C NMR (CD₃OD) 15.88, 33.72, 45.64, 52.94, 69.50, 74.55, 110.62, 117.41, 125.65, 132.36, 134.44, 137.83, 144.33, 156.43, 172.88; HPLC a) column: Phenominex C18 4.6×50 mm, 4 min gradient, 10% MeOH/90% H₂O/0.1% TFA to 90% MeOH/10% H₂O/0.1% TFA; 1 min hold, 4 mL/min UV detection at 220 nm, 2.30 min retention time; HPLC b) column: Shimadzu Shim-Pack VP-ODS C18 4.6×50 mm, 4 min gradient, 10% MeOH/90% H₂O/0.1% TFA to 90% MeOH/10% H₂O/0.1% TFA, 1 min hold; 4 mL/min, UV detection at 220 nm, 2.13 min retention time (97%); HPLC c) column: Daicel Chiralcel OD 4.6×250 mm, Isocratic 25% Isopropanol/Hexanes, 30 min, 1 mL/min, UV detection at 220 nm, 9.03 min retention time (98%); MS (ES) m/z 338 [M+H]⁺.

54B. (2S,3S)-1-(3-Chloro-4-cyano-2-methylphenylcarbamoyl)-3-hydroxy-pyrrolidine-2-carboxylic acid

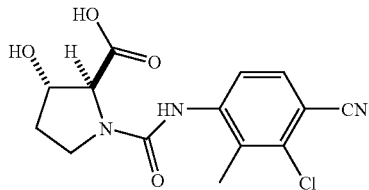

A suspension of ester 54A (260 mg, 0.770 mmol) in 20 mL of 1.6 N NaOH was stirred at rt for 45 min. The reaction mixture was acidified to pH 2 with 10% HCl and extracted with EtOAc (3×). The combined organic layers were dried (MgSO$_4$), filtered and the filtrate concentrated under reduced pressure to afford the title compound (260 mg) as a beige solid. A portion (50 mg) of the residue was purified by preparative HPLC (reverse phase silica gel, 10% MeOH/90% H$_2$O/0.1% TFA to 90% MeOH/10% H$_2$O/0.1% TFA) to afford the title compound (25 mg) as a colorless oil. $^1$H NMR (CD$_3$OD) 2.02-2.05 (m, 1H), 2.17-2.22 (m, 1H), 2.35 (s, 3H), 3.73-3.76 (m, 2H), 4.40 (br s, 1H), 4.49 (br s, 1H), 7.47 (d, J=8.80, 1H), 7.58 (d, J=8.25, 1H); $^{13}$C NMR (CD$_3$OD) 15.83, 33.59, 45.61, 69.53, 74.73, 110.40, 117.45, 125.45, 132.34, 137.80, 144.42, 156.50, 159.95, 173.94; HPLC a) column: Phenominex ODS C18 4.6×50 mm, 4 min gradient, 10% MeOH/90% H$_2$O/0.1% TFA to 90% MeOH/10% H$_2$O/0.1% TFA; 1 min hold, 4 mL/min UV detection at 220 nm, 1.97 min retention time; HPLC b) column: Shimadzu Shim-Pack VP-ODS C18 4.6×50 mm, 4 min gradient, 10% MeOH/90% H$_2$O/0.1% TFA to 90% MeOH/10% H$_2$O/0.1% TFA, 1 min hold; 4 mL/min, UV detection at 220 nm, 1.79 min retention time (92%); HPLC c) column: Daicel Chiralcel OD 4.6×250 mm, Isocratic 25% isopropanol/hexanes, 30 min, 1 mL/min, UV detection at 220 nm, 6.96 min retention time (98%); MS (ES) m/z 324 [M+H]$^+$.

54C. (7S,7aS)-2-Chloro-4-(7-hydroxy-1,3-dioxotetrahydropyrrolo[1,2-c]imidazol-2-yl)-3-methylbenzonitrile.

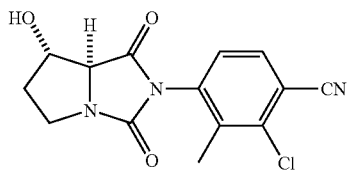

To a suspension of acid 54B (210 mg, 0.649 mmol) in 15 mL of acetonitrile at rt was added DCC (134 mg, 0.649 mmol) followed by p-nitrophenol (180 mg, 1.30 mmol). The suspension was refluxed for 1 h, cooled to rt and filtered. The filtrate was concentrated under reduced pressure and the residue dissolved in EtOAc, washed with water and brine, dried (MgSO$_4$), filtered and concentrated under reduced pressure. The residue was purified by flash chromatography (silica gel, EtOAc/hexanes, 75:25) to afford the title compound (121 mg) as a white foam. $^1$H NMR (CD$_3$OD) 1.94-2.05 (m, 1H), 2.18, 2.22 (s, 3H), 2.24-2.33 (m, 1H), 3.34-3.40 (m, 1H), 3.67-3.75 (m, 1H), 4.08, 4.16 (d, J=6.05, 1H), 4.35, 4.42 (m, 1H), 7.33, 7.38 (d, J=8.25, 1H), 7.70 (m, 1H); $^{13}$C NMR (CD$_3$OD) 15.90, 16.11, 36.95, 37.05, 44.88, 45.06, 70.91, 70.94, 72.46, 72.90, 115.19, 115.53, 116.60, 116.66, 129.30, 129.46, 132.74, 133.03, 137.41, 137.61, 138.08, 138.37, 138.42, 138.53, 159.69, 159.97, 172.10, 172.43; HPLC a) column: Phenominex LUNA C18 4.6×50 mm, 4 min gradient, 10% MeOH/90% H$_2$O/0.1% TFA to 90% MeOH/10% H$_2$O/0.1% TFA; 1 min hold, 4 mL/min UV detection at 220 nm, 2.32 min retention time; HPLC b) column: Shimadzu Shim-Pack VP-ODS C18 4.6×50 mm, 4 min gradient, 10% MeOH/90% H$_2$O/0.1% TFA to 90% MeOH/10% H$_2$O/0.1% TFA, 1 min hold; 4 mL/min, UV detection at 220 nm, 2.15 min retention time (100%); HPLC c) column: Daicel Chiralcel OD 4.6×250 mm, Isocratic 25% Isopropanol/Hexanes, 30 min, 1 mL/min, UV detection at 220 nm, 17.65 min retention time (99%); MS (ES) m/z 306 [M+H]$^+$.

EXAMPLE 55

2-Chloro-4-[(7S,7aR)-7-hydroxy-3-oxo-tetrahydro-1H-pyrrolo[1,2-c]imidazol-2(3H)-yl]-3-methylbenzonitrile

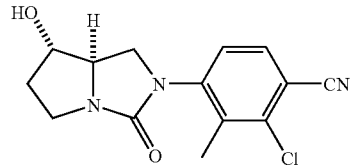

55A. Methyl-(2S,3S)-1-{[(3-Chloro-4-cyano-2-methylphenyl)amino]-carbonyl}-3-hydroxypyrrolidine-2-carboxylate

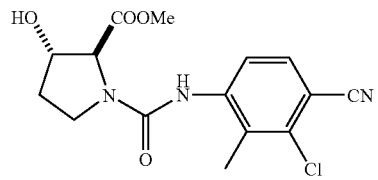

A solution of ester 1A (500 mg, 2.75 mmol) in dry CH$_2$Cl$_2$ (10 mL) was cooled to 0° C., treated with Hunig's base (0.53 mL, 3.04 mmol) and stirred at 0° C. for 30 min. The solution was treated with isocyanate 23E (505 mg, 2.62 mmol), and the resulting suspension was stirred at rt for 3 h. The insoluble solids were filtered off and the filtrate was partitioned between aqueous NH$_4$Cl (6.0 mL) and CH$_2$Cl$_2$ (3×60 mL). The combined organic phases were washed with brine, dried (Na$_2$SO$_4$), filtered and concentrated under reduced pressure. The residue and insoluble solids were combined and chromatographed (silica gel; EtOAc/hexane gradient) to yield the title compound (177.2 mg, 75.3%) as a white solid, mp 189-191° C. HPLC: 1.72 min (retention time) (Conditions: YMC S-5 C-18 (4.6×50 mm), eluting with 0-100% B, 4 min gradient. (A=90% H$_2$O—10% CH$_3$CN—0.1% TFA and B=10% H$_2$O—90% CH$_3$CN—0.1% TFA); Flow rate at 4 mL/min. UV detection at 220 nm). Chiral HPLC: retention time=22.2 min (100%); Conditions: AD (4.6×250 mm); Eluted with 20% isopropanol in heptane for 30 min at 1 mL/min. MS (ES) m/z 338 [M+H]$^+$.

55B. Methyl-(2S,3S)-1-{[(3-chloro-4-cyano-2-methylphenyl)amino]-carbonyl}-3-(tert-butyl-dimethylsilanyloxy)-pyrrolidine-2-carboxylate

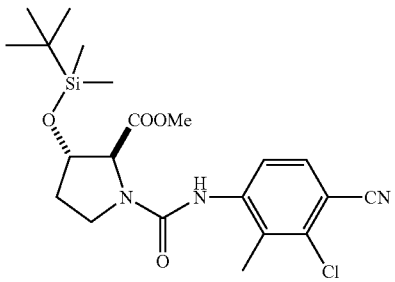

A cooled (0° C.) solution of compound 55A (510.1 mg, 1.51 mmol) and imidazole (516 mg, 7.58 mmol) in dry DMF (2.6 mL) was treated with 97% tert-butyldimethylsilyl chloride (572 mg, 3.68 mmol), stirred at 0° C. for 5 min then at rt for 24 h. Methanol (3.5 mL) was added and the solution stirred at rt for another 24 h. The mixture was partitioned between 10% citric acid (5.3 mL) and EtOAc (3×50 mL). The combined organic phases were washed with brine, dried (Na$_2$SO$_4$), filtered and concentrated under reduced pressure. The resulting syrup was chromatographed (silica gel; EtOAc/hexane gradient) to yield the title compound (732.3 mg, 100%) as a white solid, mp 123-125° C. HPLC: 3.38 min (retention time) (Conditions: YMC S-5 C-18 (4.6×50 mm), eluting with 0-100% B, 4 min gradient. (A=90% H$_2$O—10% CH$_3$CN—0.1% TFA and B=10% H$_2$O—90% CH$_3$CN—0.1% TFA); Flow rate at 4 mL/min. UV detection at 220 nm. Chiral HPLC: retention time=9.30 min (98.6%); Conditions: AD (4.6×250 mm); Eluted with 20% isopropanol in heptane for 30 min at 1 mL/min. MS (ES) m/z 452 [M+H]$^+$.

55C. (2R,3S)—N-(3-Chloro-4-cyano-2-methylphenyl)3-(tert-butyldimethylsilanyloxy)-2-(hydroxymethyl)pyrrolidine-1-carboxamide

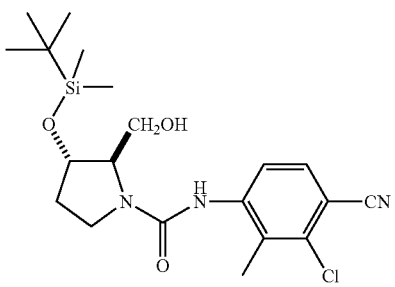

To a solution of compound 55B (300 mg, 0.66 mmol) in anhydrous THF (6.7 mL) at −25° C. was added 1 N LAH in THF (1.34 mL, 1.34 mmol) over a period of 10 min. The solution was then warmed to 0° C. and stirred for 2.0 h before quenching with H$_2$O (0.05 mL), 15% NaOH (0.05 mL) and H$_2$O (0.16 mL). After warming to rt, the mixture was extracted with EtOAc (2×40 mL). The combined organic phases were washed with brine, dried (Na$_2$SO$_4$), filtered and concentrated under reduced pressure. The resultant off-white solid was chromatographed (silica gel; EtOAc/hexane gradient) to yield the title compound (217.2 mg, 78%) as a white solid, mp 174-176° C. HPLC: 3.23 min (retention time) (Conditions: YMC S-5 C-18 (4.6×50 mm), eluting with 0-100% B, 4 min gradient. (A=90% H$_2$O—10% CH$_3$CN—0.1% TFA and B=10% H$_2$O—90% CH$_3$CN—0.1% TFA); Flow rate at 4 mL/min. UV detection at 220 nm. Chiral HPLC: retention time=7.11 min (96.1%); Conditions: AD (4.6×250 mm); Eluted with 20% isopropanol in heptane for 30 min at 1 mL/min. MS (ES) m/z 424 [M+H]$^+$.

55D. 2-Chloro-4-[(7S,7aR)-7-(tert-butyldimethylsilanyloxy)-3-oxo-tetrahydro-1H-pyrrolo[1,2c]imidazol-2-(3H)yl]methylbenzonitrile

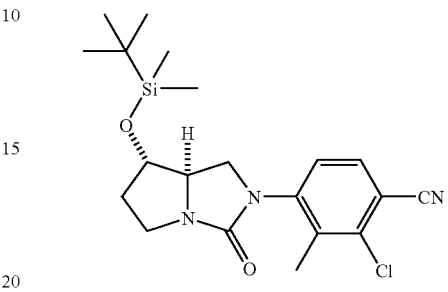

A solution of compound 55C (150 mg, 0.35 mmol) in anhydrous THF (4.8 mL) at 0° C. was treated with 97% tert-BuOK (104.2 mg, 0.86 mmol) and stirred at 0° C. for 5 min. To the solution was added a solution of toluenesulfonyl chloride (81.6 mg, 0.43 mmol) in anhydrous THF, and the mixture was stirred at 0° C. for another 10 min as described in by Taek Heon Kim and Gue-Jae Lee *J. Org. Chem.* 64, 2941-2943 (1999). The reaction mixture was then quenched with H$_2$O (4.8 mL), removed from the bath and extracted with EtOAc (2×15 mL). The combined organic phases were dried (Na$_2$SO$_4$), filtered and concentrated under reduced pressure. The residue was chromatographed (silica gel; EtOAc/hexane gradient) to yield the title compound (128.9 mg, 90%) as a white foam. HPLC: 3.61 min (retention time) (Conditions: YMC S-5 C-18 (4.6×50 mm), eluting with 0-100% B, 4 min gradient. (A=90% H$_2$O—10% CH$_3$CN—0.1% TFA and B=10% H$_2$O—90% CH$_3$CN—0.1% TFA); Flow rate at 4 mL/min. UV detection at 220 nm. Chiral HPLC: retention time=9.54 min (99.3%); Conditions: AD (4.6×250 mm); Eluted with 20% isopropanol in heptane for 30 min at 1 mL/min. MS (ES) m/z 406 [M+H]$^+$.

55E. 2-Chloro-4-[(7S,7aR)-7-hydroxy-3-oxotetrahydro-1H-pyrrolo[1,2-c]imidazol-2(3H)-yl]-3-methylbenzonitrile.

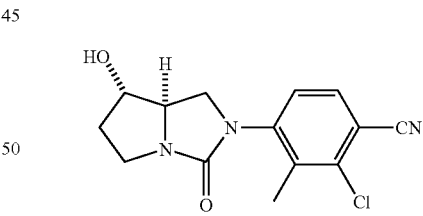

To a solution of compound 55D (112.4 mg, 0.28 mmol) in anhydrous THF (5.0 mL) at 0° C. was added 1.0 M TBAF in THF (0.32 mL, 0.32 mmol). The solution was stirred at 0° C. for 10 min, at rt for 19 h, then partitioned between 25% NH$_4$Cl (7.0 mL) and EtOAc (3×40 mL). The combined organic phases were washed with brine, dried (Na$_2$SO$_4$), filtered and concentrated under reduced pressure. The resultant off-white solid was chromatographed (silica gel; EtOAc/hexane gradient) to yield the title compound (77.4 mg, 95%) as a white solid, mp 148-149° C. HPLC: 5.4 min (retention time) (Conditions: Zorbax C-18 (4.6×75 mm), eluting with 0-100% B, 8 min gradient. (A=90% H$_2$O—10% CH$_3$OH—0.2% H$_3$PO$_4$ and B=10% H$_2$O—90% CH$_3$OH—0.2% H$_3$PO$_4$); Flow rate at 2.5 mL/min. UV detection at 220 nm. Chiral HPLC: retention time=19.9 min (99.7%); Conditions: AD (4.6×250 mm); Eluted with 20% isopropanol in heptane for 30 min at 1 mL/min. MS (ES) m/z 290 [M−H]⁻.

EXAMPLE 56

2-Chloro-4-[(6R,7aS)-6-hydroxy-3-oxotetrahydropyrrolo[1,2-c]imidazol-2(3H)-yl]-3-methylbenzonitrile.

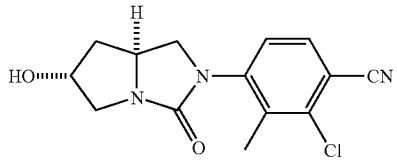

56A. 4-Hydroxypyrrolidine-2-carboxylic acid methyl ester, hydrochloride salt

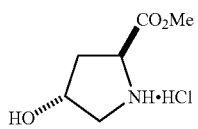

The title compound was prepared from trans-4-hydroxy-L-proline (5.0 g, 38.1 mmol) by procedures analogous to those described for Example 1A to afford a white solid (6.97 g, 100%), mp 164-166° C.

56B. Methyl (2S,4R)-1-{[(3-Chloro-4-cyano-2-methylphenyl)amino]-carbonyl}-4-hydroxypyrrolidine-2-carboxylate

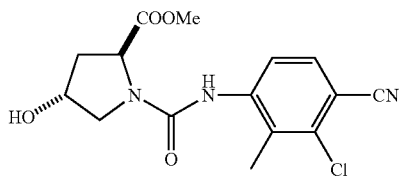

The title compound was prepared from compound 56A (300 mg, 1.65 mmol) and isocyanate 23E (312 mg, 1.62 mmol) by procedures analogous to that described for Example 55A to afford a white foam (375.6 mg, 69%). HPLC: 1.68 min (retention time) (Conditions: YMC S-5 C-18 (4.6×250 mm), eluting with 0-100% B, 4 min gradient. (A=90% H₂O—10% CH₃CN—0.1% TFA and B=10% H₂O—90% CH₃CN—0.1% TFA); Flow rate at 4 mL/min. UV detection at 220 nm. Chiral HPLC: retention time=12.92 min (98.9%); Conditions: AD (4.6×250 mm); Eluted with 20% isopropanol in heptane for 30 min at 1 mL/min. MS (ES) m/z 338 [M+H]⁺.

56C. Methyl (2S,4R)-1-{[(3-chloro-4-cyano-2-methylphenyl)amino]-carbonyl}4-(tert-butyldimethylsilanyloxy)pyrrolidine-2-carboxylate.

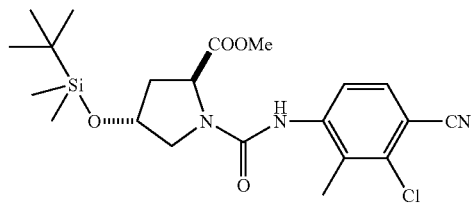

The title compound was prepared from compound 56B (150 mg, 0.44 mmol) in a manner analogous to that described for compound 55B to afford a white solid (156.3 mg, 79%), mp 129-131° C. HPLC: 3.38 min (retention time) (Conditions: YMC S-5 C-18 (4.6×250 mm), eluting with 0-100% B, 4 min gradient. (A=90% H₂O—10% CH₃CN—0.1% TFA and B=10% H₂O—90% CH₃CN—0.1% TFA); Flow rate at 4 mL/min. UV detection at 220 nm. Chiral HPLC: retention time=9.80 min (99.9%); Conditions: AD (4.6×250 mm); Eluted with 20% isopropanol in heptane for 30 min at 1 mL/min. MS (ES) m/z 452 [M+H]⁺.

56D. (2S,4R)—N-(3-Chloro-4-cyano-2-methylphenyl)-4-(tert-butyldimethylsilanyloxy)-2-(hydroxymethyl)pyrrolidine-1-carboxamide

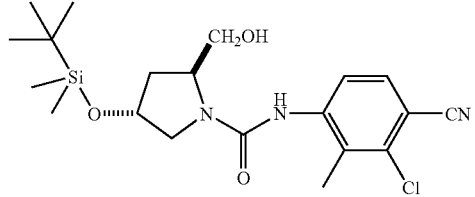

To a solution of compound 56C (145 mg, 0.32 mmol) in anhydrous THF (3.0 mL) at 0° C. was added dropwise a solution of 2 M LiBH₄ in THF (0.24 ml, 0.48 mmol) as described by Terry Rosen et. al. *J. Med. Chem.* 31 (8), 1598-1611 (1988). The solution was stirred at 0° C. for 2.5 h, quenched with 1.0 M K₂CO₃ (1.0 mL) and extracted with EtOAc (2×25 mL). The combined organic phases were washed with 1 M K₂CO₃, brine, dried (Na₂SO₄), filtered and concentrated under reduced pressure. The residue was chromatographed (silica gel; EtOAc/hexane gradient) to yield the title compound (125.4 mg, 93%) as a white solid, mp 169-171° C. HPLC: 3.31 min (retention time) (Conditions: YMC S-5 C-18 (4.6×250 mm), eluting with 0-100% B, 4 min gradient. (A=90% H₂O—10% CH₃CN—0.1% TFA and B=10% H₂O—90% CH₃CN—0.1% TFA); Flow rate at 4 mL/min. UV detection at 220 nm. Chiral HPLC: retention time=7.01 min (99.96%); Conditions: AD (4.6×250 mm); Eluted with 20% isopropanol in heptane for 30 min at 1 mL/min. MS (ES) m/z 424 [M+H]⁺.

56E. 2-Chloro-4-[(6R,7aS)-6-(tert-butyldimethylsilanyloxy)-3-oxotetrahydro-1H-pyrrolo[1,2-c]imidazol-2(3H)-yl]-3-methylbenzonitrile

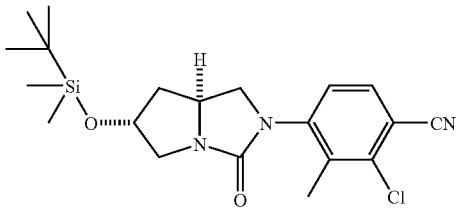

The title compound was prepared from compound 56D (124 mg, 0.29 mmol) in a manner analogous to that described for compound 1E to give a colorless syrup (104.9 mg, 89%). HPLC: 3.58 min (retention time) (Conditions: YMC S-5 C-18 (4.6×250 mm), eluting with 0-100% B, 4 min gradient. (A=90% H₂O—10% CH₃CN—0.1% TFA and B=10% H₂O—90% CH₃CN—0.1% TFA); Flow rate at 4 mL/min. UV detection at 220 nm. Chiral HPLC: retention time=12.53 min (99.96%); Conditions: AD (4.6×250 mm); Eluted with 20% isopropanol in heptane for 30 min at 1 mL/min. MS (ES) m/z 406 [M+H]⁺.

56F. 2-Chloro-4-[(6R,7aS)-6-hydroxy-3-oxotetrahydropyrrolo[1,2-c]imidazol-2(3H)-yl]-3-methylbenzonitrile

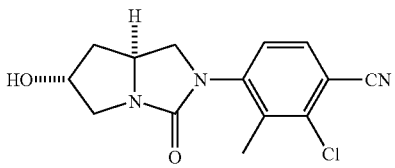

The title compound was prepared from compound 56E (95.9 mg, 0.24 mmol) in a manner analogous to that described for compound 1E to give a white foam (69.8 mg, 100%). HPLC: 1.66 min (retention time) (Conditions: YMC S-5 C-18 (4.6×250 mm), eluting with 0-100% B, 4 min gradient. (A=90% H₂O—10% CH₃CN—0.1% TFA and B=10% H₂O—90% CH₃CN—0.1% TFA); Flow rate at 4 mL/min. UV detection at 220 nm. Chiral HPLC: retention time=15.42 min (100%); Conditions: AD (4.6×250 mm); Eluted with 20% isopropanol in heptane for 30 min at 1 mL/min. MS (ES) m/z 290 [M−H]⁻.

EXAMPLE 57

(7S,7aS)-2-Chloro-4-(7-hydroxy-3-oxotetrahydropyrrolo[1,2-c]imidazol-2-yl)-3-methylbenzonitrile

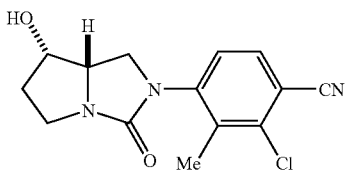

To a suspension of (7S,7aR)-2-Chloro-4-(7-hydroxy-1,3-dioxotetrahydropyrrolo[1,2-c]imidazol-2-yl)-3-methylbenzonitrile (23C) (5.00 g, 16.36 mmol) in THF (164 mL) was added LAH (620 mg, 16.34 mmol) in two portions. After 30 min, the reaction was quenched by the slow addition of the following: water (0.62 mL) in THF (2 mL), 1.86 mL 15% aqueous NaOH, then 1.86 mL water in THF (2 mL). After stirring for 15 min, the reaction was filtered through celite, washed with EtOAc, and concentrated under reduced pressure to obtain 4.45 g of a yellow foam. The foam was taken up in CH₂Cl₂ (142 mL) and cooled to −78° C. Triethylsilane (4.50 mL, 28.17 mmol) and boron trifluoride diethyl etherate (3.60 mL, 28.41 mmol) were then added and the cold bath was removed. After stirring for 1.5 h, the reaction mixture was poured into saturated aqueous NaHCO₃ and the layers were separated. The organic layer was dried (MgSO₄), filtered, concentrated under reduced pressure, and then purified using preparative HPLC (YMC ODS C-18, 30×250 mm, eluting with 50-70% solvent B (A=90% H₂O—10% MeOH—0.1% TFA and B=10% H₂O—90% MeOH—0.1% TFA) over 30 min; Flow rate at 20 mL/min. UV detection at 220 nm) to provide a white solid (ca. 1 g). The solid was further purified by several recrystallizations (first from MeOH/H₂O then EtOH until purity >99% by ¹H NMR) to provide 236 mg of the desired racemic product as white needles. A portion of this material (28 mg) was further purified using chiral preparative HPLC (Chiracel OD, 5×50 cm, eluting with 20% isopropanol/hexane, Flow rate=56 mL/min, UV detection at 220 nm) to afford 57 (6.8 mg) (Chiral HPLC: retention time=10.68 min; Daicel Chiralcel OD, 4.6×250 mm, eluting with 20% isopropanol in hexane over 30 min; Flow rate at 1 mL/min, UV detection at 220 nm; LC/MS m/z 292 [M+1]⁺) and 11.5 mg of a white solid which was purified by chiral preparative HPLC as above followed by preparative HPLC to provide the title compound (3.3 mg) (Chiral HPLC: retention time=12.91 min; Daicel Chiralcel OD, 4.6×250 mm, eluting with 20% isopropanol/hexane over 30 min; Flow rate at 1 mL/min, UV detection at 220 nm). LC/MS m/z 292 [M+1]⁺.

EXAMPLE 58

(7R,7aR)-Chloro-4-(7-hydroxy-7a-methyl-3-oxotetrahydropyrrolo-[1,2c]imidazol-2-yl)-3-methylbenzonitrile

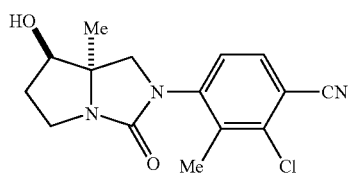

58A. (2S,3R)-3-(tert-Butyldimethylsilanyloxy)-2-methylpyrrolidine-1,2-dicarboxylic acid 1-tert-butyl ester-2-methyl ester

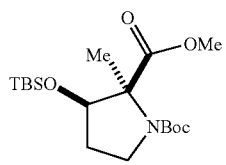

To a solution of (2S,3R)-3-Hydroxy-2-methylpyrrolidine-1,2-dicarboxylic acid 1-tert-butyl ester-2-methyl ester (25A) (362 mg, 1.39 mmol) in CH₂Cl₂ (4 mL) was added imidazole (284 mg, 4.17 mmol) then tert-butydimethylsilyl chloride (1.05 g, 6.95 mmol). After stirring overnight, the reaction was partitioned between H₂O and CH₂Cl₂. The CH₂Cl₂ layer was washed with 1M H₃PO₄ (2×) and brine, dried (MgSO₄), then filtered and concentrated under reduced pressure. The residue was chromatographed (silica gel) eluting with 30% EtOAc/hexane to yield the title compound (456 mg) as a white solid.

58B. (2R,3R)-3-(tert-Butyldimethylsilanyloxy)-2-hydroxymethyl-2-methylpyrrolidine-1-carboxylic acid tert-butyl ester

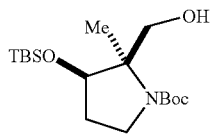

To a solution of (2S,3R)-3-(tert-Butyldimethylsilanyloxy)-2-methylpyrrolidine-1,2-dicarboxylic acid 1-tert-butyl ester-2-methyl ester (58A) (1.08 g, 2.90 mmol) in THF (12 mL) at −78° C. was added a 1 M solution of Super-Hydride® in THF (14.50 mL, 14.50 mmol) in three portions over 15 min. After 10 min, the cold bath was removed and the reaction was allowed to warm to rt and was stirred for 18 h. The reaction was cooled again to −78° C. and more Super-Hydride® (7 mL) was added. After stirring an additional 24 h, the reaction was poured into a 1-L Erlenmeyer flask containing ice water and was then diluted with EtOAc. The layers were separated and the organic layer washed with 1 M H₃PO₄ (2×), NaHCO₃ and brine, dried (MgSO₄), filtered and concentrated under reduced pressure. The residue was diluted with CH₂Cl₂, stirred with silica gel for 10 min, then concentrated under reduced pressure and purified via flash chromatography, eluting with 20% EtOAc/hexane to obtain the title compound (0.54 g) as a clear oil. MS m/z 346 [M+H]⁺.

58C. (2R,3R)-[3-(tert-Butyldimethylsilanyloxy)-2-methylpyrrolidin-2-yl]methanol trifluoroacetic acid salt

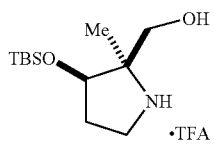

(2R,3R)-3-(tert-Butyldimethyl-silanyloxy)-2-hydroxymethyl-2-methylpyrrolidine-1-carboxylic acid tert-butyl ester (58B) (269 mg, 0.78 mmol) was stirred in 17% TFA/CH₂Cl₂ (6 mL) for 30 min. The reaction was concentrated to provide a brown oil (334 mg). LC/MS m/z 246 [M+H]⁺

58D. (2R,3R)-3-(tert-Butyldimethylsilanyloxy)-2-hydroxymethyl-2-methylpyrrolidine-1-carboxylic acid (3-chloro-4-cyano-2-methyl-phenyl)-amide

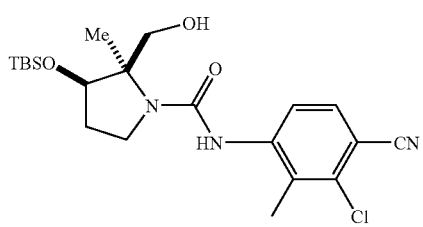

To a solution of (2R,3R)-[3-(tert-Butyldimethylsilanyloxy)-2-methylpyrrolidin-2-yl]methanol trifluoroacetic acid salt (58C) (167 mg, 0.61 mmol) in CH₂Cl₂ (2.5 mL) at 0° C. were added molecular sieves followed by Hunig's base (0.21 mL, 1.22 mL). After stirring for 15 min, 2-Chloro-4-isocyanato-3-methylbenzonitrile (23A) was added and the ice bath was removed. After 10 min, the reaction was stirred for 2 h and then diluted with water and CH₂Cl₂. The layers were separated and the organic layer was washed with brine, dried (MgSO₄), filtered and concentrated. The resulting solid was purified via preparative HPLC (Luna C-18, 250×21.2 mm, eluting with 60-100% solvent B (A=90% H₂O—10% MeOH—0.1% TFA and B=10% H₂O—90% MeOH—0.1% TFA) over 15 min; Flow rate at 10 mL/min; UV detection at 220 nm) to provide the title compound (17 mg) as a white film (LC/MS m/z 438 [M+H]⁺) and di-acylated product (80 mg) as a white solid (LC/MS m/z 630 [M+H]⁺). The di-acylated product (80 mg, 0.13 mmol) was dissolved in EtOH (2 mL) and treated with 21% NaOEt (48 □L, 0.13 mmol) at rt for 4 h. The reaction was concentrated under reduced pressue then diluted with water and EtOAc. The layers were separated, and the aqueous layer acidified with 1 N HCl then re-extracted with EtOAc. The combined organic layers were washed with brine, dried (MgSO₄), filtered and concentrated under reduced pressure. The residue was purified via preparative HPLC (Luna C-18, 100×21.2 mm, eluting with 40-100% solvent B (A=90% H₂O—10% MeOH—0.1% TFA and B=10% H₂O—90% MeOH—0.1% TFA) over 10 min; Flow rate at 20 mL/min; UV detection at 220 nm) to provide the title compound (43 mg) as a white film. LC/MS m/z 438 [M+H]⁺.

58E. (7R,7aR)-4-[7-(tert-Butyldimethylsilanyloxy)-7a-methyl-3-oxotetrahydropyrrolo[1,2-c]imidazol-2-yl]-2-chloro-3-methyl-benzonitrile

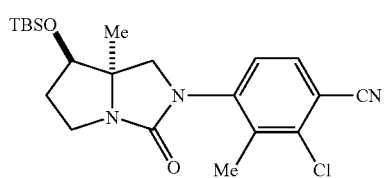

To a solution of (2R,3R)-3-(tert-Butyldimethylsilanyloxy)-2-hydroxymethyl-2-methylpyrrolidine-1-carboxylic acid (3-chloro-4-cyano-2-methyl-phenyl)-amide (58D) (43 mg, 0.10 mmol) in THF (1 mL) at 0° C. was added a 1 M solution of potassium tert-butoxide in THF (0.24 mL, 0.24 mmol) followed by a solution of p-toluenesulfonyl chloride (22 mg, 0.12 mmol) in THF (0.5 mL). After 10 min, additional potassium tert-butoxide (50 □L) and p-toluenesulfonyl chloride (3 mg) were added. After another 10 min, the reaction was diluted with water and EtOAc and the layers were separated. The organic layer was washed with brine, dried (MgSO₄), filtered and concentrated and purified via preparative HPLC (Luna C-18, 100×21.2 mm, eluting with 60-100% solvent B (A=90% H₂O—10% MeOH—0.1% TFA and B=10% H₂O—90% MeOH—0.1% TFA) over 12 min; Flow rate at 20 mL/min; UV detection at 220 nm) to provide the title compound (17 mg). LC/MS m/z 420 [M+H]⁺.

58F. (7R,7aR)-2-Chloro-4-(7-hydroxy-7a-methyl-3-oxotetrahydropyrrolo[1,2-c]imidazol-2-yl)-3-methylbenzonitrile

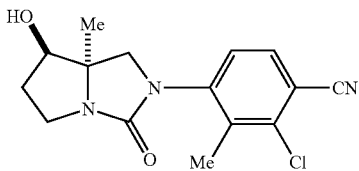

To a solution of (7R,7aR)-4-[7-(tert-Butyldimethylsilanyloxy)-7a-methyl-3-oxotetrahydropyrrolo[1,2-c]imidazol-2-yl]-2-chloro-3-methylbenzonitrile (58E) (17 mg, 0.04 mmol) in THF (2 mL) was added acetic acid (100 □L) and a 1 M solution of TBAF in THF (122 □L, 0.12 mmol). After stirring at rt for 11 h, additional TBAF solution was added (100 □L), and after stirring for another 6 h, 200 □L TBAF solution was added. The reaction was stirred overnight, then 100 □L TBAF was added and the reaction stirred an additional 1.5 h. The reaction was then quenched with saturated aqueous NH₄Cl and extracted with EtOAC. The organic layer was washed with brine, dried (MgSO₄), filtered, and concentrated under reduced pressure. The resulting residue was purified via preparative HPLC (Luna C-18, 100×21.2 mm, eluting with 40-100% solvent B (A=90% H₂O—10% MeOH—0.1% TFA and B=10% H₂O—90% MeOH—0.1% TFA) over 10 min; Flow rate at 20 mL/min; UV detection at 220 nm) to provide the title compound (11 mg). LC/MS m/z 306 [M+H]⁺.

EXAMPLE 59

(7aR)-2-Chloro-3-methyl-4-(7a-methyl-3,7-dioxotetrahydropyrrolo[1,2-c]imidazol-2-yl)benzonitrile

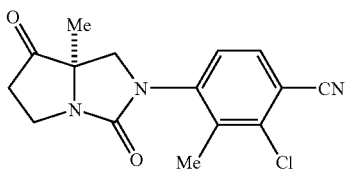

To a 2 M CH₂Cl₂ solution of oxalyl chloride (68 □L, 0.13 mmol) in CH₂Cl₂ (2 mL) at −78° C. was added DMSO (17□L, 0.25 mmol). After 20 min, a solution of (7R,7aR)-2-chloro-4-(7-hydroxy-7a-methyl-3-oxotetrahydropyrrolo[1,2-c]imidazol-2-yl)-3-methylbenzonitrile (58F) (17 mg, 0.06 mmol) in CH₂Cl₂ (1 mL) was added. After an additional 20 min at −78° C., triethylamine (62 □L, 0.47 mmol) was added, the cold bath was removed, and the reaction mixture was stirred for 20 min. Water was added and the layers were separated. The organic layer was washed with brine then dried (MgSO₄), filtered and concentrated. The resulting residue was purified via preparative HPLC (YMC ODS C-18, 100×20 mm, eluting with 30-80% solvent B (A=90% H₂O—10% CH₃CN—0.1% TFA and B=10% H₂O—90% CH₃CN—0.1% TFA) over 15 min; Flow rate at 20 mL/min; UV detection at 220 nm) to provide the title compound (6.3 mg) as a white solid. LC/MS m/z 629 [2M+23]⁺.

EXAMPLE 60

(7R,7aR)-2-Chloro-4-(7-hydroxy-7a-methyl-1,3-dioxotetrahydropyrrolo[1,2-c]imidazol-2-yl)-3-methylbenzonitrile

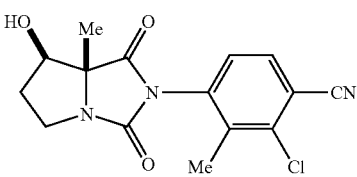

60A. (2R,3R)-3-(tert-Butyldimethylsilanyloxy)-2-methylpyrrolidine-1,2-dicarboxylic acid 1-tert-butyl ester-2-methyl ester

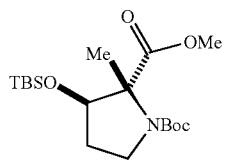

To a solution of (2S,3R)-3-(tert-Butyldimethylsilanyloxy) pyrrolidine-1,2-dicarboxylic acid 1-tert-butyl ester 2-methyl ester (51A) (195 mg, 0.54 mmol) in THF (6 mL) at −78° C. was added a 1.8 M solution of LDA (0.66 mL, 1.19 mmol). After stirring for 1.5 h at −78° C. and 0.5 h at −30° C., the reaction was cooled again to −78° C. and iodomethane (0.2 mL, 3.21 mmol) was added. The mixture was stirred at −78° C. for 1 h and at −20° C. for 4 h. After warming to rt, water and EtOAc were added and the layers were separated. The organic layer was washed with brine, dried (Na₂SO₄), filtered then concentrated under reduced pressure. The resulting residue was purified via preparative HPLC (Luna C-18, 21.1×100 mm, eluting with 75-100% solvent B (A=90% H₂O—10% MeOH—0.1% TFA and B=10% H₂O—90% MeOH—0.1% TFA) over 12 min; Flow rate at 20 mL/min. UV detection at 220 nm) to provide the title compound (36 mg). LC/MS m/z 374 [M+H]⁺.

60B. (7R,7aR)-4-[7-(tert-Butyldimethylsilanyloxy)-7a-methyl-1,3-dioxotetrahydropyrrolo[1,2-c]imidazol-2-yl]-2-chloro-3-methyl-benzonitrile

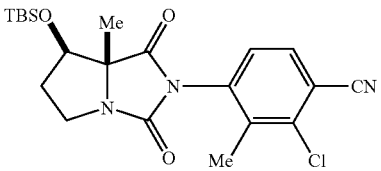

A solution of (2R,3R)-3-(tert-Butyldimethylsilanyloxy)-2-methyl-pyrrolidine-1,2-dicarboxylic acid 1-tert-butyl ester-2-methyl ester (60A) (52 mg, 0.14 mmol) in CH₂Cl₂ (1.5 mL) and TFA (0.5 mL) was stirred at rt for 2 h. The reaction was concentrated under reduced pressure and dried under vacuum. The residue was dissolved in CH₂Cl₂ (1.5 mL) and Hunig's base (60 μL, 0.35 mmol) was added. After stirring at rt for 10 min, 2-chloro-4-isocyanato-3-methylbenzonitrile (34 mg, 0.18 mmol) was added and the reaction was stirred at rt overnight. The reaction was treated with DBU (40 μL, 0.27 mmol) and was stirred for 4 h at rt then concentrated under reduced pressure. The residue was purified via chromatography (silica gel) eluting with 30% EtOAc in hexane to provide the title compound (54 mg). LC/MS m/z 434 [M+H]+.

60C. (7R,7aR)-2-Chloro-4-(7-hydroxy-7a-methyl-1,3-dioxotetrahydropyrrolo[1,2-c]imidazol-2-yl)-3-methylbenzonitrile

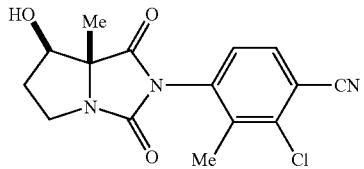

A solution of (7R,7aR)-4-[7-(tert-Butyldimethylsilanyloxy)-7a-methyl-1,3-dioxotetrahydropyrrolo[1,2-c]imidazol-2-yl]-2-chloro-3-methylbenzonitrile (60B) (32 mg, 0.07 mmol) in THF (2 mL) in a plastic vial was cooled to 0° C. HF/pyridine complex (0.12 mL) was added and the reaction was stirred at 0° C. for 1 h and at rt overnight. Saturated aqueous NaHCO3 and CH2Cl2 were added. The layers were separated and the organic layer was concentrated under reduced pressure. The residue was purified via chromatography (silica gel) eluting with 75% EtOAc in hexane to provide the title compound (16 mg). LC/MS m/z 320 [M+H]+.

EXAMPLE 61

4-[(1S,7S,7aR)-7-hydroxy-1-methyl-3-oxo-hexahydro-pyrrolo[1,2-c]imidazol-2-yl]-2-chloro-3-methyl-benzonitrile

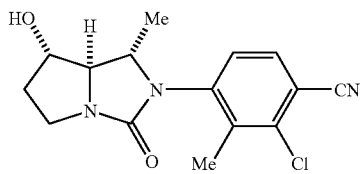

61A. (2R,3S)—N-tert-Butyloxycarbonyl-3-(tert-butyldimethylsilanyloxy)-2-hydroxymethylpyrrolidine

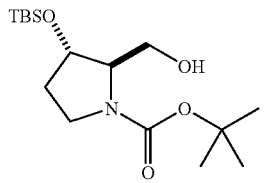

Following procedures described for the preparation of (2S,3R)—N-tert-butyloxycarbonyl-3-(tert-butyldimethylsilanyloxy)proline methyl ester (51A), (2S,3S)-3-hydroxyproline was converted to (2S,3S)—N-tert-butyloxycarbonyl-3-(tert-butyldimethylsilanyloxy)proline methyl ester. To this material (4.3 g, 12 mmol) in THF (75 mL) at −78° C. under nitrogen was added dropwise 1.0 M lithium triethylborohydride in THF (60 mL, 60 mmol). The reaction was allowed to warm to rt and was stirred for 4 h. The reaction was quenched by pouring over ice (150 g) and stirring for 30 min. The product was extracted into EtOAc and washed with saturated aqueous NaHCO3. The organics were dried over MgSO4, filtered and concentrated. Purification by flash chromatography (silica gel, 0-15% EtOAc in hexanes) provided the title compound (3.3 g).

61B. (2S,3S)—N-tert-Butyloxycarbonyl-3-(tert-butyldimethylsilanyloxy)-2-formyl-pyrrolidine

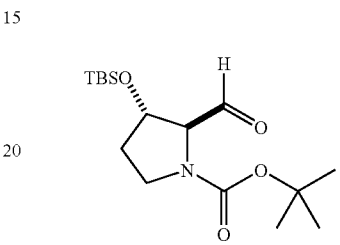

To a solution of 61A (3.3 g, 9.97 mmol) in 10% CH3CN in CH2Cl2 (50 mL) at rt was added NMO (3.0 g, 25.6 mmol) followed by tetrapropyl ammonium perruthenate (300 mg, 0.85 mmol). After a mild exotherm, the reaction was stirred at rt for 4 h. The reaction was diluted with hexane (50 mL), mixed well and filtered through a plug of silica gel (~50 g). The silica plug was washed liberally with 30% EtOAc in hexane (500 mL). Solvents were removed under vacuum. Purification by flash chromatography (silica gel, 0-15% EtOAc in hexanes) provided the title compound (2.94 g).

61C. (2R,3S)—N-tert-Butyloxycarbonyl-3-(tert-butyldimethylsilanyloxy)-2-(1-hydroxyethyl)pyrrolidine

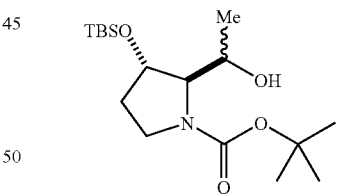

To a solution of intermediate 61B (~0.05 M in THF) at −78° C. was added dropwise MeMgBr (3.0 M in Et2O, 3 equiv). The reaction was stirred at −78° C. for 1.5-2 h (quench small aliquot in 10% MeOH/DCM, spot TLC-silica gel, 30% EtOAc/Hex—stain with 5% HCl/MeOH, heat and then ninhydrin, heat). Quench reaction by addition of HOAc (3 equiv) at −78° C. Warm to rt, dilute with EtOAc and wash with a 1:1 mixture of sat'd aq. NaHCO3 and brine. Back extract aqueous layer. Combine organic extracts, dry over MgSO4, filter and concentrate. Purification by flash chromatography (silica gel, step gradient 0-10-20% EtOAc in hexane) provided the title compound.

61D. (2S,3S)—N-tert-Butyloxycarbonyl-3-(tert-butyldimethylsilanyloxy)-2-(1-hydroxyethyl)pyrrolidine

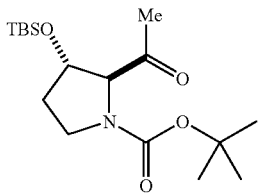

To intermediate 61C (0.1 M solution in 10% CH₃CN in DCM) add NMO (2 equiv) followed by TPAP (0.05 equiv). Provide sufficient ventilation and take care to watch for exotherm. Stir reaction at rt for 3-5 h. Dilute by half with hexane and allow TPAP to precipitate. Flash filter through silica gel plug (20 fold mass of starting alcohol) and elute with 10% EtOAc/Hex until product is not observed in eluent. Removal of solvents gave the title compound. MS (ES) m/z 344.31 [M+H]$^+$ 61E. (2R,3S)—N-tert-Butyloxycarbonyl-3-(tert-butyldimethylsilanyloxy)-2-(1-hydroxyiminoethyl)pyrrolidine

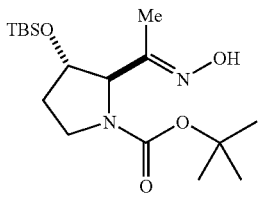

To a solution of 61D (3.86 g, 11.3 mmol) in methanol:water (2:1, 50 mL) was added hydroxylamine HCl salt (3.0 g) followed by pyridine (5.0 mL). The reaction was stirred at rt for 18 h. Extract product into EtOAc, washing once with sat'd aqueous NaHCO₃ and once with water. Back extract the aqueous washings with EtOAc and combine this with the initial extract. Dry organic extract over MgSO₄, filter and concentrate. Dilute residue in toluene and remove solvent under vacuum to provide the title compound as a white solid (2.9 g). MS (ES) m/z 359.30 [M+H]$^+$ 61F. (2R,3S)—N-tert-Butyloxycarbonyl-3-(tert-butyldimethylsilanyloxy)-2-((1S)-1-aminoethyl)pyrrolidine

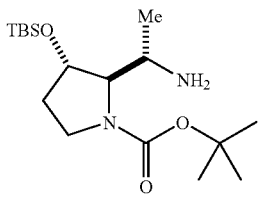

To a solution of 61E (3.6 g, 10.0 mmol) in methanol in a pressure vessel was added Raney Ni in water (~0.2 g), 10% Pd/C (Degussa type, 200 mg), water (7.5 mL) and ammonia in methanol (2.0 M, 5 mL). The reaction vessel was carefully evacuated under vacuum until the solvent bubbled gently. Hydrogen gas was then introduced to a pressure of 70 psi and the reaction was stirred for 2 min). The reaction vessel was again carefully evacuated under vacuum until the solvent bubbled gently. Hydrogen gas was then introduced to a pressure of 70 psi and the reaction was stirred for 18 h at rt. The reaction was filtered through a pad of celite, taking care to keep the captured catalyst wet with methanol at all times. The celite pad was washed with methanol until the product could no longer be detected in the eluent (TLC, 5% MeOH in CH₂Cl₂, stain with ninhydrin and heat). Solvent was removed under vacuum and purification by flash chromatography (110 g ISCO silica gel cartridge, step gradient 0%-5%-10% MeOH in CH₂Cl₂) gave the title compound (2.2 g): MS (ES) m/z 345.35 [M+H]$^+$ 61G. 2-Chloro-4-iodo-3-methylbenzonitrile

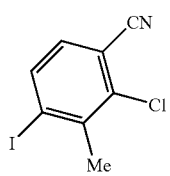

To a suspension of CuI (7.5 g, 39.3 mmol) in acetonitrile (150 mL) under N₂ at rt was added tert-butylnitrite (5.7 mL, 47.9 mmol). The reaction mixture was heated to 65° C. for 1 h and then 4-amino-2-chloro-3-methyl-benzonitrile (23D) (6.0 g, 36.0 mmol) was added and the reaction was heated at 65° C. for 3 h. The reaction was cooled to rt and filtered through a pad of celite. The celite pad was washed with EtOAc. The organics were washed twice with water, dried over MgSO₄, filtered and concentrated. Purification by flash chromatography (silica gel, 110 g ISCO, 0-5% EtOAc in hexane, step gradient) gave the title compound (4.3 g): MS (ES) m/z 278 [M+H]$^+$ 61H. (2R,3S)-1-tert-Butyloxycarbonyl-3-(tert-butyldimethylsilanyloxy)-2-[(1S)-1-(3-chloro-4-cyano-2-methyl-phenylamino)ethyl]pyrrolidine

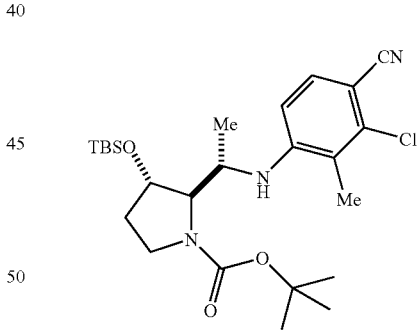

To a solution of 61F (325 mg, 0.94 mmol) in degassed toluene:DMSO (2:1, 7 mL) at rt was added 61G (260 mg, 0.94 mmol), Cs₂CO₃ (614 mg, 1.89 mmol) and a solution of Pd₂(dba)₃ and (S)—N,N-dimethyl-1-[(R)-2-(diphenyphosphino)ferrocenyl]ethylamine (1:6 ratio, 0.06 mol %) in nitrogen degassed toluene (3 mL). The reaction was degassed with nitrogen for 30 min, sealed and heated at 110° C. for 48 h. Cool to rt and extract with EtOAc (50 mL) and wash with water followed by sat'd aqueous NaHCO₃. Dry over MgSO₄, filter and concentrate. Purification by flash chromatography (40 g ISCO silica gel cartridge, 0-10% EtOAc in hexane gradient) gave the title compound (460 mg): MS (ES) m/z 494.29 [M+H]$^+$ 61I. (2R,3S)-3-(tert-Butyldimethylsilanyloxy)-2-[(1S)-1-(3-chloro-4-cyano-2-methyl-phenylamino)ethyl]pyrrolidine

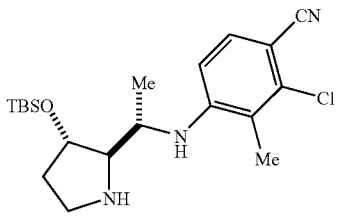

Intermediate 61H (825 mg, 1.67 mmol) was dried azeotropically with toluene (2×). The residue was taken up in 15% TFA in CH₂Cl₂ (10 mL) and stirred at rt for 5 h. Toluene (10 mL) was added and solvent was removed under vacuum. The product was purified by reverse phase HPLC (Phenoenex Luna 30×100 mm S5 C18, 10 min. grad, 25 mL/min, 20-100% B solvent, A=10% MeOH/water+0.1% TFA, B=90% MeOH/Water+0.1% TFA, 4 injections). Solvent was reduced to ~10% volume and the product was then extracted into EtOAc, washed with sat. aqueous NaHCO₃, dried over MgSO₄ and filtered. Solvents were removed to provide the title compound (371 mg): MS (ES) m/z 394.53 [M+H]⁺

61J. 4-[(1S,7S,7aR)-7-tert-Butyldimethylsilanoxy-1-methyl-3-oxo-hexahydro-pyrrolo[1,2-c]imidazol-2-yl]-2-chloro-3-methylbenzonitrile

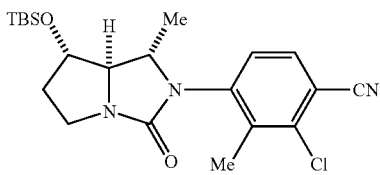

To a solution of crude 61I (~1.81 mmol) in CH₂Cl₂ (10 mL) was added i-Pr₂NEt (2 mL) followed by 20% phosgene in toluene (2.5 mL) dropwise. The reaction was stirred at rt overnight. Reaction was extracted with EtOAc (50 mL) which was washed twice with 1N HCl and then saturated NaHCO₃. The organic layer was dried over MgSO4, filtered and concentrated. Purification by flash chromatography (silica gel, 0 to 10% EtOAc in hexane) provided the title compound (369 mg): MS (ES) m/z 420.23 [M+H]⁺

61K. 4-[(1S,7S,7aR)-7-Hydroxy-1-methyl-3-oxo-hexahydropyrrolo[1,2-c]imidazol-2-yl]-2-chloro-3-methylbenzonitrile

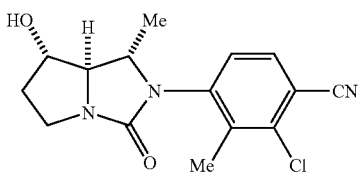

To a solution of 61J (369 mg) in THF (4 mL) was added TBAF (1.0 M in THF, 1.3 mL). The reaction was stirred at rt for 1 h. The reaction was extracted with EtOAc which was washed three times with water, dried over MgSO₄, filtered and concentrated. Purification by reverse phase HPLC (Phenoenex Luna 20×100 mm S5 C18, 10 min. grad, 20 mL/min, 20-100% B solvent, A=10% MeOH/water+0.1% TFA, B=90% MeOH/Water+0.1% TFA) provided the title compound (186 mg): MS (ES) m/z 306.42 [M+H]⁺

EXAMPLE 62

4-[(1R,7R, 7aS)-7-Hydroxy-1-methyl-3-oxo-hexahydropyrrolo[1,2-c]imidazol-2-yl]-2-chloro-3-methylbenzonitrile

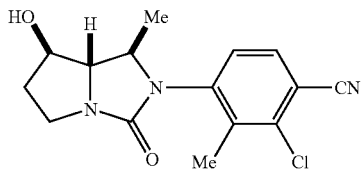

The title compound was prepared in a fashion similar to Example 61: MS (ES) m/z 306.42 [M+H]⁺

EXAMPLE 63

4-[(1R,7aS)-1-Methyl-3,7-dioxo-hexahydropyrrolo[1,2-c]imidazol-2-yl]-2-chloro-3-methylbenzonitrile

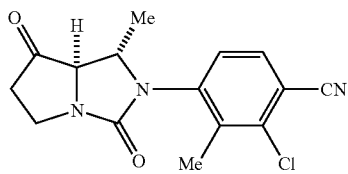

To a solution of DMSO (20 μL) in CH₂Cl₂ (1 mL) at −78° C. was added oxalyl chloride (1.0 M in CH₂Cl₂, 131 μL). This mixture was stirred at −78° C. for 30 min. and then a solution of 61K in CH₂Cl₂ (20 mg in 1 mL). The reaction was stirred at −78° C. for 1 h and then i-Pr₂NEt (100 μL) was added and the reaction was allowed to warm to rt over 1 h. The reaction was extracted with EtOAc and washed twice with 1N HCl and once with saturated NaHCO₃. The organic layer was dried over MgSO₄, filtered and concentrated. Purification by flash chromatography (silica gel, 40% EtOAc/CH₂Cl₂) provided the title compound (18 mg): MS (ES) m/z 304.42 [M+H]⁺

EXAMPLE 64

4-[(1S, 7R, 7aR)-7-Hydroxy-1-methyl-3-oxohexahydropyrrolo[1,2-c]imidazol-2-yl]-2-chloro-3-methylbenzonitrile

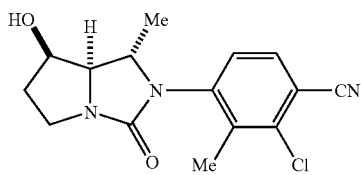

To a solution of 63 (14 mg) in THF (3 mL) at −78° C. was added K-selectride (1.0 M in THF, 100 μL). The reaction was stirred at −78° C. for 30 min. MeOH (100 μL) was added and the reaction was stirred at −78° C. for an additional 10 min. The reaction was warmed to rt, diluted with EtOAc (25 mL) and washed with saturated NaHCO$_3$. The organic layer was dried over MgSO$_4$, filtered and concentrated. Purification by preperative HPLC (Phenoenex Luna 20×100 mm S5 C18, 10 min. grad, 20 mL/min, 20-100% B solvent, A=10% MeOH/water+0.1% TFA, B=90% MeOH/Water+0.1% TFA) provided the title compound (8.3 mg): MS (ES) m/z 306.42 [M+H]$^+$

EXAMPLE 65

4-(1R,7aS)-7-Hydroxyimino-1-methyl-3-oxohexahydropyrrolo[1,2-c]imidazol-2-yl]-2-chloro-3-methylbenzonitrile

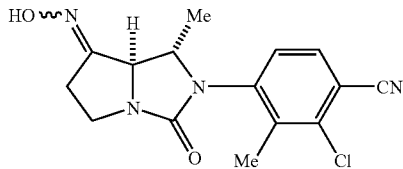

To a solution of 63 (20 mg) in MeOH/water (2:1, 3 mL) was added pyridine (0.5 mL) and NH$_2$OH.HCl (20 mg). After the reaction was stirred at rt overnight, EtOAc was added and the organic layer was washed once with water. The organic layer was dried over MgSO$_4$, filtered and concentrated. Purification by preperative HPLC (Phenoenex Luna 20×100 mm S5 C18, 10 min. grad, 20 mL/min, 20-100% B solvent, A=10% MeOH/water+0.1% TFA, B=90% MeOH/Water+0.1% TFA) provided the title compound (9.1): MS (ES) m/z 319.43 [M+H]$^+$

EXAMPLE 66

(1S,7R,7aR)-2-Chloro-4-(7-hydroxy-1-trifluoromethyl-3-oxohexahydropyrrolo[1,2-c]imidazol-2-yl)-3-methylbenzonitrile

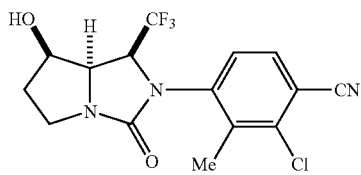

66A. (2R,3R)-3-(tert-Butyl-dimethylsilanyloxy)-2-[(1R)-(2,2,2-trifluoro-1-hydroxyethyl)]pyrrolidine-1-carboxylic acid tert-butyl ester and 66B. (2R,3R)-3-(tert-Butyl-dimethylsilanyloxy)-2-[(1S)-(2,2,2-trifluoro-1-hydroxyethyl)]pyrrolidine-1-carboxylic acid tert-butyl ester

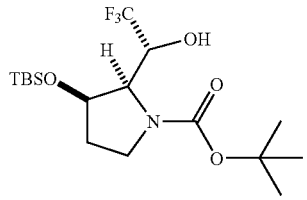

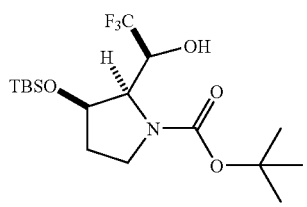

To aldehyde 51C (2.10 g, 6.38 mmol) was added trimethyl(trifluoromethyl)silane (800 μL, 6.57 mmol) and cesium fluoride (dried under high vacuum at 130° C. for 12 h) (10.0 mg, 0.0658 mmol). The reaction was stirred at rt for 24 h then heated to 50° C. for 5 h. After cooling to rt, 4 N HCl (ca. 10 mL) was added and the reaction was stirred overnight. The brown aqueous solution was decanted and the waxy yellow solid was dried under high vacuum overnight then recrystallized from hexane to provide (2R,3R)-3-(tert-butyl-dimethylsilanyloxy)-2-[(1R)-(2,2,2-trifluoro-1-hydroxy-ethyl)]-pyrrolidine-1-carboxylic acid tert-butyl ester (66A) (1.19 g) as a white solid. The mother liquor was concentrated and purified via flash chromatography eluting with 5-20% ethyl acetate/hexane to provide (2R,3R)-3-(tert-butyl-dimethyl-silanyloxy)-2-[(1S)-(2,2,2-trifluoro-1-hydroxy-ethyl)]-pyrrolidine-1-carboxylic acid tert-butyl ester (66B) (192 mg) as an oil and a mixture of 66A and starting material 51C (306 mg). The latter mixture was recrystallized from hexane to provide additional 66A (100 mg).

66C. (2R,3R)-3-(tert-Butyl-dimethylsilanyloxy)-2-[(1R)-((2,2,2-trifluoro-1-hydroxyethyl)]pyrrolidine-1-carboxylic acid (3-chloro-4-cyano-2-methylphenyl)amide

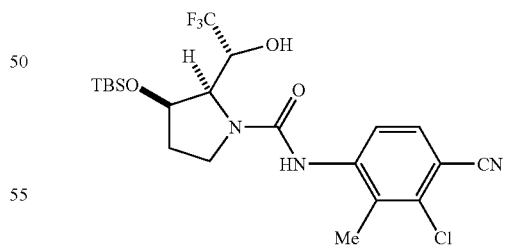

To (2R,3R)-3-(tert-butyl-dimethyl-silanyloxy)-2-[(1R)-(2,2,2-trifluoro-1-hydroxy-ethyl)]-pyrrolidine-1-carboxylic acid tert-butyl ester (66A) (1.29 g, 3.23 mmol) in CH$_2$Cl$_2$ (24 mL) was added trifluoroacetic acid (8 mL). After stirring for 30 min at rt, toluene (ca. 5 mL) was added, the reaction was concentrated under reduced pressure and the brown oil was dried under high vacuum overnight. The resulting brown waxy solid was dissolved in CH$_2$Cl$_2$ (32 mL) and was cooled to −78° C. DIPEA (1.13 mL, 6.49 mmol) was added and the whole was stirred for 15 min at −78° C. 2-chloro-4-isocyanato-3-methylbenzonitrile (23E) (621 mg, 3.23 mmol) in CH$_2$Cl$_2$ (5 mL) was then added and the cold bath was removed. After stirring for 2 h (−78° C. to rt), water was added and the layers separated. The organic layer was washed with brine, dried (MgSO$_4$), filtered and concentrated. The resulting residue was purified via flash chromatography eluting with 30-75% ethyl acetate/hexane to provide (2R,3R)-3-(tert-butyl-dimethylsilanyloxy)-2-[(1R)-((2,2,2-trifluoro-1-hydroxyethyl)]pyrrolidine-1-carboxylic acid (3-chloro-4-cyano-2-methyl-phenyl)-amide (1.47 g) as a white solid. LCMS: m/z 492 [M+H]$^+$.

66D. (1S,7R,7aR)-2-Chloro-4-(7-tert-butyl-dimethylsilanyloxy-1-trifluoromethyl-3-oxohexahydropyrrolo[1,2-c]imidazol-2-yl)-3-methylbenzonitrile

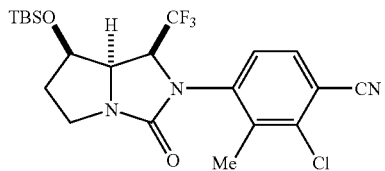

To 66C (1.44 g, 2.93 mmol) in THF (49 mL) at 0° C. was added a 1M THF solution of potassium tert-butoxide (7.04 mL, 7.04 mmol) followed by p-toluenesulfonyl chloride (670 mg, 3.52 mmol) in THF (5 mL). The cold bath was removed and additional p-toluenesulfonyl chloride was added until starting material was consumed (ca. 50 mg). The reaction was stirred at rt for 1.5 h then heated to 60° C. After 3 h, additional 1 M potassium tert-butoxide (1.00 mL) was added and the was reaction heated for an additional hour. The whole was cooled to rt and was diluted with water and EtOAc. The layers were separated and the organic layer washed with brine. The aqueous layer was acidified to pH 1 with 1 N HCl and was extracted with ethyl acetate. The organic layers were combined and dried (MgSO$_4$), filtered and concentrated. The residue was purified via flash chromatography eluting with 30-75% ethyl acetate/hexane to provide the title compound (956 mg) as a yellow foam.

66E. (1S,7R,7aR)-2-Chloro-4-(7-hydroxy-1-trifluoromethyl-3-oxohexahydropyrrolo[1,2-c]imidazol-2-yl)-3-methylbenzonitrile

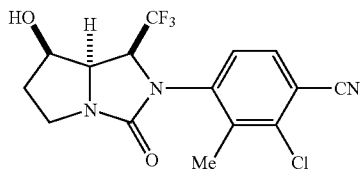

To 66D (956 mg, 2.02 mmol) in THF (20 mL) was added a 1 M THF solution of TBAF (2.02 mL, 2.02 mmol). After stirring at rt for 1 h, additional TBAF was added (500 μL) and the reaction was stirred for 45 min. Saturated aqueous ammonium chloride and EtOAc were added and the layers were separated. The organic layer was washed with brine then dried (MgSO$_4$), filtered and concentrated. The resulting residue was purified via preparative HPLC (YMC ODS C-18, 30×250 mm, eluting with 50-80% solvent B (A=90% H$_2$O—10% MeOH and B=10% H$_2$O—90% MeOH) over 15 min; Flow rate at 20 mL/min; UV detection at 220 nm) to provide the title compound (617 mg) as a white solid. MS: m/z 358 [M−H]$^-$.

EXAMPLE 67

(1R,7R,7aR)-2-Chloro-4-(7-hydroxy-1-trifluoromethyl-3-oxo-hexahydropyrrolo[1,2-c]imidazol-2-yl)-3-methylbenzonitrile

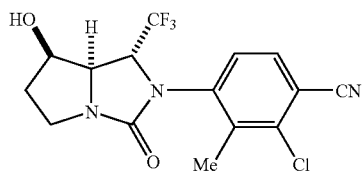

The title compound was prepared from (2R,3R)-3-(tert-butyl-dimethyl-silanyloxy)-2-[(1S)-(2,2,2-trifluoro-1-hydroxy-ethyl)]-pyrrolidine-1-carboxylic acid tert-butyl ester (66B) following procedures analogous to those found in Example 66. MS: m/z 358 [M−H]$^-$

EXAMPLE 68

(1S,7aR)-2-Chloro-4-(7-hydroxyimino-1-trifluoromethyl-3-oxohexahydropyrrolo[2-c]imidazol-2-yl)-3-methylbenzonitrile

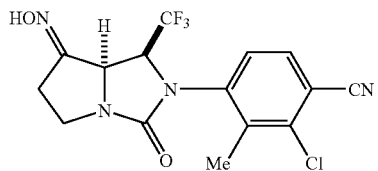

68A. (1S,7aR)-2-Chloro-4-(1-trifluoromethyl-3,7-dioxo-hexahydro-pyrrolo[1,2-c]imidazol-2-yl)-3-methyl-benzonitrile

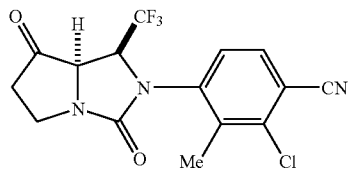

To 66E (100 mg, 0.279 mmol) in CH$_2$Cl$_2$ was added Dess-Martin periodinane (236 mg, 0.556 mmol) and the reaction was stirred at rt overnight. Saturated aqueous Na$_2$S$_2$O$_3$ and NaHCO$_3$ were added and the whole was stirred vigorously for 0.5 h. The layers were separated, the organic layer was washed with a mixture of saturated aqueous Na$_2$S$_2$O$_3$ and NaHCO$_3$ followed by brine, dried (MgSO$_4$), and was then filtered and concentrated to obtain the title compound (96.0 mg) as a white film.

68B. (1S,7aR)-2-Chloro-4-(7-hydroxyimino-1-trifluoromethyl-3-oxohexahydropyrrolo[1,2-c]imidazol-2-yl)-3-methylbenzonitrile

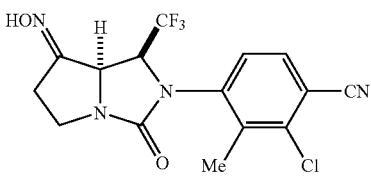

To 68A (96.0 mg, 0.269 mmol) in MeOH (2.7 mL) and water (5 drops) was added pyridine (109 µL) and hydroxylamine hydrochloride (93.0 mg, 1.34 mmol) and the whole was stirred overnight at rt. The reaction was concentrated then diluted with ethyl acetate and washed with water and brine. The organic layer was dried (MgSO$_4$), filtered and concentrated. The resulting residue was purified via preparative HPLC (YMC ODS C-18, 30×100 mm, eluting with 60-100% solvent B (A=90% H$_2$O—10% MeOH and B=10% H$_2$O—90% MeOH) over 10 min; Flow rate at 40 mL/min; UV detection at 220 nm) to provide a solid which was re-purified via preparative HPLC (YMC ODS C-18, 30×100 mm, eluting with 40-70% solvent B (A=90% H$_2$O—10% CH$_3$CN and B=10% H$_2$O—90% CH$_3$CN) over 12 min; Flow rate at 40 mL/min; UV detection at 220 nm) to provide the title compound (48.0 mg) as a white solid. MS: m/z 371 [M–H]$^-$.

EXAMPLE 69

(1S,7S,7aS)-2-Chloro-4-(7-amino-1-trifluoromethyl-3-oxohexahydropyrrolo[1,2-c]imidazol-2-yl)-3-methylbenzonitrile

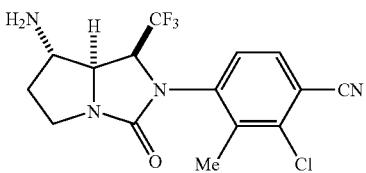

69A. (1S,7R,7aR)-2-Chloro-4-(7-methanesulfonoxy-1-trifluoromethyl-3-oxohexahydropyrrolo[1,2-c]imidazol-2-yl)-3-methylbenzonitrile

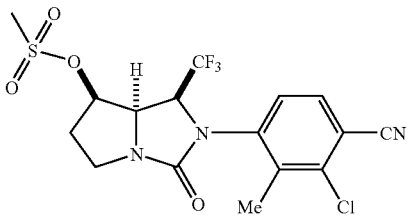

To 66E (54.0 mg, 0.150 mmol) in pyridine (1 mL) was added methanesulfonyl chloride (14.0 µL, 0.182 mmol). After stirring at rt for 3 h, additional methanesulfonyl chloride (14.0 µL) was added. The reaction was heated to 65° C. and after 5 h, additional methanesulfonyl chloride (14.0 µL) was added. After stirring at 65° C. overnight, the reaction was heated to 80° C. and additional methanesulfonyl chloride (20.0 µL) was added. After 2 h, the reaction was cooled to rt and was diluted with water and EtOAc. The layers were separated and the organic layer was washed with 1 N HCl (3×), then dried (MgSO$_4$), filtered and concentrated. The resulting residue was purified via preparative HPLC (YMC ODS C-18, 21×100 mm, eluting with 50-85% solvent B (A=90% H$_2$O—10% MeOH and B=10% H$_2$O—90% MeOH) over 15 min; Flow rate at 20 mL/min; UV detection at 220 nm) to provide starting material (22.0 mg) and the title compound 69A (14.0 mg). The recovered starting material was diluted with pyridine (2 mL) and treated with methanesulfonyl chloride (50.0 µL) at rt overnight to provide, after work-up and purification as above, additional 69A (14.0 mg).

69B. (1S,7S,7aR)-2-Chloro-4-(7-azido-1-trifluoromethyl-3-oxohexahydropyrrolo[1,2-c]imidazol-2-yl)-3-methylbenzonitrile

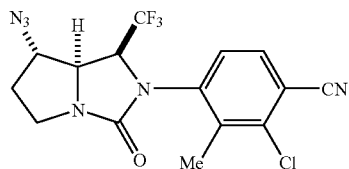

To 69A in DMF (1 mL) was added sodium azide (17.0 mg, 0.262 mmol) and the reaction was stirred overnight at 75° C. The reaction was cooled to rt then diluted with water and EtOAc. The layers were separated and the organic layer was washed with water (3×), then dried (MgSO$_4$), filtered and concentrated. The resulting residue was purified via flash chromatography eluting with 50% EtOAc/hexane to provide the title compound (15.0 mg) as a clear oil.

69C. (1S,7S,7aS)-2-Chloro-4-(7-amino-1-trifluoromethyl-3-oxohexahydro pyrrolo[1,2-c]imidazol-2-yl)-3-methylbenzonitrile

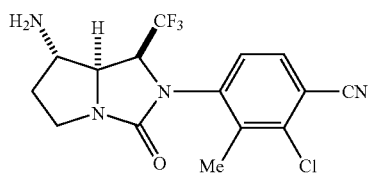

To 69B (15.0 mg, 0.0391 mmol) in EtOH (1 mL) was added platinum (IV) oxide (5 mg) and hydrogen was bubbled through the system for 10 min. The hydrogen outlet was removed and the system was stirred under a hydrogen atmosphere. After 2h, the reaction was filtered through celite and concentrated. The resulting residue was purified via preparative HPLC (YMC ODS C-18, 21×100 mm, eluting with 50-100% solvent B (A=90% H$_2$O—10% MeOH and B=10% H$_2$O—90% MeOH) over 10 min; Flow rate at 40 mL/min; UV detection at 220 nm) to provide the title compound (6.00 mg) as a clear film. MS: m/z 419 [M+HCO$_3$]$^-$

EXAMPLE 70

(1S,7R,7aS)- and (1S,7S,7aS)-2-Chloro-4-(7-hydroxy-1-trifluoromethyl-3-oxohexahydropyrrolo[1,2-c]imidazol-2-yl)-3-methylbenzonitrile

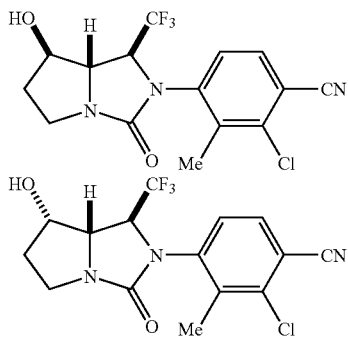

70A. (1S,7aS)- and (1S,7aR)-2-Chloro-4-(1-trifluoromethyl-3,7-dioxohexahydropyrrolo[1,2-c]imidazol-2-yl)-3-methylbenzonitrile

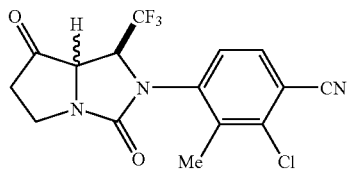

To a 2M $CH_2Cl_2$ solution of oxalyl chloride (167 µL, 0.334 mmol) in $CH_2Cl_2$ (3 mL) at −78° C. was added DMSO (43 µL, 0.555 mmol). After stirring at the same temperature for 20 min, a solution of 66E (89.0 mg, 0.248 mmol) in $CH_2Cl_2$ (1 mL) was added. After an additional 20 min at −78° C., triethylamine (156 µL, 1.12 mmol) was added then the reaction was lifted out of the cold bath and stirred for 1 h. Water was added and the were layers separated. The organic layer was washed with brine then dried ($MgSO_4$), filtered and concentrated. The resulting residue was purified via flash chromatography eluting with 30% EtOAc/hexane to provide a 3.3:1 mixture (major and minor products not assigned) of (1S,7aS)- and (1S,7aR)-2-chloro-4-(1-trifluoromethyl-3,7-dioxohexahydropyrrolo[1,2-c]imidazol-2-yl)-3-methylbenzonitrile (74.0 mg).

70B. (1S,7R,7aS)-2-Chloro-4-(7-hydroxy-1-trifluoromethyl-3-oxohexahydropyrrolo[1,2-c]imidazol-2-yl)-3-methyl-benzonitrile and 70C. (1S,7S,7aS)-2-Chloro-4-(7-hydroxy-1-trifluoromethyl-3-oxohexahydropyrrolo[1,2-c]imidazol-2-yl)-3-methylbenzonitrile

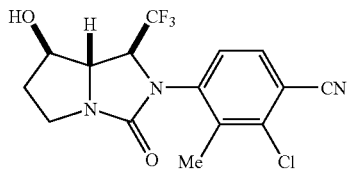

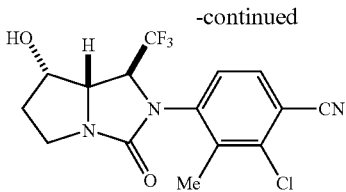

A mixture of (1S,7aS)- and (1S,7aR)-2-chloro-4-(1-trifluoromethyl-3,7-dioxohexahydropyrrolo[1,2-c]imidazol-2-yl)-3-methylbenzonitrile (70A) (74.0 mg, 0.218 mmol) in EtOAc (2 mL) was hydrogenated in the presence of platinum (IV) oxide (5 mg) for 3 h. The reaction was filtered through celite, concentrated and purified via preparative HPLC (YMC ODS C-18, 21×100 mm, eluting with 40-75% solvent B (A=90% $H_2O$—10% $CH_3CN$ and B=10% $H_2O$—90% $CH_3CN$) over 10 min; Flow rate at 40 mL/min; UV detection at 220 nm) to provide two products. To obtain analytically pure samples, the two products were purified two more times via preparative HPLC (YMC ODS C-18, 21×100 mm, first eluting with 40-70% solvent B (A=90% $H_2O$—10% $CH_3CN$ and B=10% $H_2O$—90% $CH_3CN$) over 10 min; Flow rate at 40 mL/min; UV detection at 220 nm), then using MeOH/water under similar conditions to provide (1S,7R,7aS)-2-chloro-4-(7-hydroxy-1-trifluoromethyl-3-oxo-hexahydropyrrolo[1,2-c]imidazol-2-yl)-3-methyl-benzonitrile (70B) (11.0 mg, MS: m/z 717 [2M−H]$^-$) and (1S,7S,7aS)-2-chloro-4-(7-hydroxy-1-trifluoromethyl-3-oxohexahydropyrrolo[1,2-c]imidazol-2-yl)-3-methylbenzonitrile (70C) (4.00 mg, MS: m/z 717 [2M−H]$^-$).

EXAMPLE 71

(1R,7R,7aR)-2-Chloro-4-(7-hydroxy-1-isopropyl-3-oxohexahydropyrrolo[1,2-c]imidazol-2-yl)-3-methylbenzonitrile

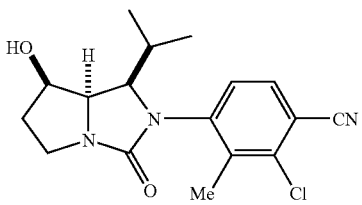

71A. (2R,3R)-3-(tert-Butyl-dimethylsilanyloxy)-2-[(1S)-(1-hydroxy-2-methylpropyl)]pyrrolidine-1-carboxylic acid tert-butyl ester

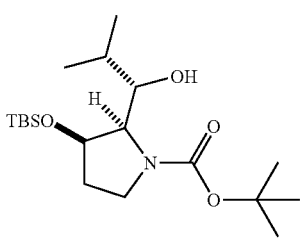

To 51C (6.50 g, 19.8 mmol) in THF (100 mL) at −78° C. was added a 2M THF solution of isopropylmagnesium chloride (30.0 mL, 60.0 mmol) over 20 min. The cold bath was removed and the reaction was stirred for 1 h. The reaction was then cooled to −60° C. and was quenched with saturated aqueous ammonium chloride. After warming to rt, the whole was diluted with EtOAc. The layers were separated and the organic layer washed with water and brine, then dried (MgSO$_4$), filtered and concentrated. The resulting residue was purified via flash chromatography eluting with 20% EtOAc/hexane to provide the title compound (5.90 g).

71B. (2R,3R)-3-(tert-Butyl-dimethylsilanyloxy)-2-[(1S)-(1-hydroxy-2-methylpropyl]pyrrolidine-1-carboxylic acid (3-chloro-4-cyano-2-methylphenyl)amide

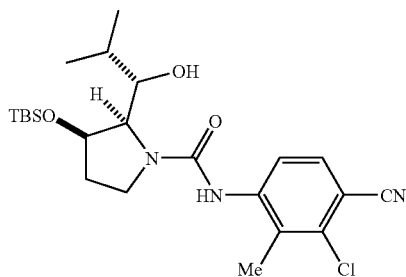

(2R,3R)-3-(tert-butyl-dimethylsilanyloxy)-2-[(1S)-(1-hydroxy-2-methylpropyl]pyrrolidine-1-carboxylic acid (3-chloro-4-cyano-2-methylphenyl)amide (71B) (5.90 g) was prepared from 71A (5.90 g) following procedures analogous to those found in Example 66 for the preparation of 66C.

71C. (1R,7R,7aR)-2-Chloro-4-(7-tert-butyl-dimethylsilanyloxy-1-isopropyl-3-oxohexahydropyrrolo[1,2-c]imidazol-2-yl)-3-methylbenzonitrile

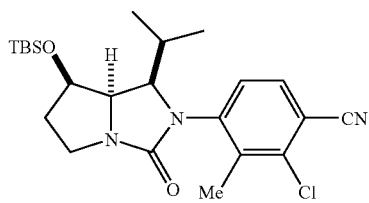

To 71B (3.00 g, 6.45 mmol) in THF (80 mL) at 0° C. was added a 1M THF solution of LiHMDS (15.5 mL, 15.5 mmol) followed by p-toluenesulfonyl chloride (1.84 g, 9.65 mmol) in THF (27 mL). The cold bath was removed and the reaction was stirred for 1 h. The reaction was diluted with water and EtOAc. The layers were separated and the organic layer washed with brine. The aqueous layer was acidified to pH 1 with 1 N HCl and was extracted with EtOAc. The organic layers were combined and dried (MgSO$_4$), filtered and concentrated. The residue was purified via flash chromatography eluting with 30-75% EtOAc/hexane to provide the title compound (2.25 g) as a light yellow solid. LCMS: m/z 448 [M+H]$^+$.

71D. (1R,7R,7aR)-2-Chloro-4-(7-hydroxy-1-isopropyl-3-oxohexahydropyrrolo[1,2-c]imidazol-2-yl)-3-methylbenzonitrile

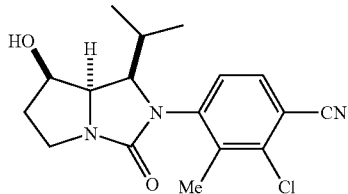

To 71C (2.00 g, 4.47 mmol) in THF (45 mL) was added a 1 M THF solution of TBAF (4.47 mL, 4.47 mmol). After stirring at rt for 45 min, saturated aqueous ammonium chloride and EtOAc were added and the layers were separated. The organic layer was washed with brine then dried (MgSO$_4$), filtered and concentrated. The resulting residue was purified via flash chromatography eluting with 75-100% EtOAc/hexane to provide the title compound (1.36 g) which contained a minor impurity (6.76%). To obtain an analytically pure sample, a portion of the product (ca. 250 mg) was purified via preparative HPLC (YMC ODS C-18, 30×100 mm, eluting with 25% solvent B (solvent B=10% H$_2$O—90% CH$_3$CN—0.1% TFA) for 25 min; Flow rate at 40 mL/min; UV detection at 220 nm) to provide, after recrystallization from MeOH/water, the title compound (106 mg) as white needles. MS: m/z 665 [2M−H]$^-$

EXAMPLE 72

(1S,7R,7aR)-2-Fluoro-4-(7-hydroxy-1-trifluoromethyl-3-oxo-hexahydropyrrolo[1,2-c]imidazol-2-yl)-3-methylbenzonitrile

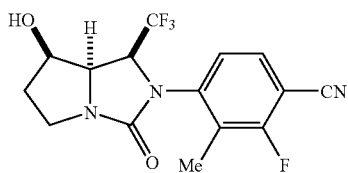

72A. N-(3-Fluoro-2-methylphenyl)acetamide

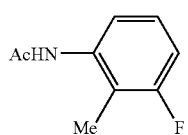

To a solution of 3-fluoro-2-methylaniline (2.65 g, 21.2 mmol) in EtOH (25 mL) at 0° C. was added acetic anhydride (2.60 g, 25.5 mmol). The mixture was stirred at rt overnight then concentrated under reduced pressure to give the title compound (3.54 g). LCMS: m/z 168 [M+H]$^+$

72B. N-(4-Bromo-3-fluoro-2-methylphenyl)acetamide

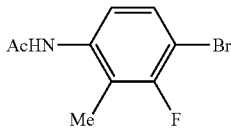

To a solution of N-(3-fluoro-2-methylphenyl)acetamide (72A) (1.71 g, 10.2 mmol) in acetic acid (15 mL) at 0° C. was added bromine (1.68 mL, 32.8 mmol) over 15 min. The mixture was stirred at rt for 2 h, and was then poured into ice (50 g). The mixture was filtered and concentrated under reduced pressure to give the title compound (2.26 g). LCMS: m/z 246 [M+H]$^+$

72C. N-(4-Cyano-3-fluoro-2-methylphenyl)acetamide

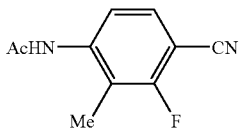

To a solution of N-(4-bromo-3-fluoro-2-methylphenyl)acetamide (72B) (2.18 g, 8.86 mmol) in DMF (20 mL) was added CuCN (2.61 g, 29.1 mmol). The mixture was stirred at 150° C. for 12 h and was then poured into ice (50 g). After warming to rt, the product was extracted with EtOAc (3×50 mL). The combined organic layers were washed with brine, dried and concentrated. The residue was purified via flash chromatography eluting with a solution of 5% methanol in 95% of EtOAc/hexane (1:1) to provide the title compound (1.51 g) as a white solid. LCMS: m/z 193 [M+H]$^+$

72D. 4-Amino-2-fluoro-3-methylbenzonitrile

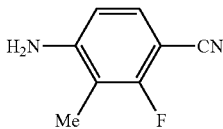

N-(4-cyano-3-fluoro-2-methyl-phenyl)-acetamide (72C) (450 mg, 2.34 mmol) was dissolved in 1:1 conc. HCl/EtOH (20 mL,) and the mixture was refluxed for 1 h. The reaction was cooled to rt and concentrated. The residue was dissolved in EtOAc (30 mL), washed with sat. aq. NaHCO$_3$ and brine, dried (MgSO$_4$), filtered and concentrated. The residue was recrystallized from EtOAc/Hexane to provide the title compound (340 mg). LC/MS: m/z 151 [M+H]$^+$

72E. 2-Fluoro-4-isocyanato-3-methylbenzonitrile

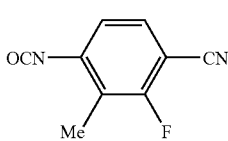

2-Fluoro-4-isocyanato-3-methylbenzonitrile was prepared from 4-amino-2-fluoro-3-methyl-benzonitrile (72D) following a procedure analogous to the procedure used in the preparation of compound 2E (Example 2).

72F. (2R,3R)-3-(tert-Butyl-dimethylsilanyloxy)-2-[(1R)-((2,2,2-trifluoro-1-hydroxyethyl)]pyrrolidine-1-carboxylic acid (3-fluoro-4-cyano-2-methylphenyl)amide

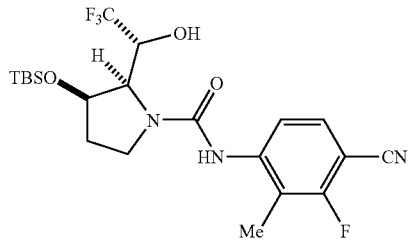

To (2R,3R)-3-(tert-butyl-dimethylsilanyloxy)-2-[(1R)-(2,2,2-trifluoro-1-hydroxyethyl)]pyrrolidine-1-carboxylic acid tert-butyl ester (66A) (233 mg, 0.584 mmol) in CH$_2$Cl$_2$ (4 mL) was added trifluoroacetic acid (1 mL). The mixture was stirred for 30 min at rt, concentrated under reduced pressure, azeotroped from toluene, then dried under high vacuum for 3 h. The resulting brown waxy solid was dissolved in CH$_2$Cl$_2$ (5 mL) and DIPEA (0.300 mL, 1.72 mmol) followed by 2-fluoro-4-isocyanato-3-methylbenzonitrile (72E) (133 mg, 0.693 mmol) were added. The mixture was stirred at rt overnight and then was filtered and concentrated. The resulting residue was purified by flash chromatography eluting with 0-40% EtOAc/hexane to provide the title compound (533 mg) as a white solid. LCMS: m/z 476 [M+H]$^+$.

72G. (2S,3R)-3-(tert-Butyl-dimethylsilanyloxy)-2-[(1R)-((2,2,2-trifluoro-1-methanesulfonoxy)]pyrrolidine-1-carboxylic acid (3-fluoro-4-cyano-2-methylphenyl)amide

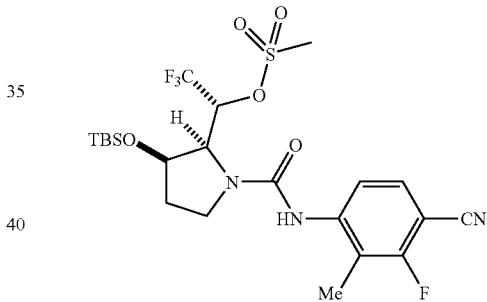

To 72F (100 mg, 0.211 mmol) in CH$_2$Cl$_2$ (3 mL) at 0° C. was added a 1M THF solution of potassium tert-butoxide (0.45 mL, 1 mmol), followed by methanesulfonyl chloride (76 mg, 0.663 mmol). The mixture was stirred at rt overnight. The reaction was concentrated and the residue was purified via flash chromatography eluting with 0-20% EtOAc/hexane to provide the title compound (117 mg) as a white solid. LCMS: m/z 554 [M+H]$^+$

72H. (1S,7R,7aR)-2-Fluoro-4-(7-tert-butyl-dimethylsilanyloxy-1-trifluoromethyl-3-oxohexahydropyrrolo[1,2-c]imidazol-2-yl)-3-methylbenzonitrile

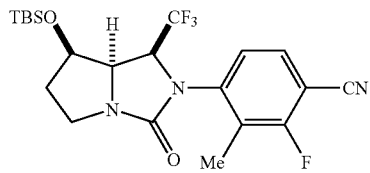

To 72G (117 mg, 0.211 mmol) in MeOH (3mL) at 0° C. was added a 25% (wt) MeOH solution of NaOMe (89.0 mg, 0.412 mmol) and the mixture was refluxed 1 h. After cooling to rt and concentrating, the residue was purified via preparative HPLC (YMC ODS C-18, 30×250 mm, eluting with 50-100% solvent B (A=90% H₂O—10% MeOH and B=10% H₂O—90% MeOH) over 15 min; Flow rate at 20 mL/min; UV detection at 220 nm) to provide the title compound (17.0 mg) as a white solid. LCMS: m/z 458 [M+H]⁺

72I. (1S,7R,7aR)-2-Fluoro-4-(7-hydroxy-1-trifluoromethyl-3-oxohexahydropyrrolo[1,2-c]imidazol-2-yl)-3-methylbenzonitrile

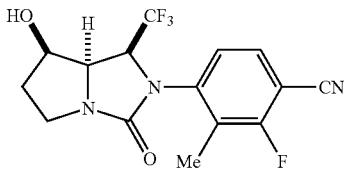

To 72H (17.0 mg, 0.0371 mmol) in THF (2mL) was added a 1 M THF solution of TBAF (0.230 mL, 0.230 mmol). After stirring at rt for 1 h, saturated aqueous ammonium chloride and EtOAc were added and the layers were separated. The organic layer was washed with brine then dried (MgSO₄), filtered and concentrated. The resulting residue was purified via flash chromatography eluting with 0-75% EtOAc/hexane to provide the title compound (12.3 mg) as a white solid. LCMS: m/z 344 [M+H]⁺

EXAMPLE 73

(1S,7R,7aR)-2-Chloro-4-(7-hydroxy-1-trifluoromethyl-3-oxo-hexahydropyrrolo[1,2-c]imidazol-2-yl)-3-fluorobenzonitrile

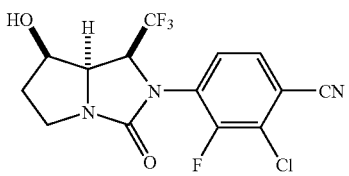

73A. 4-Amino-2-chloro-3-fluorobenzaldehyde

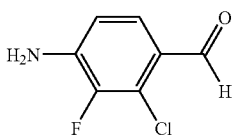

To 3-chloro-2-fluoroaniline (10.0 g, 68.7 mmol) in DMSO (500 mL) was added copper (II) chloride (18.5 g, 137.4 mmol) and conc. HCl (50 mL). The whole was heated to 90° C. for 13 h. The reaction was cooled to 0° C. and 4N NaOH was added dropwise to adjust to pH 8. The reaction was diluted with water and extracted with Et₂O/EtOAc (1:1). The organic layer was washed with brine, and was dried, filtered and concentrated. The resulting residue was purified via silica gel chromatography eluting with 5-30% EtOAc/hexane to provide 4-amino-2-chloro-3-fluorobenzaldehyde (1.00 g) as a yellow powder.

73B. 4-Amino-3-fluoro-2-chlorobenzonitrile

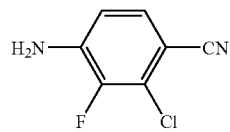

To a solution of hydroxylamine hydrochloride (336 mg, 4.84 mmol) in water (1.2 mL) was added 4-amino-2-chloro-3-fluorobenzaldehyde (73A) (0.800 g, 4.61 mmol) and pyridine (2.5 mL). After stirring at rt for 1 h, copper (II) sulfate pentahydrate (230 mg, 0.922 mmol) was added followed by a solution of triethylamine (1.40 mL, 9.68 mmol) in CH₂Cl₂ (2.5 mL). To the resulting dark green reaction mixture was then added a solution of DCC (1.14 g, 5.53 mmol) in CH₂Cl₂ (10 mL) and the reaction was stirred for 2 h. Formic acid (1 mL) was added and the reaction was stirred for 20 min, filtered through celite, and concentrated. The resulting residue was purified via silica gel chromatography eluting with 20-30% EtOAc/hexane to provide the title compound (0.780 g) as a light brown solid.

73C. 4-Isocyanato-3-fluoro-2-chlorobenzonitrile

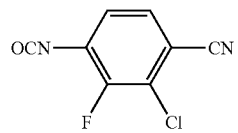

4-Isocyanato-3-fluoro-2-chlorobenzonitrile was prepared from 4-amino-3-fluoro-2-chlorobenzonitrile (73B) in a manner similar to that described in Example 2 for the preparation of 2E.

73D. (1S,7R,7aR)-2-Chloro-4-(7-hydroxy-1-trifluoromethyl-3-oxohexahydro-pyrrolo[1,2-c]imidazol-2-yl)-3-fluorobenzonitrile

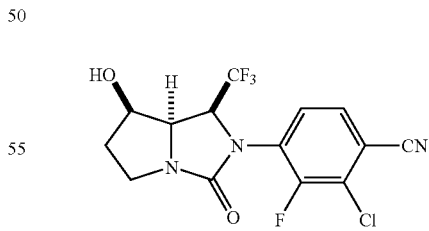

The title compound was prepared from (2R,3R)-3-(tert-butyl-dimethylsilanyloxy)-2-[(1R)-(2,2,2-trifluoro-1-hydroxyethyl)]pyrrolidine-1-carboxylic acid tert-butyl ester (66A) and 2-chloro-4-isocyanato-3-fluorobenzonitrile (73C) following procedures analogous to those found in Example 72. LCMS: m/z 364 [M+H]⁺

EXAMPLE 74

(1S,7R,7aR)-2-Trifluoromethyl-4-(7-hydroxy-1-trifluoromethyl-3-oxohexahydropyrrolo[1,2-c]imidazol-2-yl)-3-methylbenzonitrile

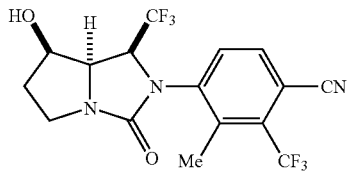

The title compound was prepared from (2R,3R)-3-(tert-butyl-dimethylsilanyloxy)-2-[(1R)-(2,2,2-trifluoro-1-hydroxyethyl)]pyrrolidine-1-carboxylic acid tert-butyl ester (66A) and isocyanate 18E following procedures analogous to those found in Example 72. LCMS: m/z 394 [M+H]$^+$

EXAMPLE 75

(1S,7S,7aR)-2-Chloro-4-(7-hydroxy-1-trifluoromethyl-3-oxohexahydropyrrolo[1,2-c]imidazol-2-yl)-3-methylbenzonitrile

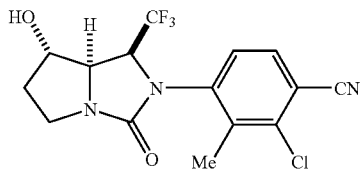

75A. (2S,3S)-3-(tert-Butyldimethylsilanyloxy)-2-formylpyrrolidine-1-carboxylic acid tert-butyl ester

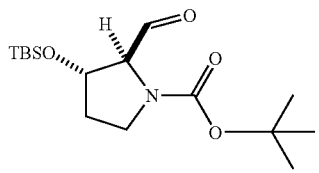

To (2R,3S)-3-(tert-butyl-dimethylsilanyloxy)-2-hydroxymethyl pyrrolidine-1-carboxylic acid tert-butyl ester (61A) (9.85 g, 29.7 mmol) in CH$_2$Cl$_2$ (200 mL) at 0° C. was added Dess-Martin periodinane. The ice bath was removed and the reaction was warmed to rt. After 2 h, saturated aqueous Na$_2$S$_2$O$_3$ and NaHCO$_3$ (ca. 100 mL each) were added and the reaction mixture was stirred vigorously for 0.5 h. The layers were separated, and the organic layer was washed with a mixture of saturated aqueous Na$_2$S$_2$O$_3$ and saturated aqueous NaHCO$_3$ followed by brine, dried (MgSO$_4$), and was then filtered and concentrated to obtain the title compound (9.23 g) as a yellow oil.

75B. (2R,3S)-3-(tert-Butyl-dimethylsilanyloxy)-2-[(1R)-(2,2,2-trifluoro-1-hydroxyethyl)]pyrrolidine-1-carboxylic acid tert-butyl ester and 75C. (2R,3S)-3-(tert-Butyl-dimethylsilanyloxy)-2-[(1S)-(2,2,2-trifluoro-1-hydroxyethyl)]pyrrolidine-1-carboxylic acid tert-butyl ester

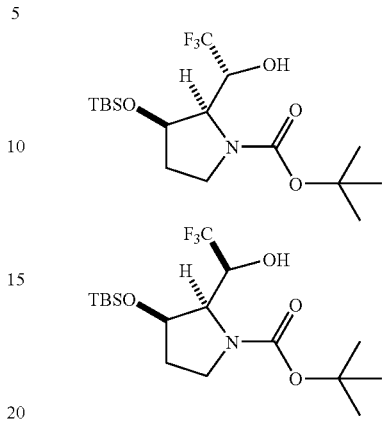

To 75A (1.00 g, 3.04 mmol) was added trimethyl(trifluoromethyl)silane (550 mg, 3.87 mmol) and cesium fluoride (10 mg, dried under high vacuum at 130° C. for 12 h). The mixture was stirred at rt for 24 h, and then was heated to 50° C. for 5 h. After cooling to rt, 4N HCl (ca. 10 mL) was added and the reaction was stirred overnight. The product was extracted with EtOAc (3×30 mL). The organic layer was washed with saturated aqueous NaHCO$_3$ and brine, then dried (MgSO$_4$), filtered and concentrated. The residue was purified via flash chromatography eluting with 0-15% ethyl acetate/hexane to provide (2R,3S)-3-(tert-butyl-dimethyl-silanyloxy)-2-[(1R)-(2,2,2-trifluoro-1-hydroxy-ethyl)]-pyrrolidine-1-carboxylic acid tert-butyl ester (75B) (357 mg) as a colorless oil and (2R,3S)-3-(tert-butyl-dimethylsilanyloxy)-2-[(1S)-(2,2,2-trifluoro-1-hydroxyethyl)]pyrrolidine-1-carboxylic acid tert-butyl ester (75C) (380 mg) as a white solid.

75D. (2R,3S)-3-(tert-Butyl-dimethylsilanyloxy)-2-[(1R)-((2,2,2-trifluoro-1-hydroxyethyl)]pyrrolidine-1-carboxylic acid (3-chloro-4-cyano-2-methylphenyl)amide

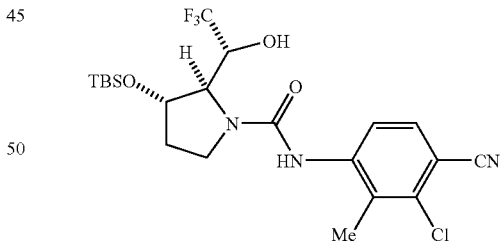

To 75B (490 mg, 1.25 mmol) in CH$_2$Cl$_2$ (10 mL) was added trifluoroacetic acid (3 mL). After stirring for 30 min at rt, the reaction was concentrated under reduced pressure, azeotroped from toluene and dried under high vacuum for 3 h. The resulting brown waxy solid was dissolved in CH$_2$Cl$_2$ (5 mL). DIPEA (0.65 mL, 3.73 mmol) was added, followed by 2-chloro-4-isocyanato-3-methylbenzonitrile (23E) (285 mg, 1.48 mmol). The mixture was stirred at rt overnight and was then filtered and concentrated. The resulting residue was purified via flash chromatography eluting with 0-40% EtOAc/hexane to provide the title compound (533 mg) as a white solid. LCMS: m/z 492 [M+H]$^+$.

75E. (2S,3S)-3-(tert-Butyl-dimethylsilanyloxy)-2-[(1R)-((2,2,2-trifluoro-1-p-toluenesulfonoxy)]pyrrolidine-1-carboxylic acid (3-chloro-4-cyano-2-methylphenyl)amide

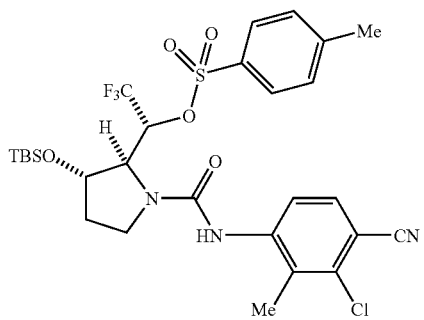

To 75D (280 mg, 0.570 mmol) in THF (3 mL) at 0° C. was added a 1 M THF solution of potassium tert-butoxide (1.14 mL, 1.14 mmol) and tosyl chloride (380 mg, 1.99 mmol) and the mixture was stirred at rt overnight. The reaction was diluted with $CH_2Cl_2$ (30 mL), washed with 1M $H_3PO_4$, sat'd $NaHCO_3$ and brine, dried ($MgSO_4$), filtered and concentrated. The resulting residue was purified via flash chromatography eluting with 0-40% EtOAc/hexane to provide the title compound. m/z 646 $[M+H]^+$.

75F. (1S,7S,7aR)-2-Chloro-4-(7-tert-butyl-dimethylsilanyloxy-1-trifluoromethyl-3-oxohexahydropyrrolo[1,2-c]imidazol-2-yl)-3-methylbenzonitrile

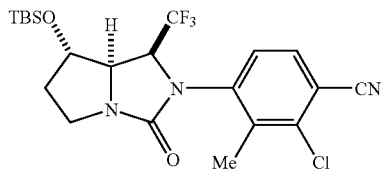

To 75E (50.0 mg, 0.0775 mmol) in 1,4-dioxane (2 mL) at 0° C. was added a 1M THF solution of potassium tert-butoxide (0.2 mL). The mixture was heated to 170° C. in a microwave oven for 15 min. The reaction was concentrated and purified via preparative HPLC (YMC ODS C-18, 30×250 mm, eluting with 50-100% solvent B (A=90% $H_2O$—10% MeOH and B=10% $H_2O$—90% MeOH) over 15 min; Flow rate at 20 mL/min; UV detection at 220 nm) to provide the title compound (7.20 mg). m/z 474 $[M+H]^+$.

75G. (1S,7S,7aR)-2-Chloro-4-(7-hydroxy-1-trifluoromethyl-3-oxohexahydropyrrolo[1,2-c]imidazol-2-yl)-3-methylbenzonitrile

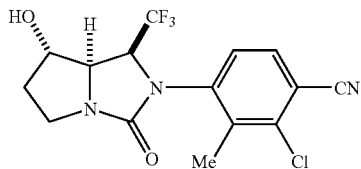

To a solution of 75F (8.20 mg, 0.173 mmol) in THF (2 mL) was added a 1 M THF solution of TBAF (0.120 mL, 0.120 mmol). After stirring at rt for 1 h, saturated aqueous ammonium chloride and EtOAc were added and the layers were separated. The organic layer was washed with brine then dried ($MgSO_4$), filtered and concentrated. The resulting residue was purified via preparative HPLC (YMC ODS C-18, 30×250 mm, eluting with 50-90% solvent B (A=90% $H_2O$—10% MeOH and B=10% $H_2O$—90% MeOH) over 15 min; Flow rate at 20 mL/min; UV detection at 220 nm) to provide the title compound (4.10 mg) as a white solid. MS: m/z 360 $[M+H]^+$

EXAMPLE 76

(1R,7S,7aR)-2-Chloro-4-(7-hydroxy-1-trifluoromethyl-3-oxohexahydropyrrolo[1,2-c]imidazol-2-yl)-3-methylbenzonitrile

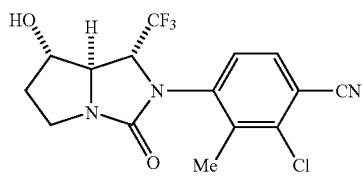

The title compound was prepared from (2R,3S)-3-(tert-butyl-dimethylsilanyloxy)-2-[(1S)-(2,2,2-trifluoro-1-hydroxyethyl)]pyrrolidine-1-carboxylic acid tert-butyl ester (75C) following procedures analogous to those found in Example 75. MS: m/z 360 $[M+H]^+$

EXAMPLE 77

4-[(8R,8aR)-8-Hydroxy-3-oxohexahydroimidazo[1,5-a]pyridin-2-yl]-2-chloro-3-methylbenzonitrile and

EXAMPLE 78

4-[(8S,8aS)-8-Hydroxy-3-oxohexahydroimidazo[1,5-a]pyridin-2-yl]-2-chloro-3-methylbenzonitrile

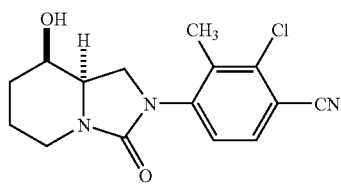

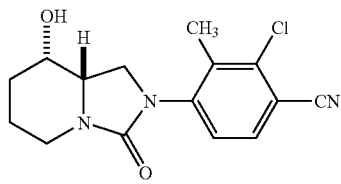

77A. (±)-(cis)-3-Hydroxypipecolic acid

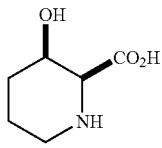

A mixture of 3-hydroxy picolinic acid (20 g, 0.14 mol), 10% rhodium hydroxide on carbon (The catalyst was prepared according to the literature procedure: William M. Pealman, Tetrahedron Letters, 1967, 8, 1663-1664) (13.2 g), 20% palladium hydroxide on carbon (4.0 g) in 30% ammonium hydroxide solution (40 mL) and water (280 mL) were stirred under hydrogen at 75 psi for 6 days. The catalysts were removed by filtration and the filtrate was concentrated to yield the crude product 77A as a white foam (18.93 g): MS (ES): m/z 146 [M+1]$^+$ 77B. (±)-(2S,3R)-3-Hydroxypipecolic acid methyl ester

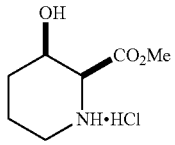

A solution of 3-hydroxy-pipecolic acid 77A (crude, 21.7g, 0.15 mol) in MeOH (420 mL) was saturated with HCl gas and heated at reflux overnight. Removal of solvent and coevaporation of the residue with diethyl ether gave the hydrochloric acid salt of the title compound 77B as a yellow foam (24.9 g).

77C. (±)-(2S,3R)-1-tert-Butoxycarbonyl-3-hydroxypipecolic acid methyl ester

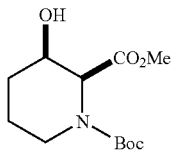

To a mixture of 3-hydroxy-pipecolic acid methyl ester 77B (10.5 g, 66 mmol) and TEA (27.6 mL, 198 mmol, 3.0 equiv) in DCM (150 mL) was added Boc$_2$O (21.6 g, 99 mmol, 1.5 equiv). The mixture was stirred at rt overnight. The mixture was concentrated and the residue was diluted with EtOAc (200 mL), washed with 0.5 N HCl (3×30 mL), saturated sodium bicarbonate solution (2×30 mL), brine (2×30 mL), dried (MgSO$_4$) and evaporated to give the crude product. Purification of the crude product by flash chromatography (0-100% EtOAc/hexane) yield the desired product 77C (5.5 g) as a racemic mixture: HPLC (Phenomenex Luna 5μ C18 4.6×50 mm, linear gradient over 4 min) retention time 2.48 min (100%).

77D. (±)-(2S,3R)-1-tert-Butoxycarbonyl-3-(tert-butyldimethylsilanyloxy)pipecolic acid methyl ester

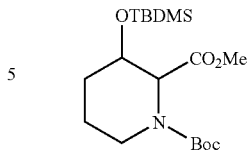

To a solution of 77C (3.3 g, 12.7 mmol) in DCM (50 mL) was added DIPEA (6.63 mL, 38.1 mmol), tert-butyldimethylsilyl chloride (3.83 g, 25.4 mmol, 2.0 equiv) and DMAP (310 mg, 5.24 mmol, 0.2 equiv). The resulting mixture was stirred at rt overnight. TLC showed no completion and therefore another 2.2 mL of DIPEA and 1.91 g of tert-butyldimethylsilyl chloride were added and stirred at rt for 3 days. The mixture was concentrated and the residue was diluted with EtOAc (100 mL), washed with 0.5 N HCl (2×30 mL), brine (2×30 mL), dried (MgSO$_4$) and evaporated to give the crude product as a light pink oil. Purification of the crude product by flash chromatography (5-10% EtOAc/hexane) gave the desired product 77D (3.8 g, 81%): R$_f$ (10% EtOAc/hexane) 0.25; HPLC (Phenomenex Luna 5 u C18 4.6×50 mm, linear gradient over 4 min) retention time 4.3 min (100%); MS (ES) m/z 374 [M+1]$^+$.

77E. (±)-(2S,3R)-1-tert-Butoxycarbonyl-3-(tert-butyldimethylsilanyloxy)-2-hydroxymethylpiperidine

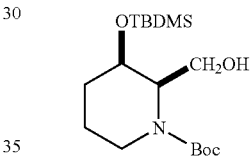

To a solution of 77D (1.0 g, 2.7 mmol) in THF (10 mL) at −78° C. was added a solution of LiEt$_3$BH (1.0 M in THF, 13.5 mL, 13.5 mmol, 5 equiv). The mixture was warmed to rt and stirred at rt for 4 h. The mixture was poured over ice and stirred vigorously for 15 min. The mixture was extracted with EtOAc (2×50 mL). The combined organic layers were washed with 0.5 N HCl (20 mL), saturated sodium bicarbonate solution (20 mL), brine (20 mL), dried (MgSO$_4$) and evaporated to give the crude product as a colorless oil. Purification of the crude product by flash chromatography (5-50% EtOAc/hexane) gave the desired product 77E (960 mg): R$_f$ (50% EtOAc/hexane) 0.64; HPLC (Phenomenex Luna 5 u C18 4.6×50 mm, linear gradient over 4 min) retention time 4.1 min (100%); MS (ES) m/z 346.1 [M+1]$^+$; HRMS calcd for C$_{17}$H$_{36}$NO$_4$Si 346.2414, Found 346.2419.

77F. (±)-(2S,3R)-1-tert-Butyloxycarbonyl-3-(tert-butyldimethylsilanyloxy)-2-formylpiperidine

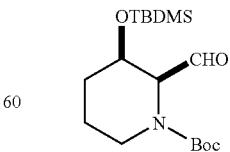

To a solution of 77E (800 mg, 2.3 mmol) in DCM (15 mL) was added 4-methylmorpholine N-oxide (541 mg, 4.6 mmol, 2 equiv) followed by the addition of TPAP (177 mg, 0.5 mmol, 0.22 equiv). The mixture was stirred at rt for 3 h. The mixture was diluted with hexane (10 mL), loaded on a layer of silica gel and eluted with 25% EtOAc/hexane. The filtrate was concentrated to gave the desired product 77F (711 mg, 90%): $R_f$ (30% EtOAc/hexane) 0.87; HPLC (Phenomenex Luna 5 u C18 4.6×50 mm, linear gradient over 4 min) retention time 4.1 min (100%); MS (ES) m/z 344.1 [M+1]$^+$; HRMS calcd for $C_{17}H_{34}NO_4Si$ 344.2257, Found 344.2259.

77G. (±)-(2R,3R)-1-tert-Butyloxycarbonyl-3-(tert-butyldimethylsilanyloxy)-2-[(3-chloro-4-cyano-2-methylphenylamino)-methyl]piperidine

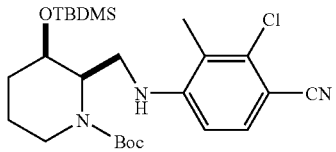

A mixture of 77F (660 mg, 1.92 mmol), 4-amino-2-chloro-3-methylbenzonitrile (384 mg, 2.3 mmol, 1.2 equiv) and HOAc (165 µL, 2.88 mmol, 1.5 equiv) in 1,2-DCE (10 mL) was stirred at rt for 30 min and Na(OAc)$_3$BH (610 mg, 2.88 mmol, 1.5 equiv) was added. The reaction was stirred at rt overnight. Another 407 mg of Na(OAc)$_3$BH (610 mg, 1.92 mmol, 1.0 equiv) was added and stirred at rt for another 24 h. The mixture was concentrated and the residue was diluted with EtOAc (30 mL), washed with saturated sodium bicarbonate solution (2×15 mL), brine (2×15 mL), dried (MgSO$_4$) and evaporated to give the crude product. Purification of the crude product by flash chromatography (0-50% EtOAc/hexane) yield the desired product 77G (192 mg, 20%) as a white foam: $R_f$ (30% EtOAc/hexane) 0.37; HPLC (Phenomenex Luna 5µ C18 4.6×50 mm, linear gradient over 4 min) retention time 4.6 min (100%); MS (ES) m/z 344.1 [M+1]$^+$; HRMS calcd for $C_{25}H_{41}N_3O_3SiCl$ 494.2606, Found 494.2613.

77H. (±)-(2S,3R)-3-(tert-Butyldimethylsilanyloxy)-2-[(3-chloro-4-cyano-2-methylphenylamino)methyl]piperidine

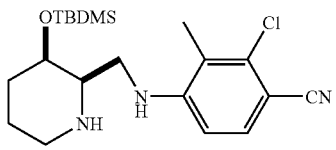

A solution of 77G (170mg, 0.34 mmol) in 5% TFA/DCM (5 mL) was stirred at rt for 5 h and LC-MS showed completion. The mixture was concentrated and the residue was dissolved in EtOAc (30 mL), washed with saturated sodium bicarbonate solution (15 mL), brine (10 mL), dried (MgSO$_4$) and evaporated to give desired product 77H (121 m, 89%) as a white solid: $R_f$ (10% MeOH/DCM) 0.39; HPLC (Phenomenex Luna 5 u C18 4.6×50 mm, linear gradient over 4 min) retention time 3.2 min (100%); MS (ES) m/z 344.1 [M+H]$^+$; HRMS calcd for $C_{20}H_{33}N_3OSiCl$ 394.2081, Found 394.2080.

77I. 4-[(8R,8aR)-8-(tert-Butyldimethylsilanyloxy)-3-oxohexahydroimidazo[1,5-a]pyridin-2-yl]-2-chloro-3-methylbenzonitrile (77Ia) and 4-[(8S,8aS)-8-8-(tert-Butyldimethylsilanyloxy)-3-oxohexahydroimidazo[1,5-a]pyridin-2-yl]-2-chloro-3-methylbenzonitrile (77Ib)

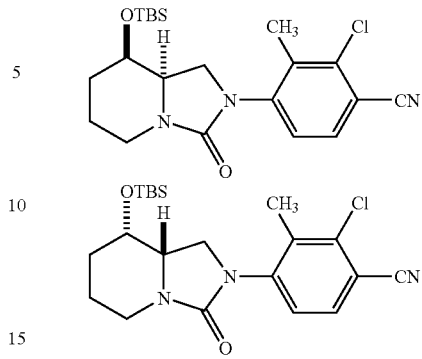

To a solution of 77H (64 mg, 0.16 mmol) in DCM (2.8 mL) at 0° C. was added DIPEA (84 µL, 0.84 mmol, 3 equiv) followed by the addition of phosgene (102 µL, 0.19 mmol, 1.2 equiv). The mixture was warmed to rt and stirred for 10 min. The reaction was concentrated and the residue was purified by flash chromatography (0-50% EtOAc/hexane) to give the racemic mixtures of 77Ia and 77Ib (60 mg). A racemic mixture of 77Ia and 77Ib (190 mg) was dissolved in IPA (5 mL) and purified by chiral preparative HPLC (Chiralpak AD 4.6× 250, 7% IPA/heptane) to give enantiomer 77Ia (87 mg) and enantiomer 77Ib (85 mg). The relative and absolute stereochemistry of 77Ia and 77Ib was assigned by separating the enantiomers of racemic intermediate 77C and transferring each enantiomer to the known (2S,3S) and (2R,3R)-3-hydroxypipecolic acids[1]. Compounds 77Ia and 77Ib were enantiomerically resynthesized from each enantiomers of intermediate 77C to confirm the stereochemistry. For 77Ia: Chiral analytical HPLC (ChiralPak AD OD 4.6×250 mm, 20% IPA/ hexane isocratic) retention time 11.0 min (100% ee); LRMS (ES$^+$) [M+H]$^+$ 420.1; HRMS calcd for $C_{21}H_{31}N_3O_2SiCl$ 420.1874, Found 420.1876. For 77Ib: Chiral analytical HPLC (ChiralPak AD OD 4.6×250 mm, 20% IPA/hexane isocratic) retention time 15.6 min (100% ee); MS (ES) m/z 420.0 [M+1]$^+$; HRMS calcd for $C_{21}H_3IN_3O_2SiCl$ 420.1874, Found 420.1859.

77J. 4-[(8R,8aR)-8-Hydroxy-3-oxohexahydroimidazo[1,5-a]pyridin-2-yl]-2-chloro-3-methylbenzonitrile To a solution of 77Ia (11 mg, 0.026 mmol) in THF (1 mL) was added TBAF (1.0 M in THF, 1.5 mL). The reaction was stirred at rt for 2 h. The reaction mixture was diluted with EtOAc, washed with water, dried (MgSO$_4$), filtered and concentrated to give the crude product. Purification by reverse phase HPLC (YMC-Pack ODS S-5 um 20×100 mm, 10 min gradient, 20 mL/min, 20-100% solvent B, A=10% MeOH/ water+0.1% TFA, B=90% MeOH/Water+0.1% TFA) provided the title compound 77J (7.1 mg): HPLC (Phenomenex Luna 5 u C18 4.6×50 mm, linear gradient over 4 min) retention time 2.30 min (100%); LC-MS [M+H]$^+$ 306; Chiral analytical HPLC (ChiralPak AD OD 4.6×250 mm, 25% IPA/ hexane isocratic) retention time 13.9 min (100% ee); MS (ES) m/z 306.1 [M+1]$^+$; HRMS calcd for $C_{15}H_{15}N_3O_2Cl$ 304.0853, Found 304.0848.

77K. 4-[(8S,8aS)-8-Hydroxy-3-oxohexahydroimidazo[1,5-a]pyridin-2-yl]-2-chloro-3-methylbenzonitrile To a solution of 77Ib (11 mg, 0.026 mmol) in THF (1 mL) was added TBAF (1.0 M in THF, 1.5 mL). The reaction was stirred at rt for 2 h. The reaction mixture was diluted with EtOAc, washed with water, dried (MgSO$_4$), filtered and concentrated to give the crude product. Purification by reverse phase HPLC (YMC-Pack ODS S-5 um 20×100 mm, 10 min gradient, 20 mL/min, 20-100% solvent B, A=10% MeOH/water+0.1% TFA, B=90% MeOH/Water+0.1% TFA) provided the title compound (24 mg): HPLC (Phenomenex Luna 5 u C18 4.6× 50 mm, linear gradient over 4 min) retention time 2.30 min (100%); LC-MS (M+H)+ 306; Chiral analytical HPLC (ChiralPak AD OD 4.6×250 mm, 25% IPA/hexane isocratic) retention time 16.1 min (100% ee); MS (ES) m/z 306.1 [M+1]+; HRMS calcd for $C_{21}H_{31}N_3O_2SiCl$ 304.0853, Found 304.0848.

[2] Lucia Battistini, Franca Zanardi et al, Tetrahedron: *Asymmetry*, 1997, 8, 2975-2987

EXAMPLE 78

4-[(8S,8aR)-8-Hydroxy-3-oxo-hexahydroimidazo[1,5-a]pyridin-2-yl]-2-chloro-3-methylbenzonitrile

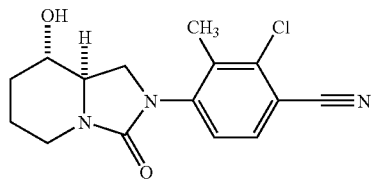

78A. 4-[(8aR)-3,8-Dioxohexahydroimidazo[1,5-a]pyridin-2-yl]-2-chloro-3-methylbenzonitrile

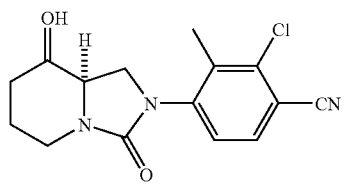

A mixture of oxalyl chloride (94 µL, 0.19 mmol) in DCM (50 µL) was cooled to −78° C. and a solution of DMSO (26 µL, 0.37 mmol) in DCM (0.7 mL) was added. The resulting mixture was stirred at −78° C. for 15 min. A solution of 4-[(8R,8aR)-8-hydroxy-3-oxohexahydroimidazo[1,5-a]pyridin-2-yl]-2-chloro-3-methylbenzonitrile (77J) (16 mg, 0.052 mmol) in DCM (0.5 mL) was followed by DCM (0.5 mL) and stirred at −78° C. for 30 min. Triethylamine (120 µL, 0.86 mmol) was added and gradually warmed to rt over 1 h. The solvent was removed and the residue was purified by flash chromatography (silica gel, 30-50% EtOAc/hexane) to give the title compound 78A (12.9 mg) as a white solid: Chiral analytical HPLC (ChiralPak AD OD 4.6×250 mm, 35% IPA/hexane isocratic) retention time 13.8 min (100% ee); MS (ES) m/z 304.1 [M+1]+; HRMS calcd for $C_{15}H_{13}ClN_3O_2$ 302.0696, Found 302.0681.

78B. 4-[(8S,8aR)-8-Hydroxy-3-oxohexahydroimidazo[1,5-a]pyridin-2-yl]-2-chloro-3-methylbenzonitrile A mixture of 78A (5 mg, 0.016 mmol) and sodium borohydride (5 mg) in MeOH:CH3CN (1:1, 1.0 mL) was stirred at rt for 2 h. The reaction was diluted with EtOAc, washed with water (2×2 mL), dried (MgSO4), filtered and concentrated to give the crude product. Purification by chiral preparative HPLC (Chiralpak AD, 25% IPA/heptane isocratic) provided 78B (4 mg): HPLC (Phenomenex Luna 5 u C18 4.6×50 mm, linear gradient over 4 min) retention time 2.40 min (100%); MS (ES) m/z 306 [M+1]+; Chiral analytical HPLC (ChiralPak AD OD 4.6×250 mm, 25% IPA/hexane isocratic) retention time 12.1 min (97.6% ee); MS (ES) m/z 306.1 [M+1]+; HRMS calcd for $C_{15}H_{15}ClN_3O_2$ 304.0853, Found 304.0846.

EXAMPLE 79

4-[(8R,8aS)-8-Hydroxy-3-oxohexahydroimidazo[1,5-a]pyridin-2-yl]-2-chloro-3-methylbenzonitrile

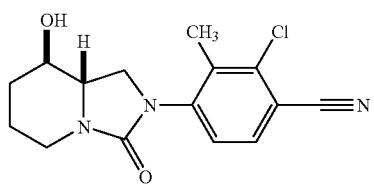

79A. 4-[(8aS)-8-Hydroxy-3,8-dioxohexahydroimidazo[1,5-a]pyridin-2-yl]-2-chloro-3-methylbenzonitrile (20A)

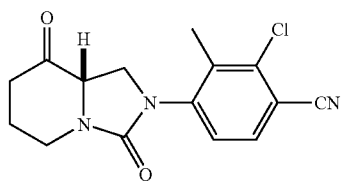

Compound 79A was prepared using the same procedure as for intermediate 78A from 77K (20 mg, 0.065 mmol), oxalyl chloride (2.0 M in DCM, 94 µL, 0.19 mmol), DMSO (26 µL, 0.37 mmol), TEA (120 µL, 0.86 mmol) and DCM (0.55 mL) and purified by flash chromatography (4 g ISCO silica gel column, 30-50% EtOAc/hexane) to give the title compound 79A (13 mg) as a white solid: Chiral analytical HPLC (ChiralPak AD OD 4.6×250 mm, 35% IPA/hexane isocratic) retention time 11.3 min (64% ee).

79B. 4-[(8R,8aS)-8-Hydroxy-3-oxohexahydroimidazo[1,5-a]pyridin-2-yl]-2-chloro-3-methylbenzonitrile A mixture of 79A (13 mg, 0.033 mmol) and sodium borohydride (11 mg) in MeOH:CH3CN (1:1, 1.0 mL) was stirred at rt overnight. The reaction was diluted with EtOAc, washed with water (2×2 mL), dried (MgSO4), filtered and concentrated to give the crude product (13 mg). Purification by chiral preparative HPLC (Chiralpak AD, 25% IPA/heptane isocratic) provided the title compound (4.5 mg): HPLC (Phenomenex Luna 5 u C18 4.6×50 mm, linear gradient over 4 min) retention time 2.40 min (100%); LC-MS [M+H]+ 306; Chiral analytical HPLC (ChiralPak AD OD 4.6×250 mm, 25% IPA/hexane isocratic) retention time 10.5 min (98% ee); MS (ES): m/z 306.1 [M+1]+; HRMS calcd for $C_{15}H_{15}ClN_3O_2$ 304.0853, Found 304.0863.

EXAMPLE 80

4-[(1S,7R,7aR)-7-Hydroxy-1-methyl-3-oxohexahydropyrrolo[1,2-c]imidazol-2-yl]-2-chloro-3-methylbenzonitrile

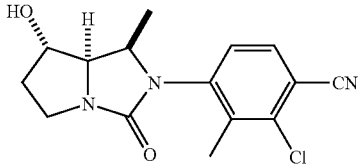

80A. (2S,3S)-N-tert-Butyloxycarbonyl-3-(tert-butyldimethylsilanyloxy)-2-((1S)-1-hydroxyethyl)pyrrolidine (80A-a) and (2S,3S)-N-tert-Butyloxycarbonyl-3-(tert-butyldimethylsilanyloxy)-2-((1R)-1-hydroxyethyl)pyrrolidine (80A-b)

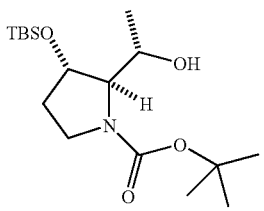

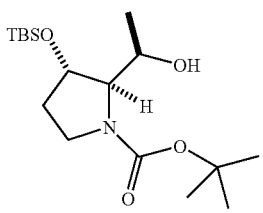

To a solution of intermediate (2S,3S)-N-tert-Butyloxycarbonyl-3-(tert-butyldimethylsilanyloxy)-2-formylpyrrolidine (4.7 g, 14.26 mmol) in THF (70 mL) at −78° C. was added dropwise MeMgBr (3.0 M in THF, 23.8 mmol). The reaction was stirred at −78° C. for 3 h and TLC (20% EtOAc/hexane) showed complete reaction. The reaction was quenched by the addition of HOAc (5.0 mL) at −78° C., warmed to rt and diluted with EtOAc (20 mL). The organic layer was separated and the aqueous layer was extracted with EtOAc (2×30 mL). The combined organic layers were washed with saturated NaHCO$_3$ solution and brine, dried (MgSO$_4$), filtered and concentrated to give the crude product. Purification by flash chromatography (120 g ISCO silica gel column, 0-30% EtOAc/hexane) provided 80A-a (760 mg) and 80A-b(1.54 g) as colorless oil. 80A-a: For (20% EtOAc/hexane) 0.29. 80A-b: For (20% EtOAc/hexane) 0.25.

80B. (2S,3S)-N-tert-Butyloxycarbonyl-3-(tert-butyldimethylsilanyloxy)-2-((1S)-1-methanesulfonyloxyethyl)pyrrolidine

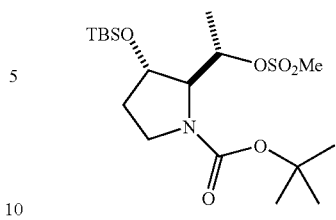

To a solution of 80A-a (728 mg, 2.10 mmol) in DCM (10 mL) at 0° C. was added DIPEA (1.46 mL, 8.4 mmol) and a catalytic amount of DMAP. The mixture was stirred at 0° C. for 20 min and warmed to rt and stirred at rt for 4 h. The reaction was diluted with EtOAc and washed a 1:1 mixture of 1 N HCl and brine (2×5 mL), saturated sodium bicarbonate solution (5 ml), brine (5 mL), dried (MgSO$_4$), filtered and concentrated to give the crude product. Purification by chromatography (10 g ISCO silica gel cartridge, 8% EtOAc/hexane) provided 80B as a yellow oil (410 mg): MS (ES) m/z 324 [M−Boc+H]$^+$.

80C. (2R,3S)-N-tert-Butyloxycarbonyl-3-(tert-butyldimethylsilanyloxy)-2-((1R)-1-azidoethyl)pyrrolidine

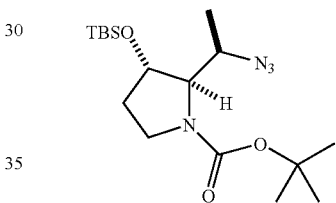

A mixture of 80B (650 mg, 1.53 mmol) and sodium azide (597 mg, 9,18 mmol) was heated at 80° C. for 2 days. The reaction was diluted with EtOAc (200 mL), washed with brine:water (1:1, 4×15 mL), dried (MgSO$_4$), filtered and concentrated to give the crude product. Purification by chromatography (40 g ISCO silica gel cartridge, 0-20% EtOAc/hexane) provided 80C as a colorless oil (410 mg). MS (ES) m/z 271 [M−Boc+H]$^+$.

80D. (2S,3S)-N-tert-Butyloxycarbonyl-3-(tert-butyldimethylsilanyloxy)-2-((1R)-1-aminoethyl)pyrrolidine

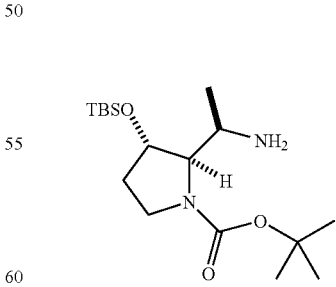

A mixture of 80C (410 mg, 1.10 mmol) and 10% Pd/C (100 mg) in MeOH:EtOAc (2:1, 15 mL) was stirred under hydrogen atmosphere for 2 h. The reaction was filtered through a pad of celite. The filtrate was concentrated and purified by flash chromatography (10 g ISCO silica gel cartridge, 0-20% MeOH/DCM) to the title compound 80D (284 mg): MS (ES) m/z 345 [M+H]+.

80E. (2S,3S)-1-tert-Butyloxycarbonyl-3-(tert-butyldimethylsilanyloxy)-2-[(1R)-1-(3-chloro-4-cyano-2-methylphenylamino)ethyl]pyrrolidine

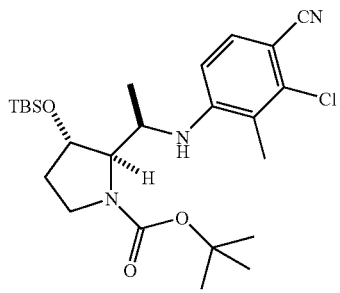

To a solution of 80D (137 mg, 0.40 mmol) in nitrogen degassed toluene (3 mL) at rt was added 2-chloro-4-iodo-3-methyl-benzonitrile (122 mg, 0.44 mmol), Cs₂CO₃ (260 mg, 0.80 mmol) and Pd₂(dba)₃ (7.3 mg, 0.008 mmol) and (S)-N,N-dimethyl-1-[(R)-2-(diphenylphosphino)ferrocenyl]ethylamine (11 mg, 0.024 mmol). The reaction was degassed with nitrogen for 30 min, sealed and heated at 140° C. for 2 h under microwave conditions. The mixture was cool to rt, diluted with hexane and filtered through a layer of celite. The filtrate was evaporated to give the crude product. Purification by flash chromatography (10 g ISCO silica gel cartridge, 0-20% EtOAc in hexane gradient) gave the title compound 80E (36 mg): MS (ES) m/z 345 [M+H]+; HRMS calcd for C₂₅H₄₁N₃O₃ClSi 494.2606, found 494.2606.

80F. (2R,3S)-3-(tert-Butyldimethylsilanyloxy)-2-[(1R)-1-(3-chloro-4-cyano-2-methylphenylamino)ethyl]pyrrolidine

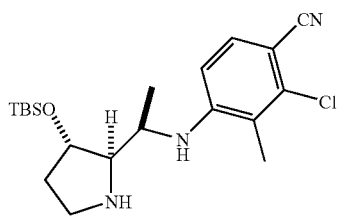

Intermediate 80E (36 mg, 0.073 mmol) was dissolved in DCM (900 µL) and TFA (100 µL) was added. The mixture was stirred at rt for 10 h. The reaction was diluted with EtOAc, washed with saturated sodium bicarbonate solution (3×5 mL), brine (5 mL), dried (MgSO₄), filtered and concentrated to give the title compound 80F (27 mg): MS (ES) m/z 394.5 [M+H]+.

80G. 4-[(1R,7S,7aR)-7-tert-Butyldimethylsilanoxy-1-methyl-3-oxohexahydropyrrolo[1,2-c]imidazol-2-yl]-2-chloro-3-methylbenzonitrile

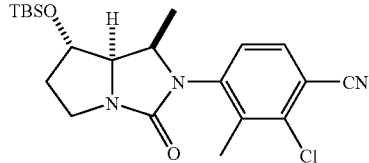

To a solution of crude 80F (~0.068 mmol) in CH₂Cl₂ (2 mL) was added i-Pr₂NEt (36 µL, 0.20 mmol) followed by 20% phosgene in toluene (50 µL, 0.1 mmol)-dropwise. The reaction was stirred at rt for 4 days and no desired product was formed. The solvent was removed and the residue was dissolved in 1,2-dichloroethane (2 mL) and treated with i-Pr₂NEt (108 µL) at 80° C. for 3 h. Reaction was concentrated and the residue was purified by preparative TLC (30% EtOAc/hexane) to provide the title compound 80G (11 mg): MS (ES) m/z 420.5 [M+H]+; HRMS calcd for C₂₁H₃₁N₃O₂ClSi 420.1874, found 420.1870.

80H. 4-[(1S,7R,7aR)-7-Hydroxy-1-methyl-3-oxohexahydropyrrolo[1,2-c]imidazol-2-yl]-2-chloro-3-methylbenzonitrile To a solution of 80G (11 mg, 0.026 mmol) in THF (1 mL) was added TBAF (1.0 M in THF, 0.26 mL). The reaction was stirred at rt for 2 h. The reaction mixture was concentrated and the residue was purified by reverse phase HPLC (Phenomenex Luna 20×100 mm S5 C18, 10 min. grad, 20 mL/min, 20-100% B solvent, A=10% MeOH/water+0.1% TFA, B=90% MeOH/Water+0.1% TFA) to provide the title compound (5.1 mg): HPLC (Phenomenex Luna 5 u C18 4.6×50 mm, linear gradient over 4 min) retention time 2.40 min (100%); Chiral analytical HPLC (ChiralPak AD 4.6×250 mm, 20% IPA/hexane isocratic) retention time 18.6 min (100% ee); MS (ES) m/z 306.1 [M+H]+; HRMS calcd for C₁₅H₁₇ClN₃O₂ 306.1009, Found 306.1010.

Examples 81–84

| Example | Structure | MS (ES) m/z [M + H]+ |
|---|---|---|
| 81 | 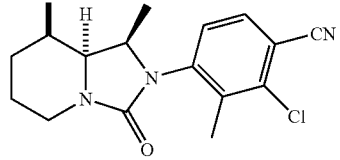 | 320.1 |
| 82 | 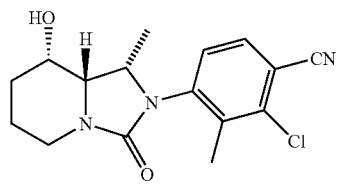 | 320.1 |

-continued

Examples 81–84

| Example | Structure | MS (ES) m/z [M + H]+ |
|---|---|---|
| 83 | 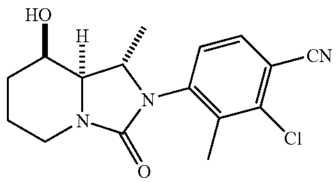 | 320.1 |
| 84 | 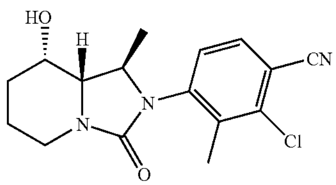 | 320.1 |

81A. (±)-(2R,3R)-1-tert-Butyloxycarbonyl-3-(tert-butyldimethylsilanyloxy)-2-[(1R)-1-(3-chloro-4-cyano-2-methylphenylamino)ethyl]piperidine (81A-a) and (±) (2R,3R)-1-tert-Butyloxycarbonyl-3-(tert-butyldimethylsilanyloxy)-2-[(1S)-1-(3-chloro-4-cyano-2-methylphenylamino)ethyl]piperidine (81A-b)

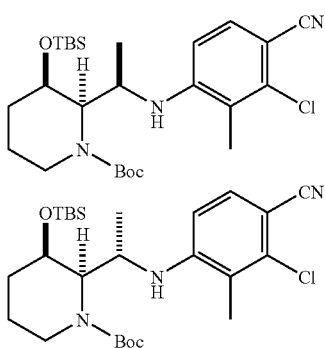

Compounds 81A-a and 81A-b were synthesized from 1-tert-butyloxycarbonyl-3-(tert-butyldimethylsilanyloxy)-2-formyl-piperidine (18F) following a procedure similar to that used for 80F to give a mixture of 81A-a and 81A-b as the crude product. Purification and separation by flash chromatography (12 g ISCO silica gel column, 0-20% EtOAc/hexane gradient) provided 81A-a as colorless film (28 mg) and 81A-b (14 mg) as a colorless film. For 81A-a: HPLC (Phenomenex Luna 5 u C18 4.6×50 mm, linear gradient over 4 min) retention time 4.85 min (100%); MS (ES) m/z 508.0 [M+H]+; HRMS calcd for $C_{26}H_{43}ClN_3O_3Si$ 508.2762, Found 508.2761. For 81A-b: HPLC (Phenomenex Luna 5 u C18 4.6×50 mm, linear gradient over 4 min) retention time 4.95 min (100%); MS (ES) m/z 508.0 [M+H]+; HRMS calcd for $C_{26}H_{43}ClN_3O_3Si$ 508.2762, Found 508.2748.

81B. Examples 81-82 and 83-84 were prepared from 81A-a and 81A-b, respectively, following the methods from Example 80. Individual enantiomers were isolated using preperative HPLC (ChiralPak 5×50 cm, isocratic 20% IPA/hexane).

EXAMPLE 85

4-[(1S,7S,7aR)-1-Ethyl-7-hydroxy-3-oxohexahydropyrrolo[1,2-c]imidazol-2-yl)-2-chloro-3-methylbenzonitrile

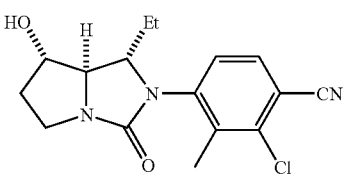

The title compound was prepared in a manner similar to that described in Example 61. Analytical HPLC with YMC Combiscreen ODS-A C18 4.6×50 mm column, 4 min gradient, 10% MeOH/90% $H_2O$/0.1% $H_3PO_4$ to 90% MeOH/10% $H_2O$/0.1% $H_3PO_4$; 1 min hold, 4 mL/min UV detection at 220 nm, 98% purity (Rt 2.86 min); MS (ESI) m/z 320 [M+H]; HRMS calcd for [M−H] 318.1009, found 318.0994.

EXAMPLE 86

4-[(1R,7S,7aR)-1-Ethyl-7-hydroxy-3-oxohexahydropyrrolo[2-c]imidazol-2-yl)-2-chloro-3-methylbenzonitrile

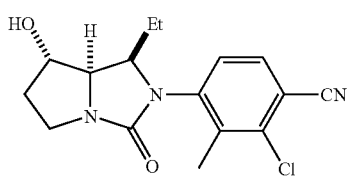

The title compound was prepared in a manner similar to that described in Example 80. Analytical HPLC with YMC Combiscreen ODS-A C18 4.6×50 mm column, 4 min gradient, 10% MeOH/90% $H_2O$/0.1% $H_3PO_4$ to 90% MeOH/10% $H_2O$/0.1% $H_3PO_4$; 1 min hold, 4 mL/min UV detection at 220 nm, 98% purity (Rt 2.67 min); MS (ESI) m/z 320 [M+H]; HRMS calcd for [M+H] 320.1166, found 320.1165.

EXAMPLE 87

4-[(1S, 7R, 7aR)-1-Ethyl-7-hydroxy-3-oxohexahydropyrrolo[1,2-c]imidazol-2-yl]-2-chloro-3-methylbenzonitrile

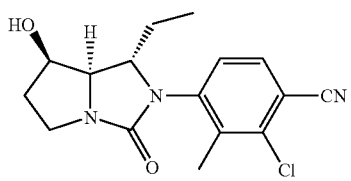

87A. 4-[(1S,7R,7aR)-7-Benzoyloxy-1-ethyl-3-oxohexahydropyrrolo[1,2-c]imidazol-2-yl]-2-chloro-3-methylbenzonitrile

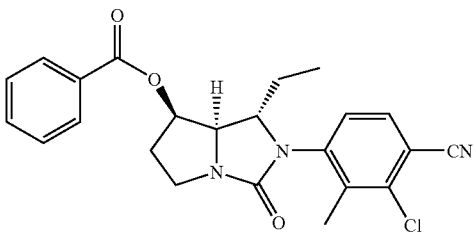

To a solution of compound 85 (51 mg, 0.16 mmol) in 2 mL THF were added triphenylphosphine (84 mg, 0.32 mmol), benzoic acid (39 mg, 0.32 mmol) followed by diisopropyl azodicarboxylate (65 mg, 0.32 mmol) at rt. The mixture was stirred at rt for 2 h. Concentration of the reaction mixture via rotary evaporator, followed by silica gel column chromatography purification yielded the title compound (64 mg).

87B. 4-[(1S,7R,7aR)-1-Ethyl-7-hydroxy-3-oxohexahydropyrrolo[1,2-c]imidazol-2-yl]-2-chloro-3-methylbenzonitrile

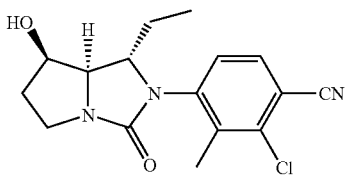

Compound 87A (64 mg, 0.15 mmol) was dissolved in 1.5 mL of THF, treated with 1N KOH in anhydrous methanol (0.32 mL, 0.32 mmol) at rt for 2 h. Diluted the reaction mixture with 30 mL EtOAc, washed with saturated aqueous NaHCO$_3$ solution (10 mL), brine (10 mL×2), dried over MgSO$_4$, filtered and concentrated. The resulting mixture was purified by reverse phase HPLC (Phenominex Luna 30×250 mm S5 C18, 30 min. gradient time, 25 mL/min, 30-100% B solvent, A=10% MeOH/water, B=90% MeOH/Water), provided the title compound (43 mg). Analytical HPLC retention time 2.947 min (purity 98%). Condition: YMC Combiscreen ODS-A C18 4.6×50 mm column, 4 min gradient, 4 mL/min flow, 0-100% B solvent, A=10% MeOH/water+0.1% H$_3$PO$_4$, B=90% MeOH/Water+0.1% H$_3$PO$_4$. MS (ES) m/z 320.24 [M+H]$^+$, HRMS calcd for [M+H] 320.1166, found 320.1152.

EXAMPLE 88

4-[(1R,7R,7aR)-1-Ethyl-7-hydroxy-3-oxohexahydropyrrolo[1,2-c]imidazol-2-yl]-2-chloro-3-methylbenzonitrile

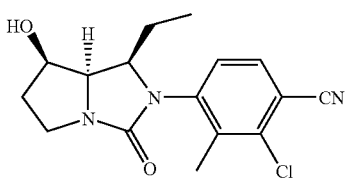

The title compound was prepared from compound 86 in a manner similar to that described in Example 87. Analytical HPLC retention time 2.750 min (purity 96%). Condition: YMC Combiscreen ODS-A C18 4.6×50 mm column, 4 min gradient, 4 mL/min flow, 0-100% B solvent, A=10% MeOH/water+0.1% H$_3$PO$_4$, B=90% MeOH/Water+0.1% H$_3$PO$_4$. MS (ES) m/z 320.22 [M+H]$^+$, HRMS calcd for [M+H] 320.1166, found 320.1168.

EXAMPLE 89

2-Chloro-4-[(7R)-7-fluoro-3-oxotetrahydro-1H-pyrrolo[1,2-c]imidazol-2(3H)-yl]-3-methylbenzonitrile

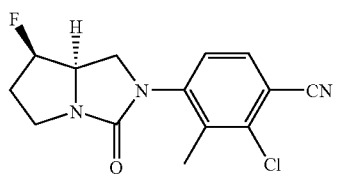

A solution of (7S,7aS)-2-chloro-4-(7-hydroxy-3-oxotetrahydropyrrolo[1,2-c]imidazol-2-yl)-3-methylbenzonitrile (WO 03/096980) (30 mg, 0.103 mmol) in dry dichloromethane (1.0 mL) was cooled to −65° C., treated with DAST (26 μL, 0.21 mmol) and stirred for 17 h, allowing the temperature to warm to rt. The reaction mixture was then cooled to 0° C., quenched with 10% sodium carbonate (0.5 mL) and extracted with CH$_2$Cl$_2$ (2×10 mL). The organic phase was washed with H$_2$O (0.5 mL), dried (Na$_2$SO$_4$), filtered and concentrated under reduced pressure. The syrup was combined with a previous batch (5.4 mg) and chromatographed 3× (silica gel; EtOAc/hexane gradient then CH$_3$OH/CH$_2$Cl$_2$ gradient) to yield the title compound (14.5 mg, 47.9%). HPLC: 99.1% at 2.04 min (retention time) (Conditions: YMC S-5 C-18 (4.6×50 mm), eluting with 0-100% B, 4 min gradient. (A=90% H$_2$O—10% CH$_3$C—0.1% TFA and B=10% H$_2$O—90% CH$_3$CN—0.1% TFA); Flow rate at 4 mL/min. UV detection at 220 nm). Chiral HPLC: retention time=20.8 min (100%); Conditions: OD (4.6×250 mm); Eluted with 20% isopropanol in heptane for 60 min at 1 mL/min. MS (ES$^+$): m/z 294 [M+H]$^+$.

EXAMPLE 90

4-[(7R)-7-Amino-3-oxotetrahydro-1H-pyrrolo[1,2-c]imidazol-2(3H)-yl]-2-chloro-3-methylbenzonitrile

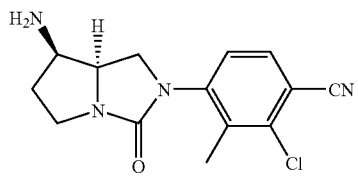

90A. (7S)-2-(3-Chloro-4-cyano-2-methylphenyl)-3-oxo-hexahydro-1H-pyrrolo[1,2-c]imidazol-7-ylmethane-sulfonate

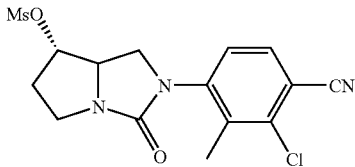

A cooled (0° C.) solution of (7S,7aS)-2-chloro-4-(7-hydroxy-3-oxotetrahydropyrrolo[1,2-c]imidazol-2-yl)-3-methylbenzonitrile (WO 03/096980) (342 mg, 1.17 mmol) and triethylamine (0.70 mL, 5.02 mmol) in dry $CH_2Cl_2$ (7.0 mL) was treated with methanesulfonyl chloride (0.21 mL, 2.71 mmol) and stirred, allowing the temperature to come up to rt over 17 h. The mixture was diluted with $CH_2Cl_2$ (100 mL), washed with saturated $NaHCO_3$ (4.0 mL) and brine (4.0 mL), dried ($Na_2SO_4$), filtered and concentrated under reduced pressure. The syrup was chromatographed (silica gel; $CH_2Cl_2/CH_3OH$ gradient) to yield the title compound (400.2 mg, 92.5%) as a white solid foam from $CH_2Cl_2$/Hexane. HPLC: 97.9% at 2.10 min (retention time) (Conditions: YMC S-5 C-18 (4.6×50 mm), eluting with 0-100% B, 4 min gradient. (A=90% $H_2O$—10% $CH_3CN$—0.1% TFA and B=10% $H_2O$—90% $CH_3CN$—0.1% TFA); Flow rate at 4 mL/min. UV detection at 220 nm. MS ($ES^+$): m/z 370 $[M+H]^+$.

90B. 2-Chloro-4-[(7R,7aR)-7-azido-3-oxotetrahydro-1H-pyrrolo[1,2-c]imidazol-2(3H)-yl]-3-methylbenzonitrile

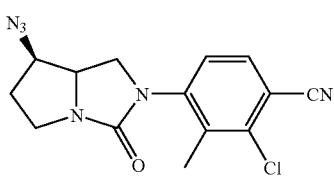

A solution of compound 90A (400 mg, 1.18 mmol) and sodium azide (309 mg, 4.75 mmol) in anhydrous DMF (3.2 mL) was placed in a pre-heated bath (75° C.) and stirred at 75° C. for 3 h. The solution was cooled, quenched with $H_2O$ (6.0 mL) and extracted with EtOAc (2×80 mL). The organic phase was washed with $H_2O$ (6.0 mL), brine (6.0 mL), dried ($Na_2SO_4$), filtered and concentrated under reduced pressure. The syrup was chromatographed (silica gel; $CH_2Cl_2/CH_3OH$ gradient) to yield the title compound (339.3 mg, 90.8%) as a white solid foam from $CH_2Cl_2$/Hexane. HPLC: 97.7% at 2.22 min (retention time) (Conditions: YMC S-5 C-18 (4.6×50 mm), eluting with 0-100% B, 4 min gradient. (A=90% $H_2O$—10% $CH_3CN$—0.1% TFA and B=10% $H_2O$—90% $CH_3CN$—0.1% TFA); Flow rate at 4 mL/min. UV detection at 220 nm. MS ($ES^+$): m/z 317 $[M+H]^+$.

90C. 4-[(7R)-7-Amino-3-oxotetrahydro-1H-pyrrolo[1,2-c]imidazol-2(3H)-yl]-2-chloro-3-methylbenzonitrile

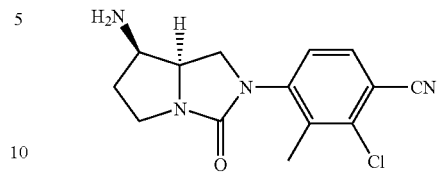

A solution of compound 90B (20.5 mg, 0.06 mmol) in dry MeOH (1.0 mL) was treated with $PtO_2$ (5.5 mg) and hydrogenated (balloon) at rt for 1.0 h. The reaction mixture was diluted with MeOH (1.0 mL) and filtered through a syringe filter, washing the syringe filter well with MeOH (3×1.0 mL). The clear filtrate was concentrated under reduced pressure and the residue was chromatographed (silica gel; $CH_2Cl_2/CH_3OH$ gradient) to yield the title compound (11.9 mg, 68.2%) as a white solid. HPLC: 100% at 1.38 min (retention time) (Conditions: YMC S-5 C-18 (4.6×50 mm), eluting with 0-100% B, 4 min gradient. (A=90% $H_2O$—10% $CH_3CN$—0.1% TFA and B=10% $H_2O$—90% $CH_3CN$—0.1% TFA); Flow rate at 4 mL/min. UV detection at 220 nm. Chiral HPLC: retention time=18.98 min (99.6%); Conditions: OD (4.6×250 mm); Eluted with 20% isopropanol in heptane for 30 min at 1 mL/min. MS ($ES^+$): m/z 291 $[M+H]^+$.

EXAMPLE 91

2-Chloro-3-methyl-4-[(7R)-7-methylamino-3-oxotetrahydro-1H-pyrrolo[1,2-c]imidazo-2(3H)-yl]benzonitrile

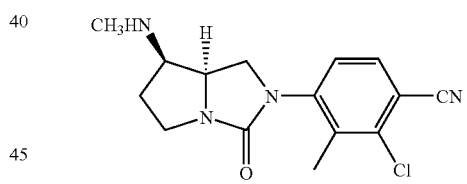

A solution of compound 90B (32 mg, 0.10 mmol) and 1.0 M $Et_3P$ in THF (0.23 mL, 0.23 mmol) in anhydrous $CH_2Cl_2$ (0.85 mL) was stirred at rt for 1.5 h, diluted with dry $CH_2Cl_2$ (0.85 mL) then treated with methyl iodide (63 μL, 1.0 mmol). The reaction mixture was stirred at rt for 3.0 h, diluted with $CH_2Cl_2$ (3.0 mL), treated with $H_2O$ (0.5 mL) and stirred at rt for another 30 min. The reaction mixture was extracted with $CH_2Cl_2$ (2×10 mL), dried over $Na_2SO_4$, filtered and concentrated under reduced pressure. The resulting syrup was chromatographed (silica gel; $CH_2Cl_2/CH_3OH$ gradient) followed by preparative HPLC and trituration of the product obtained with $Et_2O$ (2×0.5 mL) to yield the title compound (8.2 mg, 19.6%) as a light beige solid. HPLC: 98.0% at 1.35 min (retention time) (Conditions: YMC S-5 C-18 (4.6×50 mm), eluting with 0-100% B, 4 min gradient. (A=90% $H_2O$—10% $CH_3CN$—0.1% TFA and B=10% $H_2O$—90% $CH_3CN$—0.1% TFA); Flow rate at 4 mL/min. UV detection at 220 nm. MS ($ES^+$): m/z 305 $[M+H]^+$.

EXAMPLE 92

N-(7R)-2-(3-Chloro-4-cyano-2-methylphenyl)-3-oxohexahydro-1-pyrrolo[1,2-c]imidazol-7-yl]-2,2,2-trifluoroacetamide

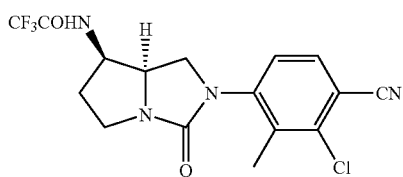

A solution of compound 90C (20 mg, 0.069 mmol) in anhydrous $CH_2Cl_2$ (0.50 mL) was cooled to 0° C., treated with trifluoroacetic anhydride (13 μL, 0.09 mmol), stirred at 0° C. for 1.0 h then at rt for 17 h. The reaction mixture was diluted with EtOAc (15 mL) and washed with 5% $NaHCO_3$ (0.5 mL). The organic phase was dried over anhydrous $Na_2SO_4$, filtered, concentrated under reduced pressure and combined with another batch from 91C (0.076 mmol). The syrup was chromatographed (silica gel; $CH_2Cl_2/CH_3OH$ gradient) to yield the title compound (38 mg, 64.5%) as a white solid foam from $CH_2Cl_2$/Hexane. HPLC: 97.0% at 2.1 min (retention time) (Conditions: YMC S-5 C-18 (4.6×50 mm), eluting with 0-100% B, 4 min gradient. (A=90% $H_2O$–10% $CH_3CN$—0.1% TFA and B=10% $H_2O$–90% $CH_3CN$–0.1% TFA); Flow rate at 4 mL/min. UV detection at 220 nm. Chiral HPLC: retention time=10.78 min (98.2%); Conditions: OD (4.6×250 mm); Eluted with 20% isopropanol in heptane for 30 min at 1 mL/min. MS (ES+): m/z 387 $[M+H]^+$.

What is claimed is:

1. A compound according to formula I

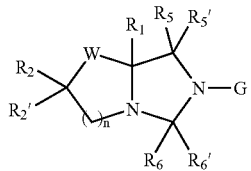

or a pharmaceutically acceptable salt thereof
wherein
$R_1$ is selected from hydrogen (H), alkenyl or substituted alkenyl, $CO_2R_4$, $CONR_4R_4'$ and $CH_2OR_4$;
$R_2$ and $R_2'$ are each independently selected from hydrogen (H), alkyl, substituted alkyl, $SR_3$, halo, $NHR_4$, $NHCOR_4$, $NHCO_2R_4$, $NHCONR_4R_4'$ and $NHSO_2R_4$;
and at least one of $R_2$ and $R_2'$ is H or alkyl;
$R_3$ in each functional group is independently selected from hydrogen (H), alkyl or substituted alkyl, $CHF_2$, $CF_3$ and $COR_4$;
$R_4$ and $R_4'$ in each functional group are each independently selected from hydrogen(H), alkyl or substituted alkyl, alkenyl or substituted alkenyl, alkynyl or substituted alkynyl, cycloalkyl or substituted cycloalkyl, arylalkyl or substituted arylalkyl, and aryl or substituted aryl;
$R_5$ and $R_5'$ are each independently selected from hydrogen (H), alkyl or substituted alkyl, alkenyl or substituted alkenyl, alkynyl or substituted alkynyl, cycloalkyl or substituted cycloalkyl and arylalkyl or substituted arylalkyl, wherein at least one of $R_5$ and $R_5'$ is hydrogen, or $R_5$ and $R_5'$ taken together can form a double bond with oxygen (O), sulfur (S), $NR_7$ or $CR_7R_7'$;
$R_6$ and $R_6'$ are each independently at each occurrence selected from hydrogen(H), alkyl or substituted alkyl, alkenyl or substituted alkenyl, alkynyl or substituted alkynyl, cycloalkyl or substituted cycloalkyl, and arylalkyl or substituted arylalkyl, wherein at least one of $R_6$ and $R_6'$ is hydrogen, or $R_6$ and $R_6'$ at each occurrence taken together form a double bond with oxygen (O), sulfur (S), or $CR_7R_7'$;
$R_7$ and $R_7'$ in each functional group are each independently selected from hydrogen(H), $OR_4$, alkyl or substituted alkyl, alkenyl or substituted alkenyl, alkynyl or substituted alkynyl, cycloalkyl or substituted cycloalkyl, arylalkyl or substituted arylalkyl, and aryl or substituted aryl;
G is an aryl group, wherein said group is mono- or polycyclic, and which is optionally substituted with one or more substitutents selected from hydrogen, halo, CN, $CF_3$, $OR_4$, $CO_2R_4$, $NR_4R_4'$, $CONR_4R_4'$, $CH_2OR_4$, alkyl or substituted alkyl, alkenyl or substituted alkenyl, alkynyl or substituted alkynyl, cycloalkyl or substituted cycloalkyl, arylalkyl or substituted arylalkyl, and aryl or substituted aryl;
W is selected from $(CR_6R_6')$, $C(R_6)OR_3$, or $C(R_6)(NR_4R_4')$; and
n is 1;
with the following provisos:
(a) when $R_5$ and $R_5'$ and/or $R_6$ and $R_6'$ form a double bond with $CR_7R_7'$, then when either $R_7$ or $R_7'$ is $OR_4$, $R_4$ is not hydrogen;
(b) when
  (i) $R_5$ and $R_5'$ are each H or taken together to be =O, =S or $=CH_2$,
  (ii) $R_6$ and $R_6'$ on the imidazolidine portion of the bicyclic structure shown are selected from hydrogen(H), alkyl or substituted alkyl, alkenyl, or substituted alkenyl, alkynyl or substituted alkynyl, cycloalkyl or substituted cycloalkyl, and arylalkyl or substituted arylalkyl, wherein at least one of $R_6$ and $R_6'$ on the imidazolidine portion of the bicyclic structure shown is hydrogen, or $R_6$ and $R_6'$ on the imidazolidine portion of the bicyclic structure shown are taken together to form a double bond with oxygen (O) or sulfur (S),
  (iii) W is $CR_6R_6'$ where $R_6$ and $R_6'$ are each independently selected from H, alkyl or substituted alkyl, alkenyl or substituted alkenyl, alkynyl or substituted alkynyl, cycloalkyl or substituted cycloalkyl and arylalkyl or substituted arylalkyl, wherein at least one of $R_6$ and $R_6'$ in W is H, and
  (iv) G has the structure:

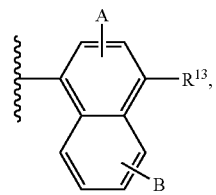

wherein,
$R_{13}$ is selected from the group consistng of H, CN, $NO_2$, halo, $OR_{14}$, $CO_2R_{15}$, $CONHR_{15}$, $COR_{15}$, S(O)$_p$R$_{15}$, SO$_2$NR$_{15}$R$_{15}$', NHCOR$_{15}$ and NHSO$_2$R$_{15}$, wherein p is an integer from 0 and 2, R$_{14}$ in each functional group is independently selected from H, alkyl or substituted alkyl, CHF$_2$, CF$_3$ and COR$_{15}$, R$_{15}$ and R$_{15}$' in each functional group are each independently selected from H, alkyl or substituted alkyl, alkenyl or substituted alkenyl, alkynyl or substituted alkynyl, cycloalkyl or substituted cycloalkyl, arylalkyl or substituted arylalkyl, aryl or substituted aryl, heteroaryl or substituted heteroaryl and -CN, and A and B are each independently selected from H, halo, CN, NO$_2$, alkyl or substituted alkyl and OR$_{14}$, then R$_2$ R$_2$' are each independently selected from SR$_3$ and NHR$_4$.

2. The compound or pharmaceutically acceptable salt thereof according to claim 1 wherein G is selected from:

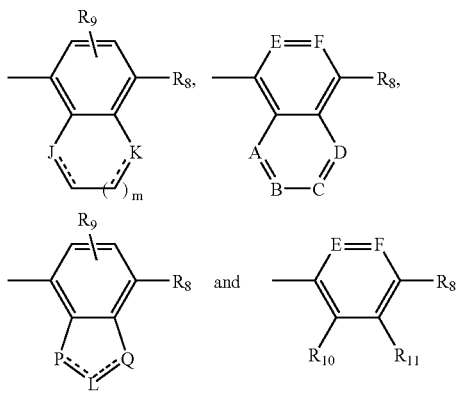

wherein

R$_8$, R$_9$, R$_{10}$ and R$_{11}$ are each independently selected from hydrogen (H), NO$_2$, CN, CF$_3$, OR$_4$, CO$_2$R$_4$, NR$_4$R$_4$', CONR$_4$R$_4$', CH$_2$OR$_4$, alkyl or substituted alkyl, alkenyl or substituted alkenyl, alkynyl or substituted alkynyl, cycloalkyl or substituted cycloalkyl, arylalkyl or substituted arylalkyl, and aryl or substituted aryl;

A to F is each independently selected from N or CR$_9$;

J, K, L, P and Q are each independently selected from CR$_{12}$R$_{12}$';

R$_{12}$ and R$_{12}$' in each functional group are each independently selected from a bond or R$_1$; and m is an integer of 0 or 1.

3. The compound or pharmaceutically acceptable salt thereof according to claim 2 wherein R$_8$ is -CN.

4. The compound according to claim 1 which is:

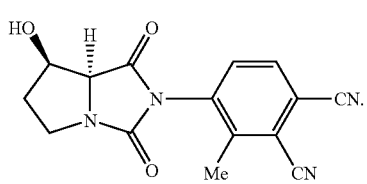

or a pharmaceutically acceptable salt thereof.

5. The compound according to claim 1 selected from:

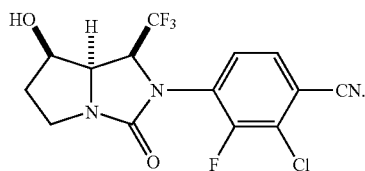

or a pharmaceutically acceptable salt thereof.

6. A pharmaceutical composition, comprising:
(a) a compound or pharmaceutically acceptable salt thereof according to claim 1; and
(b) at least one pharmaceutically acceptable diluent or carrier.

7. The compound according to claim 1 which is

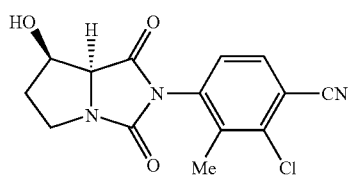

or a pharmaceutically acceptable salt thereof.

8. The compound according to claim 1 which is

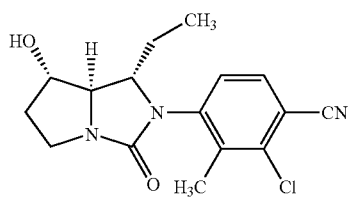

or a pharmaceutically acceptable salt thereof.

9. A pharmaceutical composition according to claim 6, wherein the compound according to claim 1 is

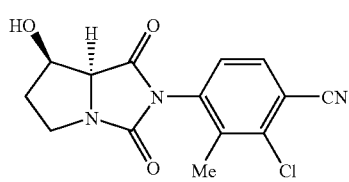

or a pharmaceutically acceptable salt thereof.

10. A pharmaceutical composition according to claim 6, wherein the compound according to claim 1 is

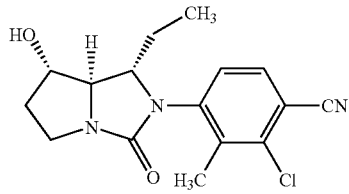

or a pharmaceutically acceptable salt thereof.

11. The compound according to claim 1 which is

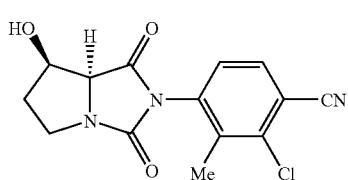

or a pharmaceutically acceptable salt thereof.

12. The compound according to claim 1 which is

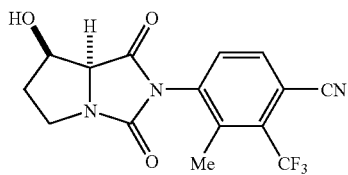

pharmaceutically acceptable salt thereof.

13. The compound according to claim 1 which is

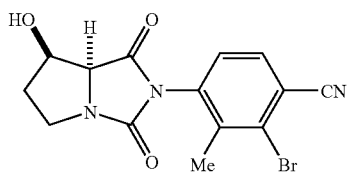

pharmaceutically acceptable salt thereof.

14. The compound according to claim 1 which is

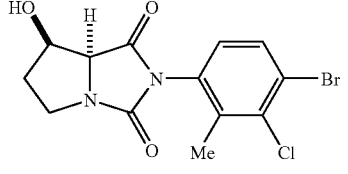

pharmaceutically acceptable salt thereof.

15. The compound according to claim 1 which is

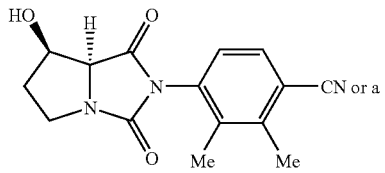

pharmaceutically acceptable salt thereof.

16. The compound according to claim 1 which is

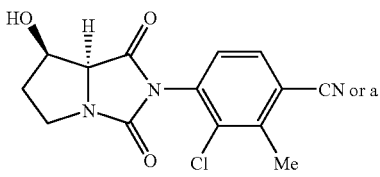

pharmaceutically acceptable salt thereof.

17. The compound according to claim 1 which is

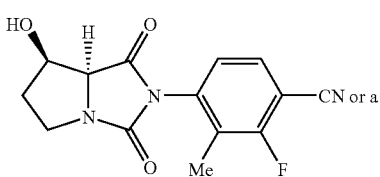

pharmaceutically acceptable salt thereof.

18. The compound according to claim 1 which is

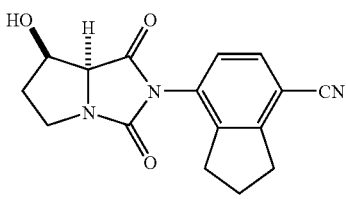

pharmaceutically acceptable salt thereof.

19. The compound according to claim 1 which is

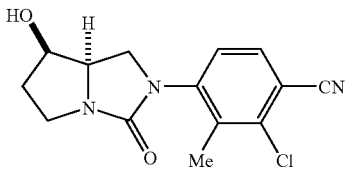

pharmaceutically acceptable salt thereof.

20. The compound according to claim 1 which is

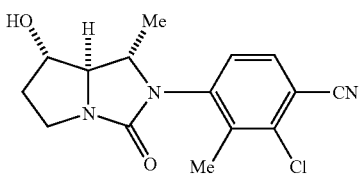

pharmaceutically acceptable salt thereof.

21. The compound according to claim 1 which is
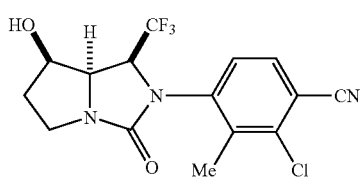
a pharmaceutically acceptable salt thereof.
22. The compound according to claim 1 which is
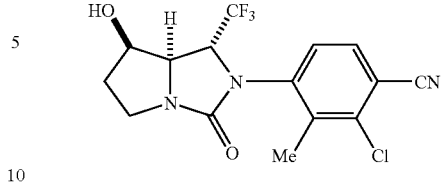
a pharmaceutically acceptable salt thereof.
* * * * *